United States Patent
Chen et al.

(10) Patent No.: US 12,121,530 B2
(45) Date of Patent: Oct. 22, 2024

(54) COMPOSITION AND METHODS FOR TREATING ARTICULATING JOINT DISORDERS WITH NUCLEOSIDE REVERSE TRANSCRIPTASE INHIBITORS

(71) Applicants: RHODE ISLAND HOSPITAL, Providence, RI (US); BROWN UNIVERSITY, Providence, RI (US)

(72) Inventors: Qian Chen, Barrington, RI (US); Yun Gao, Providence, RI (US); John M. Sedivy, Barrington, RI (US); Marco De Cecco, Pawtucket, RI (US)

(73) Assignees: RHODE ISLAND HOSPITAL, Providence, RI (US); BROWN UNIVERSITY, Providence, RI (US)

( * ) Notice: Subject to any disclaimer, the term of this patent is extended or adjusted under 35 U.S.C. 154(b) by 0 days.

(21) Appl. No.: 17/054,409

(22) PCT Filed: May 13, 2019

(86) PCT No.: PCT/US2019/032054
§ 371 (c)(1),
(2) Date: Nov. 10, 2020

(87) PCT Pub. No.: WO2019/217973
PCT Pub. Date: Nov. 14, 2019

(65) Prior Publication Data
US 2021/0379092 A1 Dec. 9, 2021

Related U.S. Application Data

(60) Provisional application No. 62/671,356, filed on May 14, 2018, provisional application No. 62/670,705, filed on May 11, 2018.

(51) Int. Cl.
| | | |
|---|---|---|
| *A01N 43/04* | (2006.01) |
| *A61K 31/675* | (2006.01) |
| *A61K 31/70* | (2006.01) |
| *A61K 31/7072* | (2006.01) |
| *A61K 31/7076* | (2006.01) |
| *A61K 31/708* | (2006.01) |
| *A61P 19/02* | (2006.01) |

(52) U.S. Cl.
CPC .......... *A61K 31/708* (2013.01); *A61K 31/675* (2013.01); *A61K 31/7072* (2013.01); *A61K 31/7076* (2013.01); *A61P 19/02* (2018.01)

(58) Field of Classification Search
None
See application file for complete search history.

(56) References Cited

U.S. PATENT DOCUMENTS

| | | |
|---|---|---|
| 4,172,896 A | 10/1979 | Uno et al. |
| 5,358,970 A | 10/1994 | Ruff et al. |
| 5,427,798 A | 6/1995 | Ludwig et al. |
| 5,541,231 A | 7/1996 | Ruff et al. |
| 5,731,000 A | 3/1998 | Ruff et al. |
| 5,763,493 A | 6/1998 | Ruff et al. |
| 6,110,973 A | 8/2000 | Young |
| 7,625,877 B2 | 12/2009 | Kohgo et al. |
| 9,221,832 B2 | 12/2015 | Hilpert et al. |
| 9,422,605 B2 | 8/2016 | Dubnau et al. |
| 9,441,223 B2 | 9/2016 | Dubnau et al. |
| 10,100,307 B2 | 10/2018 | Prochiantz et al. |
| 10,258,575 B2 | 4/2019 | Li |
| 10,363,220 B2 | 7/2019 | Li |
| 2003/0003468 A1 | 1/2003 | Crow |
| 2004/0229262 A1 | 11/2004 | Franco et al. |
| 2005/0113324 A1 | 5/2005 | Bondarev et al. |
| 2006/0020042 A1 | 1/2006 | McDonald et al. |
| 2006/0172956 A1 | 8/2006 | Bonner, Jr. et al. |
| 2010/0048726 A1 | 2/2010 | McDonald et al. |
| 2010/0292224 A1 | 11/2010 | Walter |
| 2011/0150997 A1 | 6/2011 | Shah et al. |
| 2011/0183006 A1 | 7/2011 | Yamka et al. |
| 2014/0113952 A1 | 4/2014 | Dubnau et al. |
| 2015/0018297 A1 | 1/2015 | Jo et al. |
| 2016/0339019 A1 | 11/2016 | Laberge et al. |
| 2017/0100439 A1 | 4/2017 | Harrell |
| 2017/0224680 A2 | 8/2017 | Laberge et al. |
| 2017/0335320 A1 | 11/2017 | Prochiantz et al. |
| 2018/0050000 A1 | 2/2018 | McKearn et al. |
| 2019/0038659 A1 | 2/2019 | Nath et al. |
| 2019/0388590 A1 | 12/2019 | Barrett et al. |

FOREIGN PATENT DOCUMENTS

| | | |
|---|---|---|
| JP | 2015520144 A | 7/2015 |
| WO | WO-2008054808 A2 | 5/2008 |
| WO | WO-2009153009 A1 | 12/2009 |
| WO | WO-2012068636 A1 | 5/2012 |
| WO | WO-2013167743 A1 | 11/2013 |
| WO | WO-2016005327 A1 | 1/2016 |

(Continued)

OTHER PUBLICATIONS

Zhang et al. FEBS Open Bio (2018), vol. 8, pp. 325-331.*
Lieberthal et al. Osteoarthritis and Cartilage (2015), vol. 23, No. 11, pp. 1825-1834.*
Scott, C., A. Brand, and M. Natha. "Reactive arthritis responding to antiretroviral therapy in an HIV-1-infected individual." International journal of STD & AIDS 23.5 (2012): 373-374.*
Ali, M., et al., "Overexpression of Transcripts Containing LINE-1 in the Synovia of Patients With Rheumatoid Arthritis," Annals of the Rheumatic Diseases 62(7):663-666, BMJ, England (Jul. 2003).

(Continued)

*Primary Examiner* — Patrick T Lewis
(74) *Attorney, Agent, or Firm* — Sterne, Kessler, Goldstein & Fox P.L.L.C.

(57) ABSTRACT

Described herein is are compositions and methods for treating an articulating joint disorders, comprising systemically administering to a subject a nucleoside reverse transcriptase inhibitor (NRTI).

14 Claims, 61 Drawing Sheets

Specification includes a Sequence Listing.

(56) References Cited

FOREIGN PATENT DOCUMENTS

| WO | WO-2016138425 A1 * | 9/2016 | ........... A61K 31/506 |
|---|---|---|---|
| WO | WO-2017050803 A1 | 3/2017 | |
| WO | WO-2019246422 A1 | 12/2019 | |

OTHER PUBLICATIONS

Altschul, S.F., et al., "Basic Local Alignment Search Tool," Journal of Molecular Biology 215(3):403-410, Elsevier, England (Oct. 1990).
Altschul, S.F., et al., "Gapped BLAST and Psi-Blast: A New Generation of Protein Database Search Programs," Nucleic Acids Research 25(17):3389-3402, Oxford University Press, England (Sep. 1997).
Andrianakos, A.A., et al., "Prevalence of Symptomatic Knee, Hand, and Hip Osteoarthritis in Greece. The ESORDIG Study," The Journal of Rheumatology 33(12):2507-2513, Journal of Rheumatology Publishing Co, Canada (Dec. 2006).
Ausubel., et al., Current Protocols in Molecular Biology, John Wiley & Sons, Inc., NY, (1995).
Belancio, V.P., et al., "Somatic Expression of LINE-1 Elements in Human Tissues," Nucleic Acids Research 38(12):3909-3922, Oxford University Press, England (Jul. 2010).
Berenbaum, F., "Osteoarthritis as an Inflammatory Disease (Osteoarthritis Is Not Osteoarthrosis!)," Osteoarthritis and Cartilage 21(1):16-21, W.B. Saunders For The Osteoarthritis Research Society, England (Jan. 2013).
Birren, S.J., et al., "Sympathetic Neuroblasts Undergo a Developmental Switch in Trophic Dependence," Development 119(3):597-610, Company of Biologists Limited, England (Nov. 1993).
Botter, S.M., et al., "Analysis of Osteoarthritis in a Mouse Model of the Progeroid Human DNA Repair Syndrome Trichothiodystrophy," Age 33(3):247-260, Springer, Netherlands (Sep. 2011).
Burns, K.H. and Boeke, J.D., "Human Transposon Tectonics," Cell 149(4):740-752, Cell Press, United States (May 2012).
Carlini, F., et al., "The Reverse Transcription Inhibitor Abacavir Shows Anticancer Activity in Prostate Cancer Cell Lines," Plos One 5(12):e14221, Public Library of Science, United States (Dec. 2010).
Chen, A.F., et al., "Oxidative DNA Damage in Osteoarthritic Porcine Articular Cartilage," Journal of Cellular Physiology 217(3):828-833, Wiley-Liss, United States (Dec. 2008).
Cho, Y.H., et al., "The Association of LINE-1 Hypomethylation with Age and Centromere Positive Micronuclei in Human Lymphocytes," PloS One 10(7):e0133909, Public Library of Science, United States (Jul. 2015).
Coppe, J.P., et al., "The Senescence-associated Secretory Phenotype: the Dark Side of Tumor Suppression," Annual Review of Pathology 5:99-118, Annual Reviews, United States (2010).
Dai, L., et al., "Effect of Reverse Transcriptase Inhibitors on LINE-1 and Ty1 Reverse Transcriptase Activities and on LINE-1 Retrotransposition," BMC Biochemistry 12:18, BioMed Central, England (May 2011).
D'ambrosia, R.D., "Epidemiology of Osteoarthritis," Orthopedics 28(2 Suppl):s201-s205, Slack, United States (Feb. 2005).
Davies, C.M., et al., "Reactive Nitrogen and Oxygen Species in Interleukin-1-mediated DNA Damage Associated With Osteoarthritis," Osteoarthritis and Cartilage 16(5):624-630, W.B. Saunders For The Osteoarthritis Research Society, England (May 2008).
De Cecco, M., et al., "Genomes of Replicatively Senescent Cells Undergo Global Epigenetic Changes Leading to Gene Silencing and Activation of Transposable Elements," Aging Cell 12(2):247-56, Wiley-Blackwell, England (Apr. 2013).
De Cecco, M., et al., "Transposable Elements Become Active and Mobile in the Genomes of Aging Mammalian Somatic Tissues," Aging 5(12):867-883, Impact Journals, LLC, United States (Dec. 2013).
De Koning, A.P.J., et al., "Repetitive Elements May Comprise Over Two-thirds of the Human Genome," PLos Genetics 7(12):e1002384, Public Library of Science, United States (Dec. 2011).

Duarte, J.H., "Osteoarthritis: SIRT6 Prevents Chondrocyte Senescence and DNA Damage," Nature Reviews. Rheumatology 11(5):260, Nature Pub. Group, United States (May 2015).
Erichsen, L., et al., "Genome-wide Hypomethylation of LINE-1 and Alu Retroelements in Cell-free DNA of Blood Is an Epigenetic Biomarker of Human Aging," Saudi Journal of Biological Sciences 25(6):1220-1226, Saudi Biological Society, Saudi Arabia (Sep. 2018).
Erwin, J.A., et al., "Mobile DNA Elements in the Generation of Diversity and Complexity in the Brain," Nature Reviews. Neuroscience 15(8):497-506, Nature Pub. Group, England (Aug. 2014).
Faulkner, G.J., "Retrotransposon Silencing During Embryogenesis: Dicer Cuts in LINE," PLoS Genetics 9(11):e1003944, Public Library of Science, United States (Nov. 2013).
Freund, A., et al., "Inflammatory Networks During Cellular Senescence: Causes and Consequences," Trends in Molecular Medicine 16(5):238-246, Elsevier Science Ltd., England (May 2010).
Gelber, A.C., et al., "Joint Injury in Young Adults and Risk for Subsequent Knee and Hip Osteoarthritis," Annals of Internal Medicine 133(5):321-328, American Society of Internal Medicine, United States (Sep. 2000).
GenBank, "A disintegrin and metalloproteinase with thrombospondin motifs 5 preproprotein [*Homo sapiens*]," Accession No. NP_008969.2, accessed at [https://www.ncbi.nlm.nih.gov/protein/NP_008969.2].
GenBank, "aggrecan core protein isoform 1 precursor [*Homo sapiens*]," Accession No. NP_001126.3, accessed at [https://www.ncbi.nlm.nih.gov/protein/NP_001126.3].
GenBank, "collagen alpha-1 (II) chain isoform 1 precursor [*Homo sapiens*]," Accession No. NP_001835.3, accessed at [https://www.ncbi.nlm.nih.gov/protein/NP_001835.3].
GenBank, "collagen alpha-1 (X) chain precursor [*Homo sapiens*]," Accession No. NP_000484.2, accessed at [https://www.ncbi.nlm.nih.gov/protein/NP_000484.2].
GenBank, "collagenase 3 preproprotein [*Homo sapiens*]," Accession No. NP_002418.1, accessed at [https://www.ncbi.nlm.nih.gov/protein/NP_002418.1].
GenBank, "*Homo sapiens* ADAM metallopeptidase with thrombospondin type 1 motif 5 (ADAMTS5), mRNA," Accession No. NM_007038.5, accessed at [https://www.ncbi.nlm.nih.gov/nuccore/NM_007038.5].
GenBank, "*Homo sapiens* aggrecan (ACAN), transcript variant 1, mRNA," Accession No. NM_001135.3, accessed at [https://www.ncbi.nlm.nih.gov/nuccore/NM_001135.3].
GenBank, "*Homo sapiens* collagen type II alpha 1 chain (col. 2A1), transcript variant 1, mRNA," Accession No. NM_001844.5, accessed at [https://www.ncbi.nlm.nih.gov/nuccore/NM_001844.5].
GenBank, "*Homo sapiens* collagen type X alpha 1 chain (col. 10A1), mRNA," Accession No. NM_000493.4, accessed at [https://www.ncbi.nlm.nih.gov/nuccore/NM_000493.4].
GenBank, "*Homo sapiens* Indian hedgehog signaling molecule (IHH), mRNA," Accession No. NM_002181.4, accessed at [https://www.ncbi.nlm.nih.gov/nuccore/NM_002181.4].
GenBank, "*Homo sapiens* interferon gamma receptor 1 (IFNGR1), transcript variant 1, mRNA," Accession No. NM_000416.2, accessed at [https://www.ncbi.nlm.nih.gov/nuccore/NM_000416.2].
GenBank, "*Homo sapiens* interleukin 6 (IL6), transcript variant 1, mRNA," Accession No. NM_000600.5, accessed at [https://www.ncbi.nlm.nih.gov/nuccore/NM_000600.5].
GenBank, "*Homo sapiens* matrix metallopeptidase 13 (MMP13), mRNA," Accession No. NM_002427.4, accessed at [https://www.ncbi.nlm.nih.gov/nuccore/NM_002427.4].
GenBank, "indian hedgehog protein preproprotein [*Homo sapiens*]," Accession No. NP_002172.2, accessed at [https://www.ncbi.nlm.nih.goc/protein/NP_002172.2].
GenBank, "interferon gamma receptor 1 isoform 1 precursor [*Homo sapiens*]," Accession No. NP_000407.1, accessed at [https://www.ncbi.nlm.nih.gov/protein/NP_000407.1].
GenBank, "interleukin-6 isoform 1 precursor [*Homo sapiens*]," Accession No. NP_000591.1, accessed at [https://www.ncbi.nlm.nih.gov/protein/NP_000591.1].
Goodier, J.L., "Restricting Retrotransposons: A Review," Mobile DNA 7:16, BioMed Central, England (Aug. 2016).

(56) References Cited

OTHER PUBLICATIONS

Guan, Y.J., et al., "Mir-365: A Mechanosensitive MicroRNA Stimulates Chondrocyte Differentiation Through Targeting Histone Deacetylase 4," FASEB Journal 25(12):4457-4466, Wiley, United States (Dec. 2011).
Guilak, F., "Biomechanical Factors in Osteoarthritis," Best Practice & Research. Clinical Rheumatology 25(6):815-823, Elsevier, Netherlands (Dec. 2011).
Guo, H., et al., "Autophagy Supports Genomic Stability by Degrading Retrotransposon RNA," Nature Communications 5:5276, Nature Pub. Group, England (Nov. 2014).
Hancks, D.C. and Kazazian, H.H., Jr., "Active Human Retrotransposons: Variation and Disease," Current Opinion in Genetics & Development 22(3):191-203, Elsevier, England (Jun. 2012).
Hancks, D.C. and Kazazian, H.H., Jr., "Roles for Retrotransposon Insertions in Human Disease," Mobile DNA 7:9, BioMed Central, England (May 2016).
Hardcastle, S.A., et al., "Osteoarthritis and Bone Mineral Density: Are Strong Bones Bad for Joints?," BoneKEy Reports 4:624, Nature Publishing Group, England (Jan. 2015).
Helmick, C.G., et al., "Estimates of the prevalence of arthritis and other rheumatic conditions in the United States. Part I," Arthritis and Rheumatism 58(1):15-25, Wiley-Blackwell, United States (Jan. 2008).
Henikoff, S. and Henikoff, J.G., "Amino Acid Substitution Matrices from Protein Blocks," Proceedings of the National Academy of Sciences USA 89(22):10915-10919, National Academy of Sciences, United States (Nov. 1992).
Hiruma, Y., et al., "A SQSTM1/p62 Mutation Linked to Paget's Disease Increases the Osteoclastogenic Potential of the Bone Microenvironment," Human Molecular Genetics 17(23):3708-3719, IRL Press, England (Dec. 2008).
Hochberg, M.C., et al., "Bone Mineral Density and Osteoarthritis: Data From the Baltimore Longitudinal Study of Aging," Osteoarthritis and Cartilage 12 Suppl A:S45-S48, W.B. Saunders For The Osteoarthritis Research Society, England (2004).
Hocking, L.J., et al., "Domain-specific Mutations in Sequestosome 1 (SQSTM1) Cause Familial and Sporadic Paget's Disease," Human Molecular Genetics 11(22):2735-2739, IRL Press, England (Oct. 2002).
Hoy, J.F., et al., "Immediate Initiation of Antiretroviral Therapy for HIV Infection Accelerates Bone Loss Relative to Deferring Therapy: Findings from the START Bone Mineral Density Substudy, a Randomized Trial," Journal of Bone and Mineral Research 32(9):1945-1955, Mary Ann Liebert, Inc., United States (Sep. 2017).
Hug, B.A., "HDAC4: A Corepressor Controlling Bone Development," Cell 119(4):448-449, Cell Press, United States (Nov. 2004).
International Search Report and Written Opinion for International Application No. PCT/US2019/032054, Commissioner for Patents, Virginia, dated Aug. 9, 2019.
Jones, R.B., et al., "Nucleoside Analogue Reverse Transcriptase Inhibitors Differentially Inhibit Human LINE-1 Retrotransposition," PLoS One 3(2):e1547, Public Library of Science, United States (Feb. 2008).
Kobayashi, T., et al., "Dicer-dependent Pathways Regulate Chondrocyte Proliferation and Differentiation," Proceedings of the National Academy of Sciences of the United States of America 105(6):1949-1954, National Academy of Sciences, United States (Feb. 2008).
Kobayashi, T., et al., "Early Postnatal Ablation of the MicroRNA-processing Enzyme, Drosha, Causes Chondrocyte Death and Impairs the Structural Integrity of the Articular Cartilage," Osteoarthritis and Cartilage 23(7):1214-1220, W.B. Saunders For The Osteoarthritis Research Society, England (Jul. 2015).
Laurin, N., et al., "Recurrent Mutation of the Gene Encoding Sequestosome 1 (SQSTM1/p62) in Paget Disease of Bone," American Journal of Human Genetics 70(6):1582-1588, Cell Press, United States (Jun. 2002).

Lawrence, R.C., et al., "Estimates of the Prevalence of Arthritis and Other Rheumatic Conditions in the United States. Part II," Arthritis and Rheumatism 58(1):26-35, Wiley-Blackwell, United States (Jan. 2008).
Lepetsos, P. and Papavassiliou, A.G., "ROS/oxidative Stress Signaling in Osteoarthritis," Biochimica Et Biophysica Acta 1862(4):576-591, Elsevier Pub. Co., Netherlands (Apr. 2016).
Levin, H.L. and Moran, J.V., "Dynamic Interactions Between Transposable Elements and Their Hosts," Nature Reviews. Genetics 12(9):615-627, Nature Pub. Group, England (Aug. 2011).
Loeser, R.F., et al., "Ageing and the Pathogenesis of Osteoarthritis," Nature Reviews. Rheumatology 12(7):412-420, Nature Pub. Group, United States (Jul. 2016).
Lohmander, L.S., et al., "The Long-term Consequence of Anterior Cruciate Ligament and Meniscus Injuries: Osteoarthritis," The American Journal of Sports Medicine 35(10):1756-1769, Sage Publications, United States (Oct. 2007).
Lopez-Otin, C., et al., "The Hallmarks of Aging," Cell 153(6):1194-1217, Cell Press, United States (Jun. 2013).
Lotz, M. and Loeser, R.F., "Effects of Aging on Articular Cartilage Homeostasis," Bone 51(2):241-248, Elsevier Science, United States (Aug. 2012).
Lotz, M.K. and Carames, B., "Autophagy and Cartilage Homeostasis Mechanisms in Joint Health, Aging and OA," Nature Reviews. Rheumatology 7(10):579-587, Nature Pub. Group, United States (Aug. 2011).
Maes, O.C., et al., "Stepwise Up-regulation of MicroRNA Expression Levels From Replicating to Reversible and Irreversible Growth Arrest States in WI-38 Human Fibroblasts," Journal of Cellular Physiology 221(1):109-119, Wiley-Liss, United States (Oct. 2009).
McClintock, B., "The Origin and Behavior of Mutable Loci in Maize," Proceedings of the National Academy of Sciences of the United States of America 36(6):344-355, National Academy of Sciences, United States (Jun. 1950).
Metzner, M., et al., "LINE-1 Retroelements Complexed and Inhibited by Activation Induced Cytidine Deaminase," PLoS One 7(11):e49358, Public Library of Science, United States (2012).
Meyer, P., et al., "A Model of the Onset of the Senescence Associated Secretory Phenotype After DNA Damage Induced Senescence," PLoS Computational Biology 13(12):e1005741, Public Library of Science, United States (Dec. 2017).
Michaud, C.M., et al., "The Burden of Disease and Injury in the United States 1996," Population Health Metrics 4:11, BioMed Central, England (Oct. 2006).
Moldovan, J.B. and Moran, J.V., "The Zinc-Finger Antiviral Protein ZAP Inhibits LINE and Alu Retrotransposition," PLoS Genetics 11(5):e1005121, Public Library of Science, United States (May 2015).
Morrish, T.A., et al., "DNA Repair Mediated by Endonuclease-independent LINE-1 Retrotransposition," Nature Genetics 31(2):159-165, Nature Pub. Co., United States (Jun. 2002).
Morrish, T.A., et al., "Endonuclease-Independent LINE-1 Retrotransposition at Mammalian Telomeres," Nature 446(7132):208-212, Nature Publishing Group, England (Mar. 2007).
Moss, T.J., et al., "Genome-wide Perturbations by miRNAs Map Onto Functional Cellular Pathways, Identifying Regulators of Chromatin Modifiers," NPJ Systems Biology and Applications 1:15001, Nature Publishing Group, England (Sep. 2015).
Needleman, S.B. and Wunsch, C.D., "A General Method Applicable to the Search for Similarities in the Amino Acid Sequence of Two Proteins," Journal of Molecular Biology 48(3):443-453, Academic Press, England (Mar. 1970).
O'Donnell, K.A., et al., "A Descent Into the Nuage: the Maelstrom of Transposon Control," Developmental Cell 15(2):179-181, Cell Press, United States (Aug. 2008).
Ogino, S., et al., "A Cohort Study of Tumoral LINE-1 Hypomethylation and Prognosis in Colon Cancer," Journal of the National Cancer Institute 100(23):1734-1738, Oxford University Press, United States (Dec. 2008).
Ogino, S., et al., "p21 Expression in Colon Cancer and Modifying Effects of Patient Age and Body Mass Index on Prognosis," Cancer Epidemiology, Biomarkers & Prevention 18(9):2513-2521, American Association for Cancer Research, United States (Sep. 2009).

(56) References Cited

OTHER PUBLICATIONS

Onuora, S., "Osteoarthritis: OA Chondrocytes Made Senescent by Genomic DNA Damage," Nature Reviews. Rheumatology 8(9):502, Nature Pub. Group, United States (Sep. 2012).

Ortiz-Montero, P., et al., "Senescence-associated IL-6 and IL-8 Cytokines Induce a Self-and Cross-reinforced Senescence/inflammatory Milieu Strengthening Tumorigenic Capabilities in the MCF-7 Breast Cancer Cell Line," Cell Communication and Signaling 15(1):17, BioMed Central, England (May 2017).

Ostertag, E.M. and Kazazian, H.H., Jr., "Biology of Mammalian L1 Retrotransposons," Annual Review of Genetics 35:501-538, Annual Reviews, United States (2001).

Patnala, R., et al., "Inhibition of LINE-1 Retrotransposon-encoded Reverse Transcriptase Modulates the Expression of Cell Differentiation Genes in Breast Cancer Cells," Breast Cancer Research and Treatment 143(2):239-253, Kluwer Academic, Netherlands (Jan. 2014).

Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).

Roman-Gomez, J., et al., "Promoter Hypomethylation of the LINE-1 Retrotransposable Elements Activates Sense/antisense Transcription and Marks the Progression of Chronic Myeloid Leukemia," Oncogene 24(48):7213-7223, Nature Publishing Group, England (Nov. 2005).

Sato, S., et al., "Direct and Indirect Suppression of lnterleukin-6 Gene Expression in Murine Macrophages by Nuclear Orphan Receptor REV-ERBalpha," TheScientificWorldJournal 2014:685854, Hindawi Publishing Corporation, United States (2014).

Shi, X., et al., "Cell Divisions Are Required for L1 Retrotransposition," Molecular and Cellular Biology 27(4):1264-1270, American Society for Microbiology, United States (Feb. 2007).

Smith, T.F. and Waterman, M.S., "Comparison of Biosequences," Advances in Applied Mathematics 2(4):482-489, Academic Press, Inc., United States (Dec. 1981).

St Laurent, G., 3rd., et al., "A LINE-1 Component to Human Aging: Do LINE Elements Exact a Longevity Cost for Evolutionary Advantage?," Mechanisms of Ageing and Development 131(5):299-305, Elsevier Science, Ireland (May 2010).

Xu, Z., et al., "miR-365, A Novel Negative Regulator of lnterleukin-6 Gene Expression, Is Cooperatively Regulated by Sp1 and NF-kappaB," The Journal of Biological Chemistry 286(24):21401-21412, Elsevier Inc., United States (Jun. 2011).

Yang, K., et al., "Creating Conditional Dual Fluorescence Labeled Transgenic Animals for Studying Function of Small Noncoding RNAs," Connective Tissue Research 58(1):103-115, Informa Healthcare, England (Jan. 2017).

Yang, X., et al., "Mechanical and IL-1 beta Responsive miR-365 Contributes to Osteoarthritis Development by Targeting Histone Deacetylase 4," International Journal of Molecular Sciences 17(4):436, Basel, Switzerland (Mar. 2016).

Chen, X, et al., "Photo-crosslinked HAMA hydrogel with cordycepin encapsulated chitosan microspheres for osteoarthritis treatment," Oncotarget 8(2):2835-2849, Impact Journals, United States (Dec. 2016).

Anderson, S. "Why is osteoarthritis an age-related disease?", Clinical Rheumatology, 24:15-26, Elsevier Ltd., The Netherlands (Feb. 2010).

\* cited by examiner

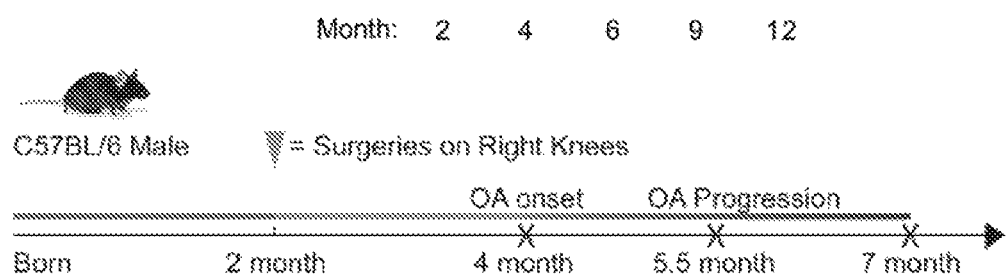
FIG. 1V
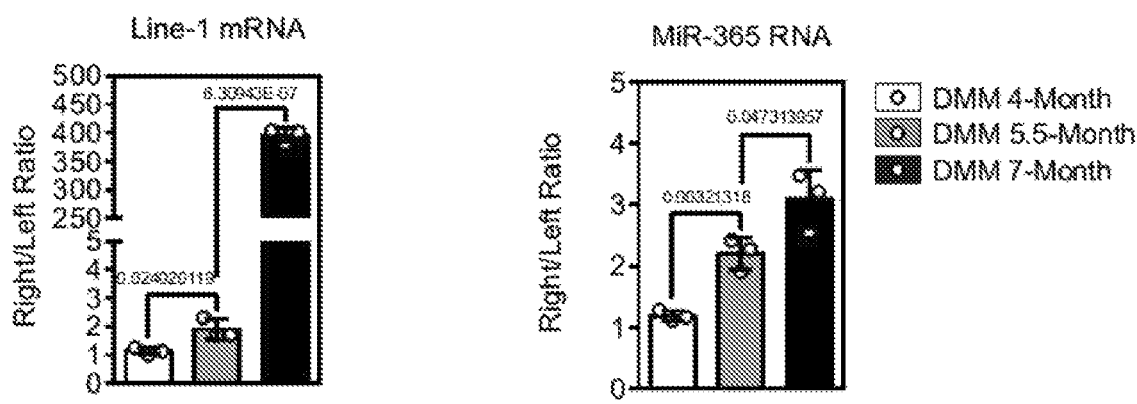
FIG. 1W  FIG. 1X

FIG. 3O     FIG. 3P

L1 suppressors predicted as miR-365 targets

| Post-transcriptional | Human | | Mouse |
|---|---|---|---|
| | miR-365 | miR-365* | miR-365 |
| AICDA | | √ | √ |
| CALCOCO2 | | | |
| HnRNPL | | √ | |
| APOBEC1 | | | √ |
| APOBEC2 | | | |
| APOBEC3A | | √ | |
| APOBEC3B | | | |
| APOBEC3C | | | |
| APOBEC3D | | | |
| APOBEC3F | √ | | |
| APOBEC3G | | | |
| APOBEC3H | | | |
| APOBEC4 | | | |
| ATG5 | | | |
| BCN1 | | | √ |
| MOV10 | | | |
| MTNR1A | | | |
| PABPC1 | | | |
| RNASEL | √ | √ | |
| SAMHD1 | | | |
| SQSTM1 | | √ | √ |
| TREX1 | | | |
| ZAP (ZC3HAV1) | √ | √ | √ |

| miRNA pathway | Human | | Mouse |
|---|---|---|---|
| | miR-365 | miR-365* | miR-365 |
| DGCR8 | | | |
| DICER1 | √ | √ | √ |
| DROSHA | | | |

| Epigenetic/Nuclear Factors | Human | | Mouse |
|---|---|---|---|
| | miR-365 | miR-365* | miR-365 |
| ATM | √ | | |
| DCLRE1C | | | |
| ERCC1 | | | |
| LIG4 | | | |
| MECP2 | √ | √ | |
| PRKDC | | √ | √ |
| SIRT6 | | | |
| XRCC4 | | | |
| XRCC6 | | | |

| KRAB zinc finger proteins (KRAB ZFPs) | Human | | Mouse |
|---|---|---|---|
| | miR-365 | miR-365* | miR-365 |
| ZBTB16 | | | √ |
| ZNF93 | | | N/A |

| Other transcriptional factors | Human | | Mouse |
|---|---|---|---|
| | miR-365 | miR-365* | miR-365 |
| RUNX3 | √ | √ | |
| SOX2 | | | |
| TP53(h) | √ | | |
| Trp53(m) | | | √ |

FIG. 8A

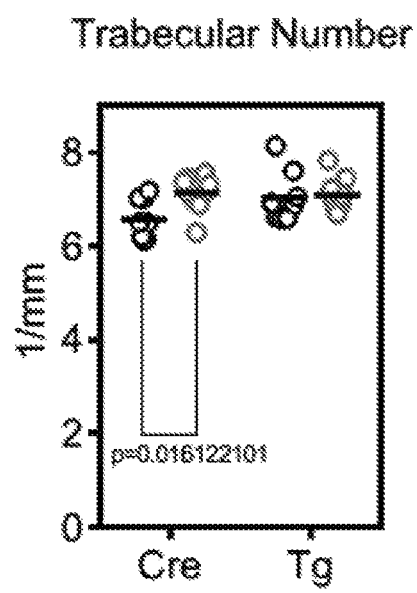
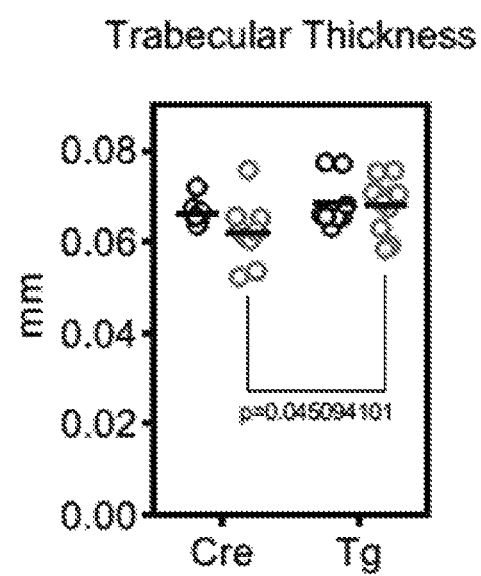
FIG. 9C     FIG. 9D

FIG. 12A

**Summary of NRTI on inhibiting strict OA
(Green/circled: Inhibiting OA, Red: Stimulating OA)**

FIG. 12B

**Summary of NRTI inhibiting expanded OA
(Green/circled: Inhibiting OA, Red: Stimulating OA)**

FIG. 12C

Summary of NRTI on expanded OA (Green/circled: Inhibiting OA, Red: Stimulating OA)

COMPOSITION AND METHODS FOR TREATING ARTICULATING JOINT DISORDERS WITH NUCLEOSIDE REVERSE TRANSCRIPTASE INHIBITORS

RELATED APPLICATIONS

This application claims the benefit of priority under 35 U.S.C. § 119(e) to U.S. Provisional Application Nos. 62/670,705, filed May 11, 2018, and 62/671,356, filed May 14, 2018, the entire contents of each of which is incorporated herein by reference in their entireties.

STATEMENT AS TO FEDERALLY SPONSORED RESEARCH

This invention was made with government support under P20 GM104937, P30 GM122732 awarded by the National Institutes of Health. The Government has certain rights in the invention.

INCORPORATION BY REFERENCE OF SEQUENCE LISTING

The contents of the sequence listing text file named "21486-641001WO_Sequence_Listing_ST25.txt", which was created on May 10, 2019 and is 131,072 bytes in size, is hereby incorporated by reference in its entirety.

FIELD OF THE INVENTION

The present invention relates to orthopedic disorders.

BACKGROUND

Arthritis affects tens of millions of patients in the U.S. annually. By 2040, an estimated 78 million (26%) of U.S. adults aged 18 years or older are projected to have physician-diagnosed arthritis. Osteoarthritis (OA) is the most common form of arthritis.

With knee OA, total or half knee replacement is a typical outcome, particularly in elderly subjects. Not infrequently, some patients have to go through secondary repair. Intramedullar infection, lethal fat embolism, surgery related fracture, unpredictable prognosis and endless post-operative physical therapy are risks shared by the patients. Moreover, patients usually have to double those aforementioned sufferings on the contralateral knee, and even for both hips.

Degenerative disorders such as osteoarthritis, osteoporosis, neurodegeneration, and tumorigenesis are often associated with aging and injury, which induce pro-inflammatory cytokines and matrix proteinases and result in tissue degeneration. For example, OA is a complicated chronic and highly prevalent degenerative joint disease. As the most common musculoskeletal disorder, OA is characterized by the degradation of articular cartilage and joint inflammation. Large numbers of individuals with OA throughout the world suffer from pain most in knees and hips joints. Current treatments are restricted to behavioral interventions and ultimately joint replacement surgery. There are still no effective pharmacological methods for prevention and treatment of OA.

SUMMARY OF THE INVENTION

The invention provides a solution to the long standing problem of treating osteoarthritic conditions in aging joints, e.g., greater than 50 year old, as well as trauma-induced joint OA, e.g., subsequent to an injury such as ligament tear/breach or cartilage, e.g., meniscus damage in an articulating joint.

Accordingly, a method for treating an articulating joint disorder comprises systemically administering to a subject a nucleoside reverse transcriptase inhibitor (NRTI). For example, the subject, e.g., a human subject, is diagnosed as comprising osteoarthritis (OA). In some embodiments, the subject does not comprises an human immunodeficiency virus (HIV, e.g., HIV-1 or HIV-2) infection. Exemplary compounds for treatment include NRTIs such as 3TC (lamivudine), FTC (Emtriva,) ABC (abacavir), TDF (tenofovir), ZDV (azidothmidine), or DD1 (Didanosine). Animal subjects such as companion animals, e.g., dogs, cats, as well as performance animals, e.g., horses, are within the scope of the inventions. Joint disorders include age-related and trauma-related OA.

As described above, it is therefore an object of the present invention to provide compounds and pharmaceutical compositions that exhibit anti-inflammation, and in particular, anti-chronic inflammation and/or anti-cartilage degeneration disease activity, as well as pharmaceutical compositions for the treatment of cartilage degeneration diseases, including all kinds of arthritis and skeletal disorders and for the treatment of cartilage degeneration diseases.

Any one or more of these and/or other objects of the invention may be readily gleaned from a review of the description of the invention which follows. Each embodiment disclosed herein is contemplated as being applicable to each of the other disclosed embodiments. Thus, all combinations of the various elements described herein are within the scope of the invention.

Despite the demographics and prevalence of osteoarthritic disease, there are still few or no effective pharmacological methods for prevention and treatment of tissue degenerative orders such OA. NRTIs are currently used for treatment of viral diseases (HIV etc.), the data described herein indicates that these NRTIs are effective for treatment of OA. The compositions and methods described herein do not require surgery or invasive means for therapy, e.g., the methods exclude surgery and/or are used in concert with a surgical intervention. Advantages of the invention include avoidance of an invasive procedure such as surgery as well an ease of use, low cost, and high patient compliance. Furthermore, the method causes neither tissue damage nor pain, and requires less patient supervision and decreased cost of care.

In aspects, provided herein are methods for treating an aging-associated joint disorder, comprising systemically administering to a subject a nucleoside nucleoside reverse transcriptase inhibitor (NRTI). In embodiments, the subject is at least 30, 40, 50, 60, 70, 80 years old or older. In other embodiments, the subject has been diagnosed with an aging-associated joint disorder (e.g., osteoarthritis (OA)). Post-traumatic OA can occur in individuals of any age. In embodiments, the method for treating an aging-associated joint disorder (OA), includes administering an NRTI, e.g., 3TC, FTC, ABC, TDF, ZDV, or DD1.

In other examples, the joint disorder originates or is associated with a trauma (post-traumatic OA), e.g., an injury to the joint or a surgery to a joint. In some embodiments, the subject does not comprise rheumatoid arthritis, an autoimmune disorder. In other embodiments, the subject comprises the auto immune disorder, rheumatoid arthritis.

In embodiments, the NRTI for treating an articulating joint disorder or an aging-associated joint disorder, inhibits the expression of osteoarthritis markers. In embodiments, the osteoarthritis markers comprise collagen type X alpha 1 chain (COL10A1), A Disintegrin and Metalloproteinase with Thrombospondin Motifs 5 (ADAMTS5), matrix metalloeptidase 13 (MMP13), senescence-associated secretory phenotype interleukin-6 (SASP IL-6), Indian hedgehog (Ihh) or interferon type 1 (IFN).

In other embodiments, the NRTI or treating an articulating joint disorder or an aging-associated joint disorder promotes the expression of anabolic markers, wherein the anabolic markers comprise aggrecan (ACAN) and Collagen, type II, alpha 1 (COL2A1).

In aspects, also provided herein are methods for treating a post-traumatic osteoarthritis (PTOA) injury in a subject, comprising systemically administering a nucleoside reverse transcriptase inhibitor (NRTI). In embodiments the subject is diagnosed as comprising osteoarthritis. In other embodiments, the NRTI comprises 3TC, FTC, ABC, TDF, ZDV, or DDl. In embodiments, the method further comprises administering 3MC.

In embodiments, the PTOA results from a high-speed impact twist, or pressure-induced trauma to the articular surface, intraarticular fractures, or joint-destabilizing soft-tissue tears. In embodiments, the PTOA injury is in a joint. In some examples, the joint includes an ankle, knee, or hip.

In embodiments, the methods for treating an articulating joint disorder, for treating an aging-associated joint disorder, or for treating a post-traumatic osteoarthritis injury, comprise administering an NRTI. In embodiments, the NRTI comprises a nucleoside analogue. In other embodiments, the NRTI comprises an adenosine analogue. In embodiments, the NRTI comprises a cytidine analog.

NTRIs include nucleoside analogues. Nucleosides are glycosylamines that can be characterized as nucleotides without a phosphate group. A nucleoside consists of a nucleobase (also termed a nitrogenous base) and a five-carbon sugar (either ribose or deoxyribose), whereas a nucleotide is composed of a nucleobase, a five-carbon sugar, and one or more phosphate groups. In a nucleoside, the anomeric carbon is linked through a glycosidic bond to the N9 of a purine or the N1 of a pyrimidine. Examples of nucleosides include cytidine, uridine, adenosine, guanosine, thymidine and inosine.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DESCRIPTION OF THE DRAWINGS

FIG. 1A-1X are a series of figures showing that MiR-365 over-expression promotes Line-1 gene expression in human OA lesion and mouse OA model.

FIG. 1A is a graph showing the gene expression of LINE-1 at the RNA level in human OA cartilage samples assessed by RT-qPCR.

FIG. 1V is a schematic representation of animal procedures: C57BL/6 mice underwent DMM or Sham surgeries on right legs at 2-month-old and were sacrificed at 4-month-old (2 months post-surgery) 5.5-month-old (3.5 months post-surgery) and 7-month-old (5 months post-surgery).

FIG. 1W is a bar graph showing the gene expression of Line-1-ORF2 at RNA level in WT C57BL/6 background mice articular cartilage was assessed by RT-qPCR. Line-1-ORF2 and miR-365 levels were significantly augmented in the cartilage of DMM knees at 3.5- and 5-month post DMM surgery when compared with 2-month post-surgery. There were 3 mice in each group. Student t-test was used for statistics. *p≤0.05, relative to appropriate control groups respectively.

FIG. 1X is a bar graph showing the gene expression of miR-365 at RNA level in WT C57BL/6 background mice articular cartilage was assessed by RT-qPCR. Line-1-ORF2 and miR-365 levels were significantly augmented in the cartilage of DMM (destabilization of medical meniscus) knees at 3.5- and 5-month post DMM surgery when compared with 2-month post-surgery. There were 3 mice in each group. Student t-test was used for statistics. *p≤0.05, relative to appropriate control groups respectively.

FIG. 2A is a schematic representation of Line-1 biogenesis and host mechanism of inhibition. n varies from 1 to 3 due to the size of human specimen. Statistics are calculated in samples with n≥3. *p≤0.05, relative to non-lesion (control) groups respectively.

FIG. 2O is an image of an immunoblot showing the protein expression of Dicer assessed by western blots analysis in human chondrocyte cell line-C28 which transiently over-expressed miR-365 mimic or miR-365 inhibitor. Dicer protein expression was down-regulated in C28 which transiently over-expressed miR-365 while inhibitor of miR-365 up-regulated Dicer protein expression. This is a representative blot form a total of 2 repeated experiments.

FIG. 3A is a bar graph showing the gene expression of Line-1 at RNA level in mouse primary chondrocytes treated with 3TC at various dosages. n=3 for all groups; *: p-value≤0.05, relative to control (saline) groups respectively.

FIG. 3O is a bar graph showing the gene expression of LINE-1 at RNA level in C28 transiently over-express miR-365 with 3TC treated at various dosages. n=3 for all groups; *: p-value≤0.05, relative to control (Mimic Ctrl) groups respectively.

FIG. 3P is a bar graph showing the gene expression of ADAMTS5 at RNA level in C28 transiently over-express miR-365 with 3TC treated at various dosages. n=3 for all groups; *: p-value≤0.05, relative to control (Mimic Ctrl) groups respectively.

FIG. 3AA is a graph showing the gene expression of Col10a1 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

FIG. 3AB is a graph showing the gene expression of Adamts5 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

FIG. 3AC is a graph showing the gene expression of miR-365 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

FIG. 4A is a graph showing the gene expression of Line-1 at RNA level in mouse PC treated with FTC at various dosages was assessed by RT-qPCR. n=3 for all groups; *: p-value≤0.05, relative to control (saline) groups respectively.

FIG. 4W is a graph showing the gene expression of miR-365 at RNA level in 129S6/SvEv mice which underwent DMM or Sham surgeries and subsequent treatment of Saline or FTC or 3TC respectively. Student t-test and one-way ANOVA test (s-w) were used for statistics. There were 6 mice in each group. *p≤0.05, relative to appropriate control groups respectively.

FIG. 5A is a bar graph showing information of sex and age of human OA patients, from whom the OA specimens were collected. Female patients (n=8) collectively had an average age of 69 yrs whilst male patients (n=4) represented an average age of 74 yrs. Student t-test was used for statistics.

FIG. 5B is a representative picture of gross morphology of a human OA specimen. Red square indicates a lesion (OA) area and green square indicates a non-lesion (healthy) area.

FIG. 5C is an image of H&E staining of sections from a non-lesion (healthy) area and a lesion (OA) area isolated from the specimen in (FIG. 5B).

FIG. 5D are images of Safranin 0/Fast Green staining of sections from a non-lesion (healthy) area and a lesion (OA) area isolated from the specimen in (FIG. 5B).

FIG. 5E are a series of images showing senescence β-Galactosidase (β-Gal) staining of sections from a non-lesion (healthy) area and a lesion (OA) area isolated from the specimen in (FIG. 5B). Arrows indicate positive β-Gal staining in chondrocytes.

FIG. 5F is a bar graph showing the number of chondrocytes that were positively stained with β-Gal from non-lesion (healthy) areas and lesion (OA) areas isolated from the specimen were counted manually by multiple researchers blind to the experiment in terms of the ratio over total cells in the field. n≥4. *p≤0.05, **p≤0.01 relative to appropriate control groups respectively.

FIG. 6A is a bar graph showing the gene expression of Line-1 expression in mouse primary chondrocytes transfected with siRNAs against Line-1 assessed by RT-qPCR. siLine-1C & D & E significantly suppressed Line-1 expression in mouse primary chondrocytes. siLine-1D was then selected for further experiments. n=3. *p≤0.05, relative to appropriate control (scramble siRNA) groups respectively. This experiment was conducted once FIG. 6B is a bar graph showing the gene expression of Acan at RNA level in mouse primary chondrocytes transfected with siRNA against Line-1 (siLine-1D) was assessed by RT-qPCR. n=2 for each treatment groups.

FIG. 6C is a bar graph showing the gene expression of Adamts5 at RNA level in mouse primary chondrocytes transfected with siRNA against Line-1 (siLine-1D) was assessed by RT-qPCR. n=2 for each treatment groups.

FIG. 6D is a bar graph showing the gene expression of Col10a1 at RNA level in mouse primary chondrocytes transfected with siRNA against Line-1 (siLine-1D) was assessed by RT-qPCR. n=2 for each treatment groups.

FIG. 6E is a bar graph showing the gene expression of IL-6 at RNA level in mouse primary chondrocytes transfected with siRNA against Line-1 (siLine-1D) was assessed by RT-qPCR. n=2 for each treatment groups.

FIG. 6F is a bar graph showing the gene expression of Mmp13 at RNA level in mouse primary chondrocytes transfected with siRNA against Line-1 (siLine-1D) was assessed by RT-qPCR. n=2 for each treatment groups.

FIG. 6G is a bar graph showing the gene expression of Tnf-α at RNA level in mouse primary chondrocytes transfected with siRNA against Line-1 (siLine-1D) was assessed by RT-qPCR. n=2 for each treatment groups.

FIG. 8A-8G are a series of images showing the Bioinformative search of potential miR-365 target genes which serve as Line-1 biogenesis inhibitors during host mechanism.

FIG. 8A are a series of tables showing bio-informative prediction of potential miR-365 targets. Genes listed here have been previously validated for their involvement in host's mechanism of Line-1 inhibition. The genes with conserved and simultaneous potential miR-365 seeding sites for post-transcriptional regulation in human and mouse are shown in red boxes, which are Aicda, Sqstm1, Zc3hav1 (Zap), Dicer1, Prkdc.

FIG. 8B is a schematic diagrams depicting the intersections of published Line-1 suppressors, predicted miR-365 targets by Targetscan and validated miR-365 in this study.

FIG. 8C is an image depicting the demonstrations of potential miR-365 seeding sites and mutations in the 3'UTR of genes in the red boxes in (FIG. 8A).

FIG. 8D is a graph showing the gene expression of Line-1 suppressor (Prkdc mRNA) at RNA level in Cre Only and miR-365 Tg mice articular cartilage was assessed. Prkdc expression was significantly down-regulated in the cartilage of miR-365 Tg mice. Student t-test was used for statistics. n=3. *p≤0.05, relative to appropriate control groups respectively.

FIG. 8E is a graph showing the gene expression of Line-1 suppressor (Dicer mRNA) at RNA level in Cre Only and miR-365 Tg mice articular cartilage was assessed. Prkdc expression was significantly down-regulated in the cartilage of miR-365 Tg mice. Student t-test was used for statistics. n=3. *p≤0.05, relative to appropriate control groups respectively.

FIG. 8F is a graph showing the gene expression of Line-1 suppressor (Sqstm1 mRNA) at RNA level in Cre Only and miR-365 Tg mice articular cartilage was assessed. Prkdc expression was significantly down-regulated in the cartilage of miR-365 Tg mice. Student t-test was used for statistics. n=3. *p≤0.05, relative to appropriate control groups respectively.

FIG. 8G is a graph showing the gene expression of Line-1 suppressor (Zc3hav1 mRNA) at RNA level in Cre Only and miR-365 Tg mice articular cartilage was assessed. Prkdc expression was significantly down-regulated in the cartilage of miR-365 Tg mice. Student t-test was used for statistics. n=3. *p≤0.05, relative to appropriate control groups respectively.

FIG. 9A-9F are a series of images depicting that 3TC treatment does not change subchondral bone morphometry in miR-365 Tg mice.

FIG. 9A are images of a 3D reconstruction of knee joints of mice being treated with saline or 3TC for 4 months FIG. 9B is a graph of a trabecular bone morphometry analysis of bone volume (BV)/total volume (TV) of subchondral bones in the knee joints of mice being treated with saline or 3TC for 4 months was assessed. n≥4. *p≤0.05, **p≤0.01 relative to appropriate control groups respectively.

FIG. 9C is a graph of the trabecular number of subchondral bones in the knee joints of mice being treated with saline or 3TC for 4 months was assessed. n≥4. *p≤0.05, **p≤0.01 relative to appropriate control groups respectively.

FIG. 9D is a graph of the trabecular thickness of subchondral bones in the knee joints of mice being treated with saline or 3TC for 4 months was assessed. n≥4. *p≤0.05, **p≤0.01 relative to appropriate control groups respectively.

FIG. 9E is a graph of the trabecular separation of subchondral bones in the knee joints of mice being treated with saline or 3TC for 4 months was assessed. n≥4. *p≤0.05, **p≤0.01 relative to appropriate control groups respectively.

FIG. 9F is a graph of the connectivity density of subchondral bones in the knee joints of mice being treated with saline or 3TC for 4 months was assessed. n≥4. *p≤0.05, **p≤0.01 relative to appropriate control groups respectively.

FIG. 10A-10I are a series of images showing that neither DMM nor Sham nor Saline nor 3TC nor FTC affected body weight of 129S6/SvEv mice.

FIG. 10A are images of a 3D reconstruction of knee joints of 129S6/SvEv mice which underwent DMM or Sham surgeries and subsequent treatment of saline or FTC or 3TC respectively.

FIG. 10B is a graph of trabecular bone morphometry analysis of bone volume (BV)/total volume (TV).

FIG. 10C is a graph of trabecular number of subchondral bones in the knee joints of 129S6/SvEv mice which underwent DMM or Sham surgeries and subsequent treatment of saline or FTC or 3TC respectively was assessed. n≥4. *p≤0.05, **p≤0.01 relative to appropriate control groups respectively.

FIG. 10D is a graph of trabecular thickness of subchondral bones in the knee joints of 129S6/SvEv mice which underwent DMM or Sham surgeries and subsequent treatment of saline or FTC or 3TC respectively was assessed. n≥4. *p≤0.05, **p≤0.01 relative to appropriate control groups respectively.

FIG. 10E is a graph of trabecular separation of subchondral bones in the knee joints of 129S6/SvEv mice which underwent DMM or Sham surgeries and subsequent treatment of saline or FTC or 3TC respectively was assessed. n≥4. *p≤0.05, **p≤0.01 relative to appropriate control groups respectively.

FIG. 10F is a graph of connectivity density of subchondral bones in the knee joints of 129S6/SvEv mice which underwent DMM or Sham surgeries and subsequent treatment of saline or FTC or 3TC respectively was assessed. n≥4. *p≤0.05, **p≤0.01 relative to appropriate control groups respectively.

Figure 10A:
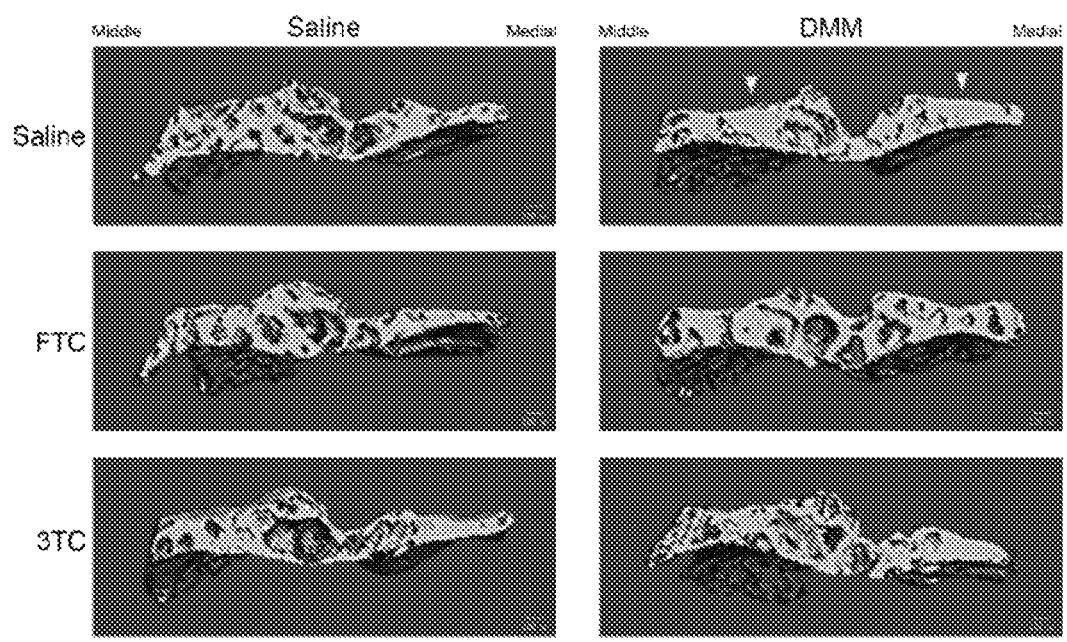
Figure 10B:
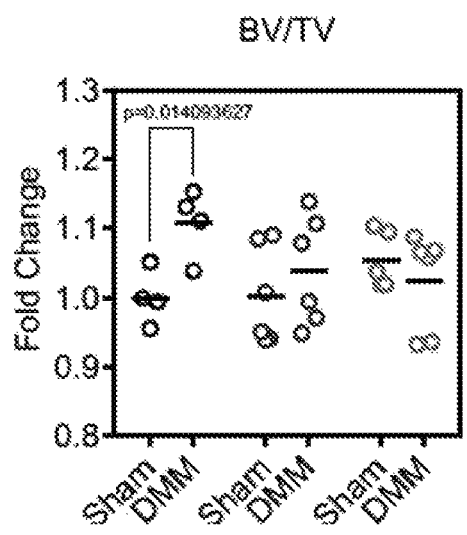
Figure 10C:
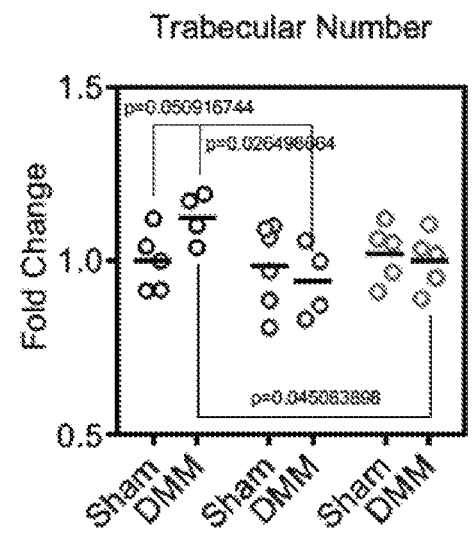
Figure 10D:
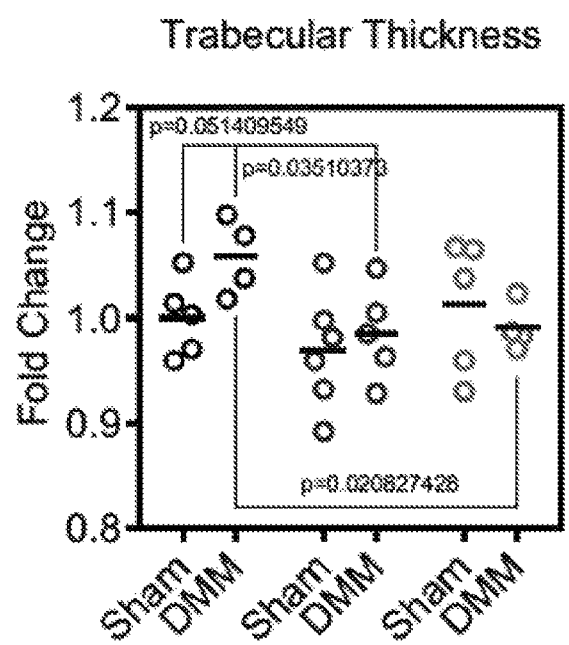
Figure 10E:
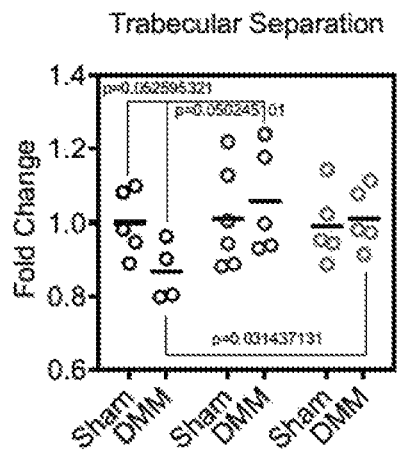
Figure 10F:
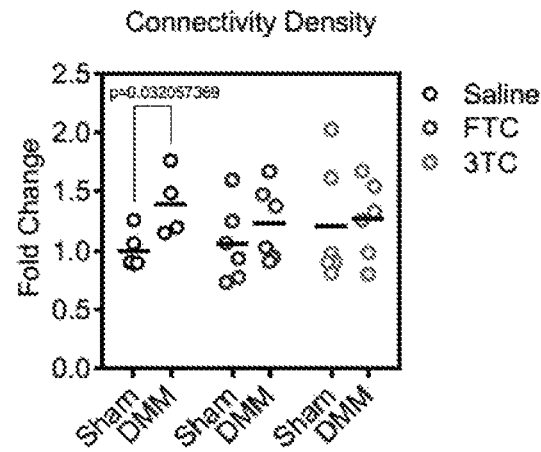
Figure 10G:
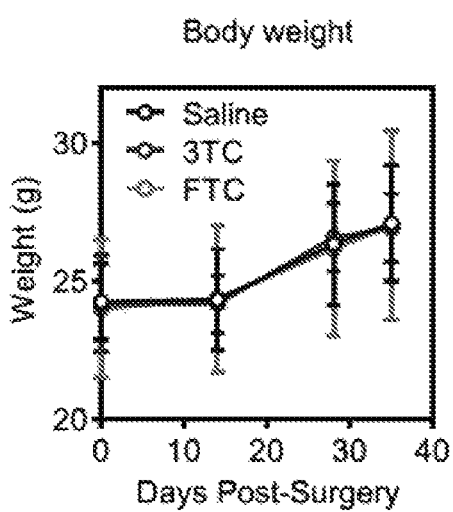

FIG. 10G is a graph of the body weight of 129S6/SvEv mice which underwent DMM or Sham surgeries and subsequent treatment of saline or FTC or 3TC respectively at various time points was assessed. No appreciable difference was observed between different treatment groups. There were 6 mice in each group respectively.

Figure 10H:
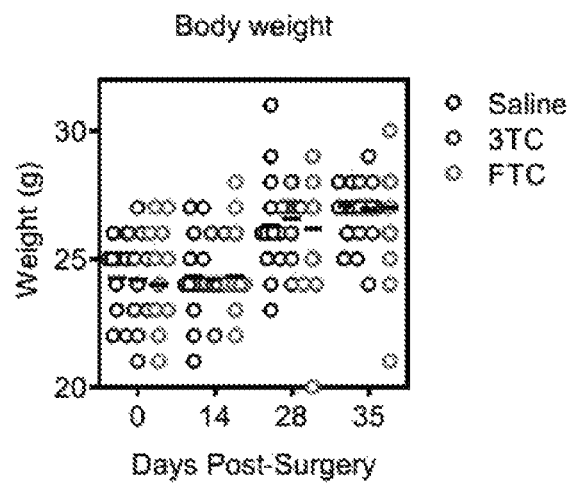

FIG. 10H is a graph of the body weight of 129S6/SvEv mice which underwent DMM or Sham surgeries and subsequent treatment of saline or FTC or 3TC respectively at various time points was assessed. No appreciable difference was observed between different treatment groups. There were 6 mice in each group respectively.

Figure 10I:
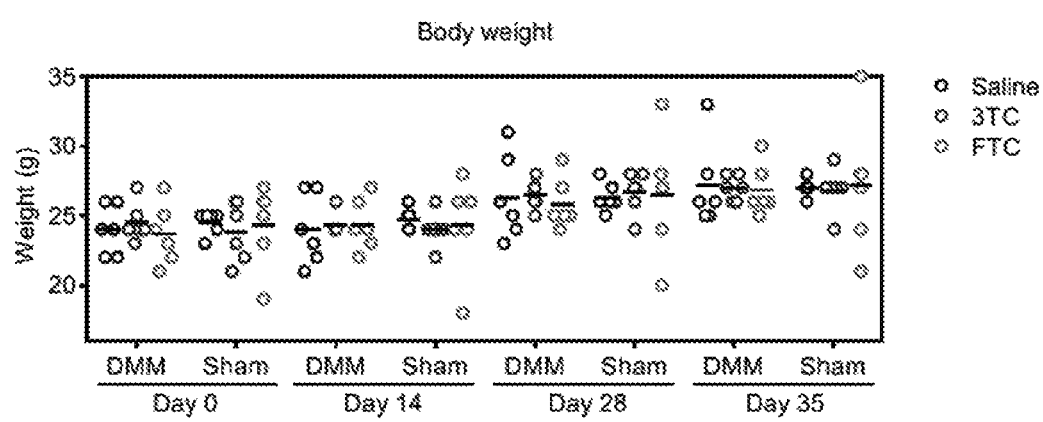

FIG. 10I is a graph of the body weight of 12956/SvEv mice which underwent DMM or Sham surgeries and subsequent treatment of saline or FTC or 3TC respectively at various time points was assessed. No appreciable difference was observed between different treatment groups. There were 6 mice in each group respectively.

Figure 11:
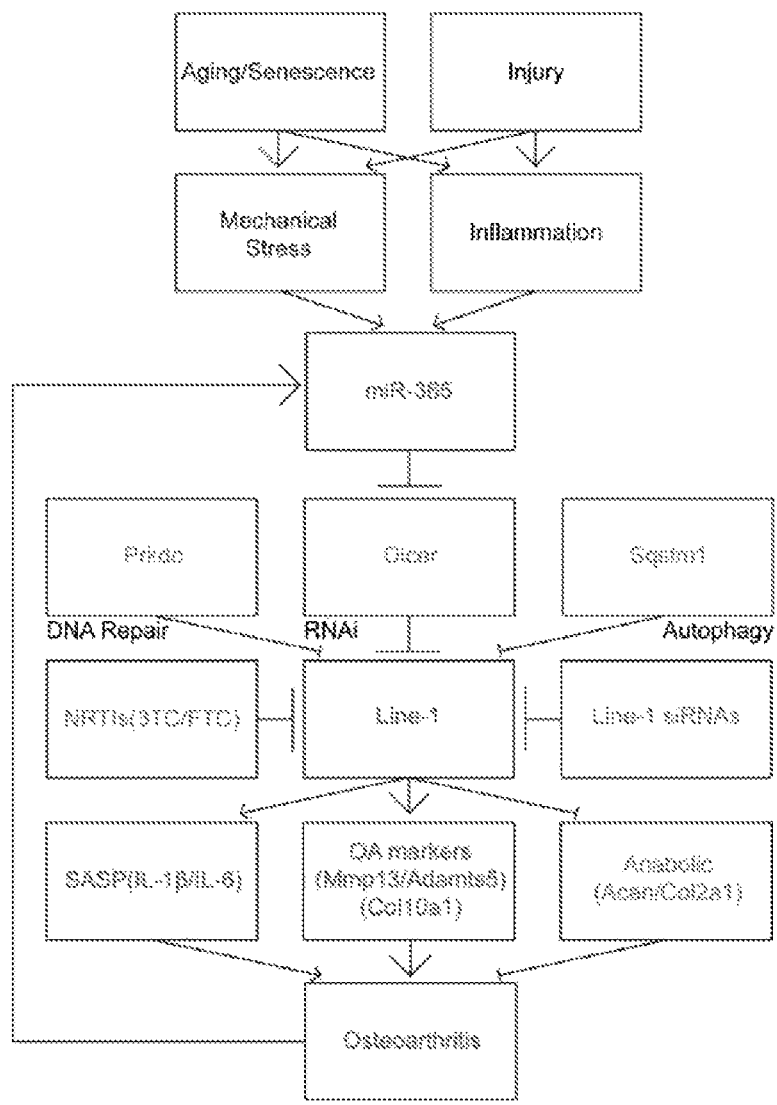

FIG. 11 is an image showing that MiR-365 over-expression in cartilage inhibited Line-1 suppressors expression thereby promoting Line-1 gene expression and subsequent OA development. A schematic representation showing the hypothesis that miR-365 increase in the cartilage caused by mechanical and inflammatory factors induced by aging/senescence or injury promotes Line-1 gene expression via post-transcriptional suppression of Line-1 inhibitors, including Dicer, Prkdc and Sqstm1, leading to Line-1 expression increase which eventually results in OA pathogenesis through up-regulation of Senescence Associated Secretory Phenotype (SASP) including IL-1β and IL-6 secretion, up-regulation of OA markers including Mmp13, Adamts5 and Col10a1 secretion and down-regulation of anabolic factors including Acan and Col2a1 synthesis. OA development will reciprocally drive miR-365 expression increase, forming a vicious cycle. Using siRNA against Line-1 or cytidine analogues (3TC and FTC) can suppress Line-1 gene expression and the development of OA, therefore interrupting the vicious cycle of miR-365-Line-1-OA.

FIGS. 12A-12C depict images of summary data of NRTI on OA, green (circled): inhibiting OA; red (shaded/non-circled): stimulating OA.

FIG. 12A is an image of summary data of Class I NRTIs (3TC, FTC or ABC) inhibiting strict OA only.

FIG. 12B is an image of summary data of Class II NRTIs (ZDV or TDF) inhibiting expanded OA.

FIG. 12C is an image of summary data of Class III NRTIs (DDL D4T) inhibiting expanded OA.

DETAILED DESCRIPTION

Treatment of joint degenerative disorders, as described herein, modulating retrotransposon(s) and/or its regulators and effectors, and their structural analogues are useful to achieve the purpose of inhibiting tissue degeneration and promoting regeneration of joint tissues. The data shown herein, demonstrate the use and efficacy of treatment of degenerative diseases by inhibiting microrna up-regulation of retrotransposon line-1 and use of NTRIs to treat OA and suppress Line-1 activities and prevent primary OA. Line is an acronym for (Long Interspersed Nuclear Element.)

Mechanical stress plays a pivotal role in osteoarthritis (OA) pathogenesis. In some cases, miR-365 expression is stimulated by mechanical loading in chondrocytes and is increased during OA pathogenesis. Moreover, transgenic mice in which miR-365 is specifically over-expressed in Col2a1 lineage cells develop early onset of OA. miR-365 over-expression is sufficient to elevate Line-1 expression in cartilage in vitro and in vivo, the resultant Line-1 expression increase is attributed to the suppression of its inhibitors including Dicer, Prkdc and Sqstm1, direct targets of miR-365. Furthermore, inhibiting Line-1 using NRTIs such as 3TC and FTC, as well as ABC, TDF, ZDV, or DDl rescue primary and secondary OA models in mice. Collectively the data indicate that NRTIs are useful for treatment of OA.

Compositions and methods were developed for inhibiting tissue degeneration and associated inflammation and matrix enzyme secretion by modulating retrotransposon and its regulatory pathways.

OA Pathogenesis

Mechanical stress and inflammation plays a pivotal role in OA pathogenesis. In contrast to rheumatoid arthritis, OA is not an autoimmune disease. The major components of osteoarthritis are not immune cells (contrary to rheumatoid arthritis, which is an autoimmune disease), and OA is associated with wear and tear. miR-365 expression is stimulated by mechanical loading and inflammation in chondrocytes and is increased during OA pathogenesis. Transgenic mice in which miR-365 is specifically over-expressed in Col2a1 lineage cells develop early onset of OA. Retrotransposon activation has been implicated in some aging-associated and chronic diseases, but its role in degenerative joint disease such as OA pathogenesis was not known prior to the invention.

Osteoarthritis occurs as a result of cumulative stress to a joint as a result of aging or as an aftermath of trauma such as an injury or surgical procedure performed on a joint, i.e., in some cases the development of OA is not age-related, e.g., occurs in subjects younger than 45 years old. Effectiveness of NRTIs on improvement of the clinical symptoms, e.g., pain or decreased mobility was a surprising observation in the treatment of age-related or trauma-related OA.

Disclosed herein is a data showing that the levels of retrotransposon Line-1 are significantly higher in the human OA cartilage lesions compared to normal cartilage. MiR-365 over-expression is sufficient to elevate retrotransposon Line-1 expression in cartilage in vitro and in vivo, the resultant Line-1 expression increase is attributed from the suppression of its inhibitors including Dicer, Prkdc and Sqstm1, which are direct targets of miR-365. Furthermore, inhibiting Line-1 using nucleoside reverse transcriptase inhibitors (NRTIs) including 3TC and FTC inhibits aging and trauma induced in art-recognized OA models in mice. OA cells secrete exosomes (vesicles), and Line-1 is present in those exosomes. Such Line-1 containing exosomes can infect non-OA cells.

Collectively the data indicate that OA is alleviated, e.g., effectively treated, by manipulating retrotransposon content and its related regulatory pathways in the cell. Therapeutic compositions include 1) inhibitors of miR-365, 2) Dicer, Prkdc, Sqstm1, or their agonists, 3) inhibiting the antagonists of Dicer, Prkdc, Sqstm1 and their respective pathways, 4) inhibitors or antagonists of retrotransposon including siRNA and NRTI small molecules. For example, NRTIs, which have been and are currently used for inhibiting viruses, can be re-purposed and used as a therapeutic medication to treat joint disease such as OA.

In addition, structural homologs or modified (e.g. methylated) NRTIs may also be used for OA treatment, even if they do not possess inhibitory properties against reverse transcriptase.

Osteoarthritis Markers

Exemplary osteoarthritis markers comprise collagen type X alpha 1 chain (COL10A1), A Disintegrin and Metalloproteinase with Thrombospondin Motifs 5 (ADAMTS5), matrix metallloeptidase 13 (MMP13), senescence-associated secretory phenotype interleukin-6 (SASP IL-6), Indian hedgehog (Ihh) or interferon type 1 (IFN).

Human Collagen type X alpha 1 chain (COL10A1) amino acid sequence is publicly available and can be found under GenBank Accession Number: NP_000484.2; SEQ ID NO: (99); GenBank Accession, incorporated herein by reference.

```
  1 mlpqipflll vslnlvhgvf yaeryqmptg ikgplpntkt qffipytiks kgiavrgeqg
 61 tpgppgpagp rghpgpsgpp gkpgygspgl ggepglpgpp gpsavgkpgv pglpgkpger
121 gpygpkgdvg paglpgprgp pgppgipgpa gisvpgkpgq qgptgapgpr gfpgekgapg
181 vpgmngqkge mgygapgrpg erglpgpqgp tgpsgppgvg krgengvpgq pgikgdrgfp
241 gemgpigppg pqgppgergp egigkpgaag apgqpgipgt kglpgapgia gppgppgfgk
301 pglpglkger gpaglpggpg akgeqgpagl pgkpgltgpp gnmgpqgpkg ipgshglpgp
361 kgetgpagpa gypgakgerg spgsdgkpgy pgkpgldgpk gnpglpgpkg dpgvggppgl
421 pgpvgpagak gmpghngeag prgapgipgt rgpigppgip gfpgskgdpg spgppgpagi
481 atkglngptg ppgppgprgh sgepglpgpp gppgppgqav mpegfikagq rpslsgtplv
541 sanqgvtgmp vsaftvilsk aypaigtpip fdkilynrqq hydprtgift cqipgiyyfs
601 yhvhvkgthv wvglykngtp vmytydeytk gyldqasgsa iidltendqv wlqlpnaesn
661 glysseyvhs sfsgflvapm
```

Exemplary landmark residues, domains, and fragments of COL10A1 include, but are not limited to residues 1-18 (signal sequence), residues 19-680 (mature protein), residues 57-519 (non-helical region), residues 155-202 (collagen triple helix repeat), or residues 520-980 (non-helical region). A fragment of a COL10A1 protein is less than the length of the full length protein, e.g., a fragment is at least 3, 4, 5, 6, 7, 8, 9, 10, 20, 30, 40, 50, 100, 200 or more residues in length, but less than e.g., COL10A1 residues in the case of COL10A1 above.

Human COL10A1 nucleic acid sequence is depicted below with start and stop codons underlined. The sequence is publicly available and can be found under GenBank Accession Number: NM_000493.4; SEQ ID NO: (100); GenBank Accession, incorporated herein by reference.

```
   1 accttctgca ctgctcatct gggcagagga agcttcagaa agctgccaag gcaccatctc
  61 caggaactcc cagcacgcag aatccatctg agaatatgct gccacaaata ccctttttgc
 121 tgctagtatc cttgaacttg gttcatggag tgtttacgc tgaacgatac aaatgccca
 181 caggcataaa aggcccacta cccaacacca agacacagtt cttcattccc tacaccataa
 241 agagtaaagg tatagcagta agaggagagc aaggtactcc tggtccacca ggccctgctg
 301 gacctcgagg gcacccaggt ccttctggac accaggaaa accaggctac ggaagtcctg
 361 gactccaagg agagccaggg ttgccaggac acccgggacc atcagctgta gggaaaccag
 421 gtgtgccagg actcccagga aaaccaggag agagaggacc atatggacca aaaggagatg
 481 ttggaccagc tggcctacca ggaccccggg gccaccagg accacctgga atccctggac
 541 cggctggaat ttctgtgcca ggaaaacctg gacaacaggg acccacagga gccccaggac
 601 ccagggctt tcctggagaa aagggtgcac caggagtccc tggtatgaat ggacagaaag
 661 gggaaatggg atatggtgct cctggtcgtc caggtgagag gggtcttcca ggccctcagg
 721 gtcccacagg accatctggc cctcctggag tgggaaaaag aggtgaaaat ggggttccag
 781 gacagccagg catcaaaggt gatagaggtt ttccgggaga aatgggacca attggcccac
 841 caggtcccca aggccctcct ggggaacgag gccagaagg cattggaaag ccaggagctg
 901 ctggagcccc aggccagcca gggattccag aacaaaagg tctccctggg gctccaggaa
 961 tagctgggcc cccagggcct cctggctttg gaaaccagg cttgccaggc ctgaagggag
1021 aaagaggacc tgctggcctt cctgggggtc caggtgccaa aggggaacaa gggccagcag
1081 gtcttcctgg gaagccaggt ctgactggac ccctgggaa tatgggaccc caaggaccaa
1141 aaggcatccc gggtagccat ggtctcccag gccctaaagg tgagacaggg ccagctgggc
1201 ctgcaggata ccctgggggct aagggtgaaa ggggttcccc tgggtcagat ggaaaaccag
```

-continued

```
1261 ggtacccagg aaaaccaggt ctcgatggtc ctaagggtaa cccagggtta ccaggtccaa 1321 aaggtgatcc tggagttgga ggacctcctg gtctcccagg ccctgtgggc ccagcaggag 1381 caaagggaat gcccggacac aatggagagg ctggcccaag aggtgcccct ggaataccag 1441 gtactagagg ccctattggg ccaccaggca ttccaggatt ccctgggtct aaagggatc 1501 caggaagtcc cggtcctcct ggcccagctg gcatagcaac taagggcctc aatggaccca 1561 ccgggccacc agggcctcca ggtccaagag gccactctgg agagcctggt cttccagggc 1621 cccctgggcc tccaggccca ccaggtcaag cagtcatgcc tgagggtttt ataaaggcag 1681 gccaaaggcc cagtctttct gggacccctc ttgttagtgc caaccagggg gtaacaggaa 1741 tgcctgtgtc tgcttttact gttattctct ccaaagctta cccagcaata ggaactccca 1801 taccatttga taaaattttg tataacaggc aacagcatta tgcccaagg actgaatct 1861 ttacttgtca gataccagga atatactatt tttcatacca cgtgcatgtg aaagggactc 1921 atgtttgggt aggcctgtat aagaatggca cccctgtaat gtacacctat gatgaataca 1981 ccaaaggcta cctggatcag gcttcaggga gtgccatcat cgatctcaca gaaaatgacc 2041 aggtgtggct ccagcttccc aatgccgagt caaatggcct atactcctct gagtatgtcc 2101 actcctcttt ctcaggattc ctagtggctc caatgtgagt acacacagag ctaatctaaa 2161 tcttgtgcta gaaaaagcat tctctaactc tacccccaccc tacaaaatgc atatggaggt 2221 aggctgaaaa gaatgtaatt tttattttct gaaatacaga tttgagctat cagaccaaca 2281 aaccttcccc ctgaaaagtg agcagcaacg taaaaacgta tgtgaagcct ctcttgaatt 2341 tctagttagc aatcttaagg ctctttaagg ttttctccaa tattaaaaaa tatcaccaaa 2401 gaagtcctgc tatgttaaaa acaaacaaca aaaacaaac aacaaaaaaa aaattaaaaa 2461 aaaaaacaga aatagagctc taagttatgt gaaatttgat ttgagaaact cggcatttcc 2521 tttttaaaaa agcctgtttc taactatgaa tatgagaact tctaggaaac atccaggagg 2581 tatcatataa ctttgtagaa cttaaatact tgaatattca aatttaaaag acactgtatc 2641 ccctaaaata tttctgatgg tgcactactc tgaggcctgt atggcccctt tcatcaatat 2701 ctattcaaat atacaggtgc atatatactt gttaaagctc ttatataaaa aagcccaaa 2761 atattgaagt tcatctgaaa tgcaaggtgc tttcatcaat gaacctttc aaactttct 2821 atgattgcag agaagctttt tatatacccca gcataacttg gaaacaggta tctgacctat 2881 tcttatttag ttaacacaag tgtgattaat ttgatttctt taattcctta ttgaatctta 2941 tgtgatatga ttttctggat ttacagaaca ttagcacatg taccttgtgc ctcccattca 3001 agtgaagtta taatttacac tgagggtttc aaaattcgac tagaagtgga gatatattat 3061 ttatttatgc actgtactgt atttttatat tgctgtttaa aacttttaag ctgtgcctca 3121 cttattaaag cacaaaatgt tttacctact ccttatttac gacgcaataa aataacatca 3181 atagattttt aggctgaatt aatttgaaag cagcaatttg ctgttctcaa ccattctttc 3241 aaggcttttc attgttcaaa gttaataaaa aagtaggaca ataaagtgat gggtggcttt 3301 ta
```

Human A Disintegrin and Metalloproteinase with Thrombospondin Motifs 5 (ADAMTS5) amino acid sequence is publicly available and can be found under GenBank Accession Number: NP_008969.2; SEQ ID NO: (101); GenBank Accession, incorporated herein by reference.

```
  1 mllgwaslll cafrlplaav gpaatpaqdk agqpptaaaa aqprrrqgee vqeraeppgh
 61 phplaqrrrs kglvgnidql ysgggkvgyl vyaggrrfll dlerdgsvgi agfvpagggt
121 sapwrhrshc fyrgtvdgsp rslavfdlcg gldgffavkh arytlkpllr gpwaeeekgr
181 vygdgsaril hvytregfsf ealpprasce tpastpeahe hapahsnpsg raalasqlld
241 qsalspaggs gpqtwwrrrr rsisrarqve lllvadasma rlygrglqhy lltlasianr
301 lyshasienh irlavvkvvv lgdkdkslev sknaattlkn fckwqhqhnq lgddheehyd
361 aailftredl cghhscdtlg madvgticsp erscaviedd glhaaftvah eighllglsh
421 ddskfceetf gstedkrlms siltsidask pwskctsati teflddghgn clldlprkqi
481 lgpeelpgqt ydatqqcnlt fgpeysvcpg mdvcarlwca vvrqgqmvcl tkklpavegt
541 pcgkgriclq gkcvdktkkk yystsshgnw gswgswgqcs rscgggvqfa yrhcnnpapr
601 nngryctgkr aiyrscslmp cppngksfrh eqceakngyq sdakgvktfv ewvpkyagvl
661 padvckltcr akgtgyyvvf spkvtdgtec rlysnsvcvr gkcvrtgcdg iigsklqydk
721 cgvcggdnss ctkivgtfnk kskgytdvvr ipegathikv rqfkakdqtr ftaylalkkk
781 ngeylingky mistsetiid ingtvmnysg wshrddflhg mgysatkeil ivqilatdpt
841 kpldvrysff vpkkstpkvn svtshgsnkv gshtsqpqwv tgpwlacsrt cdtgwhtrtv
901 qcqdgnrkla kgcplsgrps afkgcllkkc
```

Exemplary landmark residues, domains, and fragments of ADAMTS5 include, but are not limited to residues 1-18 (signal sequence), residues 67-168 (reprolysin family propeptide), residues 207-214 (cysteine switch), or residues 570-622 (thrombospondin type 1 repeats). A fragment of a ADAMTS5 protein is less than the length of the full length protein, e.g., a fragment is at least 3, 4, 5, 6, 7, 8, 9, 10, 20, 30, 40, 50, 100, 200 or more residues in length, but less than e.g., ADAMTS5 residues in the case of ADAMTS5 above.

Human ADAMTS5 nucleic acid sequence is depicted below with start and stop codons underlined. The sequence is publicly available and can be found under GenBank Accession Number: NM_007038.5; SEQ ID NO: (102); GenBank Accession, incorporated herein by reference.

```
  1 acagcgctcg cgctgctctc ggcgctcgca gctgccgact ggggatgacg gcgggcagga
 61 ggagaccgca gccgaaggga cacagacacg ccgcttcacc agctcgcctc aggctgcccc
121 cctgcatttt tgttttaatt tttacggctt tttcccctct ctttcttccc ttcctcctgg
181 tcccagcaga gccaaggaaa cccacaaaat aagaaaggaa gtgggccccg gagcttggaa
241 cctccacagc cggcttgtcc agcgcagcgc gggggcggga ggctgcgcgc accagttgcc
301 agcccggtgc gcggtacctt tccttacttt tcttgaaaca gcgatcgtgc ctgcatttgg
361 tggtttttg gttttgttt ttttcctttt cccgtatttg ctgaatctcc actatccgac
421 ttttttttt taatcttttc ttttccccccc ccccaccccc acctctttct ggagcacgaa
481 tccaaacatt ttcccaagca acaaagaaaa gttcgcacgc tggcaccgca gcccggacag
541 gctggcgctg ctgccgggcc cccctccctc cgacacttga ctcaatcctg caagcaagtg
601 tgtgtgtgtc cccatccccc gccccgttaa cttcatagca aataacaaat acccataaag
661 tcccagtcgc gcagcccctc cccgcgggca gcgcactatg ctgctcgggt gggcgtccct
721 gctgctgtgc gcgttccgcc tgcccctggc cgcggtcggc ccgccgcga cacctgccca
781 ggataaagcc gggcagcctc cgactgctgc agcagccgcc cagccccgcc ggcggcaggg
841 ggaggaggtg caggagcgag ccgagcctcc cggccacccg cacccctgg cgcagcggcg
```

-continued

```
 901  caggagcaag gggctggtgc agaacatcga ccaactctac tccggcggcg gcaaggtggg 961  ctacctcgtc tacgcgggcg gccggaggtt cctcttggac ctggagcgag atggttcggt 1021  gggcattgct ggcttcgtgc ccgcaggagg cgggacgagt gcgccctggc gccaccggag 1081  ccactgcttc tatcggggca cagtggacgg tagtccccgc tctctggctg tctttgacct 1141  ctgtggggt ctcgacggct tcttcgcggt caagcacgcg cgctacaccc taaagccact 1201  gctgcgcgga ccctgggcgg aggaagaaaa ggggcgcgtg tacggggatg ggtccgcacg 1261  gatcctgcac gtctacaccc gcgagggctt cagcttcgag ccctgccgc cgcgcgccag 1321  ctgcgaaacc cccgcgtcca caccggaggc ccacgagcat gctccggcgc acagcaaccc 1381  gagcggacgc gcagcactgg cctcgcagct cttggaccag tccgctctct cgcccgctgg 1441  gggctcagga ccgcagacgt ggtggcggcg gcggcgccgc tccatctccc gggcccgcca 1501  ggtggagctg cttctggtgg ctgacgcgtc catggcgcgg ttgtatggcc ggggcctgca 1561  gcattacctg ctgaccctgg cctccatcgc caataggctg tacagccatg ctagcatcga 1621  gaaccacatc cgcctggccg tggtgaaggt ggtggtgcta ggcgacaagg acaagagcct 1681  ggaagtgagc aagaacgctg ccaccacact caagaacttt gcaagtggc agcaccaaca 1741  caaccagctg ggagatgacc atgaggagca ctacgatgca gctatcctgt ttactcggga 1801  ggatttatgt gggcatcatt catgtgacac cctgggaatg cagacgttg gaccatatg 1861  ttctccagag cgcagctgtg ctgtgattga agacgatggc ctccacgcag ccttcactgt 1921  ggctcacgaa atcggacatt tacttggcct ctcccatgac gattccaaat tctgtgaaga 1981  gacctttggt tccacagaag ataagcgctt aatgtcttcc atccttacca gcattgatgc 2041  atctaagccc tggtccaaat gcacttcagc caccatcaca gaattcctgg atgatggcca 2101  tggtaactgt ttgctggacc taccacgaaa gcagatcctg ggccccgaag aactcccagg 2161  acagacctac gatgccaccc agcagtgcaa cctgacattc gggcctgagt actccgtgtg 2221  tcccggcatg gatgtctgtg ctcgcctgtg gtgtgctgtg gtacgccagg ccagatggt 2281  ctgtctgacc aagaagctgc ctgcggtgga agggacgcct tgtggaaagg ggagaatctg 2341  cctgcagggc aaatgtgtgg acaaaaccaa gaaaaatat tattcaacgt caagccatgg 2401  caactgggga tcttggggat cctggggcca gtgttctcgc tcatgtggag gaggagtgca 2461  gtttgcctat cgtcactgta ataaccctgc tcccagaaac aacgacgct actgcacagg 2521  gaagagggcc atctaccgct cctgcagtct catgccctgc ccacccaatg gtaaatcatt 2581  tcgtcatgaa cagtgtgagg ccaaaaatgg ctatcagtct gatgcaaaag gagtcaaaac 2641  ttttgtggaa tgggttccca aatatgcagg tgtcctgcca gcggatgtgt gcaagctgac 2701  ctgcagagcc aagggcactg gctactatgt ggtatttttct ccaaaggtga ccgatggcac 2761  tgaatgtagg ctgtacagta attccgtctg cgtccggggg aagtgtgtga gaactggctg 2821  tgacggcatc attggctcaa agctgcagta tgacaagtgc ggagtatgtg gaggagacaa 2881  ctccagctgt acaaagattg ttggaacctt taataagaaa agtaagggtt acactgacgt 2941  ggtgaggatt cctgaagggg caacccacat aaaagttcga cagttcaaag ccaaagacca 3001  gactagattc actgcctatt tagccctgaa aaagaaaaac ggtgagtacc ttatcaatgg 3061  aaagtacatg atctccactt cagagactat cattgacatc aatggaacag tcatgaacta 3121  tagcggttgg agccacaggg atgacttcct gcatgcatg ggctactctg ccacgaagga 3181  aattctaata gtgcagattc ttgcaacaga ccccactaaa ccattagatg tccgttatag 3241  ctttttttgtt cccaagaagt ccactccaaa agtaaactct gtcactagtc atggcagcaa 3301  taaagtggga tcacacactt cgcagccgca gtgggtcacg ggcccatggc tcgcctgctc
```

-continued

```
3361  taggacctgt gacacaggtt ggcacaccag aacggtgcag tgccaggatg gaaaccggaa 3421  gttagcaaaa ggatgtcctc tctcccaaag gccttctgcg tttaagcaat gcttgttgaa 3481  gaaatgttag cctgtggtta tgatcttatg cacaaagata actggaggat tcagcactga 3541  tgcagtcgtg gtgaacagga ggtctaccta acgcacagaa agtcatgctt cagtgacatt 3601  gtcaacagga gtccaattat gggcagaatc tgctctctgt gaccaaaaga ggatgtgcac 3661  tgcttcacgt gacagtggtg accttgcaat atagaaaaac ttgggagtta ttgaacatcc 3721  cctgggctta caagaaacac tgatgaatgt aaaatcaggg gacatttgaa gatggcagaa 3781  ctgtctcccc cttgtcacct acctctgata gaatgtcttt aatggtatca taatcatttt 3841  cacccataat acacagtagc ttcttcttac tgtttgtaaa tacattctcc cttggtatgt 3901  cactttatat cccctggttc tattaaaata tccatatata tttctataaa aaaagtgttt 3961  gaccaaagta ggtctgcagc tatttcaact tccttccgtt tccagaaaga gctgtggata 4021  ttttactgga aattaagaac ttgctgctgt tttaataaga tgtagtatat tttctgacta 4081  caggagataa aatttcagtc aaaaaaccat tttgacagca agtatcttct gagaaatttt 4141  gaaaagtaaa tagatctcag tgtatctagt cacttaaata catacacggg ttcatttact 4201  taaacctttg actgcctgta ttttttttcag gtagctagcc aaattaatgc ataatttcag 4261  atgtagaagt agggtttgcg tgtgtgtgtg tgatcatact caagagtcta aaaactagtt 4321  tccttgtgtt ggaaatttaa aaggaaaaaa atcgtatttc actgtgtttt caatttatat 4381  tttcacaact actttctctc tccagagctt tcatctgata tctcacaatg tatgatatac 4441  gtacaaaaca cacagcaagt tttctatcat gtccaacaca ttcaacactg gtatacctcc 4501  taccagcaag cctttaaaat gcatttgtgt ttgcttattt gttttgttca agggttcagt 4561  aagacctaca atgttttgta tttcttgact tattttatta gaaacattaa agatcacttg 4621  gtagttagcc acattgagaa gtggttatca ttgttaatgt ggttaatgcc aaaaagtggt 4681  taatattaat aagactgttt ccacaccata ggcaataatt tcttaattta aaaaatctaa 4741  gtatattcct attgtactaa atattttttcc caactggaaa gcacttgatt gtacccgtaa 4801  gtgtttgagt gatgacatgt gatgattttc agaaagttgt tgttttttgtt tccatagcct 4861  gtttaagtag gttgtaagtt tgaatagtta gacatggaaa ttatttata agcacacacc 4921  taaagatatc tttttagatg ataaaatgta cacccccccca tcaccaacct cacaacttag 4981  aaaatctaag ttgtttgatt tctttgggat ttcttttgtt gtgaaacact gcaaagccaa 5041  ttttttcttta taaaaattca tagtaatcct gccaaatgtg cctattgtta aagatttgca 5101  tgtgaagatc ttagggaacc actgtttgag ttctacaagc tcatgagagt ttatttttat 5161  tataagatgt ttttaatata aaagaattat gtaactgatc actatattac atcatttcag 5221  tgggccagga aaatagatgt cttgctgttt tcagtatttt cttaagaaat tgcttttaaa 5281  acaaataatt gttttacaaa accaataatt atcccttgaa ttttcataga ctgactttgc 5341  ttttgacgta gaaatttttt ttctcaataa attatcactt tgagaaatga ggcctgtaca 5401  aggctgataa cctatatgtg atggagatca cccaatgcca agggcagaaa gcaaacctag 5461  ttaaataggt gagaaaaaaa ataataatcc cagtgccatt tgtctgtgca aagagaatta 5521  ggagagaggt taatgttact ttttttccatt ttggaaataa ttttaatcaa gtaactcaaa 5581  tgtgacaaaa tttatttttta ttttttgtgg ttatattccc aacaacatta aaaaatactc 5641  gaggcataaa tgtagttgtc tcctactctg cttctcttac tatactcata cattttttaat 5701  atggtttatc aatgattcat gtttccctca aatagtgatg gtttacacct gtcatggaaa
```

-continued

```
5761  caatcctaga gagctcagag caattaaacc actattccat gcttttaagt agttttctcc
5821  accttttct tatgagtctc actagattga ctgaggaatg tatgtctaaa ttcctggaga
5881  agatgatatg gattggaaac tgaaattcag agaaatggag tgttcaatag ataccacgaa
5941  ttgtgaacaa agggaaaatt ctatacaact caatctaagt cagtccactt tgacttcgta
6001  ctgtctttca cctttccatt gttgcatctt gaatttttta aaatgtctag aattcaggat
6061  gctaggggct acttctttaa aaaaaaaaaa aaaaagaat tcgtctgaaa atgctcaggt
6121  ttgtaagaat ctaatctcac ttacataact aagcactcca aataagttt tattaagtac
6181  aaagggagcc agaaaaaatg acatttattt cttctagatc agaaaaattt aaattaagcc
6241  ctgccttgct gtttagaaat atgtgggcat tgttataatt tattcaataa atttatgttc
6301  ctttgccttc ctgtggaaac agttttatcc cactaaacta ggaattaggg gataaatcac
6361  aaacaaaaaa aaagttgcag cactgaaaaa aagtaattta ttgttttgc aactggtatg
6421  tgaatttgtg tgataaaatt atttattctt atttaacaaa aatatgttca aattttctta
6481  tatttaaaat gttttgctgt tgtcctactt tttaatttat gcttcatgtt tgtgtataaa
6541  gtacactttt acactttgtg agtttacata atatacagca ctggttgctt ttgtattttt
6601  ttacagaaag ctttctgtgt gaagcaggtg tatatgtata tattcctcat gtattcttat
6661  tctgatacta tcatttttct ttccaaggaa attttaatct gtcatgacca atagtgttca
6721  ttacttgtgc ctatgataat aggttttta catcacatta acactatttt ttccaagtca
6781  caaataagaa aaacacttat tcaatgaaac aaggtgcaag ttttaaattt gggtacacaa
6841  atagcctaga agcttcctac agacgctaag acacagccaa taatcagatc ctttcacttc
6901  atcgagaaac ttggacaagt cgatattgat gtattagatg aaagttgtct acacacaact
6961  tctgagggat acaaacgata ataaaaccaa atgttgtctg tttctccttt agaaacacct
7021  cctaaaatta atatcattta gtctctagtg tctgtaggat ctacagatg agcacaaata
7081  gattgggttt gtataacaaa tgctaatagt cataactgtt tctacaaata tggggtgtcc
7141  attaagagaa tgtgatgttt tcctactgct gttgaatccc atgggtgat tataggactt
7201  gaaataggca gagtcacctc tgatgacatc agcttgcctc tgtgatttca cagtctgatc
7261  ctggcaacaa gacaaagcac ccttggacac acagccaatc tctggttgtg atatttcccc
7321  attgattcct tccttgttaa caaggtcatt ttaatggttc aggtgaggac agcagccaga
7381  ttcaaagtcc agaatttgtg ctgttacata gagttcacac tgtcaaataa cattgaattt
7441  aataatgatc aaattttct agtagtcttt ggcagagtgt ataatctcat tggcatgatt
7501  ggtgaatatt actaatctct ttataatgaa agatgcttta caaataccttt atatttgcta
7561  acatttcaaa actactaaat aaatgaaata gccatgtgta cagaaatggt catttaaagc
7621  tttaatagaa ccaaattcaa gacaatgtat catttagaca cacagaaaag gaacttgtat
7681  gttttcccta ttattttct catttgccaa caatctatag ttttaggtta tcaaacagat
7741  agatcaactt aactggctag tacattgaaa aatcttccta agaatccttt gttagcataa
7801  tctatagaga taatttctca aattatatca tcatgatgca tataaactct ataatgtata
7861  attgtgtttc atttatttaa tgtatgagaa catattgaaa tacaaaacca tgcattagcc
7921  aaaaaattgg aatacaggta gtgttcagat cagcaaaaca ttcagtctgg taaatgcctg
7981  cctggggcta tgatatcatt ctcaatgcag gttttatgga aaactaaaa gaatatgttg
8041  ttagatgatg ttggttttga aaaaaaaaag acattaacat acacattagt tagcccagtt
8101  aattgcattc tactaatata gttgcacatt agcaataatt ttgctgtctc tggtctttat
8161  tttgtggctt caactaactg gaccatgtgg actgtaaagg tcaaatggaa aaaacgagca
```

```
8221  gtggccccte atcctgtaag gtactgctac atcagagtga cctaaaagtc taacactgtg 8281  aggaaaactg tgatttgtag gaaaaaaaaa aaaaacaaat aaaaaacagg gcatgcttt 8341  taattttttt ccactttcct ttggcacacc caatgaacaa ttctaattt tattgaggtg 8401  ctaacatctt tcgtgaccga ctgtcaaatg tggtatttt gagttactat ttttctacat 8461  gattttacag tttgcaagaa agacctctaa gctttgtgtc acggtagggc acaacttgat 8521  actcaaaatt tgaaaaataa gcacatccaa tgattgtttt gaccaacagt ggtcagtgac 8581  gtaaactgca tgtgcatctg aggacattta aggggtcatt aaaatttgag gagcatcagg 8641  ccggagtagc agactttag atgagtcata tttcagcatt cactaagtcc tcagcattcc 8701  attcaaactg tcgtgtatat ttggcctgat ttttttcaa gctttgcaat aattatgtt 8761  attggtaaac acttggtgac tatatctcag ccttttcttt aacaactcac aatatattag 8821  aaacacgtct acctatactg agagtatatt tacaatagaa gaacatactg tatgtgactt 8881  tgtaaagcta gactttgat taagaaatat ataatctctg gatgctattt ttgcattata 8941  cactcaggca caacgtaaac cttgatggct catcttgcta caattacgag ttgaaaaaca 9001  ctacttacgt atttgtatga cctattagtc agaggaaatc atacatatgc tttgtaaata 9061  gactttgcag ataactaaat agactgaaga aatatgttgc atttgataga agcaattgca 9121  taaatatttg gtttctatat tagagtctgt gagtaaagtc aagtaataaa cctaagtagg 9181  tataacagat ttttaaacct tgaaacttgc tttgatggta gagaaaatca ttgaagattt 9241  acatactgta tataagatgt aaaatgtacg ctgcttatta ccctcaattt tccagaagca 9301  atggtatata atgcagttga aaaaccaaaa atcttggaaa actaagacgg gtcttgttta 9361  aaatgtctct cagctttggc aaccttcaaa tcttaatcaa ctatttaaag cattactgtg 9421  tcttgtagcc tgcattccac aacagctctg ttattcaggt aaaagacttg aactgagccg 9481  tttgggacct atactgtaat attttcattg aggaacaata tcctattttg taaagcattt 9541  ccctatgtgt gactttaaac tgtaaaatta aacactgctt ttgtgggttc agtgggcata 9601  ataaatataa attgtaaact a
```

Human matrix metalloeptidase 13 (MMP13) amino acid sequence is publicly available and can be found under GenBank Accession Number: NP_002418.1; SEQ ID NO: (103); GenBank Accession, incorporated herein by reference.

```
  1  mhpgvlaafl flswthcral plpsggdedd lseedlqfae rylrsyyhpt nlagilkena 61  assmterlre mqsffglevt gklddntldv mkkprcgvpd vgeynvfprt lkwskmnlty 121  rivnytpdmt hsevekafkk afkvwsdvtp lnftrlhdgi adimisfgik ehgdfypfdg 181  psgllahafp pgpnyggdah fdddetwtss skgynlflva ahefghslgl dhskdpgalm 241  fpiytytgks hfmlpdddvq giqslygpgd edpnpkhpkt pdkcdpslsl daitslrget 301  mifkdrffwr lhpqqvdael fltksfwpel pnridaayeh pshdlififr grkfwalngy 361  dilegypkki selglpkevk kisaavhfed tgktllfsgn qvwryddtnh imdkdyprli 421  eedfpgigdk vdavyekngy iyffngpiqf eysiwsnriv rvmpansilw c
```

Exemplary landmark residues, domains, and fragments of MMP13 include, but are not limited to residues 1-19 (signal sequence), residues 32-91 (Putative peptidoglycan binding domain), or residues 112-267 (peptidase m10). A fragment of a MMP13 protein is less than the length of the full length protein, e.g., a fragment is at least 3, 4, 5, 6, 7, 8, 9, 10, 20, 30, 40, 50, 100, 200 or more residues in length, but less than e.g., MMP13 residues in the case of MMP13 above.

Human MMP13 nucleic acid sequence is depicted below with start and stop codons underlined. The sequence is publicly available and can be found under GenBank Accession Number: NM_002427.4; SEQ ID NO: (104); GenBank Accession, incorporated herein by reference.

```
   1  aacagtcccc aggcatcacc attcaagatg catccagggg tcctggctgc cttcctcttc
  61  ttgagctgga ctcattgtcg ggccctgccc cttcccagtg gtggtgatga agatgatttg
 121  tctgaggaag acctccagtt tgcagagcgc tacctgagat catactacca tcctacaaat
 181  ctcgcgggaa tcctgaagga gaatgcagca agctccatga ctgagaggct ccgagaaatg
 241  cagtctttct tcggcttaga ggtgactggc aaacttgacg ataacacctt agatgtcatg
 301  aaaaagccaa gatgcggggt tcctgatgtg ggtgaataca atgttttccc tcgaactctt
 361  aaatggtcca aaatgaattt aacctacaga attgtgaatt acacccctga tatgactcat
 421  tctgaagtcg aaaaggcatt caaaaaagcc ttcaaagttt ggtccgatgt aactcctctg
 481  aattttacca gacttcacga tggcattgct gacatcatga tctcttttgg aattaaggag
 541  catggcgact tctacccatt tgatgggccc tctggcctgc tggctcatgc ttttcctcct
 601  gggccaaatt atggaggaga tgcccatttt gatgatgatg aaacctggac aagtagttcc
 661  aaaggctaca acttgtttct tgttgctgcg catgagttcg gccactcctt aggtcttgac
 721  cactccaagg accctggagc actcatgttt cctatctaca cctacaccgg caaaagccac
 781  tttatgcttc ctgatgacga tgtacaaggg atccagtctc tctatggtcc aggagatgaa
 841  gaccccaacc ctaaacatcc aaaaacgcca gacaaatgtg acccttcctt atcccttgat
 901  gccattacca gtctccgagg agaaacaatg atctttaaag acagattctt ctggcgcctg
 961  catcctcagc aggttgatgc ggagctgttt taacgaaat cattttggcc agaacttccc
1021  aaccgtattg atgctgcata tgagcaccct tctcatgacc tcatcttcat cttcagaggt
1081  agaaaatttt gggctcttaa tggttatgac attctggaag ttatcccaa aaaaatatct
1141  gaactgggtc ttccaaaaga agttaagaag ataagtgcag ctgttcactt tgaggataca
1201  ggcaagactc tcctgttctc aggaaaccag gtctggagat atgatgatac taaccatatt
1261  atggataaag actatccgag actaatagaa gaagacttcc caggaattgg tgataaagta
1321  gatgctgtct atgagaaaaa tggttatatc tatttttttca acggaccccat acagtttgaa
1381  tacagcatct ggagtaaccg tattgttcgc gtcatgccag caaattccat tttgtggtgt
1441  taagtgtctt tttaaaaatt gttatttaaa tcctgaagag catttggggt aatacttcca
1501  gaagtgcggg gtaggggaag aagagctatc aggagaaagc ttggttctgt gaacaagctt
1561  cagtaagtta tctttgaata tgtagtatct atatgactat gcgtggctgg aaccacattg
1621  aagaatgtta gagtaatgaa atggaggatc tctaaagagc atctgattct tgttgctgta
1681  caaaagcaat ggttgatgat acttcccaca ccacaaatgg gacacatggt ctgtcaatga
1741  gagcataatt taaaaatata tttataagga aattttacaa gggcataaag taaatacatg
1801  catataatga ataaatcatt cttactaaaa agtataaaat agtatgaaaa tggaaatttg
1861  ggagagccat acataaaaga aataaaccaa aggaaaatgt ctgtaataat agactgtaac
1921  ttccaaataa ataattttca ttttgcactg aggatattca gatgtatgtg ccctttcttca
1981  cacagacact aacgaaatat caaagtcatt aaagacagga gacaaaagag cagtggtaag
2041  aatagtagat gtggcctttg aattctgttt aattttcact tttggcaatg actcaaagtc
2101  tgctctcata taagacaaat attcctttgc atattataaa ggataaagaa ggatgatgtc
2161  ttttttattaa aatatttcag gttcttcaga agtcacacat tacaaagtta aaattgttat
2221  caaaatagtc taaggccatg gcatcccttt tcataaaatt atttgattat ttaagactaa
2281  aagttgcatt ttaaccctat tttacctagc taattattta attgtccagt ttgtcttgga
2341  tatataggct attttctaaa gacttgtata gcatgaaata aaatatatct tataaagtgg
2401  aagtatgtat attaaaaaag agacatccaa atttttttttt aaagcagtct actagattgt
```

-continued

```
2461  gatcccttga gatatggaag gatgccttt tttctctgca tttaaaaaaa tcccccagca 2521  cttcccacag tgcctattga tacttgggga gggtgcttgg cacttattga atatatgatc 2581  ggccatcaag ggaagaacta ttgtgctcag agacactgtt gataaaaact caggcaaaga 2641  aaatgaaatg catatttgca aagtgtatta ggaagtgttt atgttgttta taataaaaat 2701  atattttcaa caga
```

Human senescence-associated secretory phenotype interleukin-6 (SASP IL-6) amino acid sequence is publicly available and can be found under GenBank Accession Number: NP_000591.1; SEQ ID NO: (105); GenBank Accession, incorporated herein by reference.

```
  1   mnsfstsafg pvafslglll vlpaafpapv ppgedskdva aphrgpltsseridkqiryi 61   ldgisalrke tcnksnmces skealaennl nlpkmaekdg cfqsgfneet clvkiitgll 121   efevyleylq nrfesseeqa ravqmstkvl iqflqkkakn ldaittpdpt tnaslltklq 181   aqnqwlqdmt thlilrsfke flqsslralr qm
```

Exemplary landmark residues, domains, and fragments of SASP IL-6 include, but are not limited to residues 30-212 (interleukin 6) or residue 73 (glycosylation). A fragment of a SASP IL-6 protein is less than the length of the full length protein, e.g., a fragment is at least 3, 4, 5, 6, 7, 8, 9, 10, 20, 25, 30, 40, 50, 100, 200 or more residues in length, but less than e.g., SASP IL-6 residues in the case of SASP IL-6 above.

Human SASP IL-6 nucleic acid sequence is depicted below with start and stop codons underlined. The sequence is publicly available and can be found under GenBank Accession Number: NM_000600.5; SEQ ID NO: (106); GenBank Accession, incorporated herein by reference.

```
   1  attctgccct cgagcccacc gggaacgaaa gagaagctct atctcccctc caggagccca 61  gct atg aact ccttctccac aagcgccttc ggtccagttg ccttctccct ggggctgctc 121  ctggtgttgc ctgctgcctt ccctgcccca gtaccccag gagaagattc caaagatgta 181  gccgccccac acagacagcc actcacctct tcagaacgaa ttgacaaaca aattcggtac 241  atcctcgacg gcatctcagc cctgagaaag gagacatgta acaagagtaa catgtgtgaa 301  agcagcaaag aggcactggc agaaaacaac ctgaaccttc caaagatggc tgaaaagat 361  ggatgcttcc aatctggatt caatgaggag acttgcctgg tgaaaatcat cactggtctt 421  ttggagtttg aggtatacct agagtacctc cagaacagat tgagagtag tgaggaacaa 481  gccagagctg tgcagatgag tacaaaagtc ctgatccagt tcctgcagaa aaaggcaaag 541  aatctagatg caataaccac ccctgaccca accacaaatg ccagcctgct gacgaagctg 601  caggcacaga accagtggct gcaggacatg acaactcatc tcattctgcg cagctttaag 661  gagttcctgc agtccagcct gagggctctt cggcaaatgt ag catgggca cctcagattg 721  ttgttgttaa tgggcattcc ttcttctggt cagaaacctg tccactgggc acagaactta 781  tgttgttctc tatggagaac taaaagtatg agcgttagga cactatttta attattttta 841  atttattaat atttaaatat gtgaagctga gttaatttat gtaagtcata tttatatttt 901  taagaagtac cacttgaaac atttatgta ttagttttga aataataatg gaaagtggct 961  atgcagtttg aatatccttt gtttcagagc cagatcattt cttggaaagt gtaggcttac 1021  ctcaaataaa tggctaactt atacatattt ttaaagaaat atttatattg tatttatata 1081  atgtataaat ggttttata ccaataaatg gcattttaaa aaattca
```

Human Indian hedgehog (Ihh) amino acid sequence is publicly available and can be found under GenBank Accession Number: NP_002172.2; SEQ ID NO: (107); GenBank Accession, incorporated herein by reference.

```
  1 msparlrprl hfclvlllll vvpaawgcgp grvvgsrrrp prklvplayk qfspnvpekt
 61 lgasgryegk iarsserfke ltpnynpdii fkdeentgad rlmtqrckdr lnslaisvmn
121 qwpgvklrvt egwdedghhs eeslhyegra vdittsdrdr nkygllarla veagfdwvyy
181 eskahvhcsv ksehsaaakt ggcfpagaqv rlesgarval savrpgdrvl amgedgsptf
241 sdvlifldre phrlrafqvi etqdpprrla ltpahllfta dnhtepaarf ratfashvqp
301 gqyvlvagvp glqparvaav sthvalgaya pltkhgtlvv edvvascfaa vadhhlaqla
361 fwplrlfhsl awgswtpgeg vhwypqllyr lgrllleegs fhplgmsgag s
```

Exemplary landmark residues, domains, and fragments of Ihh include, but are not limited to residues 1-27 (signal peptide), residues 28-441 (mature peptide), residues 28-202 (IHH N-product), residues 44-189 (hedgehog amino terminal signaling domain) or residues 203-411 (IHH protein C-product). A fragment of a Ihh protein is less than the length of the full length protein, e.g., a fragment is at least 3, 4, 5, 6, 7, 8, 9, 10, 20, 30, 40, 50, 100, 200 or more residues in length, but less than e.g., Ihh residues in the case of Ihh above.

Human Ihh nucleic acid sequence is depicted below with start and stop codons underlined. The sequence is publicly available and can be found under GenBank Accession Number: NM_002181.4; SEQ ID NO: (108); GenBank Accession, incorporated herein by reference.

```
   1 actcggcccc gggctgcgcc gcagacggca gcagctcccg ctccgcccga gccgcctgac
  61 cgccgggccg gggtgctaac cgcggggccc tgcagcccgc cggccccgcc agcccagccc
 121 agcccggcgg cccgcagccc cgccgcccgc cgcccccgc cgccgccgcg ttgccaaaac
 181 aaacgggccg gcctatttat tggcggccgc cgagcccggc agctcagagt cgaggcgccg
 241 aggggggacag cgcgccgcca ccagctcggg ccctgggccc ccgccccgca cttgagtccc
 301 gccggccctg gccgcaccac gccgcccatg gcgcccccgc ctggagcccc ccggagccac
 361 ccggacgcct gagccccgc agcgctcccg tcgacgcgcc tgcccatcag cccaccagga
 421 gacctcgccc gccgctcccc cgggctcccc ggccatgtct cccgcccggc tccggccccg
 481 actgcacttc tgcctggtcc tgttgctgct gctggtggtg ccggcggcat ggggctgcgg
 541 gccgggtcgg gtggtgggca gccgccggcg accgccacgc aaactcgtgc cgctcgccta
 601 caagcagttc agccccaatg tgcccgagaa gaccctgggc gccagcggac gctatgaagg
 661 caagatcgct cgcagctccg agcgcttcaa ggagctcacc cccaattaca atccagacat
 721 catcttcaag gacgaggaga acacaggcgc cgaccgcctc atgacccagc gctgcaagga
 781 ccgcctgaac tcgctggcta tctcggtgat gaaccagtgg cccggtgtga agctgcgggt
 841 gaccgagggc tgggacgagg acggccacca ctcagaggag tccctgcatt atgagggccg
 901 cgcggtggac atcaccacat cagaccgcga ccgcaataag tatggactgc tggcgcgctt
 961 ggcagtggag gccggctttg actgggtgta ttacgagtca aaggcccacg tgcattgctc
1021 cgtcaagtcc gagcactcgg ccgcagccaa gacgggcggc tgcttccctg ccggagccca
1081 ggtacgcctg gagagtgggg cgcgtgtggc cttgtcagcc gtgaggccgg gagaccgtgt
1141 gctggccatg ggggaggatg ggagcccccac cttcagcgat gtgctcattt tcctggaccg
1201 cgagcctcac aggctgagag cttccaggt catcgagact caggaccccc cacgccgcct
1261 ggcactcaca cccgctcacc tgctctttac ggctgacaat cacacggagc cggcagcccg
1321 cttccgggcc acatttgcca gccacgtgca gcctggccag tacgtgctgg tggctggggt
```

-continued

```
1381  gccaggcctg cagcctgccc gcgtggcagc tgtctctaca cacgtggccc tcggggccta
1441  cgccccgctc acaaagcatg ggacactggt ggtggaggat gtggtggcat cctgcttcgc
1501  ggccgtggct gaccaccacc tggctcagtt ggccttctgg ccctgagac tctttcacag
1561  cttggcatgg ggcagctgga ctccggggga gggtgtgcat tggtaccccc agctgctcta
1621  ccgcctgggg cgtctcctgc tagaagaggg cagcttccac ccactgggca tgtccggggc
1681  agggagctga aaggactcca ccgctgccct cctggaactg ctgtactggg tccagaagcc
1741  tctcagccag gagggagctg gccctggaag ggacctgagc tgggggacac tggctcctgc
1801  catctcctct gccatgaaga tacaccattg agacttgact gggcaacacc agcgtccccc
1861  accccgtcg tggtgtagtc atagagctgc aagctgagct ggcgagggga tggttgttga
1921  cccctctctc ctagagacct tgaggctggc acggcgactc ccaactcagc ctgctctcac
1981  tacgagtttt catactctgc ctcccccatt ggggagggcc cattccatcc atcttaggcc
2041  cctttgggtg ggcttgcgcc tcagttgatg ctgctaaatt ccctgggagc cagcatggat
2101  ctggctggac ccgatgctgt ccagaactgg gaaggccaca ggggtggggc agccatcccg
2161  gccattctga ggtatgacat tcctccccgg ccacactcct caagacacat ccagagactg
2221  ttgctgtctg tgggcagagt tctgtgttct ggccaatgtg accgtagtgc cggggactgg
2281  gggaggtggg ttggatgtgc ttgccacccc cccggctaag ctccccttc tgctgaacca
2341  tgatccccac ccctccgcc ggtcagtctc ccataccta tttattggag tggaggggga
2401  agcccatggg agaattttgg ggatgttttg gtcttttctt ccttttgtaa taaaaattat
2461  ttaagttgtt aga
```

Human interferon type 1 (IFN) amino acid sequence is publicly available and can be found under GenBank Accession Number: NP_000407.1; SEQ ID NO: (109); GenBank Accession, incorporated herein by reference.

```
  1  mallfllplv mqgvsraemg tadlgpssvp tptnvtiesy nmnpivywey qimpqvpvft
 61  vevknygvkn sewidacini shhycnisdh vgdpsnslwv rvkarvgqke sayakseefa
121  vcrdgkigpp kldirkeekq imidifhpsv fvngdeqevd ydpettcyir vynvyvrmng
181  seiqykiltq keddcdeiqc qlaipvssln sqycvsaegv lhvwgvttek skevcitifn
241  ssikgslwip vvaalllflv lslvficfyi kkinplkeks iilpkslisv vrsatletkp
301  eskyvslits yqpfslekev vceeplspat vpgmhtednp gkvehteels sitevvttee
361  nipdvvpgsh ltpieresss plssnqsepg sialnsyhsr ncsesdhsrn gfdtdsscle
421  shsslsdsef ppnnkgeikt egqelitvik aptsfgydkp hvlvdllvdd sgkesligyr
481  ptedskefs
```

Exemplary landmark residues, domains, and fragments of IFN include, but are not limited to residues 1-77 (signal peptide), residues 18-489 (mature peptide), or residues 161-317 (Interferon gamma receptor (IFNGR1)). A fragment of a IFN protein is less than the length of the full length protein, e.g., a fragment is at least 3, 4, 5, 6, 7, 8, 9, 10, 20, 30, 40, 50, 100, 200 or more residues in length, but less than e.g., IFN residues in the case of IFN above.

Human IFN nucleic acid sequence is depicted below with start and stop codons underlined. The sequence is publicly available and can be found under GenBank Accession Number: NM_000416.2; SEQ ID NO: (110); GenBank Accession, incorporated herein by reference.

```
  1  acagacccg gtgacggaag tgacgtaagg ccggggctgg agggcagtgc tgggctggtc
 61  ccgcaggcgc tcggggttgg agccagcgac cgtcggtagc agcatggctc tcctctttct
```

```
121  cctacccctt gtcatgcagg gtgtgagcag ggctgagatg ggcaccgcgg atctggggcc
181  gtcctcagtg cctacaccaa ctaatgttac aattgaatcc tataacatga accctatcgt
241  atattgggag taccagatca tgccacaggt ccctgttttt accgtagagg taaagaacta
301  tggtgttaag aattcagaat ggattgatgc ctgcatcaat atttctcatc attattgtaa
361  tatttctgat catgttggtg atccatcaaa ttctctttgg gtcagagtta aagccagggt
421  tggacaaaaa gaatctgcct atgcaaagtc agaagaattt gctgtatgcc gagatggaaa
481  aattggacca cctaaactgg atatcagaaa ggaggagaag caaatcatga ttgacatatt
541  tcacccttca gtttttgtaa atggagacga gcaggaagtc gattatgatc ccgaaactac
601  ctgttacatt agggtgtaca atgtgtatgt gagaatgaac ggaagtgaga tccagtataa
661  aatactcacg cagaaggaag atgattgtga cgagattcag tgccagttag cgattccagt
721  atcctcactg aattctcagt actgtgtttc agcagaagga gtcttacatg tgtggggtgt
781  tacaactgaa aagtcaaaag aagtttgtat taccattttc aatagcagta taaaaggttc
841  tctttggatt ccagttgttg ctgctttact actctttcta gtgcttagcc tggtattcat
901  ctgttttat attaagaaaa ttaatccatt gaaggaaaaa agcataatat tacccaagtc
961  cttgatctct gtggtaagaa gtgctacttt agagacaaaa cctgaatcaa aatatgtatc
1021 actcatcacg tcataccagc cattttcctt agaaaaggag gtggtctgtg aagagccgtt
1081 gtctccagca acagttccag gcatgcatac cgaagacaat ccaggaaaag tggaacatac
1141 agaagaactt tctagtataa cagaagtggt gactactgaa gaaaatattc ctgacgtggt
1201 cccgggcagc catctgactc aatagagag agagagtct tcacctttaa gtagtaacca
1261 gtctgaacct ggcagcatcg ctttaaactc gtatcactcc agaaattgtt ctgagagtga
1321 tcactccaga aatggttttg atactgattc cagctgtctg gaatcacata gctccttatc
1381 tgactcagaa tttcccccaa ataataaagg tgaaataaaa acagaaggac aagagctcat
1441 aaccgtaata aaagccccca cctcctttgg ttatgataaa ccacatgtgc tagtggatct
1501 acttgtggat gatagcggta aagagtcctt gattggttat agaccaacag aagattccaa
1561 agaattttca tgagatcagc taagttgcac caactttgaa gtctgatttt cctggacagt
1621 tttctgcttt aatttcatga aaagattatg atctcagaaa ttgtatctta gttggtatca
1681 accaaatgga gtgacttagt gtacatgaaa gcgtaaagag gatgtgtggc attttcactt
1741 ttggcttgta aagtacagac ttttttttt ttttaaacaa aaaaagcatt gtaacttatg
1801 aacctttaca tccagatagg ttaccagtaa cggaacagta tccagtactc ctggttccta
1861 ggtgagcagg tgatgcccca gggacctttg tagccacttc acttttttc ttttctctgc
1921 cttggtatag catatgtttt tgtaagttta tgcatacagt aattttaagt aatttcagaa
1981 gaaattctgc aagcttttca aaattggact taaaatctaa ttcaaactaa tagaattaat
2041 ggaatatgta aatagaaacg tgtatatttt ttatgaaaca ttacagttag agattttaa
2101 ataaagaatt ttaaaactcg aaaaaaaaaa aaaaaaa
```

Anabolic Markers

Exemplary osteoarthritis markers comprise aggrecan (ACAN) and Collagen, type II, alpha 1 (COL2A1).

Human aggrecan (ACAN) amino acid sequence is publicly available and can be found under GenBank Accession Number: NP_001126.3; SEQ ID NO: (111); GenBank Accession, incorporated herein by reference.

```
  1  mttllwvfvt lrvitaavtv etsdhdnsls vsipqpsplr vllgtsltip cyfidpmhpv
 61  ttapstapla prikwsrvsk ekevvllvat egrvrvnsay qdkvslpnyp aipsdatlev
```

-continued

```
 121  qslrsndsgv yrcevmhgie dseatlevvv kgivfhyrai strytldfdr aqraclqnsa 181  iiatpeqlqa ayedgfhqcd agwladqtvr ypihtpregc ygdkdefpgv rtygirdtne 241  tydvycfaee megevfyats pekftfqeaa necrrlgarl attgqlylaw qagmdmcsag 301  wladrsvryp iskarpncgg nllgvrtvyv hanqtgypdp ssrydaicyt gedfvdipen 361  ffgvggeedi tvqtvtwpdm elplprnite geargsvilt vkpifevsps plepeepftf 421  apeigatafa evenetgeat rpwgfptpgl gpataftsed lvvqvtavpg qphlpggvvf 481  hyrpgptrys ltfeeaqqac lrtgaviasp eqlqaayeag yeqcdagwlr dqtvrypivs 541  prtpcvgdkd sspgvrtygv rpstetydvy cfvdrlegev ffatrleqft fqealefces 601  hnatlattgq lyaawsrgld kcyagwladg slrypivtpr pacggdkpgv rtvylypnqt 661  glpdplsrhh afcfrgisav pspgeeeggt ptspsgveew ivtqvvpgva avpveeetta 721  vpsgettail efttepenqt ewepaytpvg tsplpgilpt wpptgaatee stegpsatev 781  psaseepsps evpfpseeps pseepfpsvr pfpsvelfps eepfpskeps pseepsasee 841  pytpsppvps wtelpssgee sgapdvsgdf tgsgdvsghl dfsgqlsgdr asglpsgdld 901  ssgltstvgs glpvesglps gdeeriewps tptvgelpsg aeilegsasg vgdlsglpsg 961  evletsasgv gdlsglpsge vlettapgve disglpsgev lettapgved isglpsgevl 1021  ettapgvedi sglpsgevle ttapgvedis glpsgevlet tapgvedisg lpsgevlett 1081  apgvedisgl psgevletaa pgvedisglp sgevletaap gvedisglps gevletaapg 1141  vedisglpsg evletaapgv edisglpsge vletaapgve disglpsgev letaapgved 1201  isglpsgevl etaapgvedi sglpsgevle taapgvedis glpsgevlet aapgvedisg 1261  lpsgevleta apgvedisgl psgevletaa pgvedisglp sgevletaap gvedisglps 1321  gevletaapg vedisglpsg evletaapgv edisglpsge vletaapgve disglpsgev 1381  letaapgved isglpsgevl ettapgveei sglpsgevle ttapgvdeis glpsgevlet 1441  tapgveeisg lpsgevlets tsavgdlsgl psggevleis vsgvedisgl psgevvetsa 1501  sgiedvselp sgegletsas gvedlsrlps geevleisas gfgdlsglps ggegletsas 1561  evgtdlsglp sgregletsa sgaedlsglp sgkedlvgsa sgdldlgklp sgtlgsgqap 1621  etsglpsgfs geysgvdlgs gppsglpdfs glpsgfptvs lvdstivevv tastaseleg 1681  rgtigisgag eisglpssel disgrasglp sgtelsgqas gspdvsgeip glfgvsgqps 1741  gfpdtsgets gvtelsglss gqpgisgeas gvlygtsqpf gitdlsgets gvpdlsgqps 1801  glpgfsgats gvpdlvsgtt sgsgessgit fvdtslveva pttfkeeegl gsvelsglps 1861  geadlsgksg mvdvsgqfsg tvdssgftsq tpefsglpsg iaevsgessr aeigsslpsg 1921  ayygsgtpss fptvslvdrt lvesvtqapt aqeagegpsg ilelsgahsg apdmsgehsg 1981  fldlsglqsg liepsgeppg tpyfsgdfas ttnvsgessv amgtsgeasg lpevtlitse 2041  fvegvtepti sgelggrppv thtpqlfess gkvstagdis gatpvlpgsg vevssvpess 2101  setsaypeag fgasaapeas redsgspdls ettsafhean lerssglgvs gstltfgege 2161  asaapevsge stttsdvgte apglpsatpt asgdrteisg dlsghtsqlg vvistsipes 2221  ewtqqtqrpa ethleiessss llysgeetht vetatsptda sipaspewkr esestaadqe 2281  vceegwnkyq ghcyrhfpdr etwvdaerrc reqqshlssi vtpeeqefvn nnagdygwig 2341  lndrtiegdf rwsdghpmqf enwrpnqpdn ffaagedcvv miwhekgewn dvpcnyhlpf 2401  tckkgtatty krrlqkrssr hprrsrpsta h
```

Exemplary landmark residues, domains, and fragments of ACAN include, but are not limited to residues 1-16 (signal sequence), residues 20-2431 (mature protein), residues 43-154 (IG Aggrecan), residues 153-247 (link domain), or residues 579-674 (link domain CSPGs). A fragment of a ACAN protein is less than the length of the full length protein, e.g., a fragment is at least 3, 4, 5, 6, 7, 8, 9, 10, 20, 30, 40, 50, 100, 200 or more residues in length, but less than e.g., ACAN residues in the case of ACAN above.

Human ACAN nucleic acid sequence is depicted below with start and stop codons underlined. The sequence is publicly available and can be found under GenBank Accession Number: NM_001135.3; SEQ ID NO: (112); GenBank Accession, incorporated herein by reference.

```
   1 cacctacctc cccgccgctc cagaggggggc tcgcagagct gaggacgcgc gcagcgctgc
  61 tcaaggtctc tctctctcag caccctcgcc ggccggcgtc tgacgcgggt gccagggtct
 121 ccgggcacct ttcagtgtcc attccctcag ccagccagga ctccgcaacc cagcagttgc
 181 cgctgcggcc acagcccgag gggacctgcg gacaggacgc cggcaggagg aggggtgcgc
 241 agcgcccgcg cagagcgtct ccctcgctac gcagcgagac ccggggcctcc cggccccagg
 301 agccccccagc tgcctcgcca ggtgtgtggg actgaagttc ttggagaagg gagtccaact
 361 cttcaaggtg aactatgacc actttactct gggttttcgt gactctgagg gtcatcactg
 421 cagctgtcac tgtagaaact tcagaccatg acaactcgct gagtgtcagc atcccccaac
 481 cgtccccgct gagggtcctc ctggggacct ccctcaccat cccctgctat ttcatcgacc
 541 ccatgcaccc tgtgaccacc gccccttcta ccgccccact ggccccaaga atcaagtgga
 601 gccgtgtgtc caaggagaag gaggtagtgc tgctggtggc cactgaaggg cgcgtgcggg
 661 tcaacagtgc ctatcaggac aaggtctcac tgcccaacta cccggccatc cccagtgacg
 721 ccaccttgga agtccagagc ctgcgctcca atgactctgg ggtctaccgc tgcgaggtga
 781 tgcatggcat cgaggacagc gaggccaccc tggaagtcgt ggtgaaaggc atcgtgttcc
 841 attacagagc catctctaca cgctacaccc tcgactttga cagggcgcag cgggcctgcc
 901 tgcagaacag tgccatcatt gccacgcctg agcagctgca ggccgcctac gaagacggct
 961 tccaccagtg tgacgccggc tggctggctg accagactgt cagataccccc atccacactc
1021 cccgggaagg ctgctatgga gacaaggatg agtttcctgg tgtgaggacg tatggcatcc
1081 gagacaccaa cgagacctat gatgtgtact gcttcgccga ggagatggag ggtgaggtct
1141 tttatgcaac atctccagag aagttcacct tccaggaagc agccaatgag tgccggcggc
1201 tgggtgcccg gctggccacc acgggccagc tctacctggc ctggcaggct ggcatggaca
1261 tgtgcagcgc cggctggctg gccgaccgca gcgtgcgcta cccatctcc aaggcccggc
1321 ccaactgcgg tggcaacctc ctgggcgtga ggaccgtcta cgtgcatgcc aaccagacgg
1381 gctaccccga cccctcatcc cgctacgacg ccatctgcta cacaggtgaa gactttgtgg
1441 acatccccaga aaacttcttt ggagtggggg gtgaggagga catcaccgtc cagacagtga
1501 cctggcctga catggagctg ccactgcctc gaaacatcac tgagggtgaa gcccgaggca
1561 gcgtgatcct taccgtaaag cccatcttcg aggtctcccc cagtccctg gaacccgagg
1621 agcccttcac gtttgcccct gaaatagggg ccactgcctt cgctgaggtt gagaatgaga
1681 ctggagaggc caccaggccc tggggctttc ccacacctgg cctgggccct gccacggcat
1741 tcaccagtga ggacctcgtc gtgcaggtga ccgctgtccc tgggcagccg catttgccag
1801 ggggggtcgt cttccactac cgcccgggac ccacccgcta ctcgctgacc tttgaggagg
1861 cacagcaggc ctgcctgcgc acggggggcgg tcattgcctc gccggagcag ctccaggccg
1921 cctacgaagc aggctatgag cagtgtgacg ccggctggct gcgggaccag accgtcagat
1981 acccccattgt gagccccccgg accccatgcg tgggtgacaa ggacagcagc caggggtca
2041 ggacctatgg cgtgcgccca tcaacagaga cctacgatgt ctactgcttt gtagacagac
2101 ttgaggggga ggtgttcttc gccacacgcc ttgagcagtt caccttccag gaagcactgg
```

-continued

```
2161 agttctgtga atctcacaat gctacgctgg ccaccacggg ccagctctac gccgcctgga
2221 gccgcggcct ggacaagtgc tatgccggct ggctggccga cggcagcctc cgctaccca
2281 tcgtcacccc aaggcctgcc tgcggtgggg acaagccagg cgtgagaacg gtctacctct
2341 accctaacca gacgggcctc ccagacccac tgtcccggca ccatgccttc tgcttccgag
2401 gcatttcagc ggttccttct ccaggagaag aagagggtgg cacacccaca tcaccctctg
2461 gtgtggagga gtggatcgtg acccaagtgg ttcctggtgt ggctgctgtc cccgtagaag
2521 aggagacaac tgctgtaccc tcaggggaga ctactgccat cctagagttc accaccgagc
2581 cagaaaacca gacagaatgg gaaccagcct ataccccagt gggcacatcc ccgctgccag
2641 ggatccttcc tacttggcct cccactggcg cagcaacaga ggaaagtaca gaaggccctt
2701 ctgcaactga agtgccctct gcctcagagg aaccatcccc ctcagaggtg ccattcccct
2761 cagaggagcc atccccctca gaggaaccat tccctcagt gaggccattc ccctcagtgg
2821 agctgttccc ctcagaggag ccattcccct caaggagcc atccccctca gaggaaccat
2881 cagcctcgga agagccgtat acaccttcac ccccgtgcc cagctggact gagctgccca
2941 gctctgggga ggaatctggg gcccctgatg tcagtggtga cttcacaggc agtggagatg
3001 tttcaggaca ccttgacttc agtgggcagc tgtcagggga cagggcaagt ggactgccct
3061 ctggagacct ggactccagt ggtcttactt ccacagtggg ctcaggcctg cctgtggaaa
3121 gtggactacc ctcaggggat gaagagagaa ttgagtggcc cagcactcct acggttggtg
3181 aactgccctc tggagctgag atcctagagg gctctgcctc tggagttggg gatctcagtg
3241 gacttccttc tggagaagtt ctagagacct ctgcctctgg agtaggagac ctcagtgggc
3301 ttccttctgg agaagttcta gagaccactg cccctggagt agaggacatc agcgggcttc
3361 cttctggaga agttctagag accactgccc ctggagtaga ggacatcagc gggcttcctt
3421 ctggagaagt tctagagacc actgccctg gagtagagga catcagcggg cttccttctg
3481 gagaagttct agagaccact gcccctggag tagaggacat cagcgggctt ccttctggag
3541 aagttctaga gaccactgcc cctggagtag aggacatcag cgggcttcct tctggagaag
3601 ttctagagac cactgccct ggagtagagg acatcagcgg gcttccttct ggagaagttc
3661 tagagaccgc tgcccctgga gtagaggaca tcagcgggct tccttctgga gaagttctag
3721 agaccgctgc cctggagta gaggacatca gcgggcttcc ttctggagaa gttctagaga
3781 ccgctgcccc tggagtagag gacatcagcg ggcttccttc tggagaagtt ctagagaccg
3841 ctgcccctgg agtagaggac atcagcgggc ttccttctgg agaagttcta gagaccgctg
3901 cccctggagt agaggacatc agcgggcttc cttctggaga agttctagag accgctgccc
3961 ctggagtaga ggacatcagc gggcttcctt ctggagaagt tctagagacc gctgcccctg
4021 gagtagagga catcagcggg cttccttctg gagaagttct agagactgct gcccctggag
4081 tagaggacat cagcgggctt ccttctggag aagttctaga gactgctgcc cctggagtag
4141 aggacatcag cgggcttcct tctggagaag ttctagagac tgctgcccct ggagtagagg
4201 acatcagcgg gcttccttct ggagaagttc tagagactgc tgcccctgga gtagaggaca
4261 tcagcgggct tccttctgga gaagttctag agactgctgc cctggagta gaggacatca
4321 gcgggcttcc ttctggagaa gttctagaga ctgctgcccc tggagtagag gacatcagcg
4381 ggcttccttc tggagaagtt ctagagactg ctgcccctgg agtagaggac atcagcgggc
4441 ttccttctgg agaagttcta gagactgctg cccctggagt agaggacatc agcgggcttc
4501 cttctggaga agttctagag actgctgccc ctggagtaga ggacatcagc gggcttcctt
```

-continued

```
4561 ctggagaagt tctagagact actgcccctg gagtagagga gatcagcggg cttccttctg 4621 gagaagttct agagactact gcccctggag tagatgagat cagtgggctt ccttctggag 4681 aagttctaga gactactgcc cctggagtag aggagatcag cgggcttcct tctggagaag 4741 ttctagagac ttctacctct gcggtagggg acctcagtgg acttccttct ggaggagaag 4801 ttctagagat ttctgtctct ggagtagagg acatcagtgg gcttccttct ggagaggttg 4861 tagagacttc tgcctctgga atagaggatg tcagtgaact tccttcagga gaaggtctag 4921 agacctctgc ttctggagta gaggacctca gcaggctccc ttctggagaa gaagttctag 4981 agatttctgc ctctggattt ggggacctca gtggacttcc ttctggagga gaaggtctag 5041 agacctctgc ttctgaagta gggactgacc tcagtgggct tccttctgga agggagggtc 5101 tagagacttc agcttctgga gctgaggacc tcagtgggtt gccttctgga aaagaagact 5161 tggtggggtc agcttctgga gacttggact tgggcaaact gccttctgga actctaggaa 5221 gtgggcaagc tccagaaaca agtggtcttc cctctggatt tagtggtgag tattctgggg 5281 tggaccttgg aagtggccca ccctctggcc tgcctgactt tagtggactt ccatctggat 5341 tcccaactgt ttccctagtg gattctacat tggtggaagt ggtcacagcc tccactgcaa 5401 gtgaactgga agggagggga accattggca tcagtggtgc aggagaaata tctggactgc 5461 cctccagtga gctggacatt agtgggagag ctagtggact cccttcagga actgaactca 5521 gtggccaagc atctgggtct cctgatgtca gtggggaaat acctggactc tttggtgtca 5581 gtggacagcc atcagggttt cctgacacta gtggggaaac atctggagtg actgagctta 5641 gcgggctgtc ctctggacaa ccaggtatta gtggagaagc atctggagtt cttatggca 5701 ctagtcaacc cttggcata actgatctga gtggagaaac atctggggtc cctgatctca 5761 gtgggcagcc ttcagggtta ccaggttca gtggggcaac atcaggagtc cctgacctgg 5821 tttctggtac cacgagtggc agcggtgaat cttctgggat tacatttgtg gacaccagtt 5881 tggttgaagt ggcccctact acatttaaag aagaagaagg cttagggtct gtggaactca 5941 gtggcctccc ttccggagag gcagatctgt caggcaaatc tgggatggtg gatgtcagtg 6001 gacagttttc tggaacagtc gattccagtg ggtttacatc ccagactccg gaattcagtg 6061 gcctaccaag tggcatagct gaggtcagtg gagaatcctc cagagctgag attgggagca 6121 gcctgccctc gggagcatat tatggcagtg gaactccatc tagtttcccc actgtctctc 6181 ttgtagacag aactttggtg gaatctgtaa cccaggctcc aacagcccaa gaggcaggag 6241 aagggccttc tggcatttta gaactcagtg gtgctcattc tggagcacca gacatgtctg 6301 gggagcattc tggatttctg gacctaagtg ggctgcagtc cgggctgata gagcccagcg 6361 gagagccacc aggtactcca tattttagtg gggattttgc cagcaccacc aatgtaagtg 6421 gagaatcctc tgtagccatg ggcaccagtg agaggcctc aggacttcca gaagttactt 6481 taatcacttc tgagttcgtg gagggtgtta ctgaaccaac tatttctcag gaactaggcc 6541 aaaggccccc tgtgacacac acacccagc tttttgagtc cagtggaaaa gtctccacag 6601 ctggggacat tagtggagct accccagtgc tccctgggtc tggagtagaa gtatcatcag 6661 tcccagaatc tagcagtgag acgtccgcct atcctgaagc tgggttcggg gcatctgccg 6721 cccctgaggc cagcagagaa gattctgggt cccctgatct gagtgaaacc acctctgcat 6781 tccacagagc taaccttgag agatccctctg gcctaggagt gagcggcagc actttgacat 6841 ttcaagaagg cgaggcgtcc gctgccccag aagtgagtgg agaatccacc accaccagtg 6901 atgtggggac agaggcacca ggcttgcctt cagccactcc cacggcttct ggagacagga 6961 ctgaaatcag cggagacctg tctggtcaca cctcgcagct gggcgttgtc atcagcacca
```

-continued

```
7021 gcatcccaga gtctgagtgg acccagcaga cccagcgccc tgcagagacg catctagaaa
7081 ttgagtcctc aagcctcctg tactcaggag aagagactca cacagtcgaa acagccacct
7141 ccccaacaga tgcttccatc ccagcttctc cggaatggaa acgtgaatca gaatcaactg
7201 ctgcagacca ggaggtatgt gaggagggct ggaacaagta ccagggccac tgttaccgcc
7261 acttcccgga ccgcgagacc tgggtggatg ctgagcgccg tgtcgggag cagcagtcac
7321 acctgagcag catcgtcacc cccgaggagc aggagtttgt caacaacaat gcccaagact
7381 accagtggat cggcctgaac gacaggacca tcgaagggga cttccgctgg tcagatggac
7441 accccatgca atttgagaac tggcgcccca accagcctga caacttttt gccgctggag
7501 aggactgtgt ggtgatgatc tggcacgaga agggcgagtg gaatgatgtt ccctgcaatt
7561 accacctccc cttcacgtgt aaaaagggca cagccaccac ctacaaacgc agactacaga
7621 agcggagctc acggcaccct cggaggagcc gccccagcac agcccactga gaagagcttc
7681 caggacgcac ccaggacgct gagcccagga gcctgccagg ctgacgtgca tcccacccag
7741 acggtgtcct cttcttgtcg cttttttgtca tataaggaat cccattaaag aaggaaaaaa
7801 ataaatccca catttgtgta tgcacccact caccctcca aatcagcaaa accgcatcta
7861 atttgtccgc cgaatgccaa agcaaagcaa acttattata acccttggac tgagttaga
7921 gacatttctt caatttccca tcgtgccttt ccagggacca gtgcagggac aggggagaa
7981 gggagggt taagttaaat aaagaagatt attttttgttt cctgacttta tccaagagca
8041 gtgcaatcgt tggttatttc acctccaggg agagctaggg aggagggagg agggctccaa
8101 aggagctgga aggagcagag gcctgagagc aggaagaact cggaaccgca gctgaatgta
8161 ttggatgaga aggagccagg agggctacac catctgtatg agggaaaagc cttgggggag
8221 aggggtgggt tcctgcctcc tgccgagggt aagccggcag gagagagcca tcagagggac
8281 ctccgctgcc tgggagttgg gttccctcca agggtccctc tttcagtgtc ctctctctca
8341 cctgggtctg ccaccctaac aggtggcaac tcggcagggc tgctgggggc acttcctgcc
8401 cagtgggggg tgccgcccaa ccttctcccc tccccacccc cgcccccggg accgtgcagg
8461 caccagggtt ccgtgcacct atttatattt ttgaaaactg aagattataa tattataata
8521 ataataaaga cattggaaga gat
```

Human Collagen, type II, alpha 1 (COL2A1) amino acid sequence is publicly available and can be found under GenBank Accession Number: NP_001835.3; SEQ ID NO: (113); GenBank Accession, incorporated herein by reference.

```
  1 mirlgapqtl vlltllvaav lrcqgqdvqe agscvqdgqr yndkdvwkpe pericvcdtg
 61 tvlcddiice dvkdclspei pfgeccpicp tdlatasgqp gpkgqkgepg dikdivgpkg
121 ppgpqgpage qgprgdrgdk gekgapgprg rdgepgtpgn pgppgppgpp gppglggnfa
181 aqmaggfdek aggaqlgvmq gpmgpmgprg ppgpagapgp qgfqgnpgep gepgvsgpmg
241 prgppgppgk pgddgeagkp gkagergppg pqgargfpgt pglpgvkghr gypgldgakg
301 eagapgvkge sgspgengsp gpmgprglpg ergrtgpaga agargndgqp gpagppgpvg
361 paggpgfpga pgakgeagpt gargpegaqg prgepgtpgs pgpagasgnp gtdgipgakg
421 sagapgiaga pgfpgprgpp gpqgatgplg pkgqtgepgi agfkgeqgpk gepgpagpqg
481 apgpageegk rgargepggv gpigppgerg apgnrgfpgq dglagpkgap gergpsglag
```

```
 541 pkgangdpgr pgepglpgar gltgrpgdag pqgkvgpsga pgedgrpgpp gpqgargqpg 601 vmgfpgpkga ngepgkagek glpgapglrg lpgkdgetga agppgpagpa gergeqgapg 661 psgfqglpgp pgppgeggkp gdqgvpgeag apglvgprge rgfpgergsp gagglqgprg 721 lpgtpgtdgp kgasgpagpp gaggppglqg mpgergaagi agpkgdrgdv gekgpegapg 781 kdggrgltgp igppgpagan gekgevgppg pagsagarga pgergetgpp gpagfagppg 841 adgqpgakge ggeagqkgda gapgpqgpsg apgpqgptgv tgpkgargaq gppgatgfpg 901 aagrvgppgs ngnpgppgpp gpsgkdgpkg argdsgppgr agepglqgpa gppgekgepg 961 ddgpsgaegp pgpqglagqr givglpgqrg ergfpglpgp sgepgkqgap gasgdrgppg 1021 pvgppgltgp agepgregsp gadgppgrdg aagvkgdrge tgavgapgap gppgspgpag 1081 ptgkqgdrge agaqgpmgps gpagargiqg pqgprgdkge agepgerglk ghrgftglqg 1141 lpgppgpsgd qgasgpagps gprgppgpvg psgkdgangi pgpigppgpr grsgetgpag 1201 ppgnpgppgp pgppgpgidm safaglgpre kgpdplqymr adqaagglrq hdaevdatlk 1261 slnnqiesir spegsrknpa rtcrdlklch pewksgdywi dpnqgctlda mkvfcnmetg 1321 etcvypnpan vpkknwwssk skekkhiwfg etinggfhfs ygddnlapnt anvqmtflrl 1381 lstegsgnit yhcknsiayl deaagnlkka lliqgsndve iraegnsrft ytalkdgctk 1441 htgkwgktvi eyrsqktsrl piidiapmdi ggpeqefgvd igpvcfl
```

Exemplary landmark residues, domains, and fragments of COL2A1 include, but are not limited to residues 1-25 (signal sequence), residues 26-1487 (mature protein), residues 201-1214 (triple helical region), or residue 1388 (glycosylation). A fragment of a COL2A1 protein is less than the length of the full length protein, e.g., a fragment is at least 3, 4, 5, 6, 7, 8, 9, 10, 20, 30, 40, 50, 100, 200 or more residues in length, but less than e.g., COL2A1 residues in the case of COL2A1 above.

Human COL2A1 nucleic acid sequence is depicted below with start and stop codons underlined. The sequence is publicly available and can be found under GenBank Accession Number: NM_001844.5; SEQ ID NO: (114); GenBank Accession, incorporated herein by reference.

```
   1 gcagagcgct gctgggctgc cgggtctccc gcttcccect cctgctccaa gggcctcctg 61 catgagggcg cggtagagac ccggacccgc gccgtgctcc tgccgtttcg ctgcgctccg 121 cccgggcccg gctcagccag gccccgcggt gagccatgat tcgcctcggg gctccccaga 181 cgctggtgct gctgacgctg ctcgtcgccg ctgtccttcg gtgtcagggc caggatgtcc 241 aggaggctgg cagctgtgtg caggatgggc agaggtataa tgataaggat gtgtggaagc 301 cggagccctg ccggatctgt gtctgtgaca ctgggactgt cctctgcgac gacataatct 361 gtgaagacgt gaaagactgc ctcagccctg agatcccctt cggagagtgc tgccccatct 421 gcccaactga cctcgccact gccagtgggc aaccaggacc aaagggacag aaaggagaac 481 ctggagacat caaggatatt gtaggaccca aaggacctcc tgggcctcag ggacctgcag 541 gggaacaagg acccagaggg gatcgtggtg acaaaggtga aaaaggtgcc cctggacctc 601 gtggcagaga tggagaacct gggaccctg gaaatcctgg ccccctggt cctcccggcc 661 cccctggtcc ccctggtctt ggtggaaact tgctgccca gatggctgga ggatttgatg 721 aaaaggctgg tggcgcccag ttgggagtaa tgcaaggacc aatgggcccc atgggacctc 781 gaggacctcc aggccctgca ggtgctcctg ggcctcaagg atttcaaggc aatcctggtg 841 aacctggtga acctggtgtc tctggtccca tgggtccccg tggtcctcct ggtccccctg 901 gaaagcctgg tgatgatggt gaagctggaa aacctggaaa agctggtgaa aggggtccgc 961 ctggtcctca gggtgctcgt ggtttcccag gaacccagg ccttcctggt gtcaaaggtc 1021 acagaggtta tccaggcctg gacggtgcta agggagaggc gggtgctcct ggtgtgaagg
```

-continued

```
1081  gtgagagtgg ttccccgggt gagaacggat ctccgggccc aatgggtcct cgtggcctgc
1141  ctggtgaaag aggacggact ggccctgctg gcgctgcggg tgcccgaggc aacgatggtc
1201  agccaggccc cgcagggcct ccgggtcctg tcggtcctgc tggtggtcct ggcttccctg
1261  gtgctcctgg agccaagggt gaagccggcc ccactggtgc cgtggtcct gaaggtgctc
1321  aaggtcctcg cggtgaacct ggtactcctg gtcccctgg gcctgctggt gcctccggta
1381  accctggaac agatggaatt cctggagcca aaggatctgc tggtgctcct ggcattgctg
1441  gtgctcctgg cttccctggg ccacggggcc ctcctggccc tcaaggtgca actggtcctc
1501  tgggcccgaa aggtcagacg ggtgaacctg gtattgctgg cttcaaaggt gaacaaggcc
1561  ccaagggaga acctggccct gctggccccc agggagcccc tggacccgct ggtgaagaag
1621  gcaagagagg tgcccgtgga gagcctggtg gcgttgggcc catcggtccc cctggagaaa
1681  gaggtgctcc cggcaaccgc ggtttcccag gtcaagatgg tctggcaggt cccaagggag
1741  cccctggaga gcgagggccc agtggtcttg ctggccccaa gggagccaac ggtgaccctg
1801  gccgtcctgg agaacctggc cttcctggag cccggggtct cactggccgc cctggtgatg
1861  ctggtcctca aggcaaagtt ggcccttctg gagccccctgg tgaagatggt cgtcctggac
1921  ctccaggtcc tcaggggggct cgtgggcagc tggtgtcat gggtttccct ggccccaaag
1981  gtgccaacgg tgagcctggc aaagctggtg agaagggact gcctggtgct cctggtctga
2041  ggggtcttcc tggcaaagat ggtgagacag gtgctgcagg accccctggc cctgctggac
2101  ctgctggtga acgaggcgag cagggtgctc ctgggccatc tgggttccag ggacttcctg
2161  gccctcctgg tccccaggt gaaggtggaa accaggtga ccagggtgtt cccggtgaag
2221  ctggagcccc tggcctcgtg gtcccaggg gtgaacgagg tttcccaggt gaacgtggct
2281  ctcccggtgc ccagggcctc caggtccccc gtggcctccc cggcactcct ggcactgatg
2341  gtcccaaagg tgcatctggc ccagcaggcc ccctggggc tcagggccct ccaggtcttc
2401  agggaatgcc tggcgagagg ggagcagctg gtatcgctgg gcccaaaggc gacaggggtg
2461  acgttggtga gaaaggccct gagggagccc ctggaaagga tggtggacga ggcctgacag
2521  gtcccattgg ccccctggc ccagctggtg ctaatggcga aagggagaa gttggaccctc
2581  ctggtcctgc aggaagtgct ggtgctcgtg gcgctccggg tgaacgtgga gagactgggc
2641  cccccggacc agcgggattt gctgggcctc ctggtgctga tggccagcct ggggccaagg
2701  gtgagcaagg agaggccggc cagaaaggcg atgctggtgc ccctggtcct cagggcccct
2761  ctggagcacc tgggcctcag gtcctactg gagtgactgg tcctaaagga gcccgaggtg
2821  cccaaggccc cccgggagcc actggattcc ctggagctgc tggccgcgtt ggaccccccag
2881  gctccaatgg caaccctgga ccccctggtc ccctggtcc ttctggaaaa gatggtccca
2941  aaggtgctcg aggagacagc ggcccccctg gccgagctgg tgaacccggc ctccaaggtc
3001  ctgctggacc ccctggcgag aagggagagc tggagatgca cggtccctct ggtgccgaag
3061  gtccaccagg tccccagggt ctggctggtc agagaggcat cgtcggtctg cctgggcaac
3121  gtggtgagag aggattccct ggcttgcctg gcccgtcggg tgagcccggc aagcagggtg
3181  ctcctggagc atctggagac agaggtcctc ctggccccgt gggtcctcct ggcctgacgg
3241  gtcctgcagg tgaacctgga cgagagggaa gcccggtgc tgatggcccc cctggcagag
3301  atggcgctgc tggagtcaag ggtgatcgtg gtgagactgg tgctgtggga gctcctggag
3361  cccctgggcc cctggctcc cctggccccg ctggtccaac tggcaagcaa ggagacagag
3421  gagaagctgg tgcacaaggc cccatgggac cctcaggacc agctggagcc cggggaatcc
```

```
-continued
3481 agggtcctca aggccccaga ggtgacaaag gagaggctgg agagcctggc gagagaggcc 3541 tgaagggaca ccgtggcttc actggtctgc agggtctgcc cggccctcct ggtccttctg 3601 gagaccaagg tgcttctggt cctgctggtc cttctggccc tagaggtcct cctggccccg 3661 tcggtccctc tggcaaagat ggtgctaatg gaatccctgg ccccattggg cctcctggtc 3721 cccgtggacg atcaggcgaa accggccctg ctggtcctcc tggaaatcct ggacccctg 3781 gtcctccagg tcccctggc cctggcatcg acatgtccgc ctttgctggc ttaggcccga 3841 gagagaaggg ccccgacccc ctgcagtaca tgcgggccga ccaggcagcc ggtggcctga 3901 gacagcatga cgccgaggtg gatgccacac tcaagtccct caacaaccag attgagagca 3961 tccgcagccc cgagggctcc cgcaagaacc ctgctcgcac ctgcagagac ctgaaactct 4021 gccaccctga gtggaagagt ggagactact ggattgaccc caaccaaggc tgcaccttgg 4081 acgccatgaa ggttttctgc aacatggaga ctggcgagac ttgcgtctac cccaatccag 4141 caaacgttcc caagaagaac tggtggagca gcaagagcaa ggagaagaaa cacatctggt 4201 ttggagaaac catcaatggt ggcttccatt tcagctatgg agatgacaat ctggctccca 4261 acactgccaa cgtccagatg accttcctac gcctgctgtc cacggaaggc tcccagaaca 4321 tcacctacca ctgcaagaac agcattgcct atctggacga agcagctggc aacctcaaga 4381 aggccctgct catccagggc tccaatgacg tggagatccg ggcagagggc aatagcaggt 4441 tcacgtacac tgccctgaag gatggctgca cgaaacatac cggtaagtgg ggcaagactg 4501 ttatcgagta ccggtcacag aagacctcac gcctccccat cattgacatt gcacccatgg 4561 acataggagg gcccgagcag gaattcggtg tggacatagg gccggtctgc ttcttgtaaa 4621 aacctgaacc cagaaacaac acaatccgtt gcaaacccaa aggacccaag tactttccaa 4681 tctcagtcac tctaggactc tgcactgaat ggctgacctg acctgatgtc cattcatccc 4741 accctctcac agttcggact tttctcccct ctctttctaa gagacctgaa ctgggcagac 4801 tgcaaaataa aatctcggtg ttctatttat ttattgtctt cctgtaagac cttcgggtca 4861 aggcagaggc aggaaactaa ctggtgtgag tcaaatgccc cctgagtgac tgcccccagc 4921 ccaggccaga agacctccct tcaggtgccg ggcgcaggaa ctgtgtgtgt cctacacaat 4981 ggtgctattc tgtgtcaaac acctctgtat tttttaaaac atcaattgat attaaaaatg 5041 aaaagattat tggaaagta
```

NTRIs for Treatment of OA

Nucleoside Analog Reverse-Transcriptase Inhibitors

Nucleoside analog reverse-transcriptase inhibitors (NARTIs or NRTIs) are a class of antiretroviral drugs. To be incorporated into the viral DNA, NRTIs must be activated in the cell by the addition of three phosphate groups to their deoxyribose moiety, to form NRTI triphosphates. This phosphorylation step is carried out by cellular kinase enzymes. Exemplary NRTIs are listed below:

Zidovudine, also called AZT, ZDV, and azidothymidine, has the trade name Retrovir.

Zidovudine was the first antiretroviral drug approved by the FDA for the treatment of HIV.

Didanosine, also called ddI, with the trade names Videx and Videx EC, was the second FDA-approved antiretroviral drug. It is an analog of adenosine.

Zalcitabine, also called ddC and dideoxycytidine, has the trade name Hivid.

Stavudine, also called d4T, has trade names Zerit and Zerit XR.

Lamivudine, also called 3TC, has the trade name Zeffix and Epivir. It is approved for the treatment of both HIV and hepatitis B.

Abacavir, also called ABC, has the trade name Ziagen, is an analog of guanosine.

Emtricitabine, also called FTC, has the trade name Emtriva (formerly Coviracil). Structurally similar to lamivudine, it is approved for the treatment of HIV and undergoing clinical trials for hepatitis B.

Entecavir, also called ETV, is a guanosine analog used for hepatitis B under the trade name Baraclude. It is not approved for HIV treatment.

Truvada, made of emtricitabine and tenofovir disoproxil fumarate, is used to treat and prevent HIV. It is approved for HIV prevention in the US and manufactured by Gilead.

Another exemplary NRTI includes Tenofovir also known as TDF is a prodrug with the active compound deactivated by a molecular side chain that dissolves in the human body allowing a low dose of tenofovir to reach the site of desired activity.

NRTIs for Treatment of Strict OA

In one example NRTIs can be used for the treatment of strict osteoarthritis ("category one" or "class one"). An exemplary NRTIs include, 3TC, a cytidine analog depicted below. 3TC is commonly referred to as lamivudine, and can be formulated in tablet form (Epivir or Zeffix).

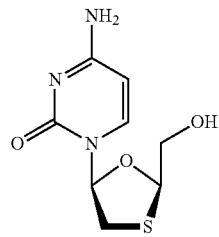

In another example, the treatment for osteoarthritis can include administration with FTC, a cytidine analog depicted below. FTC is also referred to as emtricitabine, 2',3'-dideoxy-5-fluoro-3'-thiacytidine, Emtriva or Coviracil. FTC can also be administered with tenofovir disoproxil (sold under trade name Viread).

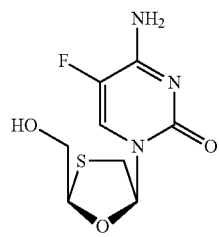

In another example, the treatment for osteoarthritis can include administration of ABC, a guanosine analog. ABC is also referred to as abacavir, or the trade name Ziagen. The structure of ABC is provided below:

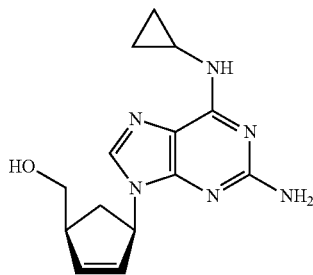 [SMILES: Nc1nc(NC2CC2)c2ncn([C@H]3C=C[C@@H](CO)C3)c2n1]

Summary data of NRTI on OA is shown in FIG. 12A. All NRTIs inhibited strict OA in age (older than 50) and dosage dependent and sex independent manner (successful for both male and female) in HIV patients. NRTIs for inhibiting strict OA were 3TC, FTC and ABC.

NRTIs for Treatment of Strict OA and Expanded OA

In another example, NRTIs can be used for the treatment of strict OA and expanded OA, e.g., partially inhibiting expanded OA ("category 2" or "class 2"). An exemplary NRTI includes, ZDV (a thymidine analog). In examples, ZDV is administered to female patients. ZDV is also commonly referred to as azidothmidine, AZT, Retrovir or Zidovudine. The structure of ZDV is provided below:

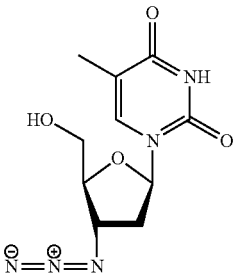

In another example, the treatment of strict OA and expanded OA comprises administering TDF (an adenosine analogue). TDF is also referred to as tenofovir, 9-(2-Phosphonyl-methoxypropyly)adenine (PMPA), Viread (Gilead Sciences). The structures of TDF, and Tenofovir dispoproxil are shown below. TDF can also be administered with FTC, which is also referred to as emtricitabine, 2',3'-dideoxy-5-fluoro-3'-thiacytidine, Emtriva or Coviracil.

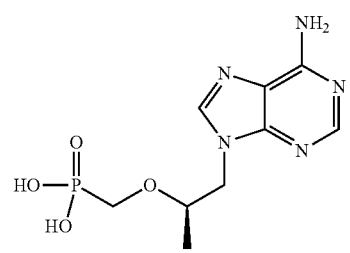

Tenofovir

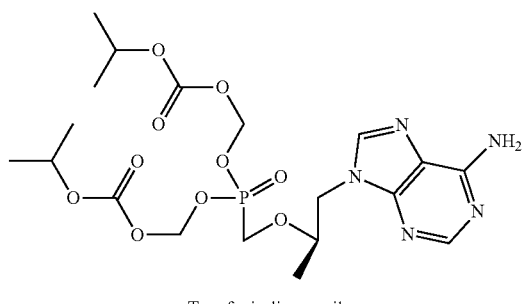

Tenofovir disoproxil

Summary data of NRTI on OA is shown in FIG. 12B. All NRTIs inhibited strict OA in age (older than 50) and dosage dependent and sex independent manner (successful for both male and female) in HIV patients. NRTIs for inhibiting strict OA and partially inhibiting expanded OA were ZDV and TDF, which was better than category one.

NRTIs for Treatment of Strict OA and Expanded OA.

In other examples, both strict OA and expanded OA are treated by administration of Didanosine, an adenosine analog (commonly referred to as DDI, ddl, Videx, Videx EC, 2',3'-dideoxyinosine) ("category 3" or "class 3"). No toxicity in a group of less than 40 years old was observed. The structure of didanosine is provided below:

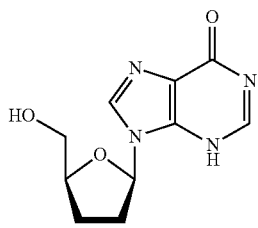

In other examples, both strict OA and expanded OA are treated by administration of Stavudine, a thymidine analog (commonly referred to as d4T, Zerit, Zerit XR, 2',3'-didehydro-2',3'-dideoxythymidine). Stavudine was the highest extent of inhibition. The structure of Stavudine is shown below:

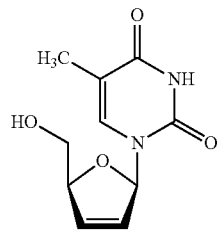 [SMILES: Cc1cn([C@H]2C=C[C@@H](CO)O2)c(=O)[nH]c1=O]

Summary data of NRTI on OA is shown in FIG. 12C. All NRTIs inhibited strict OA in age (older than 50) and dosage dependent and sex independent manner (successful for both male and female) in HIV patients. NRTIs for inhibiting both strict OA and expanded OA were DDL and D4T, which was better than category one and category 2, described above.

Osteoarthritis (OA)

Osteoarthritis is a form of arthritis that features the breakdown and eventual loss of the cartilage in one or more joints. OAs can affect the hands, feet, ankle, spine, and large weight-bearing joints, such as the hips and knees.

OA that develops secondary to a wide variety of joint injury is often grouped into a sub-category of OA called post-traumatic osteoarthritis (PTOA). Common injuries that can lead to PTOA include, but are not limited to, high-speed impact trauma to the articular surface, intraarticular fractures, and joint-destabilizing soft-tissue tears. Although the end-stage pathophysiology of PTOA may be similar, there is evidence to suggest that the early biological and mechanical events that initiate and perpetuate disease are distinct between different joints, injury types, and patient populations. The ankle, knee, and hip are the most commonly injured joints in PTOA.

The most common injury precipitating end-stage ankle OA is a severe ankle sprain, when rapid ankle inversion causes the distal tibia to impact the medial aspect of the talar dome, often resulting in an osteochondral lesion. Ligamentous injuries commonly accompany severe ankle sprains and may result in joint instability. The magnitude of the initial cartilage trauma is an important factor in development of ankle PTOA.

There is evidence implicating trauma with the likelihood of developing joint degeneration and OA. PTOA is a degenerative joint disease secondary to injury that may lead to OA years later. It is particularly prevalent in young and active individuals such as those involved in sport during which there is increased risk of sustaining such injury. It can therefore be defined as the presence of a normal joint prior to injury, structural damage at the time of injury and the joint not being compromised by systemic disease. Joint trauma affects all joint tissues leading to physiological, biomechanical and biochemical changes that may progress toward joint degeneration and subsequent development of OA.

Treatment generally involves a combination of exercise, lifestyle modification, and analgesics. If pain becomes debilitating, joint replacement surgery may be necessary to improve the quality of life. Surgical intervention is sometimes recommended after joint injury to correct abnormal joint biomechanics, reducing the risk of secondary injuries, and ideally reducing the risk of OA. Unfortunately, surgical interventions (e.g. AU (gold) reconstruction, meniscectomy, meniscal replacement) do not restore normal joint biomechanics or prevent knee OA. Therefore, it is important to understand which of these patients will develop early-onset knee OA and if this onset of knee OA can be prevented or delayed. Whilst pain management and surgery are current options, currently there are no approved therapies to address post-traumatic arthritis and its prevention.

Stages of OA

Stage 1: Minor

Small lumps of bone called osteophytes may grow in the knee area. There may be slight damage to the cartilage. There will be no apparent narrowing of the space between the bones to indicate that the cartilage is breaking down. People with stage 1 OA are unlikely to feel pain or experience discomfort. The joint will appear normal on an X-ray.

Stage 2: Mild

During this stage, a person may start to notice symptoms, and doctors can see some signs of wear. X-rays and other scans of the knee joints will clearly show more osteophyte growth, and the cartilage will begin to thin. The space between the bones will still appear normal, but the area where the bones and the tissues meet will start to harden. When the tissues harden, this makes the bone thicker and denser. A thin layer of bone will also develop beneath the cartilage in the joints. The person may experience stiffness or joint pain. The area around the knee joint may start to feel particularly stiff and uncomfortable after a person has been sitting for extended periods. Though there may be some minor damage, the bones are not rubbing or scraping against each other. Synovial fluid is present, and it helps to reduce friction and support the movement of the knee.

Stage 3: Moderate

The damage to the cartilage has progressed, the gap between the bones has narrowed, and X-rays will show cartilage loss. Pain and discomfort may occur while performing daily activities, such as running, walking, kneeling, and bending. There may be early signs of joint inflammation.

As OA progresses, the cartilage will continue to thin and break down. The bones will respond by thickening and growing outward to form lumps. The tissue that lines the joint will become inflamed, and it may produce extra synovial fluid, resulting in increased swelling. This is called synovitis, and it is commonly known as water on the knee.

Stage 4—Severe

Knee replacement surgery for OA of the knee. Knee replacement surgery may be the only option for late-stage OA of the knee. This is the most advanced stage of OA, and the symptoms are very visible. The space between the bones in the joint has continued to narrow, causing the cartilage to break down further. As a result, there is stiffness in the joint, constant inflammation, and less fluid around the joint. There is more friction in the joint and more significant pain and discomfort while moving. X-rays will show bone on bone, meaning that either the cartilage has completely worn away or there is very little left. The individual will likely develop more bone lumps and experience pain that is often intense during simple activities, such as walking. In severe cases, the bones may become deformed and angulated because of asymmetric loss of cartilage. At this stage, surgical treatment is often the only option.

Medical provider diagnoses of ICD-9-CM 715 [osteoarthrosis and allied disorders] include the following definitions: 1) strict=ICD-9-CM 715; 2) expanded=ICD-9-CM 715, 716 [other and unspecified arthropathies], OR 719 [other and unspecified disorders of joint]); and 3) probable=strict OR expanded+respondent-reported prior diagnosis of OA or other arthritis excluding rheumatoid arthritis (RA).

Mechanisms of Resistance to Reverse Transcriptase Inhibitors

While NRTIs are effective at terminating DNA synthesis and HIV replication, HIV can and eventually does develop mechanisms that confer the virus resistance to the drugs. HIV-1 RT does not have proof-reading activity. This, combined with selective pressure from the drug, leads to mutations in reverse transcriptase that make the virus less susceptible to NRTIs and NNRTIs.

NRTI Resistance

There are two major mechanisms of NRTI resistance. The first being reduced incorporation of the nucleotide analog into DNA over the normal nucleotide. This results from mutations in the N-terminal polymerase domain of the reverse transcriptase that reduce the enzyme's affinity or ability to bind to the drug. A prime example for this mechanism is the that confers resistance to lamivudine (3TC) and emtricitabine (FTC). Another well characterized set of mutations are found in multi-drug resistant HIV which decreases reverse transcriptase's efficiency at incorporating NRTIs, but does not affect natural nucleotide incorporation. A virus with the mutation is intermediately resistant to zidovudine (AZT), didanosine (ddI), zalcitabine (ddC), stavudine (d4T), and slightly resistant to abacavir (ABC). A virus with the mutation complexed with the other four mutations becomes highly resistant to the above drugs, and is additionally resistant to lamivudine (3TC) and emtricitabine (FTC).

The second mechanism is the excision or the hydrolytic removal of the incorporated drug or pyrophosphorlysis. This is a reverse of the polymerase reaction in which the pyrophosphate/PPI released during nucleotide incorporation reacts with the incorporated drug (monophosphate) resulting in the release of the triphosphate drug.

NTRIs and Treatment of OA

Osteoarthritis (OA) is an age-associated or post-traumatic degenerative joint disease involving articular cartilage degradation, chronic inflammation, and bone remodeling (Berenbaum, F. *Osteoarthritis and cartilage/OARS, Osteoarthritis Research Society* 21, 16-21 (2013)). While aging is a primary cause, it can also be caused by post-traumatic joint injury (PTOA) (Gelber, A. C., et al. *Ann Intern Med* 133, 321-328 (2000) and Lohmander, L. S., et al. *Am J Sports Med* 35, 1756-1769 (2007)). Although OA is a leading cause of disability in the elderly, there is no FDA approved disease modifying osteoarthritis drugs (DMOADs) currently. Transposons were first discovered in plant and defined as "jumping genes" (Mc, C. B. *Proc Natl Acad Sci USA* 36, 344-355 (1950)). They were subsequently discovered in all eukaryotes including animals and human (de Koning, A. P., et al. *PLoS Genet* 7, e1002384 (2011)). While human functional protein-coding exons consist merely 1% of our genome, transposons make nearly half of our genome (de Koning, A.

P., et al. *PLoS Genet* 7, e1002384 (2011)). L1, comprising 17% of entire genome, is the only active retrotransposon (Ostertag, E. M. & Kazazian, H. H., *Annu Rev Genet* 35, 501-538 (2001), Hancks, D. C. & Kazazian, H. H., Jr. *Curr Opin Genet Dev* 22, 191-203 (2012), Levin, H. L. & Moran, J. V. *Nat Rev Genet* 12, 615-627 (2011), Burns, K. H. & Boeke, J. D. *Cell* 149, 740-752 (2012), and Roman-Gomez, J., et al *Oncogene* 24, 7213-7223 (2005)). While it is active in germlines causing 124 genetic diseases, it is normally repressed in somatic cells and hence its function remains largely unknown (O'Donnell, K. A et al. *Developmental cell* 15, 179-181 (2008), Metzner, M., et al. *PloS one* 7, e49358 (2012), Faulkner, G. J. *PLoS Genet* 9, e1003944 (2013), Morrish, T. A., et al. *Nature* 446, 208-212 (2007), Morrish, T. A., et al. *Nature genetics* 31, 159-165 (2002), Guo, H., et al. *Nature communications* 5, 5276 (2014), and Moldovan, J. B. et al. *PLoS Genet* 11, e1005121 (2015)). Recently, it has been proposed that L1 plays a role in cell senescence, organism aging and neoplasia (Hancks, D. C. & Kazazian, H. H., Jr. *Curr Opin Genet Dev* 22, 191-203 (2012), De Cecco, M., et al. *Aging Cell* 12, 247-256 (2013), De Cecco, M., et al. *Aging* (Albany N.Y.) 5, 867-883 (2013), Marco De Cecco, et al. *Nature in press* (2018), and Hancks, D. C. & Kazazian, H. H., Jr. *Mob DNA* 7, 9 (2016)). Thus, as an aging associated disease, OA was hypothesized to be correlated with L1 activation in cartilage joint.

The invention provides a solution to obstacles associated with prevention and treatment of cartilage degenerative diseases. Accordingly, the invention includes methods using NRTIs to prevent, alleviate and treat cartilage degenerative diseases. Also provided herein are methods of using NRTIs for treatment of injury induced OA (also known as post-traumatic OA).

Accordingly, in some aspects, provided herein are methods for characterization of pharmaceutic efficacy in regards to alleviation OA markers and inflammatory markers. For example, the individual is diagnosed with OA, post-traumatic OA, rheumatoid arthritis, chondromatosis, costochondritis, relapsing polychondritis, herniation, chondrolysis, achondroplasia, chondrodysplasia, chondroma, chondrosarcoma, growth plate fracture and deformity, bone fracture, bone cyst, bone spur (osteophytes), bone tumor, craniosynostosis, fibrodysplasia, ossificans progressive, fibrous dysplasia, hypophosphatasia, metabolic bone disease, Paget's disease of bone, osteochondritis dissecans, osteogenesis imperfect, osteomalacia, osteopenia, osteoporosis. In experiments described herein, NRTIs are dissolved using autoclaved double distilled water. The individual to be treated is a human being; however, other subjects such as a mouse, rat, companion animals, such as a dog or a cat or working/performance animals such as a horse or a cow is also treated using the methods. RTIs suppress Long interspersed nuclear elements 1 (LINE-1, LINE1) (also, L1, Line1 and Line-1), Interferon (Inf-α) and Interleukin-6 (also IL6 and IL-6) in chondrocytes.

3TC suppresses Line-1 activities and prevent primary OA development in mice since miR-365/Line-1 axis correlates with OA development in both human OA samples and art-recognized mouse OA models Inhibition of Line-1 activity prevents and/or rescue OA onset. The class of drugs termed NRTIs are useful to treat OA pathogenesis.

To test whether NRTIs can inhibit OA markers via suppressing Line-1 in chondrocytes, human and mouse chondrocytes were treated with various concentrations of 3TC. qPCR analysis shows 3TC suppresses Line-1, Inf-α, Adamts5, Col10 expressions yet promotes Col2 expression in mouse chondrocytes. In human chondrocytes, whilst 3TC inhibits LINE-1, IHH, COL10 and ADAMTS5 expressions, 3TC promotes ACAN expression. Since Col10, Ihh and Mmp13 are induced in the articular cartilage of miR-365 Tg mice, human chondrocytes that already over-express miR-365 were treated with various concentrations of 3TC. Upon transfection, 3TC completely abolishes the miR-365 induced up-regulation of LINE-1, ADAMTS5, IHH and COL10 and rectifies ACAN suppression by miR-365.

Experiments were carried out to determine whether 3TC treatment rescues miR-365 induced Line-1 OA markers up-regulation and to determine whether 3TC can rescue OA phenotypes in primary OA model observed in miR-365 Tg mice. Starting at 2-month old, miR-365 Tg and age matched control mice (Cre only) were treated with 3TC dilution water or saline diluted water for 4 months before sacrifice. Consistently, proteoglycan loss was observed in the articular surface of miR-365 treated with saline but not of 3TC treatment. Furthermore, Line-1, Inf-α, Col10 and Adamts5 expression were significantly inhibited by 3TC treatment in miR-365 Tg mice. However, IL-6 or Acan levels are unchanged. miR-365 expression is also suppressed by oral 3TC treatment specifically in miR-365 Tg mice. Taken together, the data elucidates 3TC treatment, by inhibiting Line-1 activity, reverses Col2 lineage cell specific miR-365 over-expression induced OA markers including Col10 and Adamts5 in vivo.

3TC and FTC Prevent DMM (Destabilization of Medical Meniscus) Induced OA

Another cytidine analogue, FTC was tested. Although FTC suppresses Line-1 and Inf-α as well as inflammasome pathway like P2rx7 and Nlrp3, it induces Mmp3, Mmp13, Adamts5 and Col10 expressions whilst promotes Col2 and Acan expressions in mouse PC. 3TC was found to preferably inhibit OA markers while promoting ECM synthesis while FTC promotes both OA markers and ECM synthesis simultaneously in vitro.

The effects of 3TC and FTC using ex vivo femur organ cultures were tested. Intact femur was isolated from 21-day old WT mice into complete medium containing 3TC or FTC and was performed qPCR analysis using RNAs peeled from femur articular cartilages after 48 hrs incubation. While 3TC inhibits Line-1, Mmp13, Adamts5 and Col10, FTC inhibits Mmp13 and Adamts5 expressions. 3TC induced Col2 and Acan expressions when FTC induces the latter. Collectively, the data indicates that 3TC and/or FTC is useful to treat OA.

To test whether NRTIs can rescue secondary OA model, 12956 mice underwent either DMM or Sham surgeries with 3TC or FTC diluted water respectively from 8 weeks old for a total of 4 weeks. No appreciable difference of body weights between drug and control treatment groups are noticed. During histology assessment, treatment with 3TC and/or FTC treatments effectively prevented DMM induced proteoglycan loss in surgical knees. Meanwhile, qPCR analysis confirmed Line-1 inhibition introduced by 3TC and FTC. Chondrolytic markers including Mmp13, Adamts5 and hypertrophic maker Col10 were significantly repressed in 3TC and FTC treated DMM groups comparing with Saline treatment. Both 3TC and/or FTC treatments significantly prohibited miR-365 induction by DMM, indicating that NRTIs acts up-stream of miR-365. The data indicate that NTRIs such as 3TC and FTC prevent secondary OA onset by inhibiting Line-1 up-regulation and repressing OA markers.

miR-365 was found to target retrotransposable element suppressors including Dicer, Prkdc and Sqstm1. Through this circuit, miR-365 controls Line-1 expression thereby promoting cartilage degradation. Suppressing Line-1 expression using NRTIs, for example 3TC and FTC, through their anti-reverse transcriptional functions, prevents cartilage degradation and results in OA phenotype rescue.

The following materials and methods were used to generate the data and observations described herein.

Animals

To over-express miR-365 in cartilage tissues, C57BL/6 background miR-365fl/wt transgenic mice are crossed with Col2a1-Cre+/wt (Cre-only) mice to generate Col2a1-Cre+/wt; miR-365fl/wt mice (miR-365 Tg) (Yang, K., et al. Connect Tissue Res 58, 103-115 (2017)).

12956/SvEv strain male mice are purchased from Taconic (https://www.taconic.com/mouse-model/129s6) at their age of 7-week-old. At least 3-day (72-hrs) acclimation period must be given to mice before any further procedures occurred to them.

All strains of mice are housed with ad libitum access to food and water unless otherwise stated.

Genotyping

Genomic DNA is extracted from mouse toes or tails within 7 days after birth and performed by conventional PCR using Hot start Taq polymerase (New England BioLabs, Cat. M049S/L) using primers designed specific to miR-365 insertion or Col2a1-Cre constructs.

Mouse Model of Destabilization of Medial Meniscus (DMM)

129S6/SvEv male mice are chosen for experimental subjects at their age of 8-week-old. To create mouse injury/trauma induced osteoarthritis model, medial meniscus ligament is transected using a previously described. 8-week-old male mice are anesthetized using either intraperitoneal (IP) injection of Ketamine/Dexmedetomidine or isoflurane to carry out medial parapatellar arthrotomy. Transection is made with a stab knife (Sharpoint™, Cat. 72-1551). At Weeks 12, mice are euthanized and dissected for histological examination as well as cartilage RNA extraction. 12 mice are used for each group/time point.

Human Specimens

Cartilages are obtained from individuals diagnosed with OA and underwent total knee replacement. Samples are harvested freshly after surgeries. Pictures of specimens are taken for recording purpose. OA lesion and non-lesion areas are empirically identified by orthopedic surgeons based on direct observation. For each site of interest, a 1×1 $mm^2$ tissue with a depth ranging from 4-8 mm is harvested using sterile, RNase free Rib-Back® scalpels (Bard-Parker®, Cat. 371115) manually. Care must be taken to avoid any subchondral bone. To obtain maximal digestion efficacy, resected specimens are further minced by scalpels before submerging into 350 mL QIAzol Lysis Reagent (Qiagen, Cat No./ID: 79306). Specimens can either be stored at −80° C. or be accessed using diverse methods.

Femur Explant Organ Culture

Femurs are obtained from 21-day-old WT C57BL/6 mice. Femurs with intact articular surface and periosteum is sterilely dissected under microscope. All animal procedures are reviewed and approved by IACUC. Upon harvesting, femurs are rinsed with HBSS (Gibco®, Grand Island, N.Y. 14072 USA) and then submerged into DMEM (Gibco®, Grand Island, N.Y. 14072 USA) medium supplemented with 10% fetal bovine serum (FBS, Gibco®, Grand Island, N.Y. 14072 USA) in 12-well culture dishes. 3TC or FTC is added into the medium with desired concentrations. After a total of 48 hrs incubation at 37° C. in an atmosphere of 5% $CO_2$, femurs are rinsed with HBSS and articular cartilage is peeled off using surgical scalpels under dissecting microscope for RNA extraction.

Histology, Immunohistochemistry (IHC), and Immunofluorescence

Human cartilage tissues are fixed in 4% Paraformaldehyde (PFA) for 24 hrs at 4° C., followed by 30% DEPC-sucrose (Sigma, Cat. 50289-500G, St. Louis, Mo. 63103 USA) at 4° C. until the specimens are sunken to the bottom of the containers. Tissues are embedded in optimal cutting temperature compound (O.C.T., SAKURA FINETEK USA INC, Tissue-Tek® O.C.T. Compound, Cat. 4583). A cryosection microtome (Model: CM3050, Leica, Germany) is used to cut 6-µm-thick sections. The sections are stained by H&E staining to assess morphology. Mouse tissues are fixed in 10% formalin for 24-48 hrs depending on tissue size, followed by de-calcification process using DEPC de-calcification reagents (Ethylenediaminetetraacetic acid, Sigma, Cat. EDS-1KG, St. Louis, Mo. 63103 USA) at room temperature for 10-14 days. After de-calcification, tissues are dehydrated in ethanol before embedded in paraffin with routine procedures. A microtome (Model: FINESSE ME, Thermo Shandon, UK) is used to cut 6-µm-thick sections. For every 80 µm interval, 5 sister sections are harvested to make a total of 13-16 slices from one knee of a fully-grown mouse. Number of slides form one knee may vary due to varying sizes of the specimens. Slides are then de-paraffinized and stained GAG with Alcian blue (Sigma, Cat. A3157-10G) or Safranin O (Sigma, Cat. 58884-25G, St. Louis, Mo. 63103 USA). Morphology is assessed by H&E staining. For IHC, paraffin sections are processed with routine procedures instructed by Histostain® Plus $3^{rd}$ Gen IHC Detection Kit (Life Technologies, Cat. 859673, Frederick, Md. 21704 USA). Rabbit or mouse antibodies specifically against antigens of interest are used, followed by incubation of HRP-conjugated secondary antibodies against rabbit or mouse IgG (provided by the kit). Primary and secondary antibodies are listed herein. Signals are then visualized by a DAB-Plus Substrate Kit (Life Technologies, Cat. 002020, Frederick, Md. 21704 USA).

Safranin O Staining

Paraffin sections are de-paraffinized in 2 changes of xylene, 10 mins each, followed by re-hydration in 2 changes of 100% alcohol, 5 mins each; 2 changes of 95% alcohol, 5 mins each; 70% alcohol for 5 mins. Sections are then rinsed in running tap water for 2 mins before stained with 0.4% fast green solution (Sigma, Cat. F-7258, St. Louis, Mo. 63103 USA) for 2 mins however the latter timing must be empirically controlled to assure desired coloration. Stained sections are then quickly rinsed with 1% acetic acid solution (Sigma, Cat. 695092-500ML-GL, St. Louis, Mo. 63103 USA) for no more than 10-15 sec. 0.1% Safranin O Solution is used for staining proteoglycan however the actual timing must be carefully determined based on actual coloring condition, for maximally 10 mins. After Safranin O staining, sections are submerged in 2 changes of 95% alcohol, 2 mins each, 2 changes of 100% alcohol, 2 mins each for de-hydration. Lastly, sections are cleared in 2 changes of xylene, 2 mins each, and mounted using resinous mounting medium (ACRYMOUNT™, Cat. SL80-4, McKinney, Tex. 75069 USA).

OARSI Scoring

To histologically evaluate OA severity, we quantified Safranin O stained knee sections according to OARSI semi-quantitative system as previously described (Sato, S., et al. *TheScientificWorldJournal* 2014, 685854 (2014)).

Hematoxylin and Eosin (H&E) Staining

Paraffin sections are de-paraffinized in 2 changes of xylene, 10 mins each, followed by re-hydration in 2 changes of 100% alcohol, 5 mins each; 2 changes of 95% alcohol, 5 mins each; 70% alcohol for 5 mins. Sections are then rinsed in running tap water for 2 mins before stained in Mayer's Hematoxylin solution (NovaUltra™ H&E Stain Kit, IHC-WORLD, Cat. IW-3100) for 2 mins however the latter timing must be empirically controlled to assure desired coloration. Stained sections are then rinsed in running tap water for 5 mins before dipped into 95% alcohol for 10 times or 30 sec based on performer's preference. Eosin Solution (NovaUltra™ H&E Stain Kit, IHCWORLD, Cat. IW-3100) is used for counterstaining however the actual timing must be carefully determined based on actual coloring condition. After counterstaining, sections are dipped in 95% alcohol for 2 times before transferred through 2 changes of 100% alcohol, 5 mins each for de-hydration. Lastly, sections are cleared in 2 changes of xylene, 5 mins each, and mounted with resinous mounting medium.

For frozen sections, procedures are similar with the exception between Eosin counterstaining and 95% alcohol dipping steps. Instead, during these two steps, frozen sections must be air dried for 30 mins at room temperature and fixed in 10% formalin for 10 mins. Then the sections are taken out for another 30 mins air dry at room temperature before rinsed in water.

Homogenization

A PowerGen 125 (Fisher Scientific, Cat. 03.349248) is used to homogenize samples for RNA exaction. A cycle of 45" homogenization at speed of 5, followed by a cool down step of 15" is repeated for 5 cycles before switching to a finer drill for the same cycles. Drills/PowerGen Generator (Fisher Scientific, Cat. 14-261-15) are rinsed in DEPC-water followed by 100% ethanol rinse between different specimens to avoid cross contamination. All procedures are taken place on ice to avoid RNA degradation due to heat.

Primary Growth Plate/Articular Chondrocytes (PCs) Culture

Rib cages are sterilely isolated from neonatal mice (within 7-day-old) of desired genotypes and rinsed with HBSS for five times. To remove unspecific tissues, rib cages are digested in Collagenase D (3 µg/mL, Roche, Cat. 11088882001, Mannheim, Germany) for 2-4 hrs at 37° C. and rinsed with HBSS (Gibco®, Grand Island, N.Y. 14072 USA) for five times to remove detached unspecific tissues. To detach chondrocytes from rib cages, the samples undergo secondary digestion in Collagenase D (3 µg/mL) for at least 4 hrs at 37° C. with constant agitation (200 rpm). Detached chondrocytes are palleted to remove excessive Collagenase D and resuspended in complete medium of DMEM (Gibco®, Grand Island, N.Y. 14072 USA) which contains 10% FBS, 100 U/mL penicillin and 100 µg/mL streptomycin (Gibco®, Grand Island, N.Y. 14072 USA). Growth plate PCs are grown at 37° C. in an atmosphere of 5% $CO_2$. The media is changed on the following day to remove remaining Collagenase D and every 3 days thereafter.

Similarly, articular cartilages are sterilely isolated under dissection microscope from neonatal mice (within 7-day-old) of desired genotypes and rinsed with HBSS for five times. To remove unspecific tissues, articular cartilages are minced and digested in Collagenase D (3 µg/mL) for 2 hrs at 37° C. and rinsed with HBSS for five times to remove detached unspecific tissues. To detach chondrocytes from cartilage matrix, the samples underwent secondary digestion in Collagenase D (3 µg/mL) for at least 4 hrs at 37° C. with constant agitation (200 rpm). Detached chondrocytes are palleted to remove excessive Collagenase D and resuspended in complete medium of DMEM which contains 10% FBS, 100 U/mL penicillin and 100 µg/mL streptomycin. Articular PCs are grown at 37° C. in an atmosphere of 5%

$CO_2$. The media is changed on the following day to remove remaining Collagenase D and every 3 days thereafter.

Transient Transfection

Cells are seeded onto desired size plates to reach 70-90% confluence and transfected with miR-365 mimic or miRNA mimic negative control or miR-365 inhibitor or inhibitor negative control (Dharmacon®, Lafayette, Colo., USA). Lipofectamine 3000 (Invitrogen®, Waltham, Mass., USA) is used as transfection reagents. Medium is changed 24 hrs after transfection. 48 hrs post transfection, cells are lysated in either QIAzol for RNA purification and real-time PCR analysis or ice-cold lysis buffer containing protease inhibitor and phosphatase inhibitor for western blot analysis. MiR-365 mimic, miRNA mimic negative control, miR-365 inhibitor and inhibitor negative control are typically used at a final concentration of 25 nM unless otherwise stated.

Quantitative Real-Time PCR (qPCR)

Both miRNA and mRNA are extracted using miRNeasy Mini Kit (Qiagen®, Germantown, Md., USA) and reversely transcribed using miScriptIIRT Kit (Qiagen®, Germantown, Md., USA) according to manufacturer's instruction. qPCR is performed using SYBR Green PCR master mix (Qiagen®, Germantown, Md., USA) on a Bio-Rad CFX96 real-time PCR detection system (Bio-Rad®, Hercules, Calif., USA). Amplification conditions are as follows: 95° C. for 10 min, 40 cycles of 95° C. for 10 sec, 55° C. for 30 sec, and 72° C. for 30 sec. Sense and antisense primers are provided herein. 18S ribosomal or Gapdh RNA is used as an internal control gene to normalize the mRNAs level. The ubiquitously expressed snRNA U6 is used as an endogenous control for miRNAs level. Primers are synthesized by Integrated DNA Technologies (http://www.idtdna.com). The primers for miR-365 are purchased from Qiagen. Fold changes of mRNA and miRNAs are calculated by the $2^{\wedge(-\Delta\Delta Ct)}$ method and normalized to 18S/Gapdh or U6 snRNA, respectively.

Prediction of miR-E365 Target Genes

Targets of miR-365-5p and miR-365-3p were identified using the TargetScan (http://www.targetscan.org/) and miRanda/mirSVR (http://34.236.212.39/microrna/home.do) target prediction algorithms.

Plasmid Construction

WT Aicda, Dicer1, Prkdc, Sqstm1 and Zc3hav1 3'UTRs bearing potential response elements (REs) serving as miR-365 seeding sites predicted by microrna.org are cloned from mouse genomic DNA (50 ng-250 ng) using primers designed to introduce ideal restriction enzyme cleavage sites according to the backbone plasmid pmirGLO construct (Promega, Madison, Wis., USA). Detailed thermal cycles are: 98° C. for 30 sec, 25-35 cycles of 98° C. for 10 sec, 55-60° C. for 30 sec, and 72° C. for 15 sec and final extension at 72° C. for 10 min before holding at 4° C. Designed primers are provided herein. PmeI and XhoI are enzymes used to cleave for sticky ends. After restriction enzymes cleavage, approximately 500 bp 3'UTR sequences are annealed into pmirGLO construct (1 pg-10 ng). REs are mutated according to QuikChange Lightning Multi Site-Directed Mutagenesis Kit's instruction (Agilent, Cat. 210513/210515, Santa Clare, Calif. 95051 USA).

Luciferase Assays

ATDC5 cells are cultured at $2.5 \times 10^4$ cells/well in 24-well plates. The cells are co-transfected with miR-365 mimic (25 nM) or miRNA mimic negative control (25 nM) and 500 ng of pmirGLO-Dicer1/Zap/Sqstm1/Prkdc/Aicda 3'-UTR WT or Mut plasmids. Transfection is performed using Lipofectamine 3000 (Invitrogen, Cat. L3000-008, Carlsbad, Calif. 92008 USA) reagent. The assays are performed in triplicate unless otherwise stated. 24 hrs after transfection, cells are collected, and luciferase activity is determined using the Dual-Luciferase reporter assay system (Promega, Madison, Wis., USA) with the GLOMAX 20/20 luminometer (Model: 2031_000, Turner BioSystems, Sunnyvale, Calif. USA). Briefly, cells are rinsed with PBS and incubated with Passive Lysis Buffer (provided by the kit) for 15 mins with constant agitation at room temperature. Lysates are scraped into 1.5 mL Eppendorf tubes. 20 μl of lysates are fixed with 50 μl Luciferase Assay Buffer II to measure Firefly luciferase luminescence. 50 μl Stop & Glo buffer is then added to measure Renilla luminescence. The luciferase activity is represented by the ratio of Firefly/Renilla measurements.

Western Blot (WB)

All pre-treated samples are washed with ice-cold PBS and lysated in RIPA buffer (M-PER, Pierce, Ill.) plus protease inhibitor phenylmethylsulfonyl fluoride [Halt™, Thermo Scientific, Protease Inhibitor Single-Use Cocktail (100×), Cat. 78430] for 30 min on ice with constant agitation. The lysates are centrifuged at 12,000 g for 15 min at 4° C. The supernatants are collected, and the protein concentrations are determined using Pierce™ BCA assay (Thermo Scientific, Cat. 23225). Samples are mixed with equal volume 2× Laemmli sample buffer (Bio-Rad, Cat. 161-0737) which contains 2-Mercaptoethanol (Bio-Rad, Cat. 161-0710) and heated for 5 min at 100° C. to denature. Equal amount of proteins for each sample are separated by 8-12% SDS polyacrylamide gel depending on protein size of interest and then transferred to nitrolcellulous membrane (Bio-Rad, Cat. 162-0112) for 70 min at 100 V. The membrane is blocked with 5% bovine serum albumin (BSA, Sigma, Cat. A7906-50G) in 0.1% Tris-Buffered Saline-Tween 20 (TBS-T, BBP, Cat. IBB-581X) for 1 hr at room temperature, followed by incubation with primary antibodies against proteins of interest at 4° C. overnight. On the following day, the membrane is rinsed with TBS-T for 10 min for a total of 5 times and incubated with anti-rabbit-Alexa Fluor 680 (Molecular Probes, Eugene, Oreg., USA) for 1 hr at room temperature followed by TBS-T rinse for 10 min for a total of 5 times. The blots are then scanned using an Odyssey fluorescence scanner (LI-COR Biosciences, Lincoln, Nebr., USA) and quantitatively analyzed by ImageJ (https://imagej.nih.gov/ij/index.html).

Statistical Analysis

Data represents mean values SD (error bars). Statistical significance is calculated using student's t-test (unpaired) or ANOVA one-way test. There is a minimum of n≥3 for all groups unless otherwise stated.

MiR-365 Over-Expression Promotes Line-1 Activation in Human OA Lesion and Mouse OA Model Human long interspersed element-1 (Line-1) has been an emerging biomarker of many human cancers and chronic diseases (Ostertag, E. M. & Kazazian, H. H., Jr. *Annu Rev Genet* 35, 501-538 (2001) and Birren, S. J., Lo, L. & Anderson, D. J. S. *Development* 119, 597-610 (1993)). Line-1 activation may be associated with cellular senescence (De Cecco, M., et al. *Aging Cell* 12, 247-256 (2013), and Ali, M., et al. *Annals of the rheumatic diseases* 62, 663-666 (2003)). Since OA is an aging associated chronic disease, studies were carried out to determine whether OA pathogenesis is companied by Line-1 activation.

qPCR analysis of RNA extracted from both lesion and non-lesion areas of human cartilages specimens shows Line-1 activities are significantly up-regulated in OA lesion areas in majority of the OA patients. Yet another abundant transposable element in human genome, Alu, which exploits the machinery encoded by Line-1 to transpose itself, exhibits no uniformed trends between lesion and non-lesion areas of human OA specimens. miR-365 expressions were up-regulated in 50% of samples, indicating an association between Line-1 and miR-365 up-regulation in OA.

To test whether miR-365 is sufficient to induce Line-1, we transfected mouse primary chondrocytes (PC) with miR-365 mimic. Upon transfection, the expression of Line-1 and Ihh, a chondrocyte hypertrophic marker, are significantly induced. siRNA against Line-1 successfully rescued the miR-365 led induction of Line-1 and Ihh, indicating that not only miR-365 is sufficiently to induce Line-1, but also Ihh could act downstream of induced Line-1 activity by miR-365.

To study the relationship between miR-365 and Line-1 in cartilage in vivo, we created transgenic mice of which miR-365 is specifically over-expressed in Col2 lineage cells (miR-365 Tg mice) (Yang, K., et al. *Connect Tissue Res* 58, 103-115 (2017))). We observed that miR-365 Tg mice manifest advanced onset of OA as early as at 6-month-old (Hug, B. A. *Cell* 119, 448-449 (2004)). Therefore, studies were carried out to determine whether Line-1 is elevated in miR-365 Tg mice. In alignment with miR-365 over-expression in cartilage, Line-1 RNA expressions are significantly up-regulated 4- and 6-month old. Besides promoting Line-1 expression, miR-365 cartilage over-expression also induces Ihh, Col10 and Mmp13 expressions in miR-365 Tg mice (Hug, B. A. *Cell* 119, 448-449 (2004)). Collectively, the in vivo data indicate miR-365 over-expression in cartilage drives long-term Line-1 and OA markers up-regulation which temporarily associates with OA phenotypic onset.

To test whether this causal relationship between miR-365 up-regulation and Line-1 activation exists in secondary OA model, we built injury induced OA model by performing DMM surgery on the right knees of 12956/SvEv male mice at 2 months old. One month post DMM surgery, Line-1 activities are significantly up-regulated in the destabilized right knees comparing with Sham knees. Same pattern of miR-365 increase is observed in the same knees. Consistently, significant proteoglycan loss quantified by blinded grades using OARSI scores (Sato, S., et al. *TheScientificWorldJournal* 2014, 685854 (2014)) is observed in DMM knees, corroborating that Line-1 activation is associated with miR-365 up-regulation as well as cartilage degradation. In addition, in C57BL/6 background WT mice which underwent DMM surgeries, Line-1 activation is tightly associated with miR-365 increase and such association is further augmented as post-surgical mice age. Hence the association between miR-365 and Line-1 up-regulation is valid in secondary OA models in mice.

MiR-365 Induces Line-1 Expression via Post-Transcriptional Suppressions of Prkdc, Dicer and Sqstm1

Bio-informatic search revealed five candidates (Aicda, Dicer, Prkdc, Sqstm1 and Zc3hav1) of potential miR-365 targets that are both conserved across species and involved in Line-1 suppression. As Line-1 activation can be induced by miR-365 over-expression in cartilage and such activation has been tightly associated with primary and secondary OA in human and mice, we are interested in whether above candidates' expressions are altered in OA tissues. qPCR analysis using human OA cartilage RNA showed DICER, PRKDC, SQSTM1 and ZAP expressions are decreased in majority of OA specimens while AICDA is not detectable in human cartilage. Only Prkdc is down-regulated at the RNA level in miR-365 Tg mice articular cartilage. To further confirm in vitro, we over-expressed miR-365 in mouse PC, to evaluate wither miR-365 increase in cartilage induces Line-1 activation via post-transcriptional suppression of Line-1 inhibitors.

Aicda (Faulkner, G. J. *PLoS Genet* 9, e1003944 (2013)), Dicer (Morrish, T. A., et al. *Nature genetics* 31, 159-165 (2002)V), Prkdc (Guo, H., et al. *Nature communications* 5, 5276 (2014)), Sqstm1 (Moldovan, J. B. & Moran, J. V. *PLoS Genet* 11, e1005121 (2015)) and Zc3hav1 (Erwin, J. A., et al. *Nat Rev Neurosci* 15, 497-506 (2014)) are shown to be involved in inhibition of Line-1 at various biogenesis stages. WB using proteins isolated from primary mouse chondrocytes transfected with miR-365 mimic and Sqstm1 cDNA demonstrates Line-1 is significantly induced by miR-365 transient over-expression and rescued by Sqstm1 over-expression, indicating Sqstm1 is involved in miR-365 over-expression induced Line-1 activation in cartilage. Furthermore, WB shows while Dicer protein expression is suppressed by miR-365 transfection, it is induced by miR-365 inhibitor, indicating that miR-365 affects Dicer expression at post-transcriptional level.

To further test whether Prkdc, Dicer and Sqstm1 are authentic targets of miR-365, we co-transfected ATDC5 cells with luciferase genes bearing predicted binding sites of WT 3'UTR of Aicda, Dicer, Prkdc, Sqstm1 and Zc3hav1 at 3' ends as well as miR-365 mimic or mimic control respectively. Dicer, Prkdc and Sqstm1 WT 3'UTR luciferase reporter genes showed significant reduction of activities regarding to miR-365 over-expression and those reduction are completely abolished via site-directed mutagenesis of the predicted seeding sites. Hence Dicer, Prkdc and Sqstm1 are authentic targets of miR-365 in chondrocytes.

3TC Suppresses Line-1 Activities and Prevent Primary OA Development in Mice

Since miR-365/Line-1 axis snugly correlates with OA development in both human OA samples and mouse OA models, experiments were carried out to determine whether inhibition of Line-1 activity prevents or rescues OA onset. A class of drugs termed Reverse-transcriptase inhibitor (NRTI), which are popularly prescribed for controlling HIV and HBV infections attributing to their anti-retroviral function, can suppress retrotransposable elements activities in various models (Patnala, R., et al. *Breast Cancer Res Treat* 143, 239-253 (2014), Jones, R. B., et al *PloS one* 3, e1547 (2008), and Guilak, F. *Best practice & research. Clinical rheumatology* 25, 815-823 (2011)). However, prior to the invention, NRTI used to rescue OA pathogenesis had not been described.

To test whether NRTIs can inhibit OA markers via suppressing Line-1 in chondrocytes, we treated human and mouse chondrocytes with various concentrations of 3TC. qPCR analysis shows 3TC suppresses Line-1, Inf-α, Adamts5, Col10 expressions yet promotes Col2 expression in mouse chondrocytes. In human chondrocytes, whilst 3TC inhibits LINE-1, IHH, COL10 and ADAMTS5 expressions, 3TC promotes ACAN expression. Since Col10, Ihh and Mmp13 are induced in the articular cartilage of miR-365 Tg mice, we treated human chondrocytes that already over-express miR-365 with various concentrations of 3TC. Upon transfection, 3TC completely abolishes the miR-365 induced up-regulation of LINE-1, ADAMTS5, IHH and COL10 and rectifies ACAN suppression by miR-365.

Because 3TC treatment rescues miR-365 induced Line-1 OA markers up-regulation, we tested whether 3TC can rescue OA phenotypes in primary OA model observed in miR-365 Tg mice. Starting at 2-month old, miR-365 Tg and age matched control mice (Cre only) are treated with 3TC dilution water or saline diluted water for 4 months before sacrifice. Consistently, proteoglycan loss is observed in the articular surface of miR-365 treated with saline but not of 3TC treatment. Furthermore, Line-1, Inf-α, Col10 and Adamts5 expressions are significantly inhibited by 3TC treatment in miR-365 Tg mice. However, IL-6 or Acan levels are unchanged. miR-365 expression is also suppressed by oral 3TC treatment specifically in miR-365 Tg mice. The data elucidates 3TC treatment, by inhibiting Line-1 activity, can appreciably reverse Col2 lineage cell specific miR-365 over-expression induced OA markers including Col10 and Adamts5 in vivo.

3TC and FTC Prevent DMM Induced OA

In the light of the promising anti-OA activity of 3TC, we evaluated another widely prescribed cytidine analogue, FTC. Although FTC suppresses Line-1 and Inf-α as well as inflammasome pathway like P2rx7 and Nlrp3, it induces Mmp3, Mmp13, Adamts5 and Col10 expressions whilst promotes Col2 and Acan expressions in mouse PC. Taken together, 3TC preferably inhibits OA markers while promoting ECM synthesis, while FTC promotes both OA markers and ECM synthesis simultaneously in vitro.

Next, we tested the effects of 3TC and FTC using ex vivo femur organ cultures. We incubated intact femur isolated from 21-day old WT mice into complete medium containing 3TC or FTC and performed qPCR analysis using RNAs peeled from femur articular cartilages after 48 hrs incubation. While 3TC consistently does a promising job in terms in inhibiting Line-1, Mmp13, Adamts5 and Col10, FTC inhibits Mmp13 and Adamts5 expressions. 3TC induces Col2 and Acan expressions when FTC induces the latter. Collectively, the data further indicates the potential anti-OA role of 3TC and FTC.

To test whether NRTIs can rescue secondary OA model, we treated 129S6 mice which underwent either DMM or Sham surgeries with 3TC or FTC diluted water respectively from 8 weeks old for a total of 4 weeks. No appreciable difference of body weights between drug and control treatment groups were noticed. During histology assessment, we found both 3TC and FTC treatments effectively prevent DMM induced proteoglycan loss in surgical knees. Meanwhile, qPCR analysis confirmed Line-1 inhibition introduced by 3TC and FTC. Chondrolytic markers including Mmp13, Adamts5 and hypertrophic maker Col10 are significantly repressed in 3TC and FTC treated DMM groups comparing with Saline treatment. Both 3TC and FTC treatments significantly prohibit miR-365 induction by DMM, providing intriguing hints that NRTIs may act up-stream of miR-365. Therefore, 3TC and FTC prevents secondary OA onset by inhibiting Line-1 up-regulation and repressing OA markers.

The data indicate that miR-365 targets retrotransposable element suppressors including Dicer, Prkdc and Sqstm1. Through this circuit, miR-365 controls Line-1 expression thereby promoting cartilage degradation. Suppressing Line-1 expression using NRTIs, for example 3TC and FTC, through their anti-reverse transcriptional functions, prevents cartilage degradation and results in OA phenotype rescue.

Osteoarthritis is Treated by Inhibiting MicroRNA Up-Regulation of Retrotransposon LINE-1

Prior to the invention, retrotransposable element activation has not been associated with OA pathogenesis. Our results for the first time unearth the correlation between OA development and Line-1 activation in both human OA specimens and mouse in vivo models.

OA is a multi-factor as well as polygenic disease as etiology indicates there is no single cause of OA pathogenesis (Birren, et al. *Development* 119, 597-610 (1993)). Human OA specimens are of heterogeneous etiologies as the entire information of human donors are difficult to trace back. The up-regulation of miR-365 and activation of Line-1 are consistent in majority of the human OA specimens, indicating the strong association between these two exists in most human cases. As Line-1 activation may also correlate with aging (De Cecco, M., et al. *Aging Cell* 12, 247-256 (2013), Ali, M., et al. *Annals of the rheumatic diseases* 62, 663-666 (2003)), given that the human donors are of various ages, the basal Line-1 levels are difficult to unify. Yet OA development in WT mouse hardly occur. miR-365 Tg mice represent mono-factor OA model which is specifically triggered by the over-expression of miR-365 in Col2-lineage cells, which comprise the most population in cartilage. In addition, all mouse experimental subjects are age- and gender-matched, thus making rodent results more uniform and more consistent between individual subjects. The art recognized mouse models described herein are indicative of the human disease/disorder.

Data from miR-365 Tg mice treated with 3TC indicates 3TC inhibits Col10 and Adamts5 expressions specifically via suppressing Line-1 pathways as IL-6 expressions, which is a down-stream gene of miR-365, are left unchanged. miR-365 and Line-1 expressions are significantly suppressed by 3TC specifically in miR-365 Tg. miR-365 expression is significantly suppressed by 3TC and FTC in DMM induced OA models. The data indicate that NRTIs affect miR-365 expression. For example 3TC and FTC treatments specifically suppress supra-physical miR-365/Line-1 expressions in non-injury OA model, because physical miR-365 expression is required during mechanical signal transduction, which is a good indicator for the effective usage of 3TC and FTC in treating both primary and secondary OA without delivering adverse effects.

Both siLine-1 and 3TC suppress not only Line-1 but also Ihh in vitro while 3TC suppresses only Line-1 but not Ihh in vivo. This difference may be attributed to contrast between in vitro condition and in vivo environment. For instance, PC are isolated from neonatal mice while in vivo 3TC treatment are conducted in near fully developed mice from 2-month old till 6-month old when the qPCRs are performed. The effect of Line-1 inhibition in chondrocytes at different stages might be various. Furthermore, while the former experiment is transient, the latter is a long-term treatment. Last but only least, 3TC treatment, beyond inhibiting Line-1 specifically, might alter other pathways. Ihh pathway might parallel with Line-1 pathway in cartilage in vivo, at least during long-term 3TC treatment. Similar explanation may also underly miR-365 induced Mmp13 results.

In this study, we have demonstrated a regulatory role for miR-365 through inducing retrotransposable element, Line-1, to promote OA pathogenesis. In order to reduce the severity of and/or prevent OA, feasible methods to suppress Line-1 including administration of 3TC and FTC and siRNA against Line-1 are useful as therapeutic approaches in counteracting osteoarthritis.

Pharmaceutical Compositions

The present invention provides also pharmaceutical compositions comprising a nucleoside reverse transcriptase inhibitor (NRTI) (e.g., 3TC or FTC) and at least one pharmaceutically acceptable excipient or carrier. In examples, the pharmaceutical composition comprises an effective amount of the NRTI (e.g., 3TC or FTC) as described herein in connection with the methods of the invention.

In one embodiment, the composition (e.g., a composition comprising an NRTI) is further combined with at least one additional therapeutic agent in a single dosage form.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

For treatment of articulating joint disorders such as OA (or RA-rheumatoid arthritis), the NRTIs are administered intra-articularly (directly into a joint), intravenously, orally, or transcutaneously.

The parenteral and/or intra-articular preparation can be enclosed in ampules, disposable syringes or multiple dose vials made of glass or plastic. Intra-articular administration is useful for local treatment of disease and flare-up, e.g. pain in joints, osteoarthritis, synovitis and the like. A complex of the present invention may also be administered as a bolus, electuary or paste. Exemplary administrations include: Intra-articular, Peri-articular, Intra-bursal, Intra-muscular, or Soft tissue—tendon ruptures. Exemplary administration volumes for adult human are shown below, and are proportionally smaller for a human child.

| Joint | Volume |
|---|---|
| Shoulder | 10 ml |
| Elbow | 5 ml |
| Wrist/thumb | 2 ml |
| Fingers | 1 ml |
| Hip | 5 ml |
| Knee | 10 ml |
| Ankle, foot | 5 ml |
| Toes | 1 ml |

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). Exemplary doses and dosages regimens for the compositions in methods of treating muscle diseases or disorders are described herein.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In embodiments, the pharmaceutical composition comprises an injectable form.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

A pharmaceutical composition can be in the form of a sterile aqueous solution or dispersion suitable for systemic administration.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Kits Comprising the NRTI

In aspects, a kit for an NRTI is provided. In embodiments, the kit comprises the NRTI and reagents.

In embodiments, components of the kit are suitable for delivery (e.g., systemic administration) to a subject.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention (e.g., a joint diseases such as osteoarthritis), one or more syringes, one or more applicators, or a sterile solution suitable for reconstituting a pharmaceutical composition of the present invention.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means ±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated nucleoside, nucleoside analog, e.g., NRTI, polynucleotide (ribonucleic acid (RNA) or deoxyribonucleic acid (DNA)) of nucleotides or nucleosides that flank it in its naturally occurring states. A purified or isolated polypeptide is free of the amino acid sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice.

The term "subject" as used herein includes a human or animal diagnosed with an osteoarthritic disorder.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Compared to other methods, an illustrative non-limiting method in the Example that follows uses three commercially available mediums to generate beige adipocytes, which are largely serum/xeno free, which resulted in more consistent results. These beige adipocytes were functionally similar to brown adipocytes, but are developmentally distinct. In embodiments, serum characteristics can change from lot to lot, and mediums that are highly quality controlled are preferably used.

Example 1: Activation of L1 in OA and its Dependency on miR-365

Figure 5A:
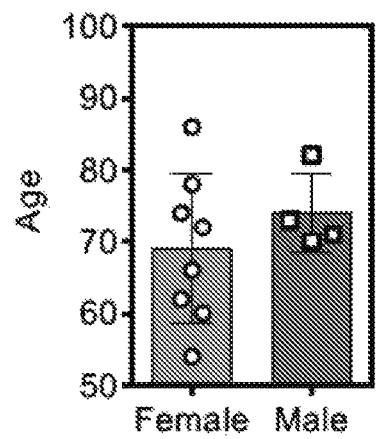
FIG. 5A-5F are a series of images that show characterization of human OA specimens.
Figure 5B:
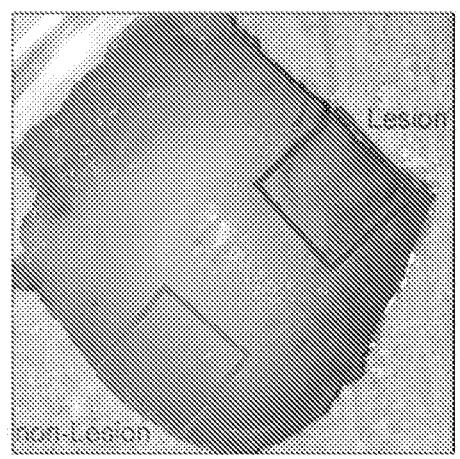
Figure 5C:
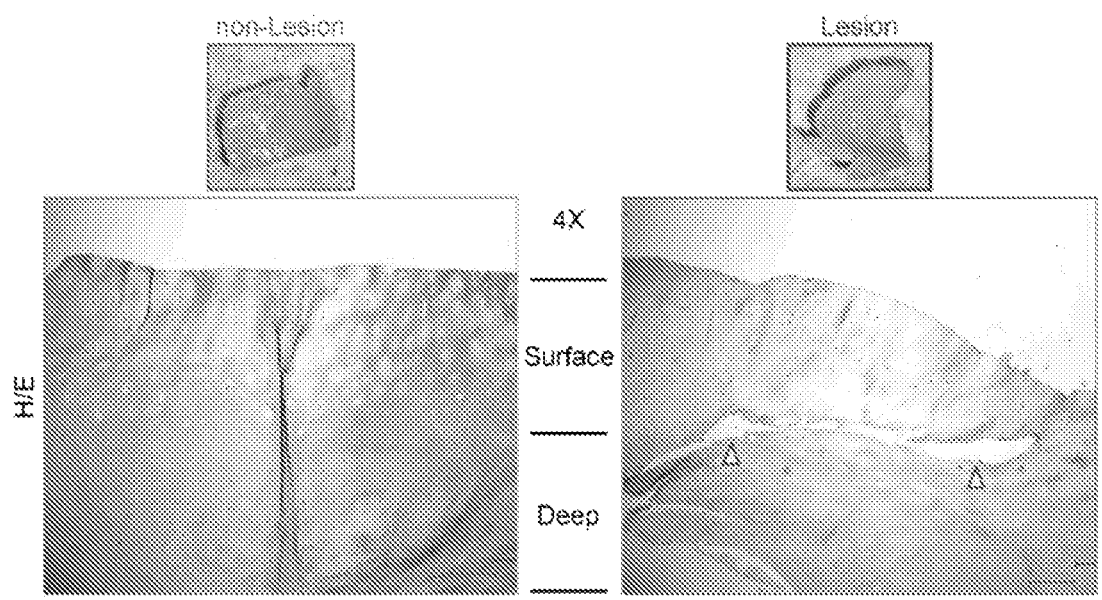
Figure 5D:
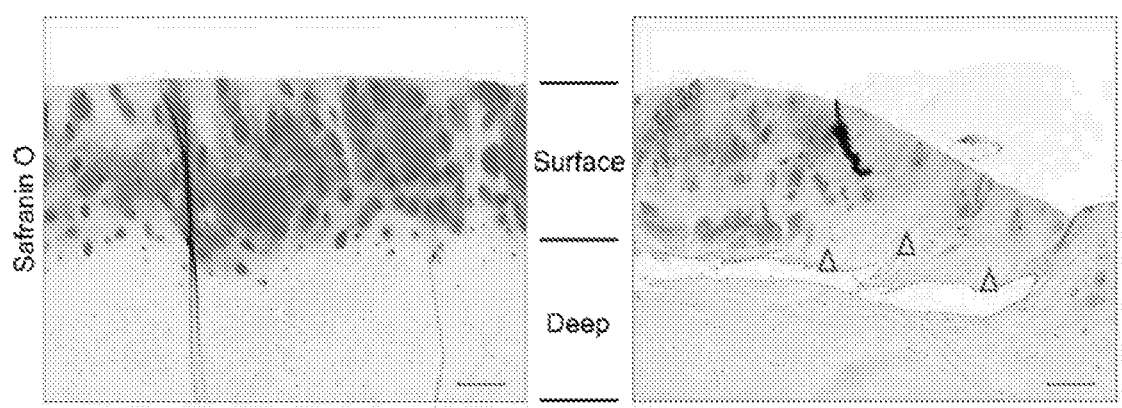
Figure 5E:
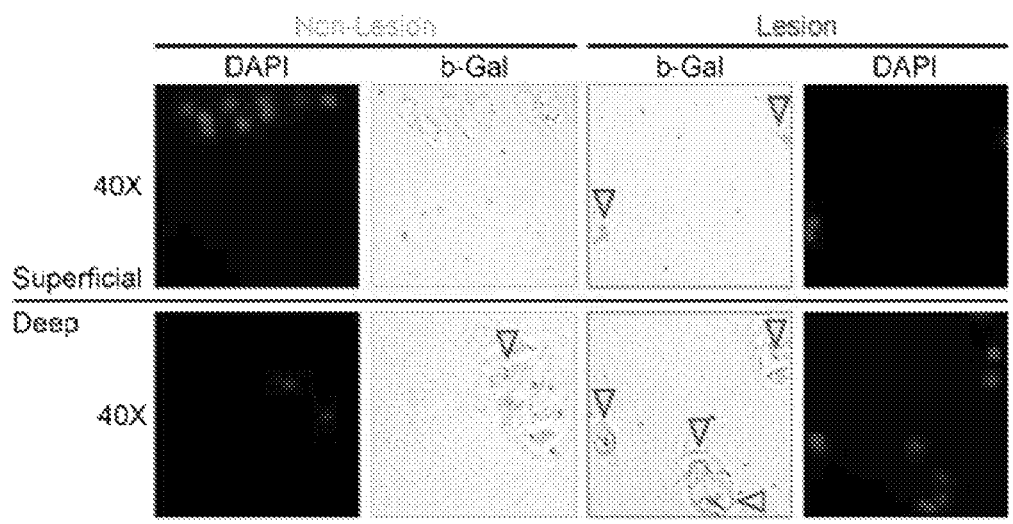
Figure 5F:
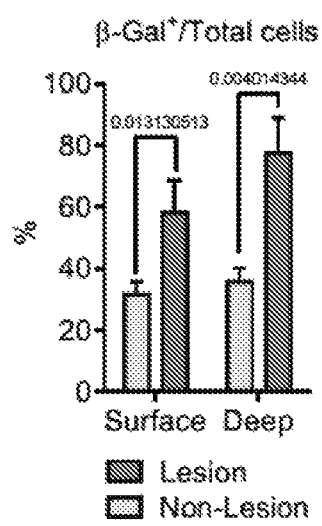

To determine whether L1 levels were elevated in OA joint, RNA was extracted from an OA lesion and non-lesion area (FIG. 5B) in the same human OA cartilage specimen collected from joint replacement surgery of aged patients (Female: 68±12; Male: 73±5) (FIG. 5A). This eliminated individual variations of LI levels in different patients. OA lesions exhibited fissures (FIG. 5C), more pronounced loss of proteoglycan (FIG. 5D), and significant increase of the percentage of senescent cells (FIG. 5E) compared to non-lesions.

Figure 1A:
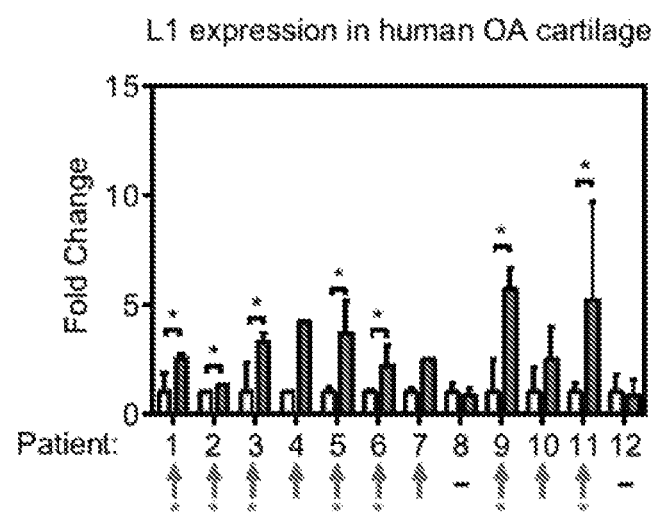
Figure 1B:
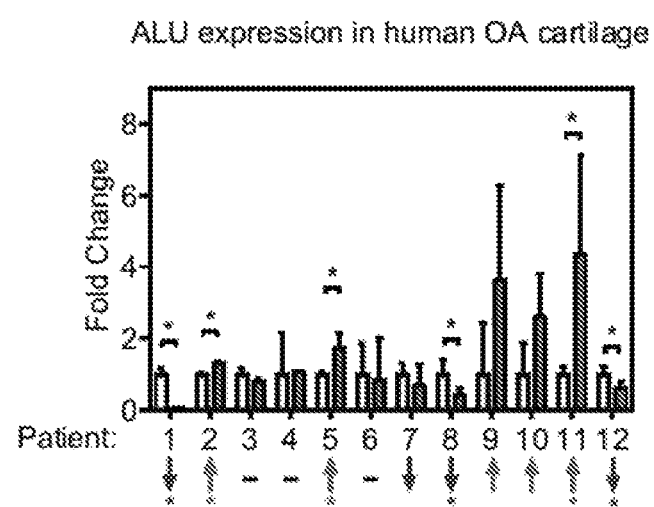
FIG. 1B is a graph showing the gene expression of ALU at the RNA level in human OA cartilage samples assessed by RT-qPCR.
Figure 1C:
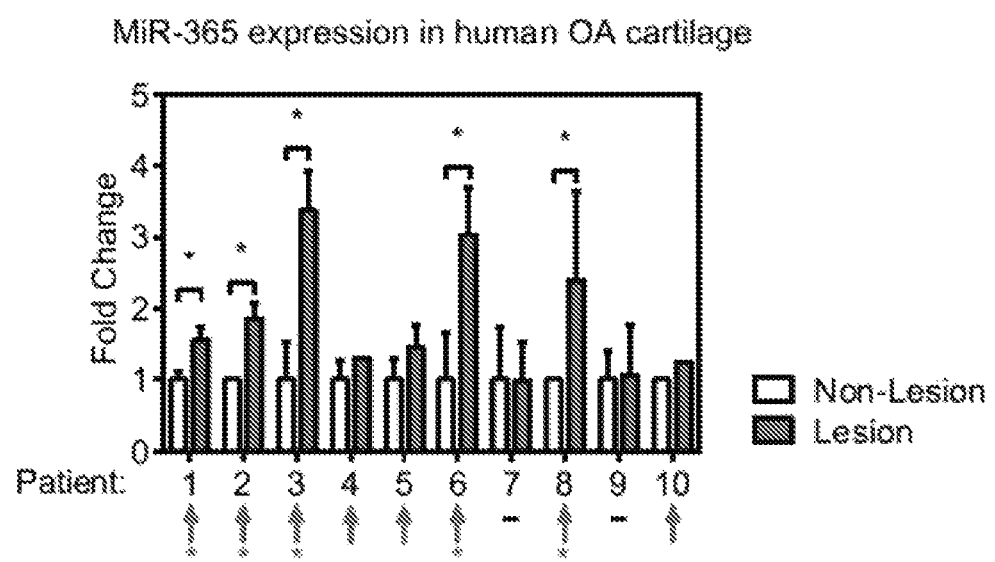
FIG. 1C is a graph showing the gene expression of miR-365 at the RNA level in human OA cartilage samples assessed by RT-qPCR. LINE-1 levels were significantly elevated in $7/12$ (58.33%) patients (FIG. 1A); ALU levels were significantly elevated in $3/12$ (25.00%) patients, while were significantly decreased in $3/12$ (25.00%) patients (FIG. 1B). MiR-365 levels were significantly elevated in $5/8$ (62.50%) patients (FIG. 1C). n varies from 1 to 3 due to the size of human specimen. Statistics are calculated in samples with n≥3. *p≤0.05, relative to appropriate non-lesion (control) groups respectively.
Figure 1D:
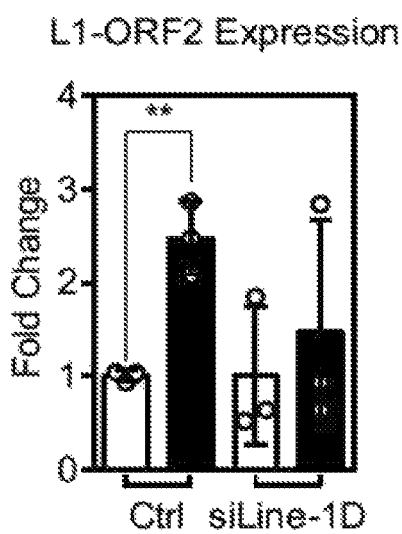
FIG. 1D is a graph showing the gene expression of Line-1-ORF2 at RNA level in mouse chondrocytes co-transfected with siRNAs against Line-1 (siLine-1D) as well as miR-365 assessed by RT-qPCR. n=3. *p≤0.05, relative to appropriate control groups respectively.
Figure 1E:
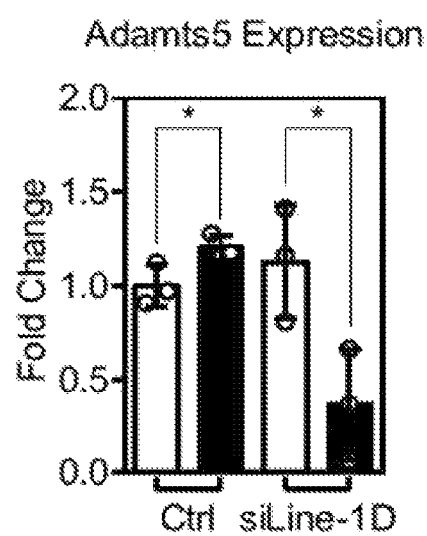
FIG. 1E is a graph showing gene expression of Adamts5 at RNA level in mouse chondrocytes co-transfected with siRNAs against Line-1 (siLine-1D) as well as miR-365 assessed by RT-qPCR. n=3. *p≤0.05, relative to appropriate control groups respectively.

L1 levels were significantly up-regulated in the OA lesion area than a non-lesion area in the majority of OA patients (FIG. 1A). In contrast, another abundant transposon in human genome, Arthrobacter luteus elements (Alu), exhibited no uniformed up-regulation in human OA lesions (FIG. 1B). MiRNA-365, a mechanical and inflammation sensitive microRNA (Yang, X., et al. *Int J Mol Sci* 17, 436 (2016), and Guan, Y. J., et al. *FASEB journal* 25, 4457-4466 (2011)), was up-regulated in the majority of OA patients (FIG. 1C), suggesting an association between L1 and miR-365 in OA cartilage.

Figure 1F:
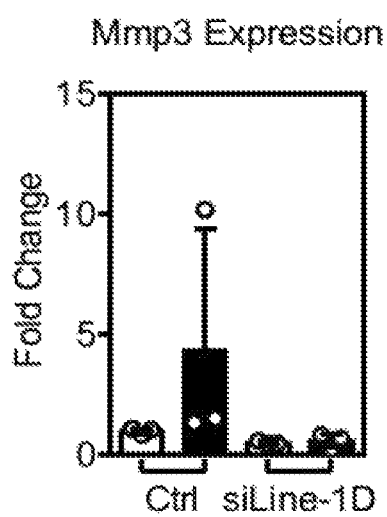
FIG. 1F is a graph showing gene expression of Mmp3 at RNA level in mouse chondrocytes co-transfected with siRNAs against Line-1 (siLine-1D) as well as miR-365 assessed by RT-qPCR. n=3. *p≤0.05, relative to appropriate control groups respectively.
Figure 1G:
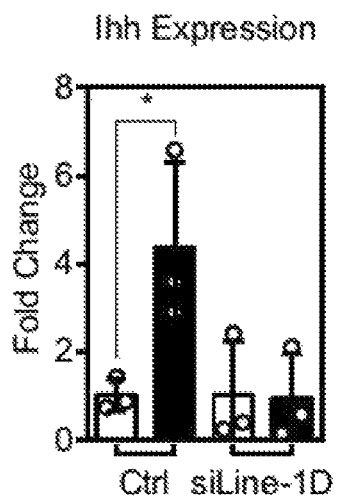
FIG. 1G is a graph showing the gene expression of Ihh at RNA level in mouse chondrocytes co-transfected with siRNAs against Line-1 (siLine-1D) as well as miR-365 assessed by RT-qPCR. n=3. *p≤0.05, relative to appropriate control groups respectively.
Figure 1H:
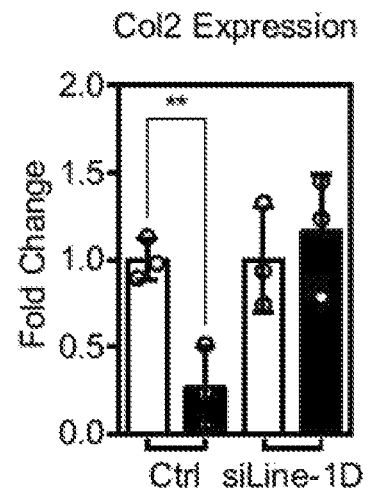
FIG. 1H is a graph showing the gene expression of Col2a1 at RNA level in mouse chondrocytes co-transfected with siRNAs against Line-1 (siLine-1D) as well as miR-365 was assessed by RT-qPCR. n=3. *p≤0.05, relative to appropriate control groups respectively.
Figure 1I:
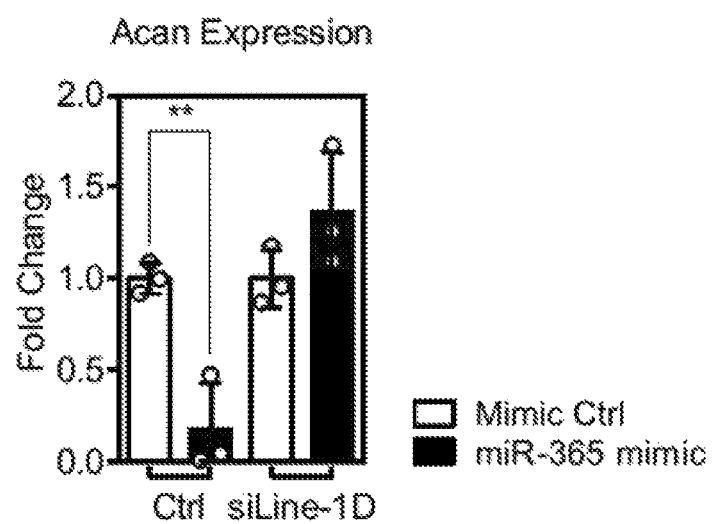
FIG. 1I is a graph showing the gene expression of Acan at RNA level in mouse chondrocytes co-transfected with siRNAs against Line-1 (siLine-1D) as well as miR-365 assessed by RT-qPCR. n=3. *p≤0.05, relative to appropriate control groups respectively.
Figure 6A:
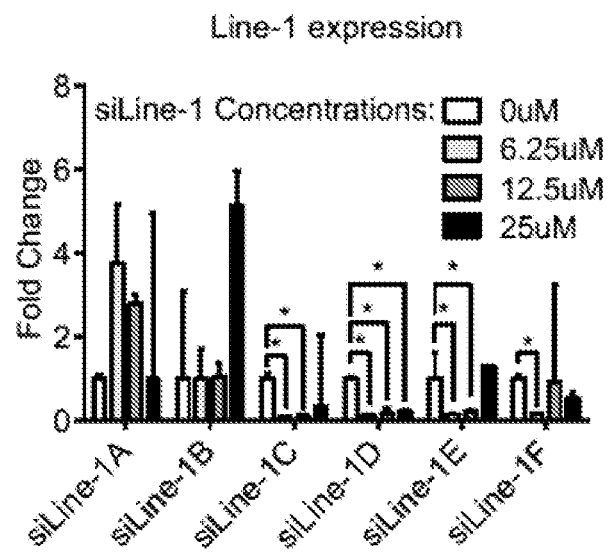
FIG. 6A-6G are a series of images showing screening of siRNA against Line-1 (siLine-1).
Figure 6B:
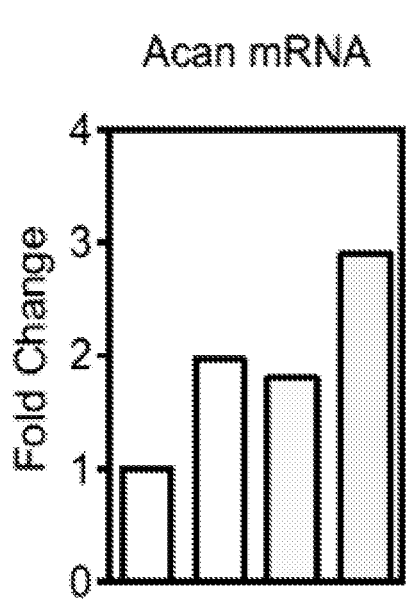
Figure 6C:
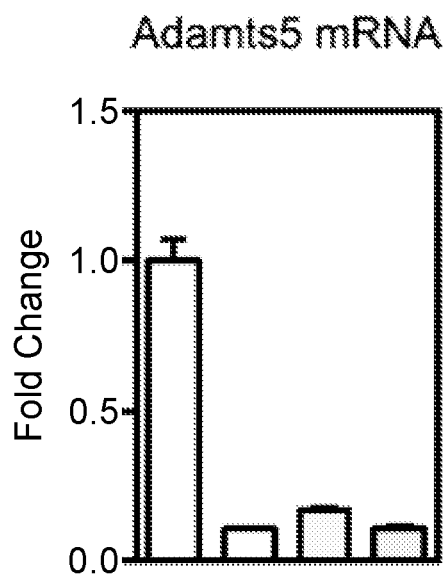
Figure 6D:
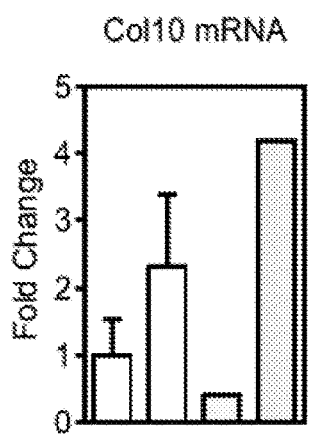
Figure 6E:
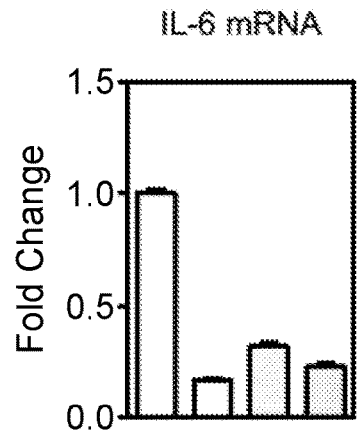
Figure 6F:
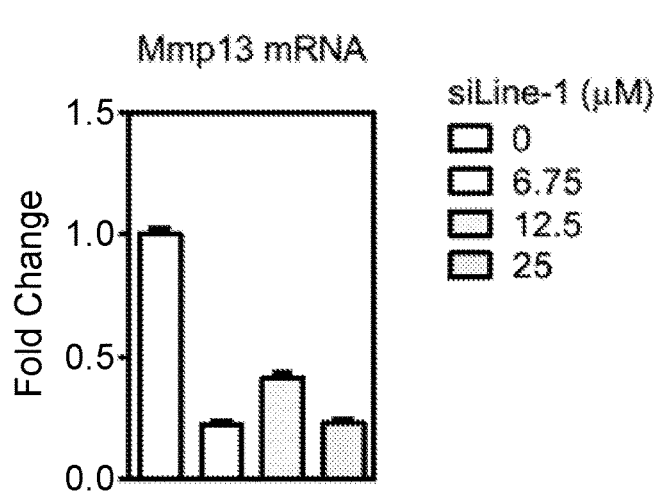
Figure 6G:
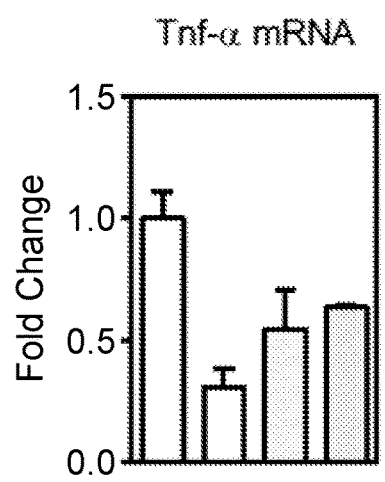

To test this association, mouse primary chondrocytes were transfected with miR-365 mimic. MiR-365 significantly induced L1 (FIG. 1D), OA markers Indian hedgehog (Ihh) and ADAMTS-5 (FIGS. 1E and 1G), and senescence associated secretory phenotype (SASP) marker MMP-3 (FIG. 1F). It also significantly decreased anabolic extracellular matrix (ECM) Col2a1 and Acan (FIGS. 1H and 1I). To determine whether miR-365-elicited gene expression changes depend on L1, siRNA was screened against L1 (FIG. 6A). Knocking down L1 with L1 siRNA (siLine-1D) abolished miR-365-elicited gene expression changes (FIG. 1D-1I). Therefore, L1 activation depended on miR-365 in vitro.

Figure 1J:
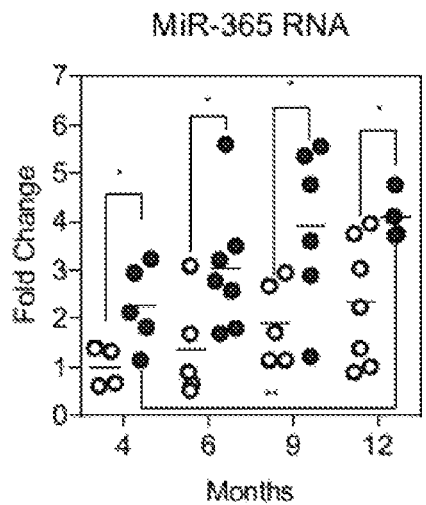
FIG. 1J is a graph showing gene expression of miR-365 in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1K:
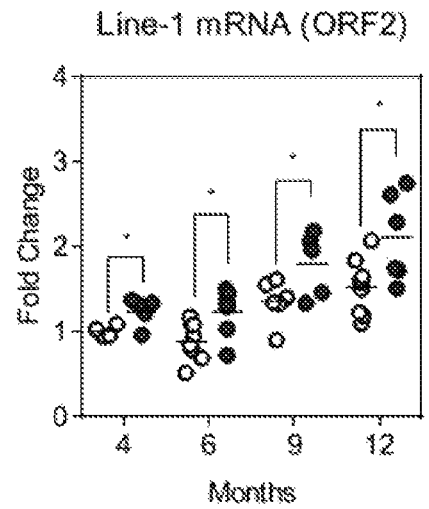
FIG. 1K is a graph showing gene expression of Line-1 mRNA in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1L:
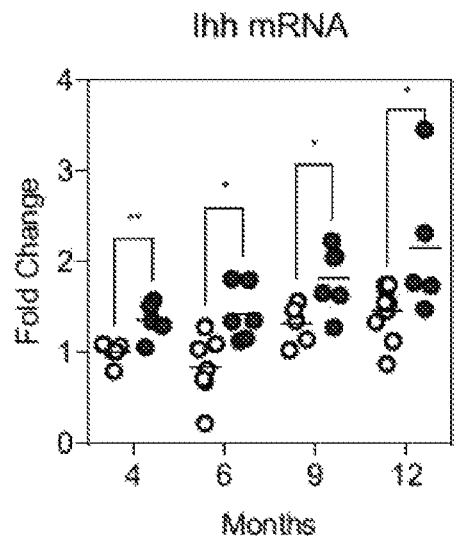
FIG. 1L is a graph showing gene expression of Ihh in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1M:
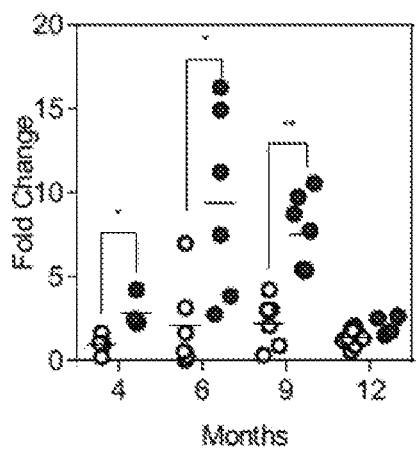
FIG. 1M is a graph showing gene expression of collagen type x alpha 1 chain (Col10a1) in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1N:
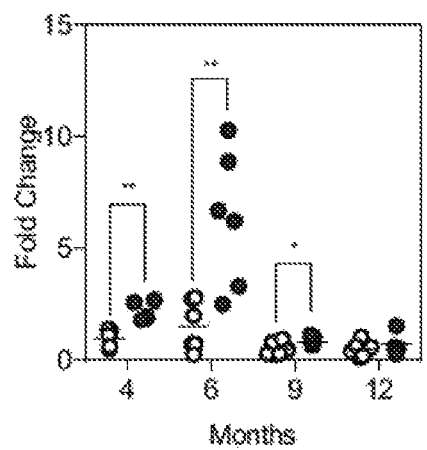
FIG. 1N is a graph showing gene expression of Adamts5 in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1O:
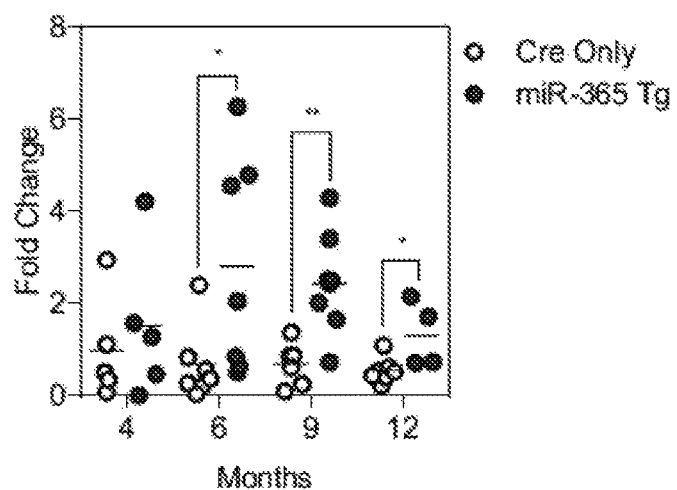
FIG. 1O is a graph showing gene expression of Mmp13 at RNA level in Cre only and miR-365 Tg mice cartilage at 2-, 6-, 9- and 12-month of age was assessed by RT-qPCR. n≥4. *p≤0.05, relative to age-matched control (Cre-only) groups respectively.
Figure 1P:
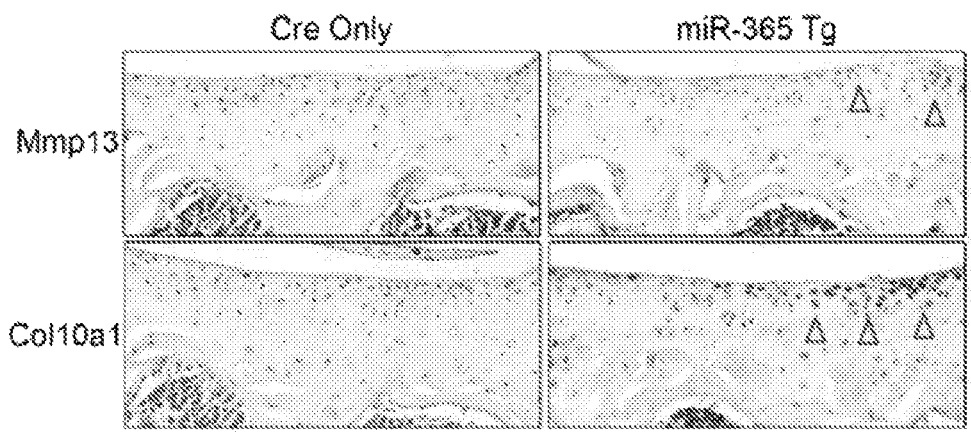
FIG. 1P are IHC staining images of Col10a1 and Ihh expression at protein level on joint sections from 6-month-old Cre only and miR-365 Tg mice. Both Col10a1 and Ihh protein expressions were up-regulated in the articular surface of miR-365 Tg mice.
Figure 1Q:
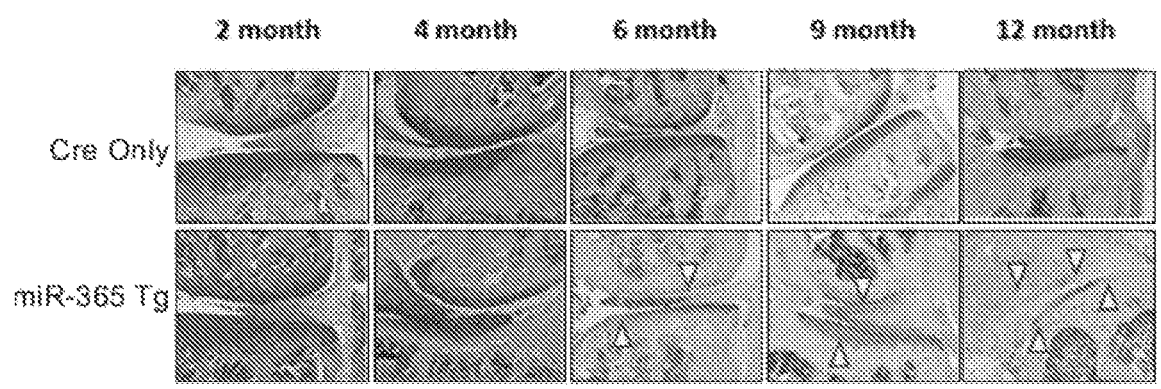
FIG. 1Q are a series of Safranin O staining images of mouse knees harvested from 2- to 12-month-old miR-365 Tg and age-matched control (Cre only) mice, showing obvious articular cartilage degradation in miR-365 Tg mice knees since 6-month old.
Figure 1R:
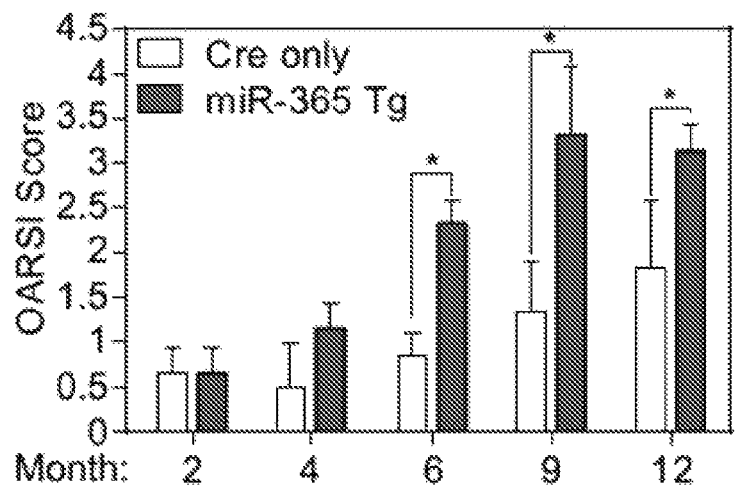
FIG. 1R is a bar graph depicting results of OARSI quantification of mouse knees harvested from 2- to 12-month-old miR-365 Tg and age-matched control (Cre only) mice, showing obvious articular cartilage degradation in miR-365 Tg mice knees since 6-month old.

To determine whether L1 activation also depends on miR-365 in vivo, mice were generated harboring the miR-365-Flox transgene in an intergenic region on chromosome 4 (Yang, K., et al. *Connect Tissue Res* 58, 103-115 (2017)). Crossing of miR-356-Flox mice with Col2a1 Cre mice generated transgenic mice (miR-365 Tg) in which miR-365 transgene was specifically expressed in cartilage (FIG. 7) (Yang, K., et al. *Connect Tissue Res* 58, 103-115 (2017)). These mice had up to six-fold increase of miR-365 levels in cartilage in comparison to their littermates Cre only (FIG. 1J). L1 RNA levels were consistently up-regulated for up to three-fold increase in cartilage throughout adulthood (FIG. 1K). The cartilage in these mice was phenotypically normal until 6 months old, when they developed early onset of OA, characterized by thinning and loss of articular cartilage (FIGS. 1Q and 1R) and expression of OA markers Col10a1 and Mmp13 (FIG. 1P). Real-time PCR analysis indicated that the mRNA levels of OA markers Ihh, Col10a1, Adamts5, and Mmp13 were up-regulated in cartilage (FIG. 1O). Thus, miR-365 activated L1 and caused early onset of OA in vivo.

Figure 1S:
FIG. 1S is a schematic representation of animal procedures: 129S6/SvEv mice underwent destabilizing medial meniscus (DMM) or Sham surgeries on right legs at 2-month-old and were sacrificed at 3-month-old (1-month post-surgery).
Figure 1S:
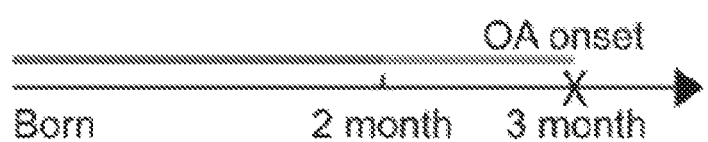
Figure 1T:
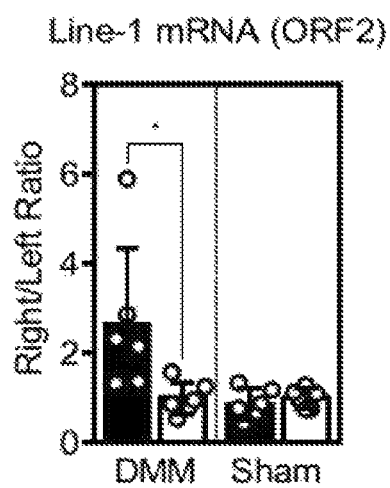
FIG. 1T is a bar graph showing the gene expression of Line-1-ORF2 at RNA level in 12956/SvEv background mice articular cartilage was assessed by RT-qPCR. Line-1 and miR-365 levels were significantly elevated in the cartilage of DMM (right) knees at 1-month post-surgery when normalized to non-surgery (left) knees. There were 6 mice in each group
Figure 1U:
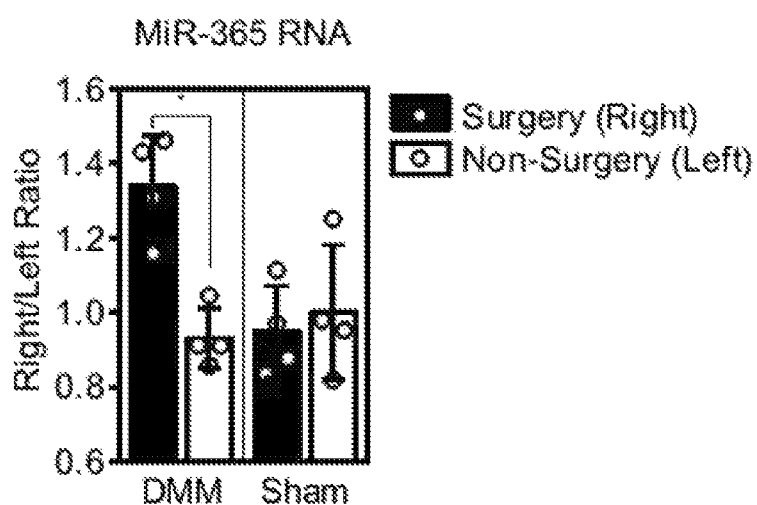
FIG. 1U is a graph showing gene expression of miR-365 at RNA level in 12956/SvEv background mice articular cartilage was assessed by RT-qPCR. Line-1 and miR-365 levels were significantly elevated in the cartilage of DMM (right) knees at 1-month post-surgery when normalized to non-surgery (left) knees. There were 6 mice in each group.

To determine whether L1 activation was also associated with injury induced PTOA, joint injury was generated by performing destabilizing medial meniscus (DMM) surgery in two genetic strains of mice (129s6/SvEv and C57BL/6) that have different OA development periods (FIGS. 1S and 1V). Joint injury significantly increased both L1 and miR-365 levels in the injured knee during PTOA onset (3-month-old) in comparison to the non-injured knee of 129s6/SvEv mice (FIGS. 1T and 1U). Thus joint injury induced L1 and miR-365 levels in cartilage.

To determine the effects of aging process on L1 levels, DMM surgery was performed on C57BL/6 mice and let them age for additional five months (FIG. 1V). While the L1 level almost doubled in the first 1.5 months period (4-5.5 months) following the onset of OA at 4-month-old, it increased almost 200 fold in the subsequent 1.5 months period (5.5-7 months) (FIG. 1W). This was in contrast to miR-365, which had linear accumulation during these two periods (FIG. 1X). It indicated that L1 were amplified during OA progression. Thus, L1 is activated by injury and amplified during aging.

Example 2: Mechanisms of miR-Dependent L1 Activation

Figure 2A:
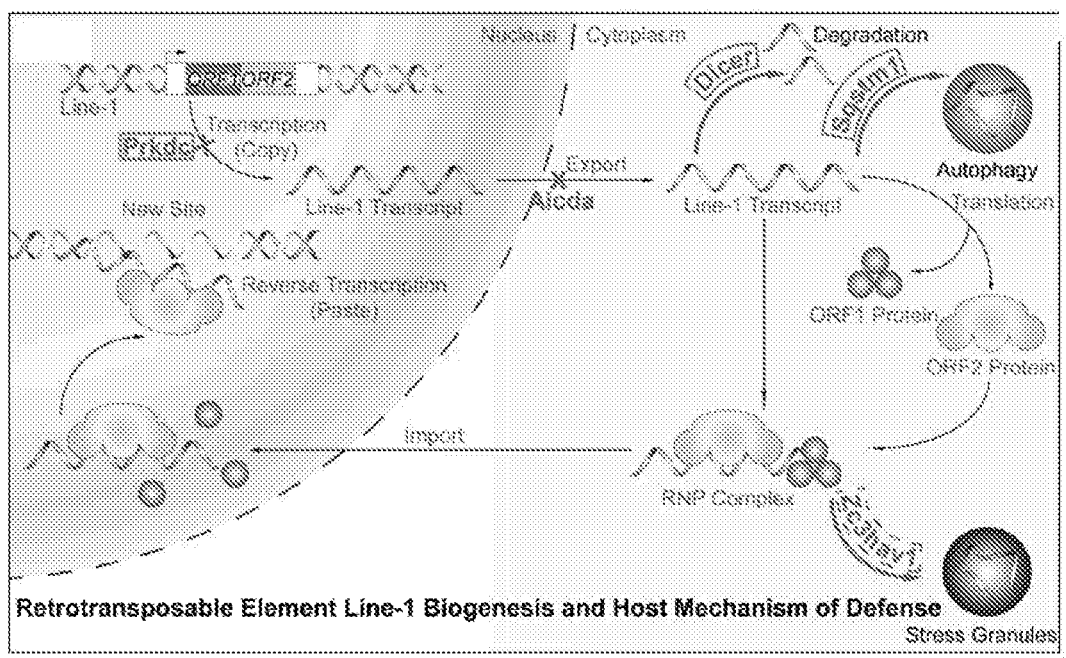
FIGS. 2A-2O are a series of images indicating that MiR-365 induced Line-1 gene expression via post-transcriptional suppressions of Prkdc (protein kinase DNA-activated catalytic subunit), Dicer and Sqstm1 (sequestosome 1).
Figure 2B:
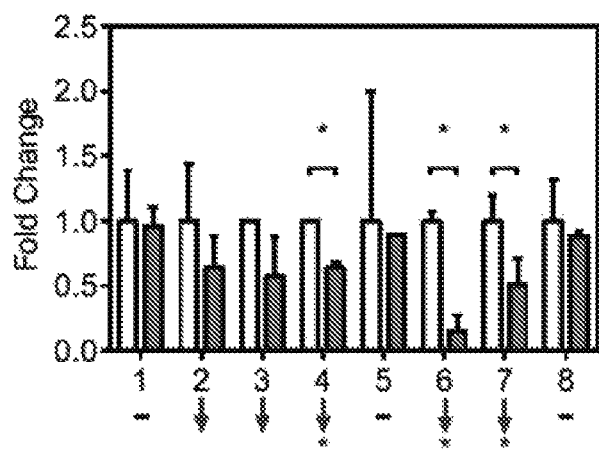
FIG. 2B is a graph showing the gene expression of DICER at RNA level in human OA cartilage was assessed by RT-qPCR. The DICER level was significantly down-regulated in 3/8 (37.50%) specimens. n varies from 1 to 3 due to the size of human specimen. Statistics are calculated in samples with n≥3. *p≤0.05, relative to non-lesion (control) groups respectively.
Figure 2C:
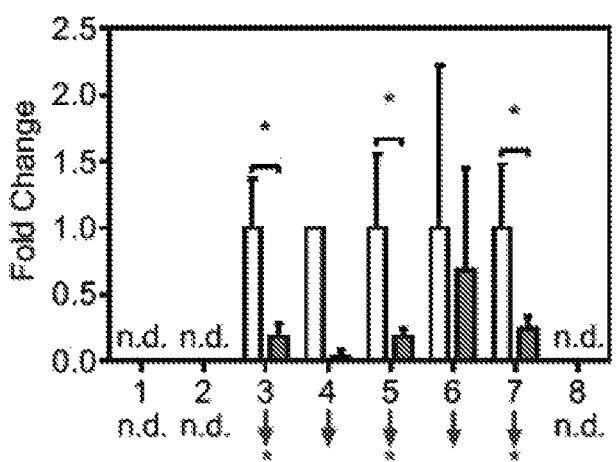
FIG. 2C is a graph showing the gene expression of PRKDC at RNA level in human OA cartilage was assessed by RT-qPCR. The PRKDC level was significantly down-regulated in 3/8 (37.50%) specimens. n varies from 1 to 3 due to the size of human specimen. Statistics are calculated in samples with n≥3. *p≤0.05, relative to non-lesion (control) groups respectively.
Figure 2D:
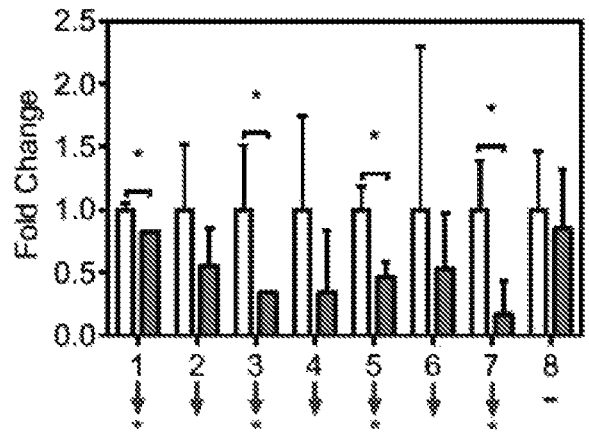
FIG. 2D is a graph showing the gene expression of SQSTM1 at RNA level in human OA cartilage was assessed by RT-qPCR. The SQSTM1 level was significantly down-regulated in 4/8 (50.00%) specimens. n varies from 1 to 3 due to the size of human specimen. Statistics are calculated in samples with n≥3. *p≤0.05, relative to non-lesion (control) groups respectively.
Figure 2E:
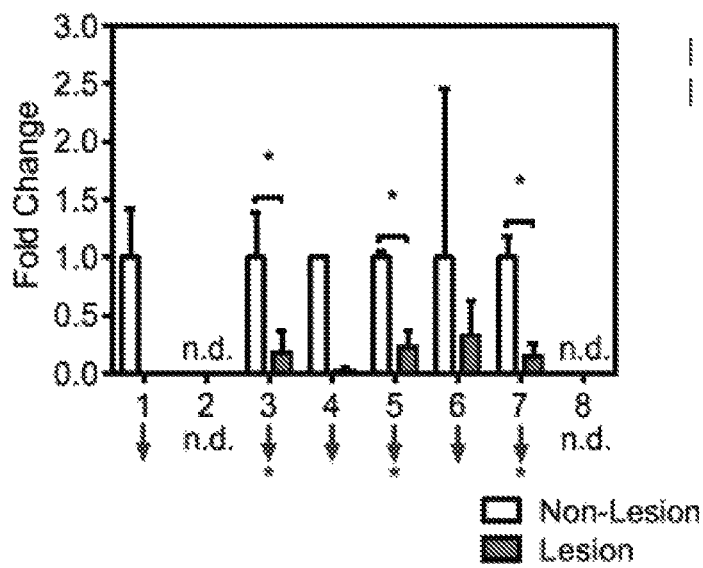
FIG. 2E is a graph showing the gene expression of ZC3HAV1 (zinc finger CCCH-Type Containing, Antiviral 1) at RNA level in human OA cartilage was assessed by RT-qPCR. The ZC3HAV1 level was significantly down-regulated in 3/8 (37.50%) specimens. n varies from 1 to 3 due to the size of human specimen. Statistics are calculated in samples with n≥3. *p≤0.05, relative to non-lesion (control) groups respectively.
Figure 2F:
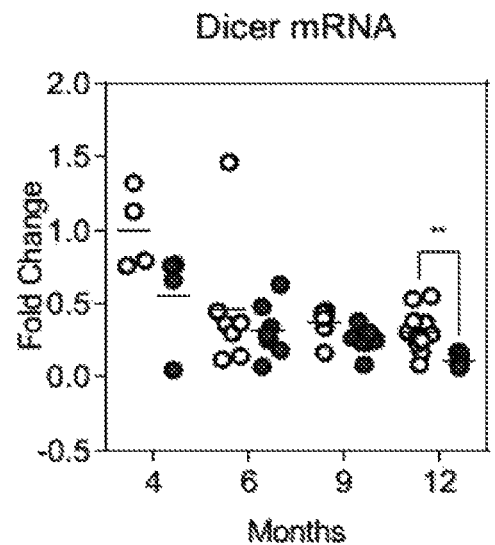
FIG. 2F is a bar graph showing the gene expression of Line-1 suppressor (Dicer) at RNA level in Cre only and miR-365 Tg mice cartilage at 2-, 6-, 9- and 12-month of age was assessed by RT-qPCR. n≥3. *p≤0.05, **p≤0.01 relative to age-matched control (Cre only) groups respectively.
Figure 2G:
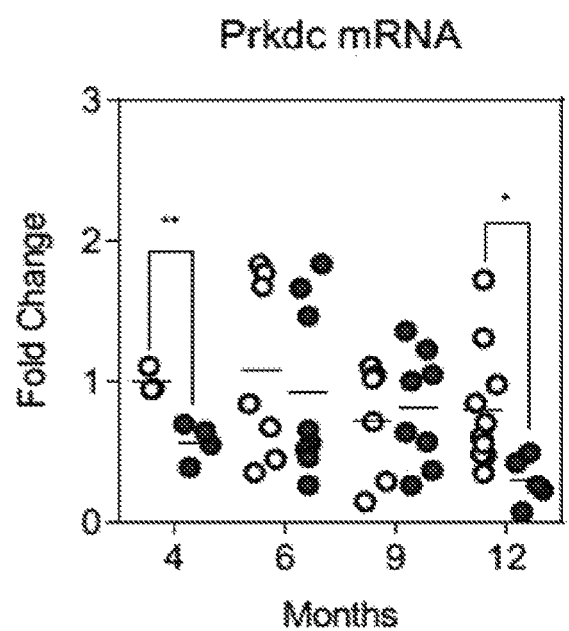
FIG. 2G is a bar graph showing the gene expression of Line-1 suppressor (Prkdc) at RNA level in Cre only and miR-365 Tg mice cartilage at 2-, 6-, 9- and 12-month of age was assessed by RT-qPCR. n≥3. *p≤0.05, **p≤0.01 relative to age-matched control (Cre only) groups respectively.
Figure 2H:
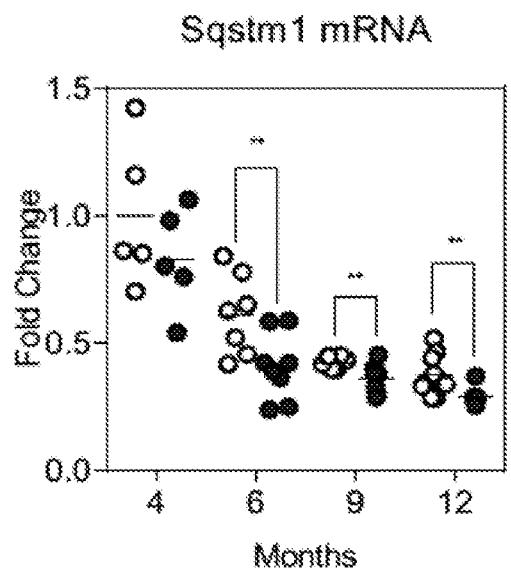
FIG. 2H is a bar graph showing the gene expression of Line-1 suppressor (SQSTM1) at RNA level in Cre only and miR-365 Tg mice cartilage at 2-, 6-, 9- and 12-month of age was assessed by RT-qPCR. n≥3. *p≤0.05, **p≤0.01 relative to age-matched control (Cre only) groups respectively.
Figure 2I:
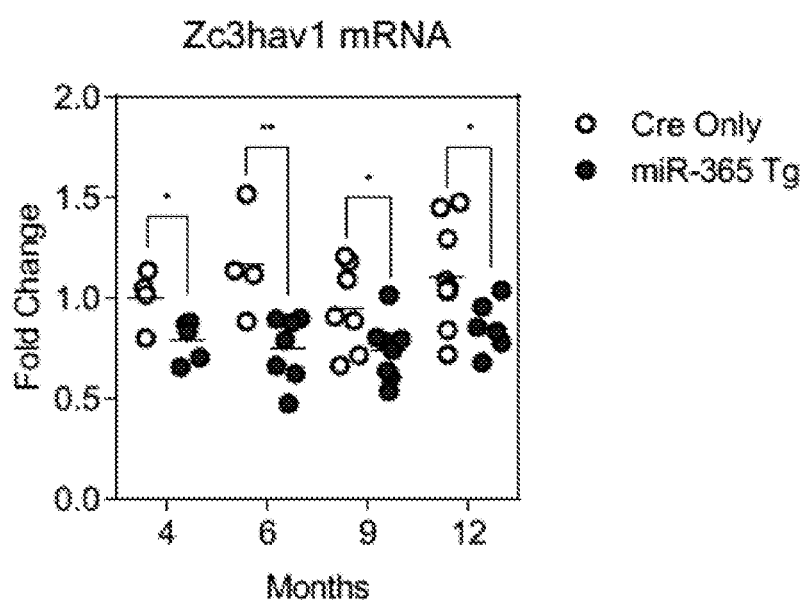
FIG. 2I is a bar graph showing the gene expression of Line-1 suppressor (Zc3hav1) at RNA level in Cre only and miR-365 Tg mice cartilage at 2-, 6-, 9- and 12-month of age was assessed by RT-qPCR. n≥3. *p≤0.05, **p≤0.01 relative to age-matched control (Cre only) groups respectively.

MiR365 could be induced by mechanical stress and inflammatory cytokines (Yang, X., et al. *Int J Mol Sci* 17, 436 (2016), and Guan, Y. J., et al. *FASEB journal* 25, 4457-4466 (2011)), however, it was not known how it could activate L1. It was hypothesized that miR-365 activated L1 by targeting L1 inhibitors in the host defense pathways in a post-transcription manner. Through bioinformatics analysis of 40 L1 inhibitors based on published literature (Goodier, J. L. *Mob DNA* 7, 16 (2016)), five L1 inhibitors were identified that harbored potential miR-365 binding sites in its 3' UTR of mRNA in both human and mouse (FIG. 8A). They are Prkdc of DNA repair (Morrish, T. A., et al. *Nature* 446, 208-212 (2007) and Morrish, T. A., et al. *Nature genetics* 31, 159-165 (2002)), Aicda of DNA editing (Metzner, M., et al. *PloS one* 7, e49358 (2012)), Dicer of RNA interference (Faulkner, G. J. *PLoS Genet* 9, e1003944 (2013)), Sqstm1 of autophagy (Guo, H., et al. *Nature communications* 5, 5276 (2014)), and Zc3hav1 of viral inhibition (Moldovan, J. B. et al. *PLoS Genet* 11, e1005121 (2015)) (FIG. 2A).

Figure 2J:
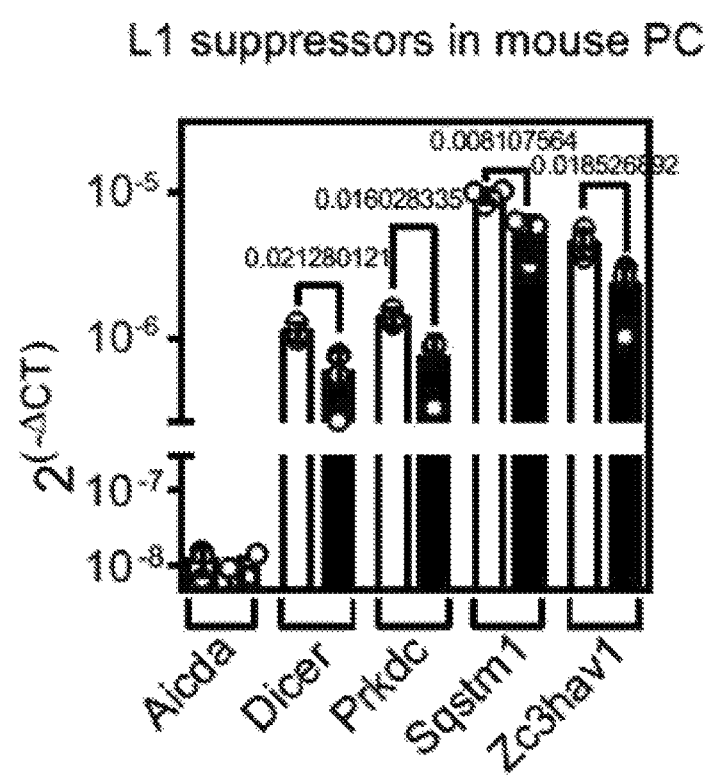
FIG. 2J is a bar graph showing the gene expression of Line-1 suppressors at RNA level in mouse primary chondrocytes transfected with miR-365 mimic assessed by RT-qPCR. Dicer, Prkdc, Sqstm1 and Zc3hav1 levels were significantly down-regulated in mouse primary chondrocytes which transiently over-express miR-365. n=3. *p≤0.05, relative to Mimic ctrl groups respectively.
Figure 2K:
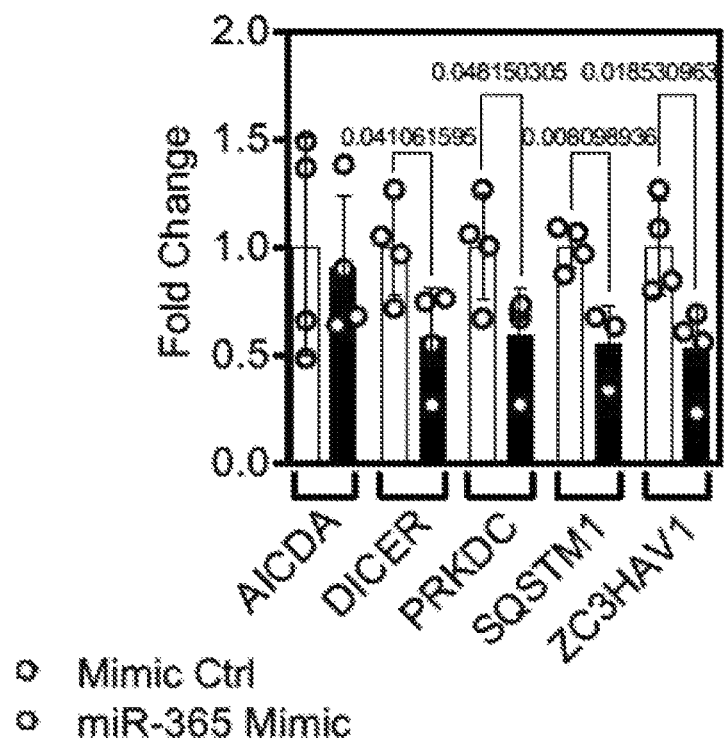
FIG. 2K is a graph showing the gene expression of Line-1 suppressors at RNA level in a human chondrocyte cell line-C28 transfected with miR-365 mimic was assessed by RT-qPCR. Dicer, Prkdc, Sqstm1 and Zc3hav1 levels were significantly down-regulated in mouse primary chondrocytes which transiently over-express miR-365. n≥3. *p≤0.05, relative to Mimic ctrl groups respectively.
Figure 2L:
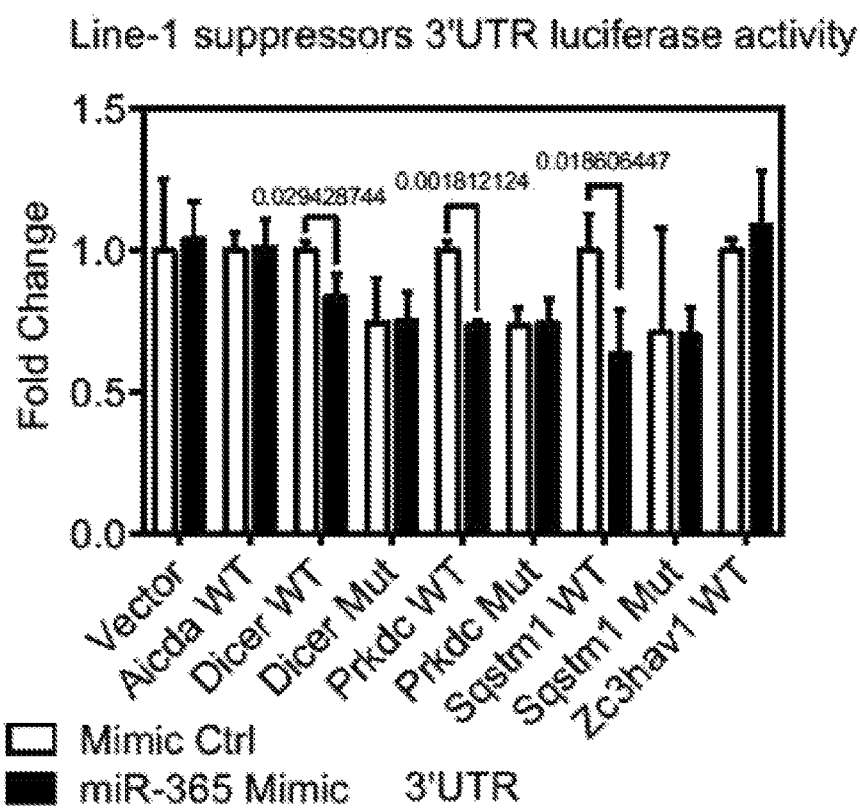
FIG. 2L is a graph showing the quantification of luciferase gene activity in ATDC5 cells co-transfected with miR-365 mimic as well as WT or mutated (Mut) 3'UTR response elements (REs) from Aicda, Dicer, Prkdc, Sqstm1 and Zc3hav1 was assessed by luciferase reporter assay. Luciferase activities were significantly down-regulated when WT REs in 3'UTR of Dicer1, Prkdc and Sqstm1 are down-stream of luciferase gene in ATDC5 cells which transiently over-express miR-365, while mutation of RE in Dicer1, Prkdc and Sqstm1 3'UTR completely abolished luciferase activity suppression in ATDC5 cells which transiently over-express miR-365. n≥3. *p≤0.05, relative to appropriate control groups respectively.
Figure 2M:
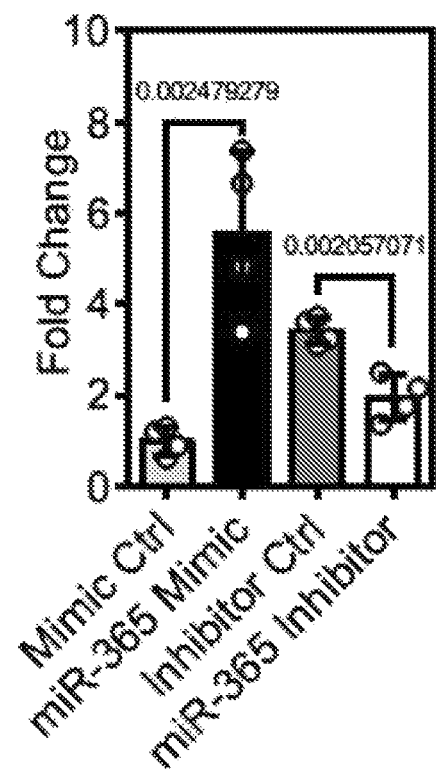
FIG. 2M is a graph showing the gene expression of Line-1-ORF2 at RNA level assessed by RT-qPCR in mouse primary chondrocytes which transiently over-expressed miR-365 mimic or miR-365 inhibitor. Line-1-ORF2 expression was significantly up-regulated in mouse primary chondrocytes which transiently over-expressed miR-365 while inhibitor of miR-365 significantly down-regulated Line-1-ORF2 expression.
Figure 2N:
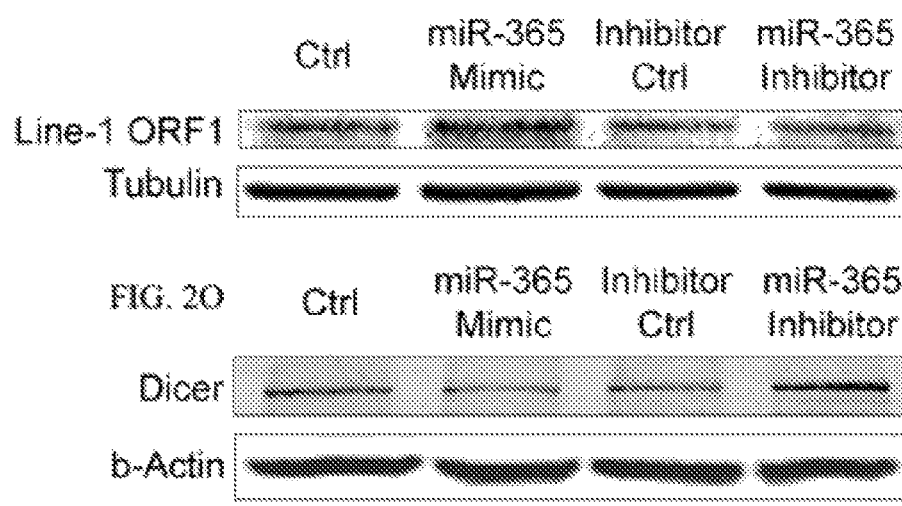
FIG. 2N is an image of an immunoblot showing the protein expression of Line-1-ORF1 assessed by western blots analysis in human chondrocyte cell line-C28 which transiently over-expressed miR-365 mimic or miR-365 inhibitor. Line-1-ORF1 expression was significantly up-regulated in C28 which transiently over-expressed miR-365 while inhibitor of miR-365 did not alter Line-1-ORF1 protein expression. This is a representative blot form a total of 3 repeated experiments. This is a representative blot form a total of 2 repeated experiments.
Figure 2O:
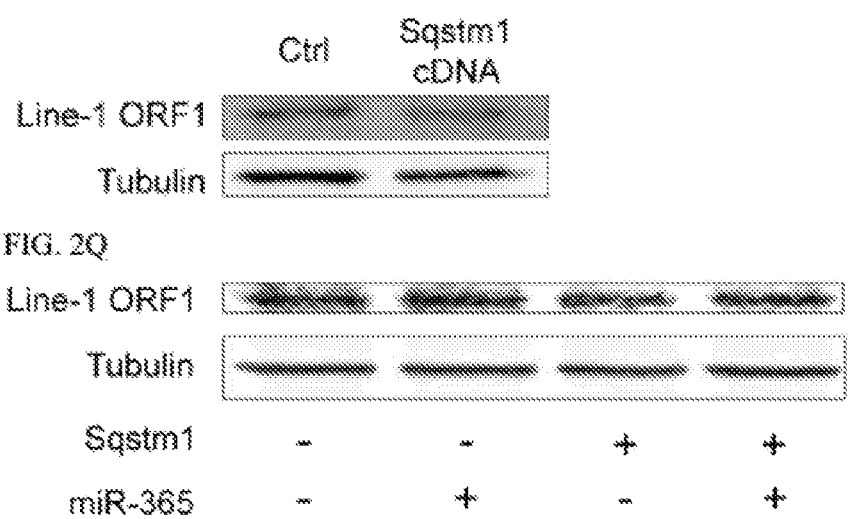
Figures 8B, 8C:
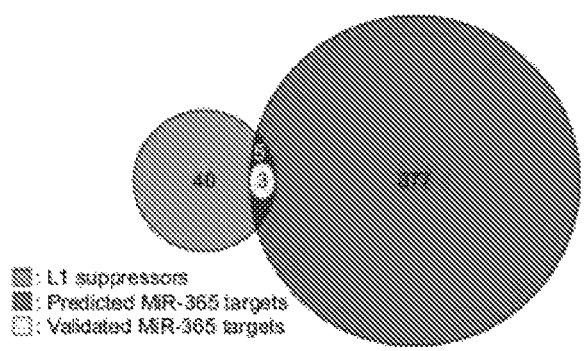

These targets were further screened in three ways (FIG. 8B). First, their expression in human and mouse OA cartilage was quantified. The mRNA of DICER, PRKDC, SQSTM1, and ZC3HAV1 were uniformly down-regulated in human OA cartilage lesions (FIG. 2B-2E), while Dicer, Prkdc, Sqstm1 and Zc3hav1 were down-regulated in miR-365 Tg mouse cartilage (FIG. 2F-2I). However, AICDA was not detected in human cartilage and expressed at very low levels in mouse chondrocytes (FIG. 2J). Thus, multiple L1 inhibitors including DICER, PRKDC, SQSTM1, and ZC3HAV1 in the host defense pathway were suppressed in OA cartilage. Second, miR-365 was transfected in both mouse and human chondrocytes. MiR-365 inhibited mRNAs of DICER, PRKDC, SQSTM1, and ZC3HAV1 in both mouse and human cells, while it did not inhibit AICDA mRNA in either species (FIGS. 2J and 2K). Thus, miR-365 induction was sufficient to suppress multiple L1 inhibitors including DICER, PRKDC, SQSTM1, and ZC3HAV1 simultaneously. Third, luciferase reporter constructs were made harboring putative miR-365 binding site in the 3'UTR of these five mRNA. Transfection of miR-365 inhibited the 3'UTR reporter activity of Dicer, Prkdc, and Sqstm1, but not that of Aicda and Zc3hav1 (FIG. 2L). Mutation of the miR-365 binding site in the 3'UTR region of Dicer, Prkdc, and Sqstm1 abolished the miR-365 inhibition of the reporter activity (FIG. 2L). Thus, miR-365 inhibited multiple L1 inhibitors including DICER, PRKDC, SQSTM1 through a post-transcriptional mechanism. Based on these data, it was concluded that 1) among L1 inhibitors, DICER, PRKDC, SQSTM1, and ZC3HAV1 were targets of miR-365; and 2) miR-365 inhibits DICER, PRKDC, SQSTM1 through its binding site in the 3'UTR of mRNAs.

miR-365 activated L1 through inhibiting Dicer and Sqstm1. While transfection of miR-365 mimic stimulated L1 at both RNA and protein levels (FIGS. 2M and 2N), it inhibited Dicer protein (FIG. 2O). Conversely, transfection of miR-365 inhibitor repressed L1 (FIGS. 2M and 2N), but increased Dicer protein levels (FIG. 2O). Thus, miR-365 regulated L1 and Dicer protein levels.

Example 3: Repressing L1 Inhibits Early Onset of OA

L1 can be repressed by nucleoside reverse transcriptase inhibitors (NRTIs) (Dai, L., Huang, Q. & Boeke, J. D. *BMC Biochem* 12, 18 (2011), Patnala, R., et al. *Breast Cancer Res Treat* 143, 239-253 (2014), and Jones, R. B., et al. *PLoS One* 3, e1547 (2008)). To determine whether repressing L1 by NRTI is sufficient to inhibit OA gene expression, chondrocytes were treated with Lamivudine (3TC) in a series of concentrations (FIG. 3A-3AC). 3TC inhibited L1 expression at both RNA and protein levels in mouse (FIGS. 3A and 3H) and human (FIG. 3I) chondrocytes. Repressing L1 with 3TC inhibited expression of OA markers including COL10A1, ADAMTS5, and MMP13 and stimulated anabolic markers including ACAN and COL2A1 in mouse (FIG. 3B-3G) and human (FIG. 3J-3N) chondrocytes. To determine whether 3TC could abolish the effect of miR-365 on chondrocytes, miR-365 was treated with transfected human chondrocytes with 3TC. Transfection of miR-365 significantly increased L1 as well as OA markers ADAMTS5, IHH, and COL10A1, and decreased ACAN levels (FIG. 3O-3T). 3TC treatment abolished and in some cases even reversed the effect of miR-365 (FIG. 3O-3T). Thus, 3TC treatment was sufficient to suppress OA gene expression in vitro.

The gene expression of Prkdc at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

Also, the gene expression of Dicer at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

The gene expression of Sqstm1 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

The gene expression of Zc3hav1 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.

Figure 3A:
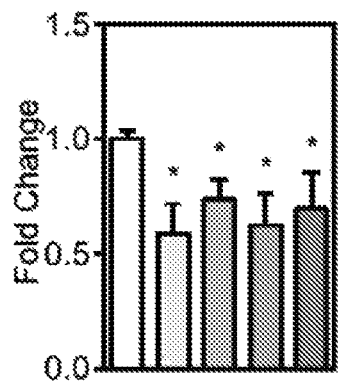
FIG. 3A-3AC are a series of images depicting that 3TC suppressed Line-1 gene expression and prevented primary OA development in mice.
Figure 3B:
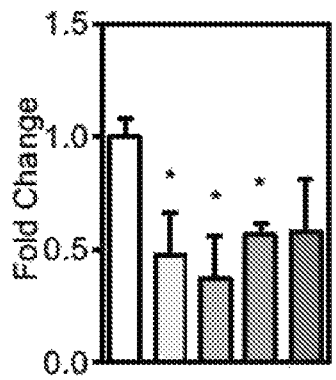
FIG. 3B is a bar graph showing the gene expression of Ifn-α at RNA level in mouse primary chondrocytes treated with 3TC at various dosages. n=3 for all groups; *: p-value≤0.05, relative to control (saline) groups respectively.
Figure 3C:
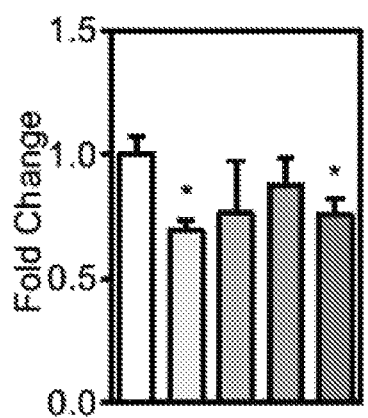
FIG. 3C is a bar graph showing the gene expression of Adamts5 at RNA level in mouse primary chondrocytes treated with 3TC at various dosages. n=3 for all groups; *: p-value≤0.05, relative to control (saline) groups respectively.
Figure 3D:
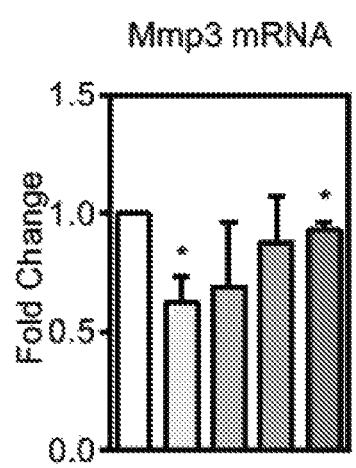
FIG. 3D is a bar graph showing the gene expression of Mmp3 at RNA level in mouse primary chondrocytes treated with 3TC at various dosages. n=3 for all groups; *: p-value≤0.05, relative to control (saline) groups respectively.
Figure 3E:
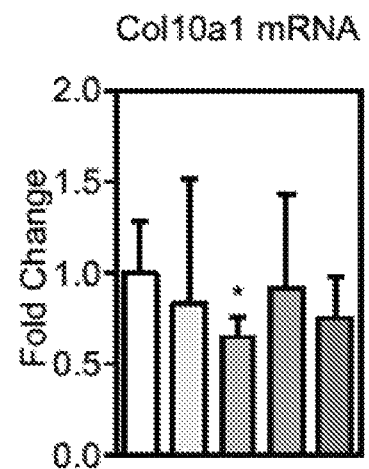
FIG. 3E is a bar graph showing the gene expression of Col10a1 at RNA level in mouse primary chondrocytes treated with 3TC at various dosages. n=3 for all groups; *: p-value≤0.05, relative to control (saline) groups respectively.
Figure 3F:
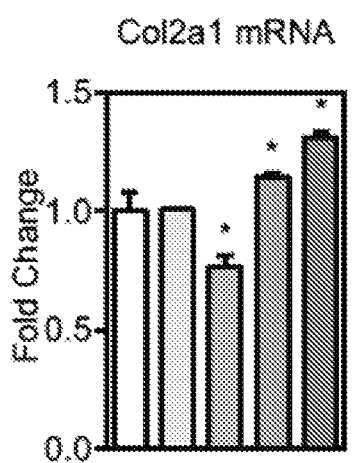
FIG. 3F is a bar graph showing the gene expression of Col2a1 at RNA level in mouse primary chondrocytes treated with 3TC at various dosages. n=3 for all groups; *: p-value≤0.05, relative to control (saline) groups respectively.
Figure 3G:
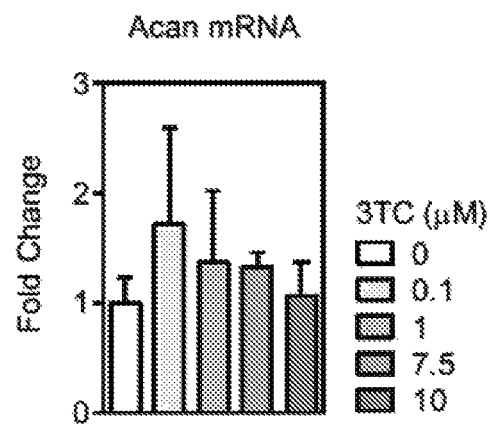
FIG. 3G is a bar graph showing the gene expression of Acan at RNA level in mouse primary chondrocytes treated with 3TC at various dosages. n=3 for all groups; *: p-value≤0.05, relative to control (saline) groups respectively.
Figure 3H:
FIG. 3H is an image of an immunoblot showing the protein expression of Line-1-ORF1 assessed by western blot analysis in C28 treated with 3TC. This is a representative blot from a total of 3 repeated experiments.
Figure 3I:
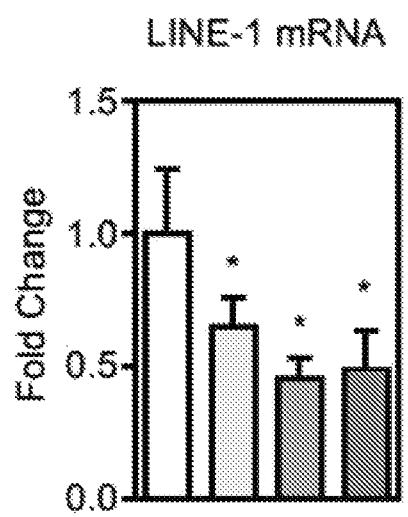
FIG. 3I is a bar graph showing the gene expression of LINE-1 at RNA level in C28 treated with 3TC at various dosages. n=3 for all groups; *: p-value≤0.05, relative to control (saline) groups respectively.
Figure 3J:
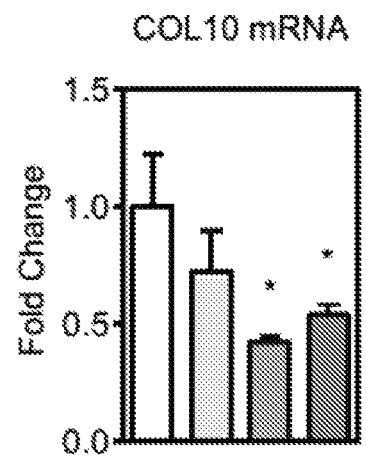
FIG. 3J is a bar graph showing the gene expression of IHH at RNA level in C28 treated with 3TC at various dosages. n=3 for all groups; *: p-value≤0.05, relative to control (saline) groups respectively.
Figure 3K:
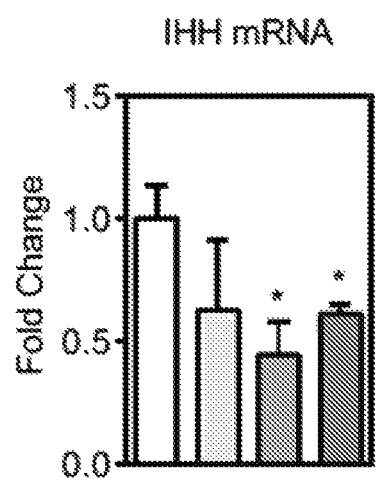
FIG. 3K is a bar graph showing the gene expression of COL10A1 at RNA level in C28 treated with 3TC at various dosages. n=3 for all groups; *: p-value≤0.05, relative to control (saline) groups respectively.
Figure 3L:
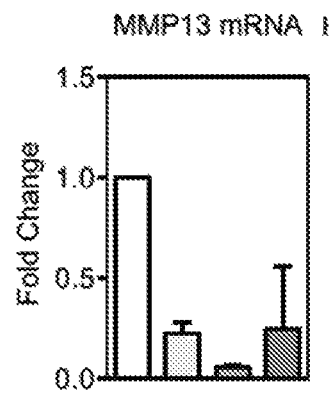
FIG. 3L is a bar graph showing the gene expression of MMP13 at RNA level in C28 treated with 3TC at various dosages. n=3 for all groups; *: p-value≤0.05, relative to control (saline) groups respectively.
Figure 3M:
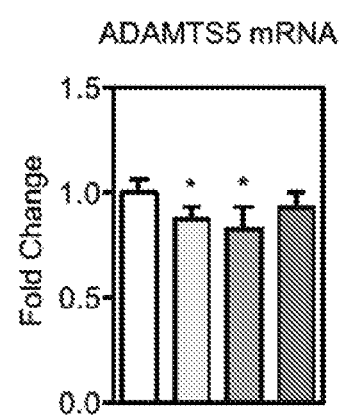
FIG. 3M is a bar graph showing the gene expression of ADAMTS5 at RNA level in C28 treated with 3TC at various dosages. n=3 for all groups; *: p-value≤0.05, relative to control (saline) groups respectively.
Figure 3N:
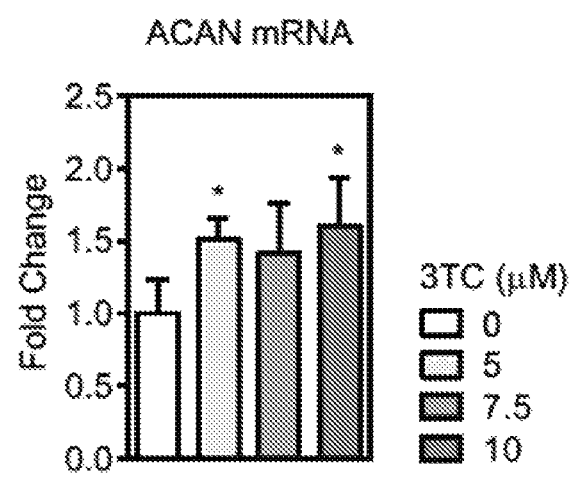
FIG. 3N is a bar graph showing the gene expression of ACAN at RNA level in C28 treated with 3TC at various dosages. n=3 for all groups; *: p-value≤0.05, relative to control (saline) groups respectively.
Figure 3Q:
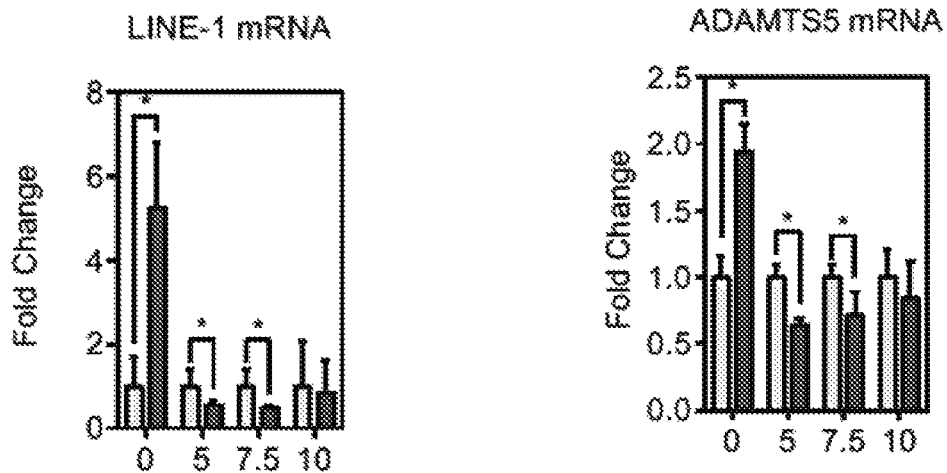
FIG. 3Q is a bar graph showing the gene expression of COL10A1 at RNA level in C28 transiently over-express miR-365 with 3TC treated at various dosages. n=3 for all groups; *: p-value≤0.05, relative to control (Mimic Ctrl) groups respectively.
Figure 3Q:
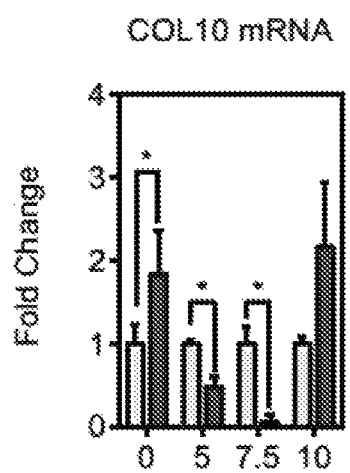
Figure 3R:
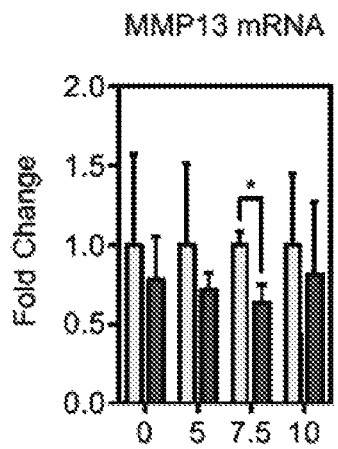
FIG. 3R is a bar graph showing the gene expression of MMP13 at RNA level in C28 transiently over-express miR-365 with 3TC treated at various dosages. n=3 for all groups; *: p-value≤0.05, relative to control (Mimic Ctrl) groups respectively.
Figure 3S:
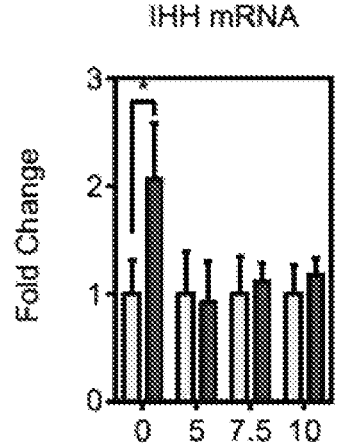
FIG. 3S is a bar graph showing the gene expression of IHH at RNA level in C28 transiently over-express miR-365 with 3TC treated at various dosages. n=3 for all groups; *: p-value≤0.05, relative to control (Mimic Ctrl) groups respectively.
Figure 3T:
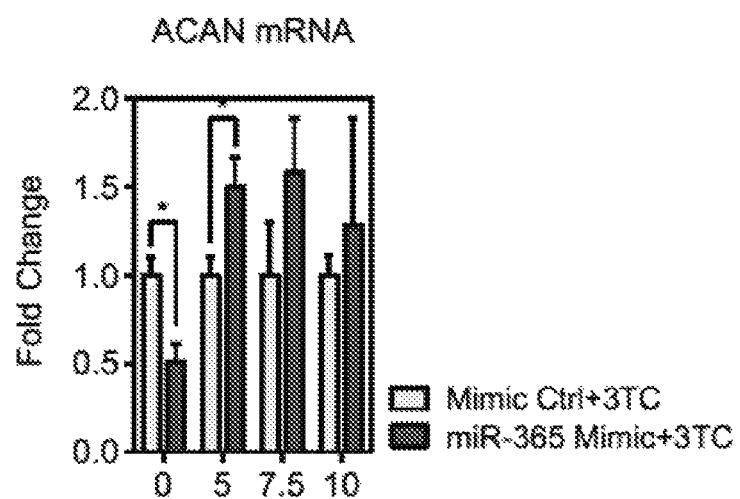
FIG. 3T is a bar graph showing the gene expression of ACAN at RNA level in C28 transiently over-express miR- 365 with 3TC treated at various dosages. n=3 for all groups; *: p-value≤0.05, relative to control (Mimic Ctrl) groups respectively.
Figure 3U:
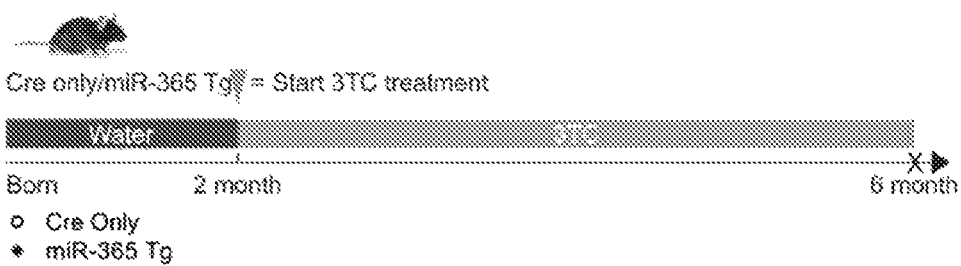
FIG. 3U is a schematic representation of animal procedures: age-matched miR-365 Tg and control mice (Cre Only) were treated with 3TC diluted water from 2-month-old for 4 months and were sacrificed at 6-month-old.
Figure 3V:
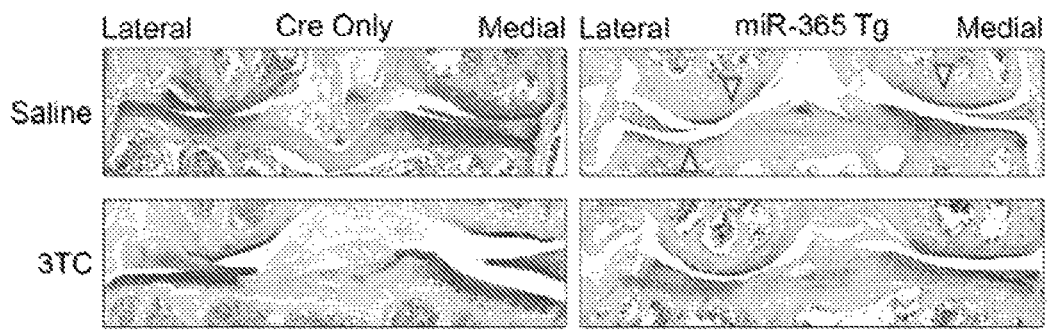
FIG. 3V are a series of Safranin O staining images of mouse knees harvested from 6-month-old miR-365 Tg and Cre only mice with 3TC or saline treatments respectively. 3TC treatment prevented early onset of OA in miR-365 Tg mice
Figure 3W:
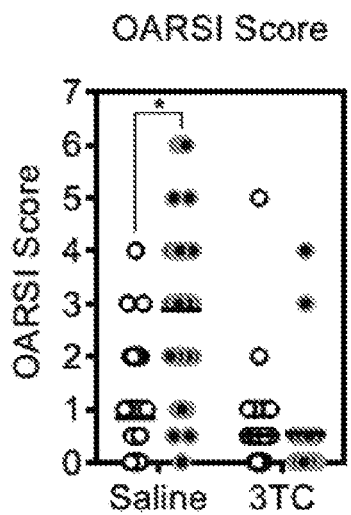
FIG. 3W is a graph of OARSI quantification of mouse knees harvested from 6-month-old miR-365 Tg and Cre only mice with 3TC or saline treatments respectively. 3TC treatment prevented early onset of OA in miR-365 Tg mice.
Figure 3X:
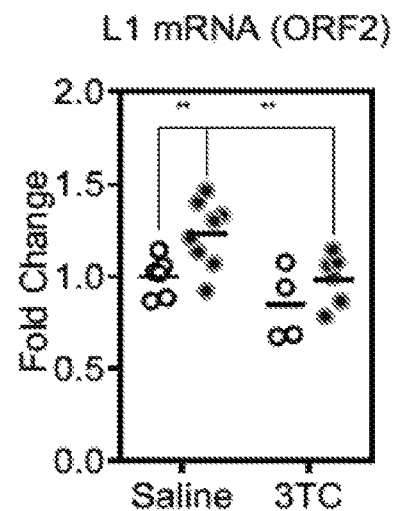
FIG. 3X is a graph showing the gene expression of Line-1-ORF2 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.
Figure 3Y:
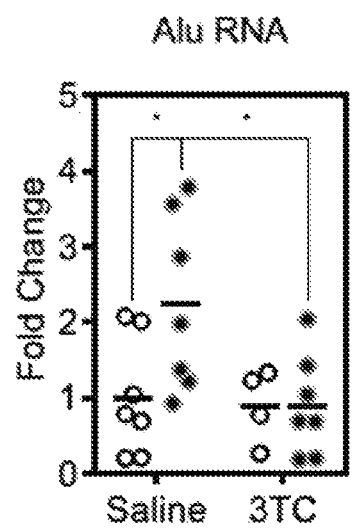
FIG. 3Y is a graph showing the gene expression of Alu at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.
Figure 3Z:
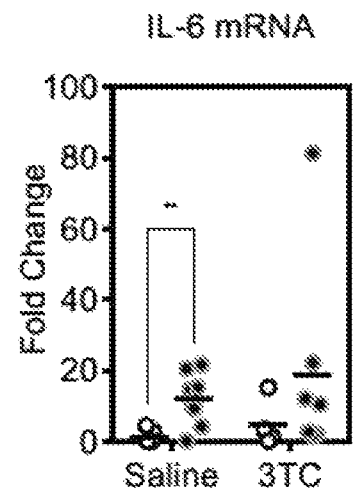
FIG. 3Z is a graph showing the gene expression of IL-6 at RNA level in mouse articular cartilage treated with 3TC for 4 months was assessed by RT-qPCR. Line-1-ORF2, Alu, IL-6, Col10a1, Adamts5 and miR-365 expression was significantly suppressed in miR-365 Tg mice treated with 3TC comparing with elevated Line-1 expression in Saline treated miR-365 Tg mice. 3TC treatment significantly up-regulated Sqstm1 and Zac3hav1 expression in miR-365 Tg mice. Student t-test and one-way ANOVA test (x-ac) were used for statistics. n≥4. *p≤0.05, **p≤0.01 relative to appropriate control groups respectively.
Figure 3A:
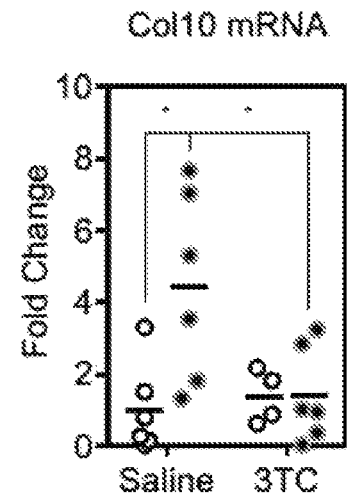
Figure 3A:
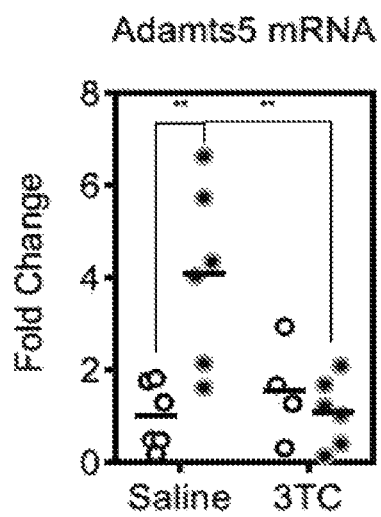
Figure 3A:
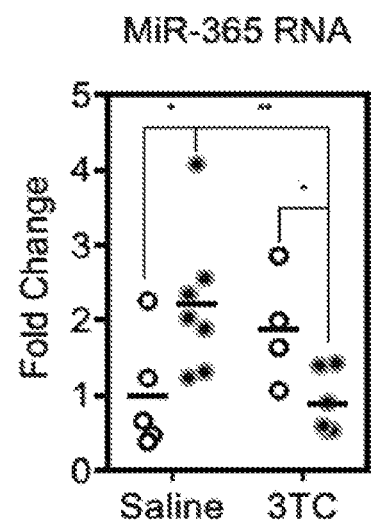

To determine whether 3TC was sufficient to suppress OA pathogenesis in vivo, miR-365 Tg mice were treated with oral administration of 3TC for four months starting from 2-months old (FIG. 3U). While saline-treated miR-365 Tg mice had elevated L1 levels (FIG. 3X) and developed early onset of OA at 6 months old (FIGS. 3V and 3W), 3TC treatment abolished L1 elevation (FIG. 3X) and OA pathogenesis (FIGS. 3V and 3W). 3TC treatment inhibited the expression of OA markers Col10a1 and Adamts5 (FIGS. 3AA and 3AB) and SASP IL-6 (FIG. 3Z). 3TC treatment also abolished the elevation of miR-365 levels in OA cartilage (FIG. 3AC), suggesting NRTI treatment inhibited OA pathogenesis by breaking the vicious cycle of miR-365-induced L1 that results in OA pathogenesis, which in turn stimulates miR-365 in cartilage (FIG. 11).

Figure 8D:
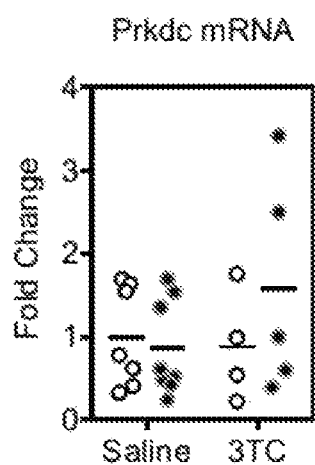
Figure 8E:
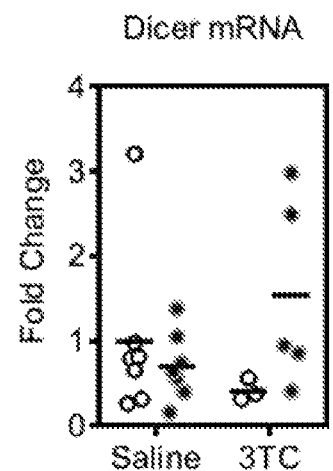
Figure 8F:
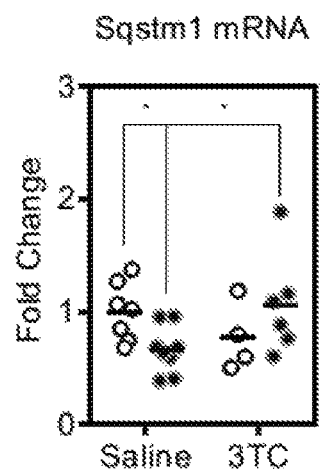
Figure 8G:
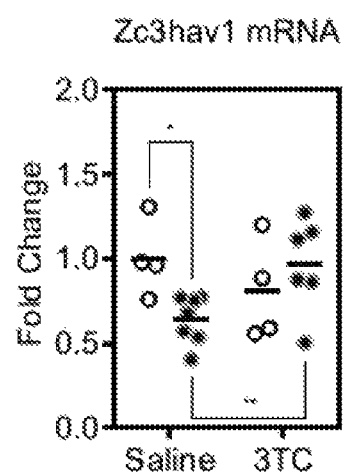
Figure 9A:
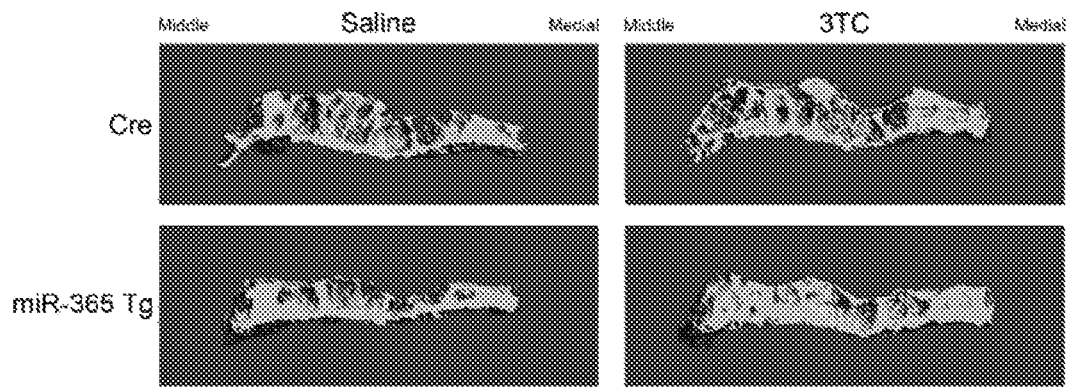
Figure 9B:
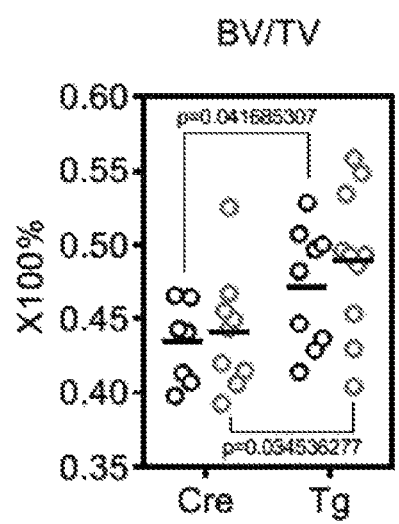
Figure 9E:
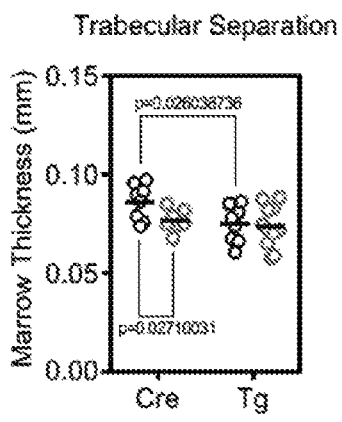
Figure 9F:
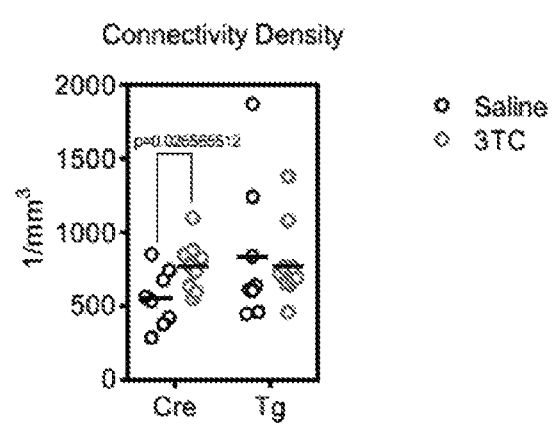

To determine whether 3TC treatment abolished the miR-365 inhibition of L1 inhibitors, the mRNA levels of Dicer, Prkdc, Sqstm1, and Zc3hav1 were quantified in miR-365 Tg mice after 3TC treatment for four months. While the expression levels of these inhibitors were inhibited in the 6-months old miR-365 Tg mice (FIG. 2F-2I), such inhibition was abolished by 3TC treatment (FIG. 8D). Thus, 3TC stimulated multiple host defense molecules against L1 by overcoming the effect of miR-365 (FIG. 11).

NRTIs may decrease bone mineral density (BMD) in human HIV patients (Hoy, J. F., et al. *J Bone Miner Res* 32, 1945-1955 (2017)). OA pathogenesis can be associated with increased BMD in subchondral bone (Hochberg, M. C., *Osteoarthritis and cartilage/OARS, Osteoarthritis Research Society* 12 Suppl A, S45-48 (2004) and Hardcastle, S. A., et al., *Bonekey Rep* 4, 624 (2015)). To determine whether 3TC affected BMD in miR-365 Tg mice, microCT was performed to quantify subchondral bone properties. Although tibial subchondral BV/TV was increased in miR-365 Tg mice (FIG. 9B), 3TC treatment did not alter BV/TV significantly in either Cre control mice or miR-365 Tg mice (FIG. 9B). 3TC treatment increased trabecular number (FIG. 9C) and connectivity density (FIG. 9F) and decreased trabecular separation (FIG. 9E) in the Cre mice, but had no effect on miR-365 Tg mice (FIG. 9B-9C and FIG. 9E-9F). Thus, 3TC inhibited cartilage degeneration without decreasing subchondral BMD in miR-365 Tg mice.

Example 4: NRTIs Inhibit OA Pathogenesis in Mice

Figures 4A, 4B:
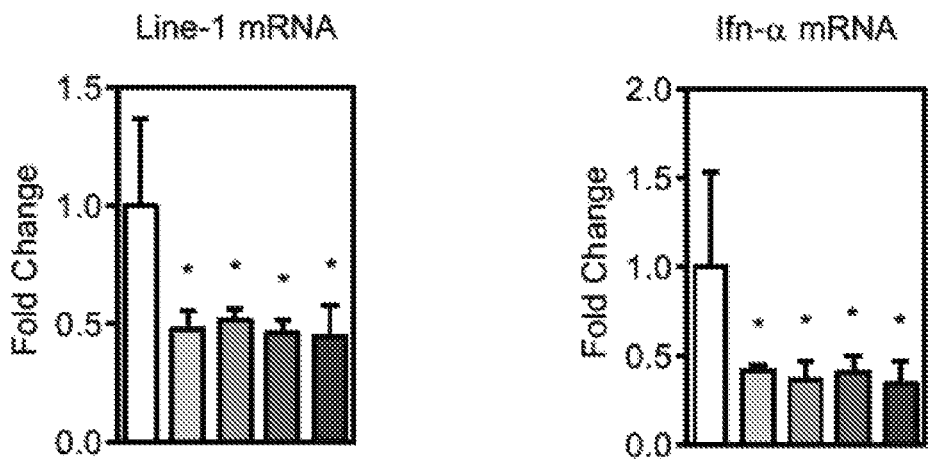
FIG. 4A-4W are a series of images depicting that 3TC and FTC prevented DMM induced OA.
FIG. 4B is a graph showing the gene expression of Ifn-α at RNA level in mouse PC treated with FTC at various dosages was assessed by RT-qPCR. n=3 for all groups; *: p-value≤0.05, relative to control (saline) groups respectively.
Figure 4C:
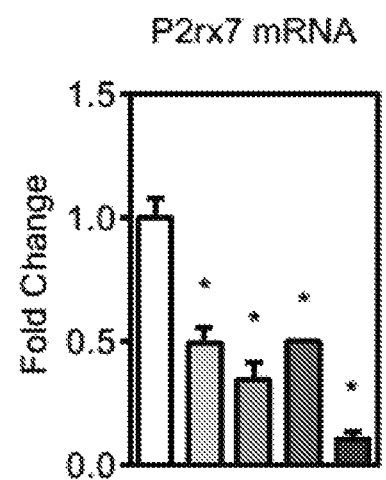
FIG. 4C is a graph showing the gene expression of P2rx7 at RNA level in mouse PC treated with FTC at various dosages was assessed by RT-qPCR. n=3 for all groups; *: p-value≤0.05, relative to control (saline) groups respectively.
Figure 4D:
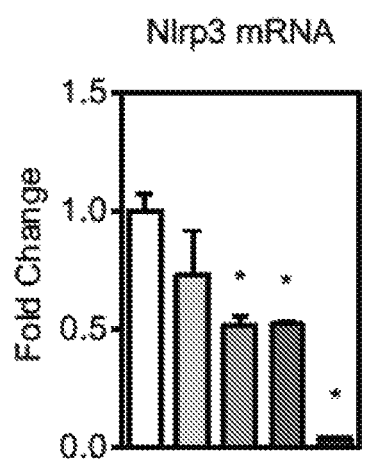
FIG. 4D is a graph showing the gene expression of Nlrp3 at RNA level in mouse PC treated with FTC at various dosages was assessed by RT-qPCR. n=3 for all groups; *: p-value≤0.05, relative to control (saline) groups respectively.
Figure 4E:
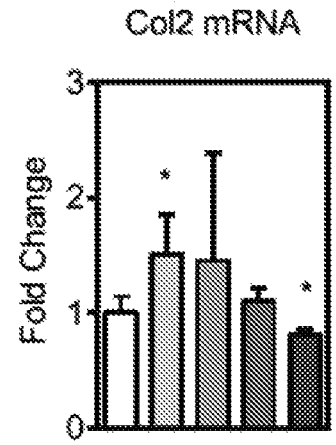
FIG. 4E is a graph showing the gene expression of Col2a1 at RNA level in mouse PC treated with FTC at various dosages was assessed by RT-qPCR. n=3 for all groups; *: p-value≤0.05, relative to control (saline) groups respectively.
Figure 4F:
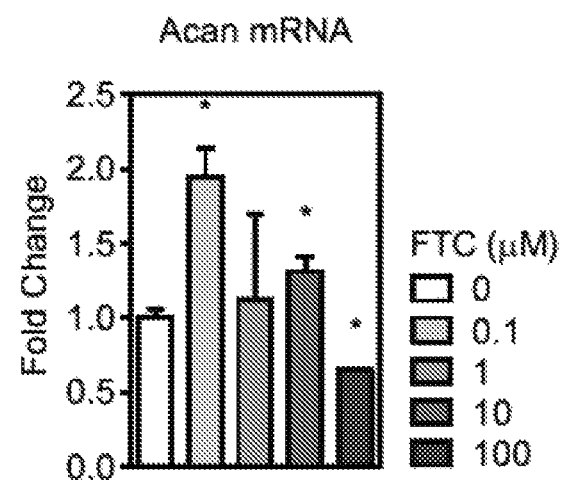
FIG. 4F is a graph showing the gene expression of Acan at RNA level in mouse PC treated with FTC at various dosages was assessed by RT-qPCR. n=3 for all groups; *: p-value≤0.05, relative to control (saline) groups respectively.
Figure 4G:
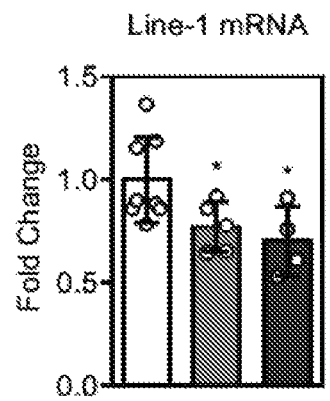
FIG. 4G is a graph showing the gene expression of Line-1 at RNA level in mouse femurs treated with 3TC or FTC for 48 hrs was assessed by RT-qPCR. n≥3 for all groups; *: p-value≤0.05, relative to control (saline) groups respectively.
Figure 4H:
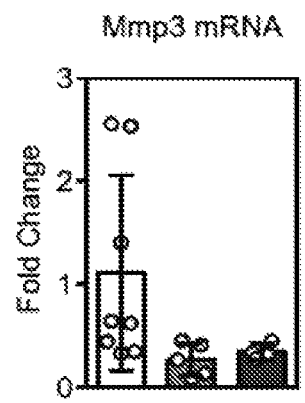
FIG. 4H is a graph showing the gene expression of Mmp3 at RNA level in mouse femurs treated with 3TC or FTC for 48 hrs was assessed by RT-qPCR. n≥3 for all groups; *: p-value≤0.05, relative to control (saline) groups respectively.
Figure 4I:
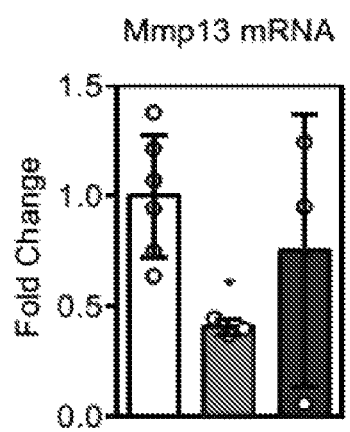
FIG. 4I is a graph showing the gene expression of Mmp13 at RNA level in mouse femurs treated with 3TC or FTC for 48 hrs was assessed by RT-qPCR. n≥3 for all groups; *: p-value≤0.05, relative to control (saline) groups respectively.
Figure 4J:
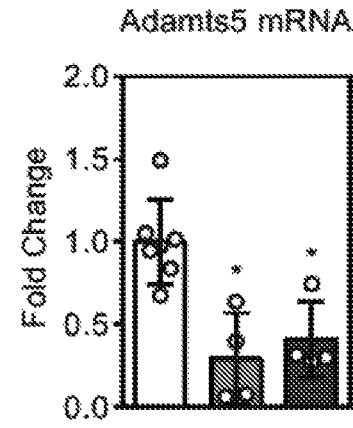
FIG. 4J is a graph showing the gene expression of Adamts5 at RNA level in mouse femurs treated with 3TC or FTC for 48 hrs was assessed by RT-qPCR. n≥3 for all groups; *: p-value≤0.05, relative to control (saline) groups respectively.
Figure 4K:
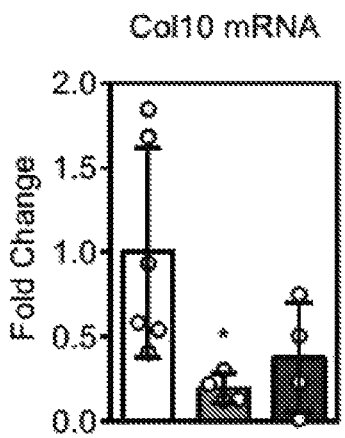
FIG. 4K is a graph showing the gene expression of Col10a1 at RNA level in mouse femurs treated with 3TC or FTC for 48 hrs was assessed by RT-qPCR. n≥3 for all groups; *: p-value≤0.05, relative to control (saline) groups respectively.
Figure 4L:
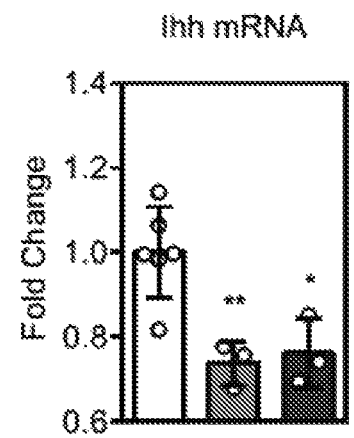
FIG. 4L is a graph showing the gene expression of Col2a1 at RNA level in mouse femurs treated with 3TC or FTC for 48 hrs was assessed by RT-qPCR. n≥3 for all groups; *: p-value≤0.05, relative to control (saline) groups respectively.
Figure 4M:
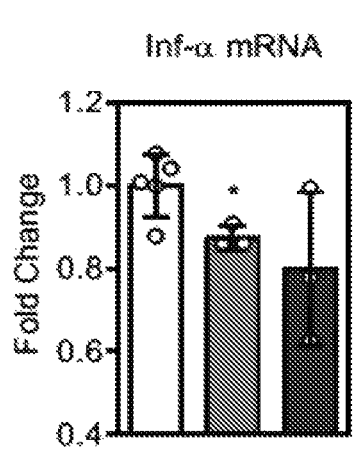
FIG. 4M is a graph showing the gene expression of Acan at RNA level in mouse femurs treated with 3TC or FTC for 48 hrs was assessed by RT-qPCR. n≥3 for all groups; *: p-value≤0.05, relative to control (saline) groups respectively.
Figure 4N:
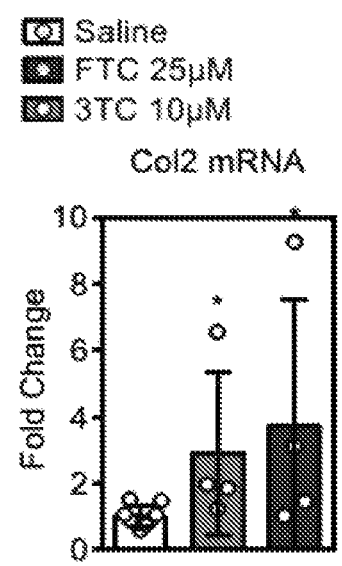
FIG. 4N is a graph showing the gene expression of Ihh at RNA level in mouse femurs treated with 3TC or FTC for 48 hrs was assessed by RT-qPCR. n≥3 for all groups; *: p-value≤0.05, relative to control (saline) groups respectively.
Figure 4O:
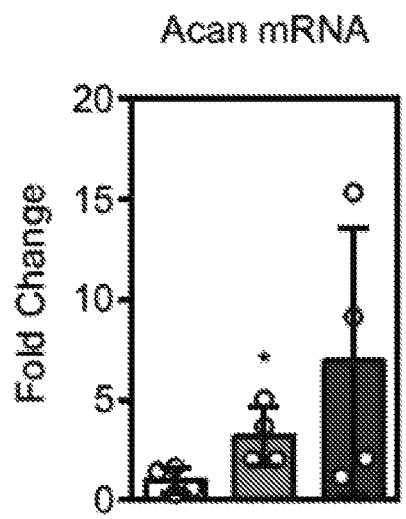
FIG. 4O is a graph showing the gene expression of Ifn-α at RNA level in mouse femurs treated with 3TC or FTC for 48 hrs was assessed by RT-qPCR. n≥3 for all groups; *: p-value≤0.05, relative to control (saline) groups respectively.

To determine whether other NRTIs also inhibited OA gene expression, mouse chondrocytes were treated with Emtricitabine (FTC) in a series of concentrations (FIG. 4A-4F). FTC treatment significantly inhibited L1 levels (FIG. 4A) and the expression of inflammasome Nlrp3, P2rx7 and Ifn-α mRNA (FIG. 4B-4D). FTC treatment at lower than 100 µM concentrations also increased anabolic ECM Col2a1 and Acan levels in chondrocytes (FIGS. 4E and 4F). To compare the effect of different NRTIs, tibia cartilage was treated with either 10 µM 3TC or 25 µM FTC in bone organ culture (FIG. 4G-4O). 3TC or FTC treatment significantly inhibited L1 levels (FIG. 4G), OA markers Adamts5, Col10a1, Ihh, and Mmp13, and SASP Mmp3 and Ifn-α mRNA levels (FIG. 4H-4M). 3TC or FTC treatment also increased Col 2a1 and Acan mRNA levels (FIGS. 4N and 4O). Thus, NRTIs inhibited OA gene expression and promoted anabolic gene expression in cartilage.

Figure 4P:
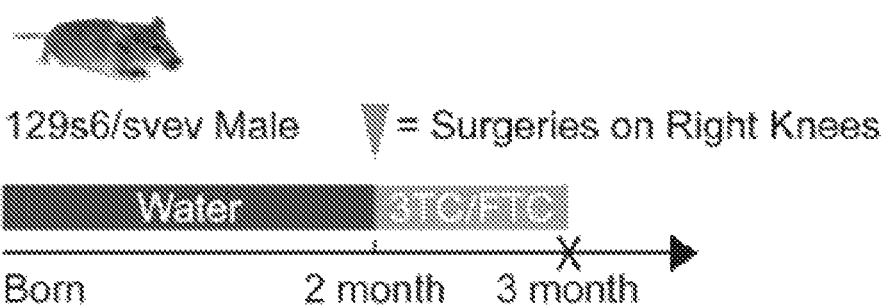
FIG. 4P is a schematic representation of animal procedures: 129S6/SvEv mice which underwent DMM or Sham surgeries were treated with Saline or 3TC or FTC diluted in water from 2-month-old for 1 month and were sacrificed at 3-month-old.
Figure 4Q:
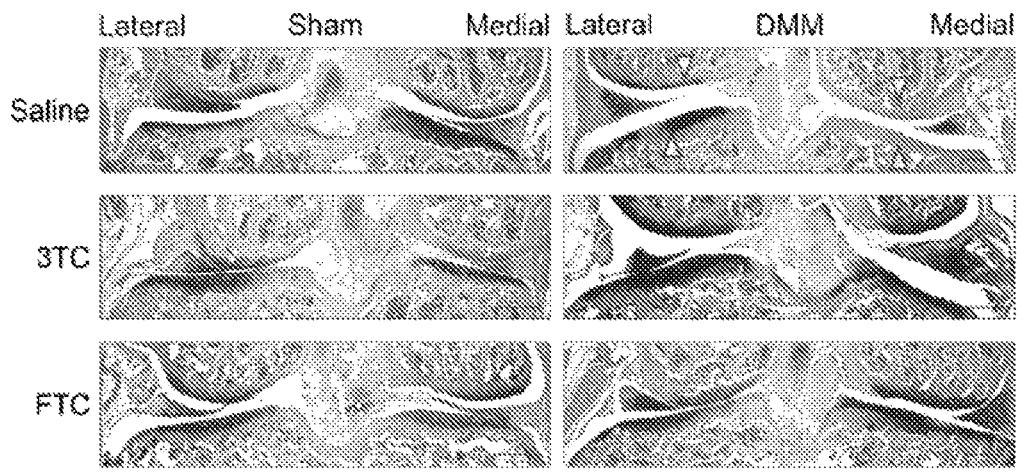
FIG. 4Q are a series of Safranin O staining images of mouse knees harvested from 3-month-old 129S6/SvEv mice which underwent DMM or Sham surgeries and subsequent treatment with Saline or 3TC or FTC diluted water from 2-month-old for 1 month. 3TC and FTC treatments significantly prevented DMM induced OA in 129S6/SvEv mice.
Figure 4R:
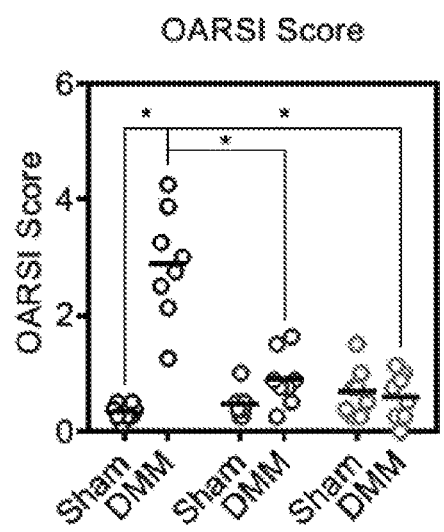
FIG. 4R is a graph showing OARSI quantification of mouse knees harvested from 3-month-old 129S6/SvEv mice which underwent DMM or Sham surgeries and subsequent treatment with Saline or 3TC or FTC diluted water from 2-month-old for 1 month. 3TC and FTC treatments significantly prevented DMM induced OA in 129S6/SvEv mice.
Figure 4S:
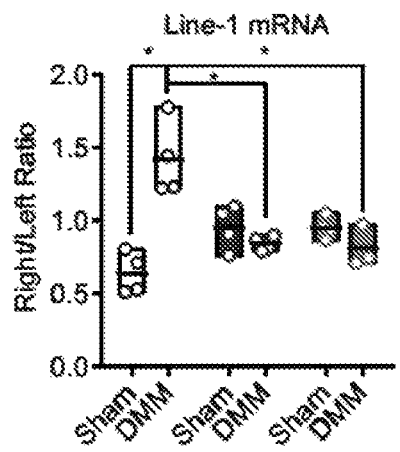
FIG. 4S is a graph showing the gene expression of Line-1 mRNA at RNA level in 129S6/SvEv mice which underwent DMM or Sham surgeries and subsequent treatment of Saline or FTC or 3TC respectively. Student t-test and one-way ANOVA test (s-w) were used for statistics. There were 6 mice in each group. *p≤0.05, relative to appropriate control groups respectively.
Figure 4T:
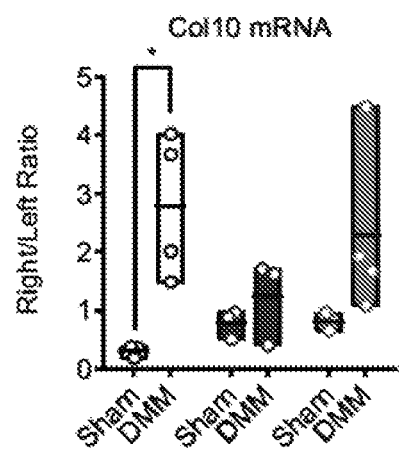
FIG. 4T is a graph showing the gene expression of Col10a1 at RNA level in 129S6/SvEv mice which underwent DMM or Sham surgeries and subsequent treatment of Saline or FTC or 3TC respectively. Student t-test and one-way ANOVA test (s-w) were used for statistics. There were 6 mice in each group. *p≤0.05, relative to appropriate control groups respectively.
Figure 4U:
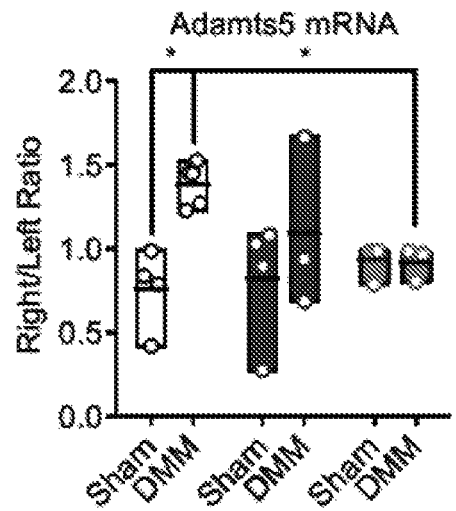
FIG. 4U is a graph showing the gene expression of Adamts5 mRNA at RNA level in 129S6/SvEv mice which underwent DMM or Sham surgeries and subsequent treatment of Saline or FTC or 3TC respectively. Student t-test and one-way ANOVA test (s-w) were used for statistics. There were 6 mice in each group. *p≤0.05, relative to appropriate control groups respectively.
Figure 4V:
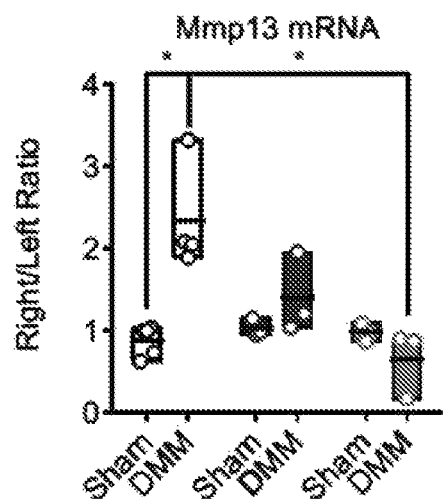
FIG. 4V is a graph showing the gene expression of Mmp13 at RNA level in 129S6/SvEv mice which underwent DMM or Sham surgeries and subsequent treatment of Saline or FTC or 3TC respectively. Student t-test and one-way ANOVA test (s-w) were used for statistics. There were 6 mice in each group. *p≤0.05, relative to appropriate control groups respectively.
Figure 4W:
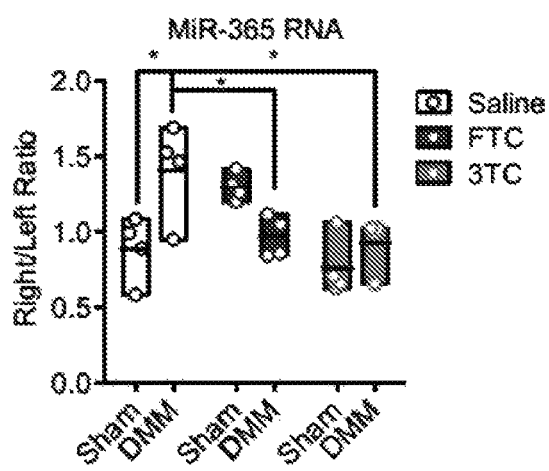

To determine whether NRTIs inhibited PTOA, DMM surgery was performed to induce PTOA in 129s6/SvEv mice (FIG. 4P). Oral administration of 3TC or FTC for a month significantly inhibited cartilage joint degeneration (FIGS. 4Q and 4R). NRTIs inhibited L1 levels and ADAMTS-5, Col 10a1, Mmp13 mRNA levels in cartilage (FIG. 4S-4V). They also inhibited miR-365, which was elevated in OA cartilage (FIG. 4W).

Whether NRTIs inhibited subchondral bone mineral density in PTOA mice was also determined. Local bone sclerosis could be seen under the cartilage OA lesion in DMM mice (FIG. 10A). BV/TV, trabecular number and thickness, and connectivity density were increased (FIGS. 10B-10D and 10F) while trabecular separation was decreased in DMM mice (FIG. 10E). NRTIs treatment abolished bone sclerosis and the increase of BV/TV, trabecular number and thickness, and connectivity density in DMM mice (FIG. 10A-10F). Thus, NRTIs inhibited both cartilage degeneration and subchondral bone sclerosis during PTOA.

The de-repression of endogenous L1 in cartilage lesions, as disclosed herein, is a mechanism responsible for initiation and progression of OA, a common human degenerative joint disease (Berenbaum, F. *Osteoarthritis and cartilage/OARS, Osteoarthritis Research Society* 21, 16-21 (2013), and Helmick, C. G., et al. *Arthritis and rheumatism* 58, 15-25 (2008), Lawrence, R. C., et al. *Arthritis and rheumatism* 58, 26-35 (2008), Michaud, C. M., et al. *Popul Health Metr* 4, 11 (2006), Andrianakos, A. A., et al. *The Journal of rheumatology* 33, 2507-2513 (2006), and D'Ambrosia, R. D. *Orthopedics* 28, s201-205 (2005)). The data suggested that it is at least a two-step pathogenic process. L1, the only cell autonomous retrotransposon, could be activated initially by mechanical and/or inflammation stress signals in tissue wound due to joint injury (FIG. 11S). Time, as during aging, appears to be critical for amplifying the cellular L1 content (FIG. 1V) and eliciting an inflammatory response including SASP IL-6 and IL-1β (Coppe, J. P., et al. *Annu Rev Pathol* 5, 99-118 (2010), Meyer, P., et al. *PLoS Comput Biol* 13, e1005741 (2017), and Ortiz-Montero, P., et al. *Cell Commun Signal* 15, 17 (2017)) and interferon-α (Marco De Cecco, et al. *Nature Medicine* (2018)). Such aging dependent "sterile inflammation" (Freund, A., et al. *Trends Mol Med* 16, 238-246 (2010) and Lopez-Otin, C., et al. The hallmarks of aging. Cell 153, 1194-1217 (2013)) leads to progression of OA pathogenesis including activation of matrix degradation proteases MMP-13 and ADMTS-5, suppression of anabolic ECM COL II and ACAN, and degradation of cartilage joint (Lotz, M. & Loeser, R. F. Bone 51, 241-248 (2012)). Repression of L1 using anti-retroviral drug NRTIs that block reverse transcriptase required for biogenesis and amplification of L1 (Dai, L., Huang, Q. & Boeke, J. D. *BMC Biochem* 12, 18 (2011), Patnala, R., et al. *Breast Cancer Res Treat* 143, 239-253 (2014), and Jones, R. B., et al. *PLoS One* 3, e1547 (2008)), reversed the tissue degeneration process by suppressing matrix degradation proteases, stimulating ECM synthesis, and inhibiting joint degradation (FIG. 3A-3AC).

The efficacy of NRTIs for the treatment of joint degeneration has been demonstrated at cell and tissue levels, in vitro and in vivo, for OA and PTOA, in mice and human, and by basic and clinical research approaches (FIG. 4A-4W) in this study.

Activation of L1 in senescent cells during aging was a recent discovery and its mechanisms to cause aging associated disease were largely unknown Belancio, V. P., et al. *Nucleic acids research* 38, 3909-3922 (2010), Erichsen, L., et al. *Saudi J Biol Sci* 25, 1220-1226 (2018), Shi, X., Seluanov, A. & Gorbunova, V. *Molecular and cellular biology* 27, 1264-1270 (2007), Cho, Y. H., et al *PloS one* 10, e0133909 (2015), St Laurent, G., 3rd, Hammell, N. & McCaffrey, *Mech Ageing Dev* 131, 299-305 (2010), Carlini, F., et al. *PloS one* 5, e14221 (2010), Ogino, S., et al. *J Natl Cancer Inst* 100, 1734-1738 (2008), and Ogino, S., et al. *Cancer Epidemiol Biomarkers Prev* 18, 2513-2521 (2009)). Herein, it was shown that miR-365 could be an activator of L1 in response to mechanical and inflammatory stress signals during tissue injury in vivo (FIG. 1A-1X). MiR-365 was the first mechano-sensitive microRNA identified in chondrocytes (Guan, Y. J., et al. *FASEB journal* 25, 4457-4466 (2011)). Its expression was exquisitely sensitive to inflammatory cytokines including IL-6 (Xu, Z., et al. *The Journal of biological chemistry* 286, 21401-21412 (2011)) and IL-1 (Yang, X., et al. *Int J Mol Sci* 17, 436 (2016)), correlated with cell hypertrophy[24], and quiescence and senescence (Maes, O. C., JBC *Journal of cellular physiology* 221, 109-119 (2009)). MiR-365 was one of the top microR- NAs identified to play a critical role in chromatin modification and oncogenesis (Moss, T. J., et al. *NPJ Syst Biol Appl* 1, 15001 (2015)).

Herein, miR-365 induced L1 by targeting multiple cellular surveillance molecules responsible for repressing L1 in cell defense pathways post-transcriptionally (FIG. 2A-2Q). They included PRKDC in DNA repair (Morrish, T. A., et al. *Nature* 446, 208-212 (2007) and Morrish, T. A., et al. Nature genetics 31, 159-165 (2002)), DICER in RNA interference (Faulkner, G. J. *PLoS Genet* 9, e1003944 (2013)), and SQSTM1 in autophagy (Guo, H., et al. *Nature communications* 5, 5276 (2014)). Recently published literatures support the notion that these pathways are critical to maintaining cartilage health and preventing OA pathogenesis (Chen, A. F. et al *Journal of cellular physiology* 217, 828-833 (2008), Davies, C. M., et al. *Osteoarthritis and cartilage/OARS, Osteoarthritis Research Society* 16, 624-630 (2008), Botter, S. M., et al. *Age (Dordr)* 33, 247-260 (2011), Kobayashi, T., et al. *PNAS* 105, 1949-1954 (2008), Kobayashi, T., et al. *Osteoarthritis and cartilage/OARS, Osteoarthritis Research Society* 23, 1214-1220 (2015), Lotz, M. K. & Carames, B. *Nature reviews. Rheumatology* 7, 579-587 (2011)). DNA damage has been identified in OA patient samples (Duarte, J. H. *Nature reviews. Rheumatology* 11, 260 (2015), Loeser, R. F., et al. *Nature reviews. Rheumatology* 12, 412-420 (2016), Onuora, S. *Nature reviews. Rheumatology* 8, 502 (2012) and Lepetsos, P. & Papavassiliou, A. G. *Biochim Biophys Acta* 1862, 576-591 (2016)). DICER null mice have cartilage defects during development and adulthood (Kobayashi, T., et al. *PNAS* 105, 1949-1954 (2008)). Autophagy appears to be an important mechanism to inhibit cartilage and bone degeneration, and the mutations in SQSTM1 results in Paget's disease, an inflammatory bone disease, and osteoarthritis (Hiruma, Y., et al. *Hum Mol Genet* 17, 3708-3719 (2008), Hocking, L. J., et al. *Hum Mol Genet* 11, 2735-2739 (2002) and Laurin, N., et al. *Am J Hum Genet* 70, 1582-1588 (2002))

Thus, this study has revealed a molecular mechanism by which L1 retrotransposons are activated by stress signals, amplified during aging, and resulting in tissue degeneration. OA is the first degenerative disease associated with L1 activation.

The following materials and methods were used to generate data described herein.

Animals

The use of animals is approved by Lifespan IACUC animal studies committee and all animal studies were performed in accordance with institutional guidelines. To overexpress miR-365 in cartilage tissues, C57BL/6 background miR-365fl+/− transgenic mice were crossed with miR-365 fl−/−; Col2a1-cre+/− (Cre-only) mice to generate miR-365 fl+/−; Col2a1-cre+/− mice (miR-365 Tg)1. Cre-only and miR-365 Tg mice were used in the studies regardless of their sexes as OA is not a sex-specific disease.

12956/SvEv strain male mice were purchased from Taconic (https://www.taconic.com/mouse-model/129s6) at their age of 7-week-old. At least 3-day (72-hrs) acclimation period must be given to mice before any further procedures occurred to them. All 12956/SvEv strain mice throughout the studies were male.

All strains of mice were housed with ad libitum access to food and water unless otherwise stated.

Genotyping

Genomic DNA was extracted from mouse toes or tails within 7 days after birth and conventional PCR was performed using Hot start Taq polymerase (New England BioLabs, Cat. M049S/L) using primers designed specific to miR-365 insertion or Col2a1-Cre constructs (Table 1, below) (Berenbaum, F. *Osteoarthritis and cartilage/OARS, Osteoarthritis Research Society* 21, 16-21 (2013)).

TABLE 1

Primer List

| GENES | DIRECTION | SEQUENCES (5' TO 3') |
|---|---|---|
| Mouse | | |
| GAPDH | Forward | CGGCCGCATCTTCTTGTG (SEQ ID NO: 1) |
|  | Reverse | GTGACCAGGCGCCCAATA (SEQ ID NO: 2) |
| 18S | Forward | CGGCTACCACATCCAAGGAA (SEQ ID NO: 3) |
|  | Reverse | GCTGGAATTACCGCGGCT (SEQ ID NO: 4) |
| COL2-CRE | Forward | TCCAATTTACTGACCGTACACCAA (SEQ ID NO: 5) |
|  | Reverse | CCTGATCCTGGCAATTTCGGCTA (SEQ ID NO: 6) |
| MIR-365 INSERTION | Forward | AGACCCACAAGGCCCTGAAGCTGA (SEQ ID NO: 7) |
|  | Reverse | CACATCTGCCCCCAAAAGTC (SEQ ID NO: 8) |
| LINE-1 | Forward | TGAGTGGAACACAACTTCTGC (SEQ ID NO: 9) |
|  | Reverse | CAGGCAAGCTCTCTTCTTGC (SEQ ID NO: 10) |
| ALU | Forward | GAGGCTGAGGCAGGAGAATCG (SEQ ID NO: 11) |
|  | Reverse | TGTCGCCCAGGCTGGAGTG (SEQ ID NO: 12) |
| 5S | Forward | CTCGTCTGATCTCGGAAGCTAAG (SEQ ID NO: 13) |
|  | Reverse | GCGGTCTCCCATCCAAGTAC (SEQ ID NO: 14) |
| MMP13 | Forward | GGACCTTCTGGTCTTCTGGC (SEQ ID NO: 15) |
|  | Reverse | GGATGCTTAGGGTTGGGGTC (SEQ ID NO: 16) |
| MMP3 | Forward | GACTCAAGGGTGGATGCTGT (SEQ ID NO: 17) |
|  | Reverse | CCAACTGCGAAGATCCACTG (SEQ ID NO: 18) |
| COLX | Forward | CTGCTGCTAATGTTCTTGAC (SEQ ID NO: 19) |
|  | Reverse | ACTGGAATCCCTTTACTCTTT (SEQ ID NO: 20) |

TABLE 1-continued

Primer List

| GENES | DIRECTION | SEQUENCES (5' TO 3') |
|---|---|---|
| IHH | Forward | GCTCGTGCCTCTTGCCTACA (SEQ ID NO: 21) |
|  | Reverse | CGTGTTCTCCTCGTCCTTGA (SEQ ID NO: 22) |
| IL-1B | Forward | AACCTGCTGGTGTGTGACGTTC (SEQ ID NO: 23) |
|  | Reverse | CAGCACGAGGCTTTTTTGTTGT (SEQ ID NO: 24) |
| IL-6 | Forward | TCCAGTTGCCTTCTTGGGAC (SEQ ID NO: 25) |
|  | Reverse | GTACTCCAGAAGACCAGAGG (SEQ ID NO: 26) |
| P2RX7 | Forward | CAACTATGAACGGCTCTTGTACCT (SEQ ID NO: 27) |
|  | Reverse | TCGATACCCATGATTCCTCCCT (SEQ ID NO: 28) |
| NLRP3 | Forward | CAGCGATCAACAGGCGAGAC (SEQ ID NO: 29) |
|  | Reverse | AGAGATATCCCAGCAAACCTATCCA (SEQ ID NO: 30) |
| IFN-A | Forward | TCTGATGCAGCAGGTGGG (SEQ ID NO: 31) |
|  | Reverse | AGGGCTCTCCAGACTTCTGCTCTG (SEQ ID NO: 32) |
| AICDA | Forward | TTGTTGTTCCTACGCTACATCTC (SEQ ID NO: 33) |
|  | Reverse | CCGGGCACAGTCATAGCAC (SEQ ID NO: 34) |
| DICER | Forward | GAAGACGTTCATCGCGGTC (SEQ ID NO: 35) |
|  | Reverse | GCTGACACTTGTTGAGCAACC (SEQ ID NO: 36) |
| PRKDC | Forward | AGCCATTGCTATTCGCGGATA (SEQ ID NO: 37) |
|  | Reverse | CGGAACCGTGTCAAGGTAAAG (SEQ ID NO: 38) |
| SQSTM1 | Forward | GAGGCACCCCGAAACATGG (SEQ ID NO: 39) |
|  | Reverse | ACTTATAGCGAGTTCCCACCA (SEQ ID NO: 40) |
| ZC3HAV1 | Forward | CCCGAAGCGCAACTCTACG (SEQ ID NO: 41) |
|  | Reverse | CGCTGGGACTGTGCATAGTG (SEQ ID NO: 42) |
| AICDA 3'UTR | Forward | GCGCGCGTTTAAACGAACAAGACTTAAAGGAGCC (SEQ ID NO: 43) |
|  | Reverse | CGCGCTCGAGTCTATGTTGGTTTCCTACAT (SEQ ID NO: 44) |
| DICER 3'UTR | Forward | GCGCGTTTAAACTAGATGCCCGGTTTTCCTCA (SEQ ID NO: 45) |
|  | Reverse | CGCGCGCTCGAGCCATACAGCATTTTTAAATG (SEQ ID NO: 46) |
| PRKDC 3'UTR | Forward | GCGCGTTTAAACAGTCTGTGGTGTCACCAATC (SEQ ID NO: 47) |
|  | Reverse | CGCGCGCGCGCTCGAGAGAAATATTTGTCATATTCT (SEQ ID NO: 48) |
| SQSTM1 3'UTR | Forward | CCAGTGTCTTTTAATTCTTGTAGAATCTTCAGG (SEQ ID NO: 49) |
|  | Reverse | CCTGAAGATTCTACAAGAATTAAAAGACACTGG (SEQ ID NO: 50) |
| ZC3HAV1 3'UTR | Forward | GCGCGTTTAAACCAGTGTGACATAACTGAAAG (SEQ ID NO: 51) |
|  | Reverse | CGCGCTCGAGCGAACAATGAGATTTTACTG (SEQ ID NO: 52) |
| DICER 3'UTR MUT | Forward | GTAAAGCTGTTTATTAATTTGCTGAAGGTCTCGC (SEQ ID NO: 53) |
|  | Reverse | GCGAGACCTTCAGCAAATTAATAAACAGCTTTAC (SEQ ID NO: 54) |
| PRKDC 3'UTR MUT | Forward | GTCAGATAAATTAATTTGTTACCAATGCTAATGGC (SEQ ID NO: 55) |
|  | Reverse | GCCATTAGCATTGGTAACAAATTAATTTATCTGAC (SEQ ID NO: 56) |
| SQSTM1 3'UTR MUT | Forward | CCAGTGTCTTTTAATTCTTGTAGAATCTTCAGG (SEQ ID NO: 57) |
|  | Reverse | CCTGAAGATTCTACAAGAATTAAAAGACACTGG (SEQ ID NO: 58) |
| ACAN | Forward | TGCTACTTCATCGACCCCAT (SEQ ID NO: 59) |
|  |  | Reverse AAAGACCTCACCCTCCATCT (SEQ ID NO: 60) |

TABLE 1-continued

Primer List

| GENES | DIRECTION | SEQUENCES (5' TO 3') |
|---|---|---|
| ADAMTS5 | Forward | TCAGCCACCATCACAGAA (SEQ ID NO: 61) |
|  | Reverse | CCAGGGCACACCGAGTA (SEQ ID NO: 62) |
| COL2* | Forward | CTCCCAGAACATCACCTACCA (SEQ ID NO: 63) |
|  | Reverse | CGTGAACCTGCTATTGCCCT (SEQ ID NO: 64) |

Human

| GENES | DIRECTION | SEQUENCES (5' TO 3') |
|---|---|---|
| IHH | Forward | GGAGAACACAGGCGCCGACC (SEQ ID NO: 65) |
|  | Reverse | CGGTCACCCGCAGCTTCACA (SEQ ID NO: 66) |
| ACAN | Forward | CCATCATTGCCACGCCTGAG (SEQ ID NO: 67) |
|  | Reverse | TCCTTGTCTCCATAGCAGCCTTC (SEQ ID NO: 68) |
| COLX | Forward | GCCCACAGGCATAAAAGGCCC (SEQ ID NO: 69) |
|  | Reverse | GCCCACAGGCATAAAAGGCCC (SEQ ID NO: 70) |
| MMP13 | Forward | ATGCGGGGTTCCTGATGTGG (SEQ ID NO: 71) |
|  | Reverse | GGCCCAGGAGGAAAAGCATG (SEQ ID NO: 72) |
| ADAMTS5 | Forward | GGCCGTGGTGAAGGTGGTGG (SEQ ID NO: 73) |
|  | Reverse | GCTGCGTGGAGGCCATCGTC (SEQ ID NO: 74) |
| 18S | Forward | CGGCTACCACATCCAAGGAA (SEQ ID NO: 75) |
|  | Reverse | GCTGGAATTACCGCGGCT (SEQ ID NO: 76) |
| LINE-1 | Forward | CAAACACCGCATATTCTCACTCA (SEQ ID NO: 77) |
|  | Reverse | CTTCCTGTGTCCATGTGATCTCA (SEQ ID NO: 78) |
| ALU | Forward | GAGGCTGAGGCAGGAGAATCG (SEQ ID NO: 79) |
|  | Reverse | TGTCGCCCAGGCTGGAGTG (SEQ ID NO: 80) |
| ZC3HAV1 | Forward | TCACGAACTCTCTGGACTGAA (SEQ ID NO: 81) |
|  | Reverse | ACTTTTGCATATCTCGGGCATAA (SEQ ID NO: 82) |
| SQSTM1 | Forward | GCACCCCAATGTGATCTGC (SEQ ID NO: 83) |
|  | Reverse | CGCTACACAAGTCGTAGTCTGG (SEQ ID NO: 84) |
| DICER | Forward | AAAATTGTCCATCATGTCCTCGC (SEQ ID NO: 85) |
|  | Reverse | CCACCAGGTCAGTTGCAGTT (SEQ ID NO: 86) |
| PRKDC | Forward | CTGTGCAACTTCACTAAGTCCA (SEQ ID NO: 87) |
|  | Reverse | CAATCTGAGGACGAATTGCCT (SEQ ID NO: 88) |
| AICDA | Forward | GAGGCGTGACAGTGCTACATC (SEQ ID NO: 89) |
|  | Reverse | CAGGGTCTAGGTCCCAGTCC (SEQ ID NO: 90) |
| IL-6 | Forward | TGTCTGAGGCTCATTCTGC (SEQ ID NO: 91) |
|  | Reverse | TGGGGCAGGGAAGGCA (SEQ ID NO: 92) |

*For mouse and human

TABLE 2 siRNA Sequences
A TABLE OF SILINE-1S SEQUENCES. SEQUENCES ARE DESIGNED AND ARE ARBITRARILY NAMED A THROUGH F.

| NAME | SEQUENCES (5' TO 3') |
|---|---|
| SILINE-1A | AAC CTG GAC GAA ATG GAC AAA (SEQ ID NO: 93) |
| SILINE-1B | AAG TAG ACC AAT GGA ATA GAA (SEQ ID NO: 94) |
| SILINE-1C | AAG CCA CTA TTA CTC TGA TAC (SEQ ID NO: 95) |
| SILINE-1D | AAG GTC AAA TCT AAG TGG ATC (SEQ ID NO: 96) |
| SILINE-1E | AAG TTT CTG CAA GGC AAA AGA (SEQ ID NO: 97) |
| SILINE-1F | AAT GGC TAA GAT CAA AAA TTC (SEQ ID NO: 98) |

Mouse Model of Destabilization of Medial Meniscus (DMM)

129S6/SvEv male mice were chosen for experimental subjects at their age of 8-week-old. To create mouse injury/trauma induced OA model, medial meniscus ligament was transected using a previously described method (Lohmander, L. S., et al. *Am J Sports Med* 35, 1756-1769 (2007)). Briefly, 8-week-old male mice were anesthetized using either intraperitoneal (IP) injection of Ketamine/Dexmedetomidine or isoflurane to carry out medial parapatellar arthrotomy. Transection was made with a stab knife (Sharpoint™, Cat. 72-1551). At Weeks 12, mice were euthanized and dissected for histological examination as well as cartilage RNA extraction. 12 mice were used for each group/time point.

Human Specimens

Figure 7:
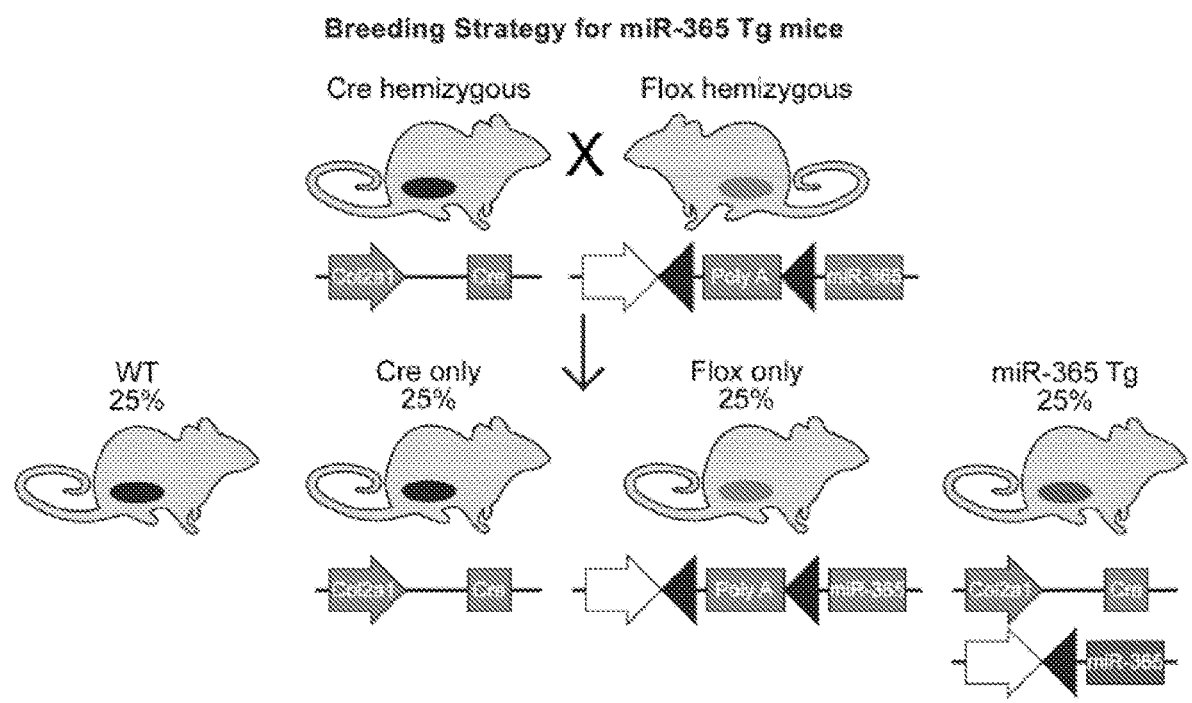
FIG. 7 is a schematic showing the breeding strategy for Col2a1-Cre+/−; miR-365 fl+/−(miR-365 Tg) mice. A schematic representation of breeding strategy to achieve cartilage specific miR-365 over-expression model in mouse (miR-365 Tg mice); In brief, miR-365 fl hemizygote (+/−) mice were crossed with Col2a1-Cre hemizygote (+/−) mice which yielded four genotypes in progeny. Double positive Col2a1-Cre+/−; miR-365 fl+/− mice had miR-365 overexpressed in cartilage tissues. Cre positive only Col2a1-Cre+/−; miR-365 fl−/− mice, flox only Col2a1-Cre−/−; miR-365 fl+/− and wild type (WT) Col2a1-Cre−/−; miR-365 fl−/− mice didn't have miR-365 over-expression. "Green" circle indicates green fluorescence, "red" circle indicates red fluorescence while "black" circle indicates no fluorescence.

Cartilages were prospectively gathered from consenting individuals who had been diagnosed with OA and underwent total knee replacement. All the procedures were prior approved by IRB. For the sake of patients' identity protection, all the information was confidential except for those relevant to experiments, such as information of gender and age. Samples were harvested immediately after surgeries. Pictures of specimens were taken for recording purpose (FIG. 7). OA lesion and non-lesion areas were empirically identified by orthopedic surgeons based on direct observation. For each site of interest, a 1×1 mm$^2$ tissue with a depth ranging from 4-8 mm was harvested using sterile, RNase free Rib-Back® scalpels (Bard-Parker®, Cat. 371115) manually. Care must be taken to avoid any subchondral bone. To obtain maximal digestion efficacy, resected specimens were further minced by scalpels before submerging into 350 mL QIAzol Lysis Reagent (Qiagen, Cat No./ID: 79306). Specimens can either be stored at −80° C. or be accessed using diverse methods.

Femur Explant Organ Culture

Femurs were obtained from 21-day-old WT C57BL/6 mice. Femurs with intact articular surface and periosteum was sterilely dissected under microscope. Upon harvesting, femurs were rinsed with HBSS (Gibco®, Grand Island, N.Y. 14072 USA) and then submerged into DMEM (Gibco, Grand Island, N.Y. 14072 USA) medium supplemented with 10% fetal bovine serum (FBS, Gibco®, Grand Island, N.Y. 14072 USA) in 12-well culture dishes. The first-generation cytidine analogue/NRTI-3TC or newest-generation cytidine analogue/NRTI-FTC was added into the medium with desired concentrations. After a total of 48 hrs incubation at 37° C. in an atmosphere of 5% $CO_2$, femurs were rinsed with HBSS and articular cartilage was peeled off using surgical scalpels under dissecting microscope for RNA extraction.

Histology, Immunohistochemistry (IHC), and Immunofluorescence

Human cartilage tissues were fixed in 4% Paraformaldehyde (PFA) for 24 hrs at 4° C., followed by 30% Diethyl pyrocarbonate (DEPC)-sucrose (Sigma, Cat. 50289-500G, St. Louis, Mo. 63103 USA) at 4° C. until the specimens were sunken to the bottom of the containers. Tissues were embedded in optimal cutting temperature compound (O.C.T., SAKURA FINETEK USA INC, Tissue-Tek® O.C.T. Compound, Cat. 4583). A cryo-section microtome (Model: CM3050, Leica, Germany) was used to cut 6-μm-thick sections. The sections were stained by H&E staining to assess morphology. Mouse tissues were fixed in 10% formalin for 24-48 hrs depending on tissue size, followed by de-calcification process using DEPC de-calcification reagents (Ethylenediaminetetraacetic acid, Sigma, Cat. EDS-1KG, St. Louis, Mo. 63103 USA) at room temperature for 10-14 days. After de-calcification, tissues were dehydrated in ethanol before embedded in paraffin with routine procedures. A microtome (Model: FINESSE ME, Thermo Shandon, UK) was used to cut 6-μm-thick sections. For every 80 μm interval, 5 sister sections were harvested to make a total of 13-16 slices from one knee of a fully-grown mouse. Number of slides form one knee may vary due to varying sizes of the specimens. Slides were then de-paraffinized and stained GAG with Alcian blue (Sigma, Cat. A3157-10G) or Safranin O (Sigma, Cat. 58884-25G, St. Louis, Mo. 63103 USA). Morphology is assessed by H&E staining. For IHC, paraffin sections were processed with routine procedures instructed by Histostain® Plus 3$^{rd}$ Gen IHC Detection Kit (Life Technologies, Cat. 859673, Frederick, Md. 21704 USA). Rabbit or mouse antibodies specifically against antigens of interest were used, followed by incubation of HRP-conjugated secondary antibodies against rabbit or mouse IgG (provided by the kit). Primary and secondary antibodies are listed in Table 3 below. Signals are then visualized by a DAB-Plus Substrate Kit (Life Technologies, Cat. 002020, Frederick, Md. 21704 USA).

TABLE 3

Antibody List

| PROTEINS | VENDOR | CATALOG# | ORIGIN | MW (KD) |
| --- | --- | --- | --- | --- |
| B-ACTIN | Cell Signaling | cs-4970S | Rabbit | 45 |
| LINE-1 ORF1 | Cell Signaling | cs-88701S | Rabbit | 42 |
| SQSTM1 | Santa Cruz | sc-28359 | Rabbit | 65 |
| DICER | Abcam | ab14601 | Mouse | 240 |
| IHH | Abcam | ab52919 | Rabbit | 45 |
| PRKDC | Abcam | ab32566 | Rabbit | 469 |

Safranin O Staining

Paraffin sections were de-paraffinized in 2 changes of xylene, 10 mins each, followed by re-hydration in 2 changes of 100% alcohol, 5 mins each; 2 changes of 95% alcohol, 5 mins each; 70% alcohol for 5 mins. Sections were then rinsed in running tap water for 2 mins before stained with 0.4% fast green solution (Sigma, Cat. F-7258, St. Louis, Mo. 63103 USA) for 2 mins however the latter timing must be empirically controlled to assure desired coloration. Stained sections were then quickly rinsed with 1% acetic acid solution (Sigma, Cat. 695092-500ML-GL, St. Louis, Mo. 63103 USA) for no more than 10-15 sec. 0.1% Safranin O Solution was used for staining proteoglycan however the actual timing must be carefully determined based on actual coloring condition, for maximally 10 mins. After Safranin O staining, sections were submerged in 2 changes of 95% alcohol, 2 mins each, 2 changes of 100% alcohol, 2 mins each for de-hydration. Lastly, sections were cleared in 2 changes of xylene, 2 mins each, and mounted using resinous mounting medium (ACRYMOUNT™, Cat. SL80-4, McKinney, Tex. 75069 USA).

OARSI Scoring

To histologically evaluate OA severity, we quantified Safranin O stained knee sections according to OARSI semi-quantitative system as previously described[3]. Detailed scoring standards are summarized in Table 4 below:

TABLE 4

OASRI Scoring Guideline:

| GRADE | OSTEOARTHRITIC DAMAGE |
| --- | --- |
| 0 | Normal |
| 0.5 | Loss of Safranin-O without structural changes |
| 1 | Small fibrillations without loss of cartilage |

TABLE 4-continued

OASRI Scoring Guideline:

| GRADE | OSTEOARTHRITIC DAMAGE |
|---|---|
| 2 | Vertical clefts down to the layer immediately below the superficial layer and some loss of surface lamina |
| 3 | Vertical clefts/erosion to the calcified cartilage extending to <25% of the articular surface |
| 4 | Vertical clefts/erosion to the calcified cartilage extending to 25-50% of the articular surface |
| 5 | Vertical clefts/erosion to the calcified cartilage extending to 50-75% of the articular surface |
| 6 | Vertical clefts/erosion to the calcified cartilage extending >75% of the articular surface |

Hematoxylin and Eosin (H&E) Staining

Paraffin sections were de-paraffinized in 2 changes of xylene, 10 mins each, followed by re-hydration in 2 changes of 100% alcohol, 5 mins each; 2 changes of 95% alcohol, 5 mins each; 70% alcohol for 5 mins. Sections were then rinsed in running tap water for 2 mins before stained in Mayer's Hematoxylin solution (NovaUltra™ H&E Stain Kit, IHCWORLD, Cat. IW-3100) for 2 mins however the latter timing must be empirically controlled to assure desired coloration. Stained sections were then rinsed in running tap water for 5 mins before dipped into 95% alcohol for 10 times or 30" based on performer's preference. Eosin Solution (NovaUltra™ H&E Stain Kit, IHCWORLD, Cat. IW-3100) was used for counterstaining however the actual timing must be carefully determined based on actual coloring condition. After counterstaining, sections were dipped in 95% alcohol for 2 times before transferred through 2 changes of 100% alcohol, 5 mins each for de-hydration. Lastly, sections are cleared in 2 changes of xylene, 5 mins each, and mounted with resinous mounting medium.

For frozen sections, procedures were similar with the exception between Eosin counterstaining and 95% alcohol dipping steps. Instead, during these two steps, frozen sections must be air dried for 30 mins at room temperature and fixed in 10% formalin for 10 mins. Then the sections were taken out for another 30 mins air dry at room temperature before rinsed in water.

Homogenization

A PowerGen 125 (Fisher Scientific, Cat. 03.349248) was used to homogenize samples for RNA extraction. A cycle of 45" homogenization at speed of 5, followed by a cool down step of 15" was repeated for 5 cycles before switching to a finer drill for the same cycles. Drills/PowerGen Generator (Fisher Scientific, Cat. 14-261-15) were rinsed in DEPC-water followed by 100% ethanol rinse between different specimens to avoid cross contamination. All procedures took place on ice to avoid RNA degradation due to heat.

Primary Growth Plate/Articular Chondrocytes (PCs) Culture

Rib cages were sterilely isolated from neonatal mice (within 7-day-old) of desired genotypes and rinsed with HBSS for five times. To remove unspecific tissues, rib cages were digested in Collagenase D (3 µg/mL, Roche, Cat. 11088882001, Mannheim, Germany) for 2-4 hrs at 37° C. and rinsed with HBSS (Gibco®, Grand Island, N.Y. 14072 USA) for five times to remove detached unspecific tissues. To detach chondrocytes from rib cages, the samples underwent secondary digestion in Collagenase D (3 µg/mL) for at least 4 hrs at 37° C. with constant agitation (200 rpm). Detached chondrocytes were pelleted to remove excessive Collagenase D and resuspended in complete medium of DMEM (Gibco®, Grand Island, N.Y. 14072 USA) which contains 10% FBS, 100 U/mL penicillin and 100 µg/mL streptomycin (Gibco®, Grand Island, N.Y. 14072 USA). Growth plate PCs were grown at 37° C. in an atmosphere of 5% $CO_2$. The media was changed on the following day to remove remaining Collagenase D and every 3 days thereafter.

Similarly, articular cartilages were sterilely isolated under dissection microscope from neonatal mice (within 7-day-old) of desired genotypes and rinsed with HBSS for five times. In brief, the skins of hindlimbs were removed and transections on Ilia and muscles around hip joints were made to detach hindlimbs from torsi, then transferred to a petri dish. Under a dissection microscope placed in a cell culture hood, soft tissues were cleared while knee and hip joints were exposed. Femur heads could be easily peeled off whilst a fine cut of epiphyses based on vascularization were made to isolate articular cartilage from secondary ossification center. Beyond that, isolated tissues were minced into finer fragments and then put together before undergoing HBSS rinse and subsequent Collagenase D digestion. To remove unspecific tissues, articular cartilages were minced and digested in Collagenase D (3 µg/mL) for 2 hrs at 37° C. and rinsed with HBSS for five times to remove detached unspecific tissues. To detach chondrocytes from cartilage matrix, the samples underwent secondary digestion in Collagenase D (3 µg/mL) for at least 4 hrs at 37° C. with constant agitation (200 rpm). Detached chondrocytes were pelleted to remove excessive Collagenase D and resuspended in complete medium of DMEM which contains 10% FBS, 100 U/mL penicillin and 100 µg/mL streptomycin. Articular PCs were grown at 37° C. in an atmosphere of 5% $CO_2$. The media was changed on the following day to remove remaining Collagenase D and every 3 days thereafter.

Transient Transfection

Cells were seeded onto desired size plates to reach 70-90% confluence and transfected with miR-365 mimic or miRNA mimic negative control or miR-365 inhibitor or inhibitor negative control (Dharmacon®, Lafayette, Colo., USA). Lipofectamine 3000 (Invitrogen®, Waltham, Mass., USA) was used as transfection reagents. Medium is changed 24 hrs after transfection. 48 hrs post transfection, cells were lysated in either QIAzol for RNA purification and real-time PCR analysis or ice-cold lysis buffer containing protease inhibitor and phosphatase inhibitor for western blot analysis. MiR-365 mimic, miRNA mimic negative control, miR-365 inhibitor and inhibitor negative control were typically used at a final concentration of 25 nM unless otherwise stated.

Quantitative Real-Time PCR (qPCR)

Both miRNA and mRNA were extracted using miRNeasy Mini Kit (Qiagen®, Germantown, Md., USA) and reversely transcribed using miScriptIIRT Kit (Qiagen®, Germantown, Md., USA) according to manufacturer's instruction. qPCR was performed using SYBR Green PCR master mix (Qiagen®, Germantown, Md., USA) on a Bio-Rad CFX96 real-time PCR detection system (Bio-Rad®, Hercules, Calif., USA). Amplification conditions are as follows: 95° C. for 10 min, 40 cycles of 95° C. for 10", 55° C. for 30", and 72° C. for 30". Sense and antisense primers are listed in Table 2. 18S ribosomal or GAPDH RNA was used as an internal control gene to normalize the mRNAs level. The ubiquitously expressed snRNA U6 was used as an endogenous control for miRNAs level. Primers were synthesized by Integrated DNA Technologies (http://www.idtdna.com). The primers for miR-365 were purchased from Qiagen. Fold changes of mRNA and miRNAs were calculated by the $2^{-(\Delta\Delta Ct)}$ method and normalized to 18S/GAPDH or U6 snRNA, respectively.

Prediction of miR-365 Target Genes

Potential targets of miR-365-5p and miR-365-3p were identified using the TargetScan (http://www.targetscan.org/) and miRanda/mirSVR (http://34.236.212.39/microrna/home.do) target prediction algorithms.

Plasmid Construction

WT Aicda, Dicer1, Prkdc, Sqstm1 and Zc3hav1 3'UTRs bearing potential response elements (REs) serving as miR-365 seeding sites predicted by microrna.org were cloned from mouse genomic DNA (50 ng-250 ng) using primers designed to introduce ideal restriction enzyme cleavage sites according to the backbone plasmid pmirGLO construct (Promega, Madison, Wis., USA). Detailed thermal cycles are: 98° C. for 30 sec, 25-35 cycles of 98° C. for 10 sec, 55-60° C. for 30 sec, and 72° C. for 15 sec and final extension at 72° C. for 10 min before holding at 4° C. Designed primers are summarized in Table 1, above. PmeI and XhoI were enzymes used to cleave for sticky ends. After restriction enzymes cleavage, approximately 500 bp 3'UTR sequences were annealed into pmirGLO construct (1 pg-10 ng). REs were mutated according to QuikChange Lightning Multi Site-Directed Mutagenesis Kit's instruction (Agilent, Cat. 210513/210515, Santa Clare, Calif. 95051 USA).

Luciferase Assays

ATDC5 cells were cultured at $2.5 \times 10^4$ cells/well in 24-well plates. The cells were co-transfected with miR-365 mimic (25 nM) or miRNA mimic negative control (25 nM) and 500 ng of pmirGLO-Dicer1/Zap/Sqstm1/Prkdc/Aicda 3'-UTR WT or Mut plasmids. Transfection was performed using Lipofectamine 3000 (Invitrogen, Cat. L3000-008, Carlsbad, Calif. 92008 USA) reagent. The assays were performed in triplicate unless otherwise stated. 24 hrs after transfection, cells were collected, and luciferase activity was determined using the Dual-Luciferase reporter assay system (Promega, Madison, Wis., USA) with the GLOMAX 20/20 luminometer (Model: 2031_000, Turner BioSystems, Sunnyvale, Calif. USA). Briefly, cells were rinsed with PBS and incubated with Passive Lysis Buffer (provided by the kit) for 15 mins with constant agitation at room temperature. Lysates were scraped into 1.5 mL Eppendorf tubes. 20 µl of lysates were fixed with 50 µl Luciferase Assay Buffer II to measure Firefly luciferase luminescence. 50 µl Stop & Glo buffer was then added to measure Renilla luminescence. The luciferase activity was represented by the ratio of Firefly/Renilla measurements.

Western Blot (WB)

All pre-treated samples were washed with ice-cold PBS and lysated in RIPA buffer (M-PER, Pierce, Ill.) plus protease inhibitor phenylmethylsulfonyl fluoride [Halt™, Thermo Scientific, Protease Inhibitor Single-Use Cocktail (100×), Cat. 78430] for 30 min on ice with constant agitation. The lysates are centrifuged at 12,000 g for 15 min at 4° C. The supernatants were collected, and the protein concentrations were determined using Pierce™ BCA assay (Thermo Scientific, Cat. 23225). Samples were mixed with equal volume 2×Laemmli sample buffer (Bio-Rad, Cat. 161-0737) which contains 2-Mercaptoethanol (Bio-Rad, Cat. 161-0710) and heated for 5 min at 100° C. to denature. Equal amount of proteins for each sample were separated by 8-12% SDS polyacrylamide gel depending on protein size of interest and then transferred to nitro-cellulous membrane (Bio-Rad, Cat. 162-0112) for 70 min at 100 V. The membrane was blocked with 5% bovine serum albumin (BSA, Sigma, Cat. A7906-50G) in 0.1% Tris-Buffered Saline-Tween 20 (TBS-T, BBP, Cat. IBB-581X) for 1 hr at room temperature, followed by incubation with primary antibodies against proteins of interest (antibodies are listed in Table 3, provided above) at 4° C. overnight. On the following day, the membrane was rinsed with TBS-T for 10 min for a total of 5 times and incubated with anti-rabbit-Alexa Fluor 680 (Molecular Probes, Eugene, Oreg., USA) for 1 hr at room temperature followed by TBS-T rinse for 10 min for a total of 5 times. The blots were then scanned using an Odyssey fluorescence scanner (LI-COR Biosciences, Lincoln, Nebr., USA) and quantitatively analyzed by ImageJ (https://imagej.nih.gov/ij/index.html).

Statistical Analysis

Data represents mean values±SD (error bars). Statistical significance was calculated using student's t-test (unpaired) or one-way ANOVA test. A p-value≤0.05 was considered statistically significant. There is a minimum of n≥3 for all groups unless otherwise stated.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting the progression of an articulating joint disorder by inhibiting LINE-1 expression in a subject, comprising systemically administering emtricitabine to said subject, wherein said subject does not comprise a human immunodeficiency virus (HIV) infection.

2. The method of claim 1, wherein said subject is diagnosed as comprising osteoarthritis.

3. The method of claim 1, wherein said joint disorder comprises osteoarthritis (OA).

4. A method for inhibiting the progression of an aging-associated joint disorder by inhibiting LINE-1 expression in a subject, comprising systemically administering emtricitabine to said subject, wherein said subject does not comprise a human immunodeficiency virus (HIV) infection.

5. The method of claim 4, wherein the subject is at least 50 years old.

6. The method of claim 4, wherein the joint disorder comprises osteoarthritis.

7. The method of claim 4, wherein the subject is a human.

8. The method of claim 4, wherein the emtricitabine inhibits the expression of osteoarthritis markers.

9. The method of claim 8, wherein the osteoarthritis markers comprise collagen type X alpha 1 chain (COL10A1), A Disintegrin and Metalloproteinase with Thrombospondin Motifs 5 (ADAMTS5), matrix metallopeptidase 13 (MMP13), senescence-associated secretory phenotype interleukin-6 (SASP IL-6), Indian hedgehog (Ihh) or interferon type 1 (IFN).

10. The method of claim 4, wherein the emtricitabine promotes the expression of anabolic markers.

11. The method of claim 10, wherein the anabolic markers comprise aggrecan (ACAN) and Collagen, type II, alpha 1 (COL2A1).

12. A method for inhibiting the progression of a post-traumatic osteoarthritis (PTOA) injury by inhibiting LINE-1 expression in a subject, comprising systemically administering emtricitabine to said subject, wherein said subject does not comprises a human immunodeficiency virus (HIV) infection.

13. The method of claim 12, wherein said PTOA results from a high-speed impact trauma to the articular surface, intraarticular fractures, or joint-destabilizing soft-tissue tears.

14. The method of claim 12, wherein the PTOA injury is in a joint.

* * * * *

SEQUENCE LISTING

```
<160> NUMBER OF SEQ ID NOS: 114

<210> SEQ ID NO 1
<211> LENGTH: 18
<212> TYPE: DNA
<213> ORGANISM: Artificial Sequence
<220> FEATURE:
<223> OTHER INFORMATION: Synthetic construct - primer

<400> SEQUENCE: 1
```

-continued cggccgcatc ttcttgtg                                                    18

<210> SEQ ID NO 2
<211> LENGTH: 18
<212> TYPE: DNA
<213> ORGANISM: Artificial Sequence
<220> FEATURE:
<223> OTHER INFORMATION: synthetic construct - primer

<400> SEQUENCE: 2
gtgaccaggc gcccaata                                                    18

<210> SEQ ID NO 3
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 3
cggctaccac atccaaggaa                                                  20

<210> SEQ ID NO 4
<211> LENGTH: 18
<212> TYPE: DNA
<213> ORGANISM: Artificial Sequence
<220> FEATURE:
<223> OTHER INFORMATION: synthetic construct - primer

<400> SEQUENCE: 4
gctggaatta ccgcggct                                                    18

<210> SEQ ID NO 5
<211> LENGTH: 24
<212> TYPE: DNA
<213> ORGANISM: Artificial Sequence
<220> FEATURE:
<223> OTHER INFORMATION: synthetic construct - primer

<400> SEQUENCE: 5
tccaatttac tgaccgtaca ccaa                                             24

<210> SEQ ID NO 6
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 6
cctgatcctg gcaatttcgg cta                                              23

<210> SEQ ID NO 7
<211> LENGTH: 24
<212> TYPE: DNA
<213> ORGANISM: Artificial Sequence
<220> FEATURE:
<223> OTHER INFORMATION: synthetic construct - primer

<400> SEQUENCE: 7
agacccacaa ggccctgaag ctga                                             24

<210> SEQ ID NO 8
<211> LENGTH: 20
<212> TYPE: DNA

```
<213> ORGANISM: Artificial Sequence
<220> FEATURE:
<223> OTHER INFORMATION: synthetic construct - primer

<400> SEQUENCE: 8
cacatctgcc cccaaaagtc                                              20

<210> SEQ ID NO 9
<211> LENGTH: 21
<212> TYPE: DNA
<213> ORGANISM: Artificial Sequence
<220> FEATURE:
<223> OTHER INFORMATION: synthetic construct -  primer

<400> SEQUENCE: 9
tgagtggaac acaacttctg c                                            21

<210> SEQ ID NO 10
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 10
caggcaagct ctcttcttgc                                              20

<210> SEQ ID NO 11
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 11
gaggctgagg caggagaatc g                                            21

<210> SEQ ID NO 12
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 12
tgtcgcccag gctggagtg                                               19

<210> SEQ ID NO 13
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 13
ctcgtctgat ctcggaagct aag                                          23

<210> SEQ ID NO 14
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 14
gcggtctccc atccaagtac                                              20
```

<210> SEQ ID NO 15
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 15
ggaccttctg gtcttctggc                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 16
ggatgcttag ggttggggtc                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 17
gactcaaggg tggatgctgt                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 18
ccaactgcga agatccactg                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 19
ctgctgctaa tgttcttgac                                              20

<210> SEQ ID NO 20
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 20
actggaatcc ctttactctt t                                            21

<210> SEQ ID NO 21
<211> LENGTH: 20
<212> TYPE: DNA
<213> ORGANISM: Artificial Sequence
<220> FEATURE:

```
<223> OTHER INFORMATION: synthetic construct - primer

<400> SEQUENCE: 21
gctcgtgcct cttgcctaca                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 22
cgtgttctcc tcgtccttga                                              20

<210> SEQ ID NO 23
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 23
aacctgctgg tgtgtgacgt tc                                           22

<210> SEQ ID NO 24
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 24
cagcacgagg ctttttttgtt gt                                          22

<210> SEQ ID NO 25
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 25
tccagttgcc ttcttgggac                                              20

<210> SEQ ID NO 26
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 26
gtactccaga agaccagagg                                              20

<210> SEQ ID NO 27
<211> LENGTH: 24
<212> TYPE: DNA
<213> ORGANISM: Artificial Sequence
<220> FEATURE:
<223> OTHER INFORMATION: synthetic construct - primer

<400> SEQUENCE: 27
caactatgaa cggctcttgt acct                                         24
```

```
<210> SEQ ID NO 28
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 28 tcgatacccca tgattcctcc ct                                          22

<210> SEQ ID NO 29
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 29
cagcgatcaa caggcgagac                                              20

<210> SEQ ID NO 30
<211> LENGTH: 25
<212> TYPE: DNA
<213> ORGANISM: Artificial Sequence
<220> FEATURE:
<223> OTHER INFORMATION: synthetic construct - primer

<400> SEQUENCE: 30
agagatatcc cagcaaacct atcca                                        25

<210> SEQ ID NO 31
<211> LENGTH: 18
<212> TYPE: DNA
<213> ORGANISM: Artificial Sequence
<220> FEATURE:
<223> OTHER INFORMATION: synthetic construct - primer

<400> SEQUENCE: 31
tctgatgcag caggtggg                                                18

<210> SEQ ID NO 32
<211> LENGTH: 24
<212> TYPE: DNA
<213> ORGANISM: Artificial Sequence
<220> FEATURE:
<223> OTHER INFORMATION: synthetic construct - primer

<400> SEQUENCE: 32
agggctctcc agacttctgc tctg                                         24

<210> SEQ ID NO 33
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 33
ttgttgttcc tacgctacat ctc                                          23

<210> SEQ ID NO 34
<211> LENGTH: 19
<212> TYPE: DNA
<213> ORGANISM: Artificial Sequence
<220> FEATURE:
<223> OTHER INFORMATION: synthetic construct - primer
```

```
<400> SEQUENCE: 34
ccgggcacag tcatagcac                                                  19

<210> SEQ ID NO 35
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 35
gaagacgttc atcgcggtc                                                  19

<210> SEQ ID NO 36
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 36
gctgacactt gttgagcaac c                                               21

<210> SEQ ID NO 37
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 37
agccattgct attcgcggat a                                               21

<210> SEQ ID NO 38
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 38
cggaaccgtg tcaaggtaaa g                                               21

<210> SEQ ID NO 39
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 39
gaggcacccc gaaacatgg                                                  19

<210> SEQ ID NO 40
<211> LENGTH: 21
<212> TYPE: DNA
<213> ORGANISM: Artificial Sequence
<220> FEATURE:
<223> OTHER INFORMATION: synthetic cosntruct - primer

<400> SEQUENCE: 40
acttatagcg agttcccacc a                                               21

<210> SEQ ID NO 41
<211> LENGTH: 19
```

```
<212> TYPE: DNA
<213> ORGANISM: Artificial Sequence
<220> FEATURE:
<223> OTHER INFORMATION: synthetic construct - primer

<400> SEQUENCE: 41
cccgaagcgc aactctacg                                                 19

<210> SEQ ID NO 42
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 42
cgctgggact gtgcatagtg                                                20

<210> SEQ ID NO 43
<211> LENGTH: 34
<212> TYPE: DNA
<213> ORGANISM: Artificial Sequence
<220> FEATURE:
<223> OTHER INFORMATION: synthetic construct - primer

<400> SEQUENCE: 43
gcgcgcgttt aaacgaacaa gacttaaagg agcc                                34

<210> SEQ ID NO 44
<211> LENGTH: 30
<212> TYPE: DNA
<213> ORGANISM: Artificial Sequence
<220> FEATURE:
<223> OTHER INFORMATION: synthetic construct - primer

<400> SEQUENCE: 44
cgcgctcgag tctatgttgg tttcctacat                                     30

<210> SEQ ID NO 45
<211> LENGTH: 32
<212> TYPE: DNA
<213> ORGANISM: Artificial Sequence
<220> FEATURE:
<223> OTHER INFORMATION: synthetic construct - primer

<400> SEQUENCE: 45
gcgcgtttaa actagatgcc cggttttcct ca                                  32

<210> SEQ ID NO 46
<211> LENGTH: 32
<212> TYPE: DNA
<213> ORGANISM: Artificial Sequence
<220> FEATURE:
<223> OTHER INFORMATION: synthetic construct - primer

<400> SEQUENCE: 46
cgcgcgctcg agccatacag catttttaaa tg                                  32

<210> SEQ ID NO 47
<211> LENGTH: 32
<212> TYPE: DNA
<213> ORGANISM: Artificial Sequence
<220> FEATURE:
<223> OTHER INFORMATION: synthetic construct - primer

<400> SEQUENCE: 47
``` gcgcgttttaa acagtctgtg gtgtcaccaa tc                                    32

<210> SEQ ID NO 48
<211> LENGTH: 36
<212> TYPE: DNA
<213> ORGANISM: Artificial Sequence
<220> FEATURE:
<223> OTHER INFORMATION: synthetic construct - primer

<400> SEQUENCE: 48
cgcgcgcgcg ctcgagagaa atatttgtca tattct                                 36

<210> SEQ ID NO 49
<211> LENGTH: 33
<212> TYPE: DNA
<213> ORGANISM: Artificial Sequence
<220> FEATURE:
<223> OTHER INFORMATION: synthetic construct - primer

<400> SEQUENCE: 49
ccagtgtctt ttaattcttg tagaatcttc agg                                    33

<210> SEQ ID NO 50
<211> LENGTH: 33
<212> TYPE: DNA
<213> ORGANISM: Artificial Sequence
<220> FEATURE:
<223> OTHER INFORMATION: synthetic construct - primer

<400> SEQUENCE: 50
cctgaagatt ctacaagaat taaaagacac tgg                                    33

<210> SEQ ID NO 51
<211> LENGTH: 32
<212> TYPE: DNA
<213> ORGANISM: Artificial Sequence
<220> FEATURE:
<223> OTHER INFORMATION: synthetic construct - primer

<400> SEQUENCE: 51
gcgcgtttaa accagtgtga cataactgaa ag                                     32

<210> SEQ ID NO 52
<211> LENGTH: 30
<212> TYPE: DNA
<213> ORGANISM: Artificial Sequence
<220> FEATURE:
<223> OTHER INFORMATION: synthetic construct - primer

<400> SEQUENCE: 52
cgcgctcgag cgaacaatga gattttactg                                        30

<210> SEQ ID NO 53
<211> LENGTH: 34
<212> TYPE: DNA
<213> ORGANISM: Artificial Sequence
<220> FEATURE:
<223> OTHER INFORMATION: synthetic construct - primer

<400> SEQUENCE: 53
gtaaagctgt ttattaattt gctgaaggtc tcgc                                   34

<210> SEQ ID NO 54
<211> LENGTH: 34
<212> TYPE: DNA
<213> ORGANISM: Artificial Sequence
<220> FEATURE:
<223> OTHER INFORMATION: synthetic construct - primer

<400> SEQUENCE: 54
gcgagacctt cagcaaatta ataaacagct ttac                                 34

<210> SEQ ID NO 55
<211> LENGTH: 35
<212> TYPE: DNA
<213> ORGANISM: Artificial Sequence
<220> FEATURE:
<223> OTHER INFORMATION: synthetic construct - primer

<400> SEQUENCE: 55
gtcagataaa ttaatttgtt accaatgcta atggc                                35

<210> SEQ ID NO 56
<211> LENGTH: 35
<212> TYPE: DNA
<213> ORGANISM: Artificial Sequence
<220> FEATURE:
<223> OTHER INFORMATION: synthetic construct - primer

<400> SEQUENCE: 56
gccattagca ttggtaacaa attaatttat ctgac                                35

<210> SEQ ID NO 57
<211> LENGTH: 33
<212> TYPE: DNA
<213> ORGANISM: Artificial Sequence
<220> FEATURE:
<223> OTHER INFORMATION: synthetic construct - primer

<400> SEQUENCE: 57
ccagtgtctt ttaattcttg tagaatcttc agg                                  33

<210> SEQ ID NO 58
<211> LENGTH: 33
<212> TYPE: DNA
<213> ORGANISM: Artificial Sequence
<220> FEATURE:
<223> OTHER INFORMATION: synthetic construct - primer

<400> SEQUENCE: 58
cctgaagatt ctacaagaat taaaagacac tgg                                  33

<210> SEQ ID NO 59
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 59
tgctacttca tcgaccccat                                                 20

<210> SEQ ID NO 60
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 60
aaagacctca ccctccatct                                                 20

```
<210> SEQ ID NO 61
<211> LENGTH: 18
<212> TYPE: DNA
<213> ORGANISM: Artificial Sequence
<220> FEATURE:
<223> OTHER INFORMATION: synthetic construct - primer

<400> SEQUENCE: 61
tcagccacca tcacagaa                                                   18

<210> SEQ ID NO 62
<211> LENGTH: 17
<212> TYPE: DNA
<213> ORGANISM: Artificial Sequence
<220> FEATURE:
<223> OTHER INFORMATION: synthetic construct - primer

<400> SEQUENCE: 62
ccagggcaca ccgagta                                                    17

<210> SEQ ID NO 63
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 63
ctcccagaac atcacctacc a                                               21

<210> SEQ ID NO 64
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 64
cgtgaacctg ctattgccct                                                 20

<210> SEQ ID NO 65
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 65
ggagaacaca ggcgccgacc                                                 20

<210> SEQ ID NO 66
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 66
cggtcacccg cagcttcaca                                                 20

<210> SEQ ID NO 67
<211> LENGTH: 20
<212> TYPE: DNA
<213> ORGANISM: Artificial Sequence
<220> FEATURE:
<223> OTHER INFORMATION: synthetic construct - primer
```

<400> SEQUENCE: 67
ccatcattgc cacgcctgag                                               20

<210> SEQ ID NO 68
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 68
tccttgtctc catagcagcc ttc                                           23

<210> SEQ ID NO 69
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 69
gcccacaggc ataaaaggcc c                                             21

<210> SEQ ID NO 70
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 70
gcccacaggc ataaaaggcc c                                             21

<210> SEQ ID NO 71
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 71
atgcggggtt cctgatgtgg                                               20

<210> SEQ ID NO 72
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 72
ggcccaggag gaaaagcatg                                               20

<210> SEQ ID NO 73
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 73
ggccgtggtg aaggtggtgg                                               20

<210> SEQ ID NO 74

```
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 74
gctgcgtgga ggccatcgtc                                            20

<210> SEQ ID NO 75
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 75
cggctaccac atccaaggaa                                            20

<210> SEQ ID NO 76
<211> LENGTH: 18
<212> TYPE: DNA
<213> ORGANISM: Artificial Sequence
<220> FEATURE:
<223> OTHER INFORMATION: synthetic construct - primer

<400> SEQUENCE: 76
gctggaatta ccgcggct                                              18

<210> SEQ ID NO 77
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 77
caaacaccgc atattctcac tca                                        23

<210> SEQ ID NO 78
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 78
cttcctgtgt ccatgtgatc tca                                        23

<210> SEQ ID NO 79
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 79
gaggctgagg caggagaatc g                                          21

<210> SEQ ID NO 80
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 80
```
tgtcgcccag gctggagtg                                              19

<210> SEQ ID NO 81
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 81
tcacgaactc tctggactga a                                           21

<210> SEQ ID NO 82
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 82
acttttgcat atctcgggca taa                                         23

<210> SEQ ID NO 83
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 83
gcaccccaat gtgatctgc                                              19

<210> SEQ ID NO 84
<211> LENGTH: 22
<212> TYPE: DNA
<213> ORGANISM: Artificial Sequence
<220> FEATURE:
<223> OTHER INFORMATION: synthetic construct - primer

<400> SEQUENCE: 84
cgctacacaa gtcgtagtct gg                                          22

<210> SEQ ID NO 85
<211> LENGTH: 23
<212> TYPE: DNA
<213> ORGANISM: Artificial Sequence
<220> FEATURE:
<223> OTHER INFORMATION: synthetic construct - primer

<400> SEQUENCE: 85
aaaattgtcc atcatgtcct cgc                                         23

<210> SEQ ID NO 86
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 86
ccaccaggtc agttgcagtt                                             20

<210> SEQ ID NO 87
<211> LENGTH: 22
<212> TYPE: DNA

```
<213> ORGANISM: Artificial Sequence
<220> FEATURE:
<223> OTHER INFORMATION: synthetic cosntruct - primer

<400> SEQUENCE: 87
ctgtgcaact tcactaagtc ca                                              22

<210> SEQ ID NO 88
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 88
caatctgagg acgaattgcc t                                               21

<210> SEQ ID NO 89
<211> LENGTH: 21
<212> TYPE: DNA
<213> ORGANISM: Artificial Sequence
<220> FEATURE:
<223> OTHER INFORMATION: synthetic construct - primer

<400> SEQUENCE: 89
gaggcgtgac agtgctacat c                                               21

<210> SEQ ID NO 90
<211> LENGTH: 20
<212> TYPE: DNA
<213> ORGANISM: Artificial Sequence
<220> FEATURE:
<223> OTHER INFORMATION: synthetic construct - primer

<400> SEQUENCE: 90
cagggtctag gtcccagtcc                                                 20

<210> SEQ ID NO 91
<211> LENGTH: 19
<212> TYPE: DNA
<213> ORGANISM: Artificial Sequence
<220> FEATURE:
<223> OTHER INFORMATION: synthetic construct - primer

<400> SEQUENCE: 91
tgtctgaggc tcattctgc                                                  19

<210> SEQ ID NO 92
<211> LENGTH: 16
<212> TYPE: DNA
<213> ORGANISM: Artificial Sequence
<220> FEATURE:
<223> OTHER INFORMATION: synthetic construct - primer

<400> SEQUENCE: 92
tggggcaggg aaggca                                                     16

<210> SEQ ID NO 93
<211> LENGTH: 21
<212> TYPE: DNA
<213> ORGANISM: Artificial Sequence
<220> FEATURE:
<223> OTHER INFORMATION: synthetic construct

<400> SEQUENCE: 93
aacctggacg aaatggacaa a                                               21
```

<210> SEQ ID NO 94
<211> LENGTH: 21
<212> TYPE: DNA
<213> ORGANISM: Artificial Sequence
<220> FEATURE:
<223> OTHER INFORMATION: synthetic construct

<400> SEQUENCE: 94
aagtagacca atggaataga a                                              21

<210> SEQ ID NO 95
<211> LENGTH: 21
<212> TYPE: DNA
<213> ORGANISM: Artificial Sequence
<220> FEATURE:
<223> OTHER INFORMATION: synthetic construct

<400> SEQUENCE: 95
aagccactat tactctgata c                                              21

<210> SEQ ID NO 96
<211> LENGTH: 21
<212> TYPE: DNA
<213> ORGANISM: Artificial Sequence
<220> FEATURE:
<223> OTHER INFORMATION: synthetic construc

<400> SEQUENCE: 96
aaggtcaaat ctaagtggat c                                              21

<210> SEQ ID NO 97
<211> LENGTH: 21
<212> TYPE: DNA
<213> ORGANISM: Artificial Sequence
<220> FEATURE:
<223> OTHER INFORMATION: synthetic construct

<400> SEQUENCE: 97
aagtttctgc aaggcaaaag a                                              21

<210> SEQ ID NO 98
<211> LENGTH: 21
<212> TYPE: DNA
<213> ORGANISM: Artificial Sequence
<220> FEATURE:
<223> OTHER INFORMATION: synthetic construct

<400> SEQUENCE: 98
aatggctaag atcaaaaatt c                                              21

<210> SEQ ID NO 99
<211> LENGTH: 680
<212> TYPE: PRT
<213> ORGANISM: Homo sapiens

<400> SEQUENCE: 99

Met Leu Pro Gln Ile Pro Phe Leu Leu Leu Val Ser Leu Asn Leu Val
1               5                   10                  15

His Gly Val Phe Tyr Ala Glu Arg Tyr Gln Met Pro Thr Gly Ile Lys
            20                  25                  30

Gly Pro Leu Pro Asn Thr Lys Thr Gln Phe Phe Ile Pro Tyr Thr Ile
        35                  40                  45

Lys Ser Lys Gly Ile Ala Val Arg Gly Glu Gln Gly Thr Pro Gly Pro

```
                50                  55                  60
Pro Gly Pro Ala Gly Pro Arg Gly His Pro Gly Pro Ser Gly Pro Pro
 65                  70                  75                  80

Gly Lys Pro Gly Tyr Gly Ser Pro Gly Leu Gln Gly Glu Pro Gly Leu
                    85                  90                  95

Pro Gly Pro Pro Gly Pro Ser Ala Val Gly Lys Pro Gly Val Pro Gly
                100                 105                 110

Leu Pro Gly Lys Pro Gly Glu Arg Gly Pro Tyr Gly Pro Lys Gly Asp
                115                 120                 125

Val Gly Pro Ala Gly Leu Pro Gly Pro Arg Gly Pro Pro Gly Pro Pro
130                 135                 140

Gly Ile Pro Gly Pro Ala Gly Ile Ser Val Pro Gly Lys Pro Gly Gln
145                 150                 155                 160

Gln Gly Pro Thr Gly Ala Pro Gly Pro Arg Gly Phe Pro Gly Glu Lys
                165                 170                 175

Gly Ala Pro Gly Val Pro Gly Met Asn Gly Gln Lys Gly Glu Met Gly
                180                 185                 190

Tyr Gly Ala Pro Gly Arg Pro Gly Glu Arg Gly Leu Pro Gly Pro Gln
                195                 200                 205

Gly Pro Thr Gly Pro Ser Gly Pro Pro Gly Val Gly Lys Arg Gly Glu
        210                 215                 220

Asn Gly Val Pro Gly Gln Pro Gly Ile Lys Gly Asp Arg Gly Phe Pro
225                 230                 235                 240

Gly Glu Met Gly Pro Ile Gly Pro Pro Gly Pro Gln Gly Pro Pro Gly
                    245                 250                 255

Glu Arg Gly Pro Glu Gly Ile Gly Lys Pro Gly Ala Ala Gly Ala Pro
                260                 265                 270

Gly Gln Pro Gly Ile Pro Gly Thr Lys Gly Leu Pro Gly Ala Pro Gly
            275                 280                 285

Ile Ala Gly Pro Pro Gly Pro Pro Gly Phe Gly Lys Pro Gly Leu Pro
        290                 295                 300

Gly Leu Lys Gly Glu Arg Gly Pro Ala Gly Leu Pro Gly Gly Pro Gly
305                 310                 315                 320

Ala Lys Gly Glu Gln Gly Pro Ala Gly Leu Pro Gly Lys Pro Gly Leu
                325                 330                 335

Thr Gly Pro Pro Gly Asn Met Gly Pro Gln Gly Pro Lys Gly Ile Pro
                340                 345                 350

Gly Ser His Gly Leu Pro Gly Pro Lys Gly Glu Thr Gly Pro Ala Gly
            355                 360                 365

Pro Ala Gly Tyr Pro Gly Ala Lys Gly Glu Arg Gly Ser Pro Gly Ser
        370                 375                 380

Asp Gly Lys Pro Gly Tyr Pro Gly Lys Pro Gly Leu Asp Gly Pro Lys
385                 390                 395                 400

Gly Asn Pro Gly Leu Pro Gly Pro Lys Gly Asp Pro Gly Val Gly Gly
                405                 410                 415

Pro Pro Gly Leu Pro Gly Pro Val Gly Pro Ala Gly Ala Lys Gly Met
                420                 425                 430

Pro Gly His Asn Gly Glu Ala Gly Pro Arg Gly Ala Pro Gly Ile Pro
            435                 440                 445

Gly Thr Arg Gly Pro Ile Gly Pro Pro Gly Ile Pro Gly Phe Pro Gly
        450                 455                 460

Ser Lys Gly Asp Pro Gly Ser Pro Gly Pro Pro Gly Pro Ala Gly Ile
465                 470                 475                 480
```

```
Ala Thr Lys Gly Leu Asn Gly Pro Thr Gly Pro Pro Gly Pro Pro Gly
                485                 490                 495

Pro Arg Gly His Ser Gly Glu Pro Gly Leu Pro Gly Pro Pro Gly Pro
            500                 505                 510

Pro Gly Pro Pro Gly Gln Ala Val Met Pro Glu Gly Phe Ile Lys Ala
        515                 520                 525

Gly Gln Arg Pro Ser Leu Ser Gly Thr Pro Leu Val Ser Ala Asn Gln
    530                 535                 540

Gly Val Thr Gly Met Pro Val Ser Ala Phe Thr Val Ile Leu Ser Lys
545                 550                 555                 560

Ala Tyr Pro Ala Ile Gly Thr Pro Ile Pro Phe Asp Lys Ile Leu Tyr
                565                 570                 575

Asn Arg Gln Gln His Tyr Asp Pro Arg Thr Gly Ile Phe Thr Cys Gln
            580                 585                 590

Ile Pro Gly Ile Tyr Tyr Phe Ser Tyr His Val His Val Lys Gly Thr
        595                 600                 605

His Val Trp Val Gly Leu Tyr Lys Asn Gly Thr Pro Val Met Tyr Thr
    610                 615                 620

Tyr Asp Glu Tyr Thr Lys Gly Tyr Leu Asp Gln Ala Ser Gly Ser Ala
625                 630                 635                 640

Ile Ile Asp Leu Thr Glu Asn Asp Gln Val Trp Leu Gln Leu Pro Asn
                645                 650                 655

Ala Glu Ser Asn Gly Leu Tyr Ser Ser Glu Tyr Val His Ser Ser Phe
            660                 665                 670

Ser Gly Phe Leu Val Ala Pro Met
        675                 680

<210> SEQ ID NO 100
<211> LENGTH: 3302
<212> TYPE: DNA
<213> ORGANISM: Homo sapiens

<400> SEQUENCE: 100
accttctgca ctgctcatct gggcagagga agcttcagaa agctgccaag gcaccatctc    60
caggaactcc cagcacgcag aatccatctg agaatatgct gccacaaata ccctttttgc   120
tgctagtatc cttgaacttg gttcatggag tgttttacgc tgaacgatac caaatgccca   180
caggcataaa aggcccacta cccaacacca agacacagtt cttcattccc tacaccataa   240
agagtaaagg tatagcagta agaggagagc aaggtactcc tggtccacca ggccctgctg   300
gacctcgagg gcacccaggt ccttctggac caccaggaaa accaggctac ggaagtcctg   360
gactccaagg agagccaggg ttgccaggac caccgggacc atcagctgta gggaaaccag   420
gtgtgccagg actcccagga aaaccaggag agagaggacc atatggacca aaaggagatg   480
ttggaccagc tggcctacca ggaccccggg gcccaccagg accacctgga atccctggac   540
cggctggaat ttctgtgcca ggaaaacctg acaacaggg acccacagga gccccaggac   600 ccagggctt tcctggagaa aagggtgcac caggagtccc tggtatgaat ggacagaaag   660
gggaaatggg atatggtgct cctggtcgtc caggtgagag gggtcttcca ggccctcagg   720
gtcccacagg accatctggc cctcctggag tgggaaaaag aggtgaaaat ggggttccag   780
gacagccagg catcaaaggt gatagaggtt tccgggagag aatgggacca attggcccac   840
caggtcccca aggccctcct ggggaacgag ggccagaagg cattggaaag ccaggagctg   900
ctggagcccc aggccagcca gggattccag gaacaaaagg tctccctggg gctccaggaa   960
```

-continued

```
tagctgggcc cccagggcct cctggctttg ggaaaccagg cttgccaggc ctgaagggag    1020
aaagaggacc tgctggcctt cctggggtc caggtgccaa aggggaacaa gggccagcag    1080
gtcttcctgg gaagccaggt ctgactggac cccctgggaa tatgggaccc caaggaccaa    1140
aaggcatccc gggtagccat ggtctcccag gccctaaagg tgagacaggg ccagctgggc    1200
ctgcaggata ccctggggct aagggtgaaa ggggttcccc tgggtcagat ggaaaaccag    1260
ggtacccagg aaaaccaggt ctcgatggtc ctaagggtaa cccagggtta ccaggtccaa    1320
aaggtgatcc tggagttgga ggacctcctg gtctcccagg ccctgtgggc ccagcaggag    1380
caaagggaat gccggacac aatggagagg ctggcccaag aggtgcccct ggaataccag    1440
gtactagagg ccctattggg ccaccaggca ttccaggatt ccctgggtct aagggatc    1500 caggaagtcc cggtcctcct ggcccagctg gcatagcaac taagggcctc aatggaccca    1560
ccgggccacc agggcctcca ggtccaagag gccactctgg agagcctggt cttccagggc    1620 ccctgggcc tccaggccca ccaggtcaag cagtcatgcc tgagggtttt ataaaggcag    1680
gccaaaggcc cagtctttct gggacccctc ttgttagtgc caaccagggg gtaacaggaa    1740
tgcctgtgtc tgcttttact gttattctct ccaaagctta cccagcaata ggaactccca    1800
taccatttga taaaattttg tataacaggc aacagcatta tgacccaagg actggaatct    1860
ttacttgtca gataccagga atatactatt tttcatacca cgtgcatgtg aaagggactc    1920
atgtttgggt aggcctgtat aagaatggca cccctgtaat gtacacctat gatgaataca    1980
ccaaaggcta cctggatcag gcttcaggga gtgccatcat cgatctcaca gaaaatgacc    2040
aggtgtggct ccagcttccc aatgccgagt caaatggcct actcctct gagtatgtcc    2100 actcctcttt ctcaggattc ctagtggctc aatgtgagt acacacagag ctaatctaaa    2160
tcttgtgcta gaaaaagcat tctctaactc taccccaccc tacaaaatgc atatggaggt    2220
aggctgaaaa gaatgtaatt tttattttct gaaatacaga tttgagctat cagaccaaca    2280
aaccttcccc ctgaaaagtg agcagcaacg taaaaacgta tgtgaagcct ctcttgaatt    2340
tctagttagc aatcttaagg ctctttaagg ttttctccaa tattaaaaaa tatcaccaaa    2400
gaagtcctgc tatgttaaaa acaaacaaca aaaacaaac aacaaaaaaa aaattaaaaa    2460
aaaaaacaga aatagagctc taagttatgt gaaatttgat ttgagaaact cggcatttcc    2520
tttttaaaaa agcctgtttc taactatgaa tatgagaact tctaggaaac atccaggagg    2580
tatcatataa ctttgtagaa cttaaatact tgaatattca aatttaaaag acactgtatc    2640
ccctaaaata tttctgatgg tgcactactc tgaggcctgt atggccccctt tcatcaatat    2700 ctattcaaat atacaggtgc atatatactt gttaaagctc ttatataaaa agccccaaa    2760 atattgaagt tcatctgaaa tgcaaggtgc tttcatcaat gaaccttttc aaacttttct    2820
atgattgcag agaagctttt tataccca gcataacttg gaaacaggta tctgacctat    2880
tcttatttag ttaacacaag tgtgattaat ttgatttctt taattcctta ttgaatctta    2940
tgtgatatga ttttctggat ttacagaaca ttagcacatg taccttgtgc ctcccattca    3000
agtgaagtta taatttacac tgagggtttc aaaattcgac tagaagtgga gatatattat    3060
ttatttatgc actgtactgt atttttatat tgctgtttaa aacttttaag ctgtgcctca    3120
cttattaaag cacaaaatgt tttacctact ccttatttac gacgcaataa aataacatca    3180 atagatttt aggctgaatt aatttgaaag cagcaatttg ctgttctcaa ccattctttc    3240
aaggcttttc attgttcaaa gttaataaaa aagtaggaca ataaagtgat gggtggcttt    3300
``` ta 3302

<210> SEQ ID NO 101
<211> LENGTH: 930
<212> TYPE: PRT
<213> ORGANISM: Homo sapiens

<400> SEQUENCE: 101

```
Met Leu Leu Gly Trp Ala Ser Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Gln Gly
            35                  40                  45

Glu Glu Val Gln Glu Arg Ala Glu Pro Pro Gly His Pro His Pro Leu
50                      55                  60

Ala Gln Arg Arg Ser Lys Gly Leu Val Gln Asn Ile Asp Gln Leu
65                  70                  75                  80

Tyr Ser Gly Gly Gly Lys Val Gly Tyr Leu Val Tyr Ala Gly Gly Arg
                    85                  90                  95

Arg Phe Leu Leu Asp Leu Glu Arg Asp Gly Ser Val Gly Ile Ala Gly
                100                 105                 110

Phe Val Pro Ala Gly Gly Gly Thr Ser Ala Pro Trp Arg His Arg Ser
            115                 120                 125

His Cys Phe Tyr Arg Gly Thr Val Asp Gly Ser Pro Arg Ser Leu Ala
130                 135                 140

Val Phe Asp Leu Cys Gly Gly Leu Asp Gly Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
    290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365
```

```
Asp Leu Cys Gly His His Ser Cys Asp Thr Leu Gly Met Ala Asp Val
    370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
                420                 425                 430

Thr Glu Asp Lys Arg Leu Met Ser Ile Leu Thr Ser Ile Asp Ala
            435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln
                485                 490                 495

Cys Asn Leu Thr Phe Gly Pro Glu Tyr Ser Val Cys Pro Gly Met Asp
                500                 505                 510

Val Cys Ala Arg Leu Trp Cys Ala Val Val Arg Gln Gly Gln Met Val
            515                 520                 525

Cys Leu Thr Lys Lys Leu Pro Ala Val Glu Gly Thr Pro Cys Gly Lys
530                 535                 540

Gly Arg Ile Cys Leu Gln Gly Lys Cys Val Asp Lys Thr Lys Lys Lys
545                 550                 555                 560

Tyr Tyr Ser Thr Ser Ser His Gly Asn Trp Gly Ser Trp Gly Ser Trp
                565                 570                 575

Gly Gln Cys Ser Arg Ser Cys Gly Gly Gly Val Gln Phe Ala Tyr Arg
                580                 585                 590

His Cys Asn Asn Pro Ala Pro Arg Asn Asn Gly Arg Tyr Cys Thr Gly
            595                 600                 605

Lys Arg Ala Ile Tyr Arg Ser Cys Ser Leu Met Pro Cys Pro Pro Asn
610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
                660                 665                 670

Gly Thr Gly Tyr Tyr Val Val Phe Ser Pro Lys Val Thr Asp Gly Thr
            675                 680                 685

Glu Cys Arg Leu Tyr Ser Asn Ser Val Cys Val Arg Gly Lys Cys Val
690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
                725                 730                 735

Thr Phe Asn Lys Lys Ser Lys Gly Tyr Thr Asp Val Val Arg Ile Pro
            740                 745                 750

Glu Gly Ala Thr His Ile Lys Val Arg Gln Phe Lys Ala Lys Asp Gln
                755                 760                 765

Thr Arg Phe Thr Ala Tyr Leu Ala Leu Lys Lys Asn Gly Glu Tyr
770                 775                 780

Leu Ile Asn Gly Lys Tyr Met Ile Ser Thr Ser Glu Thr Ile Ile Asp
```

```
              785                 790                 795                 800
Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
                820                 825                 830

Gln Ile Leu Ala Thr Asp Pro Thr Lys Pro Leu Asp Val Arg Tyr Ser
                835                 840                 845

Phe Phe Val Pro Lys Lys Ser Thr Pro Lys Val Asn Ser Val Thr Ser
            850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
                900                 905                 910

Cys Pro Leu Ser Gln Arg Pro Ser Ala Phe Lys Gln Cys Leu Leu Lys
                915                 920                 925

Lys Cys
    930

<210> SEQ ID NO 102
<211> LENGTH: 9621
<212> TYPE: DNA
<213> ORGANISM: Homo sapiens

<400> SEQUENCE: 102
acagcgctcg cgctgctctc ggcgctcgca gctgccgact ggggatgacg gcgggcagga      60
ggagaccgca gccgaaggga cacagacacg ccgcttcacc agctcgcctc aggctgcccc     120
cctgcatttt tgttttaatt tttacggctt ttttccctct ctttcttccc ttcctcctgg     180
tcccagcaga gccaaggaaa cccacaaaat aagaaaggaa gtgggccccg gagcttggaa     240
cctccacagc cggcttgtcc agcgcagcgc ggggcggga ggctgcgcgc accagttgcc     300
agcccggtgc gcgtgtacctt tccttacttt tcttgaaaca gcgatcgtgc ctgcatttgg     360
tggttttttg gttttgttt ttttccttt cccgtatttg ctgaatctcc actatccgac     420
tttttttttt taatcttttc tttccccccc ccccaccccc acctctttct ggagcacgaa     480
tccaaacatt ttcccaagca acaaagaaaa gttcgcacgc tggcaccgca gcccggacag     540
gctggcgctg ctgccgggcc cccctccctc cgacacttga ctcaatcctg caagcaagtg     600
tgtgtgtgtc cccatccccc gccccgttaa cttcatagca aataacaaat acccataaag     660
tcccagtcgc gcagcccctc cccgcgggca gcgcactatg ctgctcgggt gggcgtccct     720
gctgctgtgc gcgttccgcc tgccctggc cgcggtcggc ccgccgcga cacctgccca     780 ggataaagcc gggcagcctc cgactgctgc agcagccgcc cagccccgcc ggcggcaggg     840
ggaggaggtg caggagcgag ccgagcctcc cggccaccg caccccctgg cgcagcggcg     900
caggagcaag gggctggtgc agaacatcga ccaactctac tccggcggcg gcaaggtggg     960
ctacctcgtc tacgcgggcg gccggaggtt cctcttggac ctggagcgag atggttcggt    1020
gggcattgct ggcttcgtgc ccgcaggagg cgggacgagt gcgccctggc gccaccggag    1080
ccactgcttc tatcggggca cagtggacgg tagtccccgc tctctggctg tctttgacct    1140
ctgtgggggt ctcgacggct tcttcgcggt caagcacgcg cgctacaccc taaagccact    1200
gctgcgcgga ccctgggcgg aggaagaaaa ggggcgcgtg tacggggatg ggtccgcacg    1260
```

```
gatcctgcac gtctacaccc gcgagggctt cagcttcgag gccctgccgc cgcgcgccag    1320
ctgcgaaacc cccgcgtcca caccggaggc ccacgagcat gctccggcgc acagcaaccc    1380
gagcggacgc gcagcactgg cctcgcagct cttggaccag tccgctctct cgcccgctgg    1440
gggctcagga ccgcagacgt ggtggcgcg cggcgccgc tccatctccc gggcccgcca    1500
ggtggagctg cttctggtgg ctgacgcgtc catggcgcgg ttgtatggcc ggggcctgca    1560
gcattacctg ctgaccctgg cctccatcgc aataggctg tacagccatg ctagcatcga    1620
gaaccacatc cgcctggccg tggtgaaggt ggtggtgcta ggcgacaagg acaagagcct    1680
ggaagtgagc aagaacgctg ccaccacact caagaacttt tgcaagtggc agcaccaaca    1740
caaccagctg ggagatgacc atgaggagca ctacgatgca gctatcctgt ttactcggga    1800
ggatttatgt gggcatcatt catgtgacac cctgggaatg gcagacgttg gaccatatg    1860 ttctccagag cgcagctgtg ctgtgattga agacgatggc ctccacgcag ccttcactgt    1920
ggctcacgaa atcggacatt tacttggcct ctcccatgac gattccaaat tctgtgaaga    1980
gacctttggt tccacagaag ataagcgctt aatgtcttcc atccttacca gcattgatgc    2040
atctaagccc tggtccaaat gcacttcagc caccatcaca gaattcctgg atgatggcca    2100
tggtaactgt ttgctggacc taccacgaaa gcagatcctg gccccgaag aactcccagg    2160 acagacctac gatgccaccc agcagtgcaa cctgacattc gggcctgagt actccgtgtg    2220
tcccggcatg gatgtctgtg ctcgcctgtg tgtgctgtg tacgccagg ccagatggt    2280 ctgtctgacc aagaagctgc ctgcggtgga agggacgcct tgtggaaagg ggagaatctg    2340
cctgcagggc aaatgtgtgg acaaaaccaa gaaaaatat tattcaacgt caagccatgg    2400
caactgggga tcttggggat cctggggcca gtgttctcgc tcatgtggag gaggagtgca    2460
gtttgcctat cgtcactgta ataaccctgc tcccagaaac aacggacgct actgcacagg    2520
gaagagggcc atctaccgct cctgcagtct catgccctgc ccacccaatg gtaaatcatt    2580
tcgtcatgaa cagtgtgagg ccaaaaatgg ctatcagtct gatgcaaaag gagtcaaaac    2640
ttttgtggaa tgggttccca atatgcagg tgtcctgcca gcggatgtgt gcaagctgac    2700
ctgcagagcc aagggcactg gctactatgt ggtattttct ccaaaggtga ccgatggcac    2760
tgaatgtagg ctgtacagta attccgtctg cgtccggggg aagtgtgtga gaactggctg    2820
tgacggcatc attggctcaa agctgcagta tgacaagtgc ggagtatgtg gaggagacaa    2880
ctccagctgt acaaagattg ttggaacctt taataagaaa agtaagggtt acactgacgt    2940
ggtgaggatt cctgaagggg caacccacat aaaagttcga cagttcaaag ccaaagacca    3000
gactagattc actgcctatt tagccctgaa aaagaaaaac ggtgagtacc ttatcaatgg    3060
aaagtacatg atctccactt cagagactat cattgacatc aatggaacag tcatgaacta    3120
tagcggttgg agccacaggg atgacttcct gcatggcatg gctactctg ccacgaagga    3180 aattctaata gtgcagattc ttgcaacaga ccccactaaa ccattagatg tccgttatag    3240 ctttttgtt cccaagaagt ccactccaaa agtaaactct gtcactagtc atggcagcaa    3300
taaagtggga tcacacactt cgcagccgca gtgggtcacg ggcccatggc tcgcctgctc    3360
taggacctgt gacacaggtt ggcacaccag aacggtgcag tgccaggatg gaaaccggaa    3420
gttagcaaaa ggatgtcctc tctcccaaag gccttctgcg tttaagcaat gcttgttgaa    3480
gaaatgttag cctgtggtta tgatcttatg cacaaagata actggaggat tcagcactga    3540
tgcagtcgtg gtgaacagga ggtctaccta acgcacagaa agtcatgctt cagtgacatt    3600
gtcaacagga gtccaattat gggcagaatc tgctctctgt gaccaaaaga ggatgtgcac    3660
```

-continued

```
tgcttcacgt gacagtggtg accttgcaat atagaaaaac ttgggagtta ttgaacatcc    3720
cctgggctta caagaaacac tgatgaatgt aaaatcaggg gacatttgaa gatggcagaa    3780
ctgtctcccc cttgtcacct acctctgata gaatgtcttt aatggtatca taatcatttt    3840
cacccataat acacagtagc ttcttcttac tgtttgtaaa tacattctcc cttggtatgt    3900
cactttatat cccctggttc tattaaaata tccatatata tttctataaa aaaagtgttt    3960
gaccaaagta ggtctgcagc tatttcaact tccttccgtt tccagaaaga gctgtggata    4020
ttttactgga aattaagaac ttgctgctgt tttaataaga tgtagtatat tttctgacta    4080
caggagataa aatttcagtc aaaaaaccat tttgacagca agtatcttct gagaaatttt    4140
gaaaagtaaa tagatctcag tgtatctagt cacttaaata catacacggg ttcatttact    4200
taaacctttg actgcctgta tttttttcag gtagctagcc aaattaatgc ataatttcag    4260
atgtagaagt agggtttgcg tgtgtgtgtg tgatcatact caagagtcta aaaactagtt    4320
tccttgtgtt ggaaatttaa aaggaaaaaa atcgtatttc actgtgtttt caatttatat    4380
tttcacaact actttctctc tccagagctt tcatctgata tctcacaatg tatgatatac    4440
gtacaaaaca cacagcaagt tttctatcat gtccaacaca ttcaacactg gtataccctcc   4500 taccagcaag cctttaaaat gcatttgtgt ttgcttattt gttttgttca agggttcagt    4560
aagacctaca atgttttgta tttcttgact tattttatta gaaacattaa agatcacttg    4620
gtagttagcc acattgagaa gtggttatca ttgttaatgt ggttaatgcc aaaaagtggt    4680
taatattaat aagactgttt ccacaccata ggcaataatt tcttaattta aaaaatctaa    4740
gtatattcct attgtactaa atattttttcc caactggaaa gcacttgatt gtacccgtaa    4800
gtgtttgagt gatgacatgt gatgattttc agaaagttgt tgttttttgtt tccatagcct    4860 gtttaagtag gttgtaagtt tgaatagtta gacatggaaa ttatttttata agcacacacc    4920 taaagatatc ttttttagatg ataaaatgta cacccccccca tcaccaacct cacaacttag    4980
aaaatctaag ttgtttgatt tcttttgggat ttcttttgtt gtgaaacact gcaaagccaa    5040 ttttttcttta taaaaattca tagtaatcct gccaaatgtg cctattgtta aagatttgca    5100
tgtgaagatc ttagggaacc actgtttgag ttctacaagc tcatgagagt ttattttttat   5160 tataagatgt ttttaatata aaagaattat gtaactgatc actatattac atcatttcag    5220
tgggccagga aaatagatgt cttgctgttt tcagtatttt cttaagaaat tgcttttaaa    5280
acaaataatt gttttacaaa accaataatt atcctttgaa ttttcataga ctgactttgc    5340
ttttgacgta gaaattttttt ttctcaataa attatcactt tgagaaatga ggcctgtaca    5400
aggctgataa cctatatgtg atggagatca cccaatgcca agggcagaaa gcaaacctag    5460
ttaaataggt gagaaaaaaa ataataatcc cagtgccatt tgtctgtgca aagagaatta    5520
ggagagaggt taatgttact tttttccatt ttggaaataa ttttaatcaa gtaactcaaa    5580
tgtgacaaaa tttatttttta ttttttgtgg ttatattccc aacaacatta aaaaatactc    5640
gaggcataaa tgtagttgtc tcctactctg cttctcttac tatactcata catttttaat    5700
atggtttatc aatgattcat gtttccctca aatagtgatg gtttacacct gtcatggaaa    5760
caatcctaga gagctcagag caattaaacc actattccat gcttttaagt agttttctcc    5820
acctttttct tatgagtctc actagattga ctgaggaatg tatgtctaaa ttcctggaga    5880
agatgatatg gattggaaac tgaaattcag agaaatggag tgttcaatag ataccacgaa    5940
ttgtgaacaa agggaaaatt ctatacaact caatctaagt cagtccactt tgacttcgta    6000
```

-continued

```
ctgtctttca ccttttccatt gttgcatctt gaatttttta aaatgtctag aattcaggat    6060
gctaggggct acttctttaa aaaaaaaaaa aaaaaagaat tcgtctgaaa atgctcaggt    6120
ttgtaagaat ctaatctcac ttacataact aagcactcca taataagttt tattaagtac    6180
aaagggagcc agaaaaaatg acatttattt cttctagatc agaaaaattt aaattaagcc    6240
ctgccttgct gtttagaaat atgtgggcat tgttataatt tattcaataa atttatgttc    6300
ctttgccttc ctgtggaaac agttttatcc cactaaacta ggaattaggg gataaatcac    6360
aaacaaaaaa aaagttgcag cactgaaaaa aagtaattta ttgttttttgc aactggtatg    6420 tgaatttgtg tgataaaatt atttattctt atttaacaaa aatatgttca aattttctta    6480
tatttaaaat gttttgctgt tgtcctactt tttaatttat gcttcatgtt tgtgtataaa    6540
gtacactttt acactttgtg agtttacata atatacagca ctggttgctt ttgtatttt    6600 ttacagaaag ctttctgtgt gaagcaggtg tatatgtata tattcctcat gtattcttat    6660
tctgatacta tcattttctt ttccaaggaa attttaatct gtcatgacca atagtgttca    6720
ttacttgtgc ctatgataat aggtttttta catcacatta acactattt ttccaagtca    6780 caaataagaa aaacacttat tcaatgaaac aaggtgcaag ttttaaattt gggtacacaa    6840
atagcctaga agcttcctac agacgctaag acacagccaa taatcagatc ctttcacttc    6900
atcgagaaac ttggacaagt cgatattgat gtattagatg aaagttgtct acacacaact    6960
tctgagggat acaaacgata ataaaaccaa atgttgtctg tttctccttt agaaacacct    7020
cctaaaatta atatcattta gtctctagtg tctgtaggat tctacagatg agcacaaata    7080
gattgggttt gtataacaaa tgctaatagt cataactgtt tctacaaata tggggtgtcc    7140
attaagagaa tgtgatgttt tcctactgct gttgaatccc atggggtgat tataggactt    7200
gaaataggca gagtcacctc tgatgacatc agcttgcctc tgtgatttca cagtctgatc    7260
ctggcaacaa gacaaagcac ccttggacac acagccaatc tctggttgtg atatttcccc    7320
attgattcct tccttgttaa caaggtcatt ttaatggttc aggtgaggac agcagccaga    7380
ttcaaagtcc agaatttgtg ctgttacata gagttcacac tgtcaaataa cattgaattt    7440
aataatgatc aaattttct agtagtcttt ggcagagtgt ataatctcat ggcatgatt    7500 ggtgaatatt actaatctct ttataatgaa agatgcttta caaataccttt atatttgcta    7560 acatttcaaa actactaaat aaatgaaata gccatgtgta cagaaatggt catttaaagc    7620
tttaatagaa ccaaattcaa gacaatgtat catttagaca cacagaaaag gaacttgtat    7680
gttttcccta ttatttttct catttgccaa caatctatag ttttaggtta tcaaacagat    7740
agatcaactt aactggctag tacattgaaa aatcttccta agaatccttt gttagcataa    7800
tctatagaga taatttctca aattatatca tcatgatgca tataaactct ataatgtata    7860
attgtgtttc atttatttaa tgtatgagaa catattgaaa tacaaaacca tgcattagcc    7920
aaaaaattgg aatacaggta gtgttcagat cagcaaaaca ttcagtctgg taaatgcctg    7980
cctggggcta tgatatcatt ctcaatgcag gttttatgga aaaactaaaa gaatatgttg    8040
ttagatgatg ttggttttga aaaaaaaaag acattaacat acacattagt tagcccagtt    8100
aattgcattc tactaatata gttgcacatt agcaataatt ttgctgtctc tggtctttat    8160
tttgtggctt caactaactg gaccatgtgg actgtaaagg tcaaatggaa aaacgagca    8220 gtggcccctc atcctgtaag gtactgctac atcagagtga cctaaaagtc taacactgtg    8280
aggaaaactg tgatttgtag gaaaaaaaaa aaaacaaat aaaaaacagg gcatgctttt    8340 taatttttt ccactttcct ttggcacacc caatgaacaa ttctaatttt tattgaggtg    8400
```

```
ctaacatctt tcgtgaccga ctgtcaaatg tggtattttt gagttactat ttttctacat    8460
gattttacag tttgcaagaa agacctctaa gctttgtgtc acggtagggc acaacttgat    8520
actcaaaatt tgaaaaataa gcacatccaa tgattgtttt gaccaacagt ggtcagtgac    8580
gtaaactgca tgtgcatctg aggacattta aggggtcatt aaaatttgag gagcatcagg    8640
ccggagtagc agactttag atgagtcata tttcagcatt cactaagtcc tcagcattcc    8700
attcaaactg tcgtgtatat ttggcctgat tttttttcaa gctttgcaat aatttatgtt    8760
attggtaaac acttggtgac tatatctcag ccttttcttt aacaactcac aatatattag    8820
aaacacgtct acctatactg agagtatatt tacaatagaa gaacatactg tatgtgactt    8880
tgtaaagcta gacttttgat taagaaatat ataatctctg gatgctattt ttgcattata    8940
cactcaggca caacgtaaac cttgatggct catcttgcta caattacgag ttgaaaaaca    9000
ctacttacgt atttgtatga cctattagtc agaggaaatc atacatatgc tttgtaaata    9060
gactttgcag ataactaaat agactgaaga aatatgttgc atttgataga agcaattgca    9120
taaatatttg gtttctatat tagagtctgt gagtaaagtc aagtaataaa cctaagtagg    9180
tataacagat ttttaaacct tgaaacttgc tttgatggta gagaaaatca ttgaagattt    9240
acatactgta tataagatgt aaaatgtacg ctgcttatta ccctcaatt tccagaagca    9300 atggtatata atgcagttga aaaccaaaa atcttggaaa actaagacgg gtcttgttta    9360
aaatgtctct cagctttggc aaccttcaaa tcttaatcaa ctatttaaag cattactgtg    9420
tcttgtagcc tgcattccac aacagctctg ttattcaggt aaaagacttg aactgagccg    9480
tttgggacct atactgtaat attttcattg aggaacaata tcctatttg taaagcattt    9540 ccctatgtgt gactttaaac tgtaaaatta aacactgctt ttgtgggttc agtgggcata    9600
ataaatataa attgtaaact a                                             9621
```

<210> SEQ ID NO 103
<211> LENGTH: 471
<212> TYPE: PRT
<213> ORGANISM: Homo sapiens

<400> SEQUENCE: 103

Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
                20                  25                  30

Glu Glu Asp Leu Gln Phe Ala Glu Arg Tyr Leu Arg Ser Tyr Tyr His
            35                  40                  45

Pro Thr Asn Leu Ala Gly Ile Leu Lys Glu Asn Ala Ala Ser Ser Met
        50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140

Trp Ser Asp Val Thr Pro Leu Asn Phe Thr Arg Leu His Asp Gly Ile

```
        145                 150                 155                 160
Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Glu Thr Trp Thr
            195                 200                 205

Ser Ser Ser Lys Gly Tyr Asn Leu Phe Leu Val Ala Ala His Glu Phe
210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
            260                 265                 270

Pro Asn Pro Lys His Pro Lys Thr Pro Asp Lys Cys Asp Pro Ser Leu
            275                 280                 285

Ser Leu Asp Ala Ile Thr Ser Leu Arg Gly Glu Thr Met Ile Phe Lys
290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
            340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
            420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
450                 455                 460

Ala Asn Ser Ile Leu Trp Cys
465                 470
```

<210> SEQ ID NO 104
<211> LENGTH: 2714
<212> TYPE: DNA
<213> ORGANISM: Homo sapiens

<400> SEQUENCE: 104

```
aacagtcccc aggcatcacc attcaagatg catccagggg tcctggctgc cttcctcttc      60
ttgagctgga ctcattgtcg ggccctgccc cttccagtg gtggtgatga agatgatttg     120
tctgaggaag acctccagtt tgcagagcgc tacctgagat catactacca tcctacaaat    180
ctcgcgggaa tcctgaagga gaatgcagca agctccatga ctgagaggct ccagaaaatg    240
cagtctttct tcggcttaga ggtgactggc aaacttgacg ataacacctt agatgtcatg    300
```

```
aaaaagccaa gatgcgggt tcctgatgtg ggtgaataca atgttttccc tcgaactctt    360
aaatggtcca aaatgaattt aacctacaga attgtgaatt acacccctga tatgactcat   420
tctgaagtcg aaaaggcatt caaaaaagcc ttcaaagttt ggtccgatgt aactcctctg   480
aattttacca gacttcacga tggcattgct gacatcatga tctctttttgg aattaaggag  540
catggcgact tctacccatt tgatgggccc tctggcctgc tggctcatgc ttttcctcct   600
gggccaaatt atggaggaga tgcccatttt gatgatgatg aaacctggac aagtagttcc   660
aaaggctaca acttgtttct tgttgctgcg catgagttcg gccactcctt aggtcttgac   720
cactccaagg accctggagc actcatgttt cctatctaca cctacaccgg caaaagccac   780
tttatgcttc ctgatgacga tgtacaaggg atccagtctc tctatggtcc aggagatgaa   840
gaccccaacc ctaaacatcc aaaaacgcca gacaaatgtg acccttcctt atcccttgat   900
gccattacca gtctccgagg agaaacaatg atctttaaag acagattctt ctggcgcctg   960
catcctcagc aggttgatgc ggagctgttt taacgaaat cattttggcc agaacttccc   1020
aaccgtattg atgctgcata tgagcaccct tctcatgacc tcatcttcat cttcagaggt   1080
agaaaatttt gggctcttaa tggttatgac attctggaag gttatcccaa aaaaatatct   1140
gaactgggtc ttccaaaaga agttaagaag ataagtgcag ctgttcactt tgaggataca   1200
ggcaagactc tcctgttctc aggaaaccag gtctggagat atgatgatac taaccatatt   1260
atggataaag actatccgag actaatagaa gaagacttcc caggaattgg tgataaagta   1320
gatgctgtct atgagaaaaa tggttatatc tattttttca acggacccat acagtttgaa   1380
tacagcatct ggagtaaccg tattgttcgc gtcatgccag caaattccat tttgtggtgt   1440
taagtgtctt tttaaaaatt gttatttaaa tcctgaagag catttgggt aatacttcca   1500
gaagtgcggg gtaggggaag aagagctatc aggagaaagc ttggttctgt gaacaagctt   1560
cagtaagtta tctttgaata tgtagtatct atatgactat gcgtggctgg aaccacattg   1620
aagaatgtta gagtaatgaa atggaggatc tctaaagagc atctgattct tgttgctgta   1680
caaaagcaat ggttgatgat acttcccaca ccacaaatgg gacacatggt ctgtcaatga   1740
gagcataatt taaaaatata tttataagga aattttacaa gggcataaag taaatacatg   1800
catataatga ataaatcatt cttactaaaa agtataaaat agtatgaaaa tggaaatttg   1860
ggagagccat acataaaaga aataaaccaa aggaaaatgt ctgtaataat agactgtaac   1920
ttccaaataa ataattttca ttttgcactg aggatattca gatgtatgtg cccttcttca   1980
cacagacact aacgaaatat caaagtcatt aaagacagga gacaaaagag cagtggtaag   2040
aatagtagat gtggccttg aattctgttt aattttcact tttggcaatg actcaaagtc   2100
tgctctcata taagacaaat attcctttgc atattataaa ggataaagaa ggatgatgtc   2160
tttttattaa aatatttcag gttcttcaga agtcacacat tacaaagtta aaattgttat   2220
caaaatagtc taaggccatg gcatcccttt ttcataaatt atttgattat ttaagactaa   2280
aagttgcatt ttaaccctat tttacctagc taattattta attgtccagt tgtcttgga   2340
tatataggct attttctaaa gacttgtata gcatgaaata aaatatatct tataaagtgg   2400
aagtatgtat attaaaaaag agacatccaa atttttttt aaagcagtct actagattgt   2460
gatcccttga gatatggaag gatgcctttt ttctctgca tttaaaaaa tcccccagca    2520
cttcccacag tgcctattga tacttgggga gggtgcttgg cacttattga atatatgatc   2580
ggccatcaag ggaagaacta ttgtgctcag agacactgtt gataaaaact caggcaaaga   2640
```

-continued

```
aaatgaaatg catatttgca aagtgtatta ggaagtgttt atgttgttta taataaaaat      2700
atattttcaa caga                                                        2714
```

<210> SEQ ID NO 105
<211> LENGTH: 212
<212> TYPE: PRT
<213> ORGANISM: Homo sapiens

<400> SEQUENCE: 105

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 106
<211> LENGTH: 1127
<212> TYPE: DNA
<213> ORGANISM: Homo sapiens

<400> SEQUENCE: 106

```
attctgccct cgagcccacc gggaacgaaa gagaagctct atctcccctc caggagccca       60
gctatgaact ccttctccac aagcgccttc ggtccagttg ccttctccct ggggctgctc      120
ctggtgttgc ctgctgcctt ccctgcccca gtacccccag gagaagattc caaagatgta      180
gccgccccac acagacagcc actcacctct tcagaacgaa ttgacaaaca aattcggtac      240
atcctcgacg gcatctcagc cctgagaaag gagacatgta acaagagtaa catgtgtgaa      300
agcagcaaag aggcactggc agaaaacaac ctgaaccttc caaagatggc tgaaaaagat      360
ggatgcttcc aatctggatt caatgaggag acttgcctgg tgaaaatcat cactggtctt      420
ttggagtttg aggtatacct agagtacctc cagaacagat tgagagtag tgaggaacaa      480 gccagagctg tgcagatgag tacaaaagtc ctgatccagt tcctgcagaa aaaggcaaag      540
```

```
aatctagatg caataaccac ccctgaccca accacaaatg ccagcctgct gacgaagctg      600
caggcacaga accagtggct gcaggacatg acaactcatc tcattctgcg cagctttaag      660
gagttcctgc agtccagcct gagggctctt cggcaaatgt agcatgggca cctcagattg      720
ttgttgttaa tgggcattcc ttcttctggt cagaaacctg tccactgggc acagaactta      780
tgttgttctc tatggagaac taaaagtatg agcgttagga cactatttta attattttta      840
atttattaat atttaaatat gtgaagctga gttaatttat gtaagtcata tttatatttt      900
taagaagtac cacttgaaac attttatgta ttagttttga ataataatg gaaagtggct       960 atgcagtttg aatatccttt gtttcagagc cagatcattt cttggaaagt gtaggcttac     1020
ctcaaataaa tggctaactt atacatattt ttaaagaaat atttatattg tatttatata     1080
atgtataaat ggttttttata ccaataaatg gcattttaaa aaattca                  1127
```

<210> SEQ ID NO 107
<211> LENGTH: 411
<212> TYPE: PRT
<213> ORGANISM: Homo sapiens

<400> SEQUENCE: 107

```
Met Ser Pro Ala Arg Leu Arg Pro Arg Leu His Phe Cys Leu Val Leu
1               5                   10                  15

Leu Leu Leu Val Val Pro Ala Ala Trp Gly Cys Gly Pro Gly Arg
            20                  25                  30

Val Val Gly Ser Arg Arg Arg Pro Pro Arg Lys Leu Val Pro Leu Ala
            35                  40                  45

Tyr Lys Gln Phe Ser Pro Asn Val Pro Glu Lys Thr Leu Gly Ala Ser
        50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270
```

```
Pro Ala His Leu Leu Phe Thr Ala Asp Asn His Thr Glu Pro Ala Ala
            275                 280                 285

Arg Phe Arg Ala Thr Phe Ala Ser His Val Gln Pro Gly Gln Tyr Val
        290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410
```

<210> SEQ ID NO 108
<211> LENGTH: 2473
<212> TYPE: DNA
<213> ORGANISM: Homo sapiens

<400> SEQUENCE: 108

```
actcggcccc gggctgcgcc gcagacggca gcagctcccg ctccgcccga gccgcctgac    60
cgccgggccg gggtgctaac cgcggggccc tgcagcccgc cggcccggcc agcccagccc   120
agcccggcgg cccgcagccc cgccgcccgc cgccccccgc cgccgccgcg ttgccaaaac   180
aaacgggccg gcctatttat tggcggccgg cgagcccggc agctcagagt cgaggcgccg   240
agggggacag cgcgccgcca ccagctcggg ccctgggccc ccgccccgca cttgagtccc   300
gccggccctg ccgcaccacg ccgcccatg gcgcccccgc ctggagcccc ccggagccac    360
ccggacgcct gagcccccgc agcgctcccg tcgacgcgcc tgcccatcag cccaccagga   420
gacctcgccc gccgctcccc cgggctcccc ggccatgtct cccgcccggc tccggccccg   480
actgcacttc tgcctggtcc tgttgctgct gctggtggtg ccggcggcat ggggctgcgg   540
gccgggtcgg gtggtgggca gccgccggcg accgccacgc aaactcgtgc cgctcgccta   600
caagcagttc agccccaatg tgcccgagaa gaccctgggc gccagcggac gctatgaagg   660
caagatcgct cgcagctccg agcgcttcaa ggagctcacc cccaattaca atccagacat   720
catcttcaag gacgaggaga acacaggcgc cgaccgcctc atgacccagc gctgcaagga   780
ccgcctgaac tcgctggcta tctcggtgat gaaccagtgg ccggtgtga agctgcgggt   840
gaccgagggc tgggacgagg acggccacca ctcagaggag tccctgcatt atgagggccg   900
cgcggtggac atcaccacat cagaccgcga ccgcaataag tatggactgc tggcgcgctt   960
ggcagtggag gccggctttg actgggtgta ttacgagtca aaggcccacg tgcattgctc  1020
cgtcaagtcc gagcactcgg ccgcagccaa gacgggcggc tgcttccctg ccggagccca  1080
ggtacgcctg gagagtgggg cgcgtgtggc cttgtcagcc gtgaggccgg agaccgtgt   1140
gctggccatg ggggaggatg ggagcccac cttcagcgat gtgctcattt tcctggaccg  1200
cgagcctcac aggctgagag ccttccaggt catcgagact caggaccccc acgccgcct   1260
ggcactcaca cccgctcacc tgctctttac ggctgacaat cacacggagc cggcagcccg  1320
```

-continued

```
cttccgggcc acatttgcca gccacgtgca gcctggccag tacgtgctgg tggctggggt    1380
gccaggcctg cagcctgccc gcgtggcagc tgtctctaca cacgtggccc tcggggccta    1440
cgccccgctc acaaagcatg ggacactggt ggtggaggat gtggtggcat cctgcttcgc    1500
ggccgtggct gaccaccacc tggctcagtt ggccttctgg cccctgagac tctttcacag    1560
cttggcatgg ggcagctgga ctccggggga gggtgtgcat tggtaccccc agctgctcta    1620
ccgcctgggg cgtctcctgc tagaagaggg cagcttccac ccactgggca tgtccggggc    1680
agggagctga aaggactcca ccgctgccct cctggaactg ctgtactggg tccagaagcc    1740
tctcagccag gagggagctg gccctggaag ggacctgagc tggggacac tggctcctgc    1800 catctcctct gccatgaaga tacaccattg agacttgact gggcaacacc agcgtccccc    1860 accccgtcg tggtgtagtc atagagctgc aagctgagct ggcgagggga tggttgttga    1920
cccctctctc ctagagacct tgaggctggc acggcgactc ccaactcagc ctgctctcac    1980
tacgagtttt catactctgc ctcccccatt ggggagggcc cattccatcc atcttaggcc    2040
cctttgggtg ggcttgcgcc tcagttgatg ctgctaaatt ccctgggagc cagcatggat    2100
ctggctggac ccgatgctgt ccagaactgg aaggccaca ggggtggggc agccatcccg    2160
gccattctga ggtatgacat tcctccccgg ccacactcct caagacacat ccagagactg    2220
ttgctgtctg tgggcagagt tctgtgttct ggccaatgtg accgtagtgc cggggactgg    2280
gggaggtggg ttggatgtgc ttgccacccc cccggctaag ctccccttc tgctgaacca    2340 tgatccccac cccctccgcc ggtcagtctc ccatacctta tttattggag tggagggggaa    2400 agcccatggg agaattttgg ggatgttttg gtcttttctt ccttttgtaa taaaaattat    2460
ttaagttgtt aga                                                      2473
```

<210> SEQ ID NO 109
<211> LENGTH: 489
<212> TYPE: PRT
<213> ORGANISM: Homo sapiens

<400> SEQUENCE: 109

```
Met Ala Leu Leu Phe Leu Leu Pro Leu Val Met Gln Gly Val Ser Arg
1               5                   10                  15

Ala Glu Met Gly Thr Ala Asp Leu Gly Pro Ser Ser Val Pro Thr Pro
            20                  25                  30

Thr Asn Val Thr Ile Glu Ser Tyr Asn Met Asn Pro Ile Val Tyr Trp
        35                  40                  45

Glu Tyr Gln Ile Met Pro Gln Val Pro Val Phe Thr Val Glu Val Lys
    50                  55                  60

Asn Tyr Gly Val Lys Asn Ser Glu Trp Ile Asp Ala Cys Ile Asn Ile
65                  70                  75                  80

Ser His His Tyr Cys Asn Ile Ser Asp His Val Gly Asp Pro Ser Asn
                85                  90                  95

Ser Leu Trp Val Arg Val Lys Ala Arg Val Gly Gln Lys Glu Ser Ala
            100                 105                 110

Tyr Ala Lys Ser Glu Glu Phe Ala Val Cys Arg Asp Gly Lys Ile Gly
        115                 120                 125

Pro Pro Lys Leu Asp Ile Arg Lys Glu Glu Lys Gln Ile Met Ile Asp
    130                 135                 140

Ile Phe His Pro Ser Val Phe Val Asn Gly Asp Glu Gln Glu Val Asp
145                 150                 155                 160
```

```
Tyr Asp Pro Glu Thr Thr Cys Tyr Ile Arg Val Tyr Asn Val Tyr Val
                165                 170                 175

Arg Met Asn Gly Ser Glu Ile Gln Tyr Lys Ile Leu Thr Gln Lys Glu
            180                 185                 190

Asp Asp Cys Asp Glu Ile Gln Cys Gln Leu Ala Ile Pro Val Ser Ser
        195                 200                 205

Leu Asn Ser Gln Tyr Cys Val Ser Ala Glu Gly Val Leu His Val Trp
    210                 215                 220

Gly Val Thr Thr Glu Lys Ser Lys Glu Val Cys Ile Thr Ile Phe Asn
225                 230                 235                 240

Ser Ser Ile Lys Gly Ser Leu Trp Ile Pro Val Val Ala Ala Leu Leu
                245                 250                 255

Leu Phe Leu Val Leu Ser Leu Val Phe Ile Cys Phe Tyr Ile Lys Lys
            260                 265                 270

Ile Asn Pro Leu Lys Glu Lys Ser Ile Ile Leu Pro Lys Ser Leu Ile
        275                 280                 285

Ser Val Val Arg Ser Ala Thr Leu Glu Thr Lys Pro Glu Ser Lys Tyr
    290                 295                 300

Val Ser Leu Ile Thr Ser Tyr Gln Pro Phe Ser Leu Glu Lys Glu Val
305                 310                 315                 320

Val Cys Glu Glu Pro Leu Ser Pro Ala Thr Val Pro Gly Met His Thr
                325                 330                 335

Glu Asp Asn Pro Gly Lys Val Glu His Thr Glu Leu Ser Ser Ile
            340                 345                 350

Thr Glu Val Val Thr Thr Glu Glu Asn Ile Pro Asp Val Val Pro Gly
        355                 360                 365

Ser His Leu Thr Pro Ile Glu Arg Glu Ser Ser Ser Pro Leu Ser Ser
    370                 375                 380

Asn Gln Ser Glu Pro Gly Ser Ile Ala Leu Asn Ser Tyr His Ser Arg
385                 390                 395                 400

Asn Cys Ser Glu Ser Asp His Ser Arg Asn Gly Phe Asp Thr Asp Ser
                405                 410                 415

Ser Cys Leu Glu Ser His Ser Ser Leu Ser Asp Ser Glu Phe Pro Pro
            420                 425                 430

Asn Asn Lys Gly Glu Ile Lys Thr Glu Gly Gln Glu Leu Ile Thr Val
        435                 440                 445

Ile Lys Ala Pro Thr Ser Phe Gly Tyr Asp Lys Pro His Val Leu Val
    450                 455                 460

Asp Leu Leu Val Asp Asp Ser Gly Lys Glu Ser Leu Ile Gly Tyr Arg
465                 470                 475                 480

Pro Thr Glu Asp Ser Lys Glu Phe Ser
                485

<210> SEQ ID NO 110
<211> LENGTH: 2138
<212> TYPE: DNA
<213> ORGANISM: Homo sapiens

<400> SEQUENCE: 110
acagaccccg gtgacggaag tgacgtaagg ccggggctgg agggcagtgc tgggctggtc      60
ccgcaggcgc tcggggttgg agccagcgac cgtcggtagc agcatggctc tcctctttct     120
cctacccctt gtcatgcagg gtgtgagcag ggctgagatg ggcaccgcgg atctggggcc     180
gtcctcagtg cctacaccaa ctaatgttac aattgaatcc tataacatga acccta tcgt     240
```

```
atattgggag taccagatca tgccacaggt ccctgttttt accgtagagg taaagaacta    300
tggtgttaag aattcagaat ggattgatgc ctgcatcaat atttctcatc attattgtaa    360
tatttctgat catgttggtg atccatcaaa ttctctttgg gtcagagtta aagccagggt    420
tggacaaaaa gaatctgcct atgcaaagtc agaagaattt gctgtatgcc agatggaaa    480
aattggacca cctaaactgg atatcagaaa ggaggagaag caaatcatga ttgacatatt    540
tcacccttca gtttttgtaa atggagacga gcaggaagtc gattatgatc ccgaaactac    600
ctgttacatt agggtgtaca atgtgtatgt gagaatgaac ggaagtgaga tccagtataa    660
aatactcacg cagaaggaag atgattgtga cgagattcag tgccagttag cgattccagt    720
atcctcactg aattctcagt actgtgtttc agcagaagga gtcttacatg tgtgggtgt    780
tacaactgaa aagtcaaaag aagtttgtat taccattttc aatagcagta taaaaggttc    840
tctttggatt ccagttgttg ctgctttact actctttcta gtgcttagcc tggtattcat    900
ctgtttttat attaagaaaa ttaatccatt gaaggaaaaa agcataatat acccaagtc    960
cttgatctct gtggtaagaa gtgctacttt agagacaaaa cctgaatcaa aatatgtatc    1020
actcatcacg tcataccagc cattttcctt agaaaggag gtggtctgtg aagagccgtt    1080
gtctccagca acagttccag gcatgcatac cgaagacaat ccaggaaaag tggaacatac    1140
agaagaactt tctagtataa cagaagtggt gactactgaa gaaatattc ctgacgtggt    1200
cccgggcagc catctgactc aatagagag agagagttct tcacctttaa gtagtaacca    1260
gtctgaacct ggcagcatcg ctttaaactc gtatcactcc agaaattgtt ctgagagtga    1320
tcactccaga aatggttttg atactgattc cagctgtctg gaatcacata gctccttatc    1380
tgactcagaa tttcccccaa ataataaagg tgaaataaaa acagaaggac aagagctcat    1440
aaccgtaata aaagccccca cctcctttgg ttatgataaa ccacatgtgc tagtggatct    1500
acttgtggat gatagcggta aagagtcctt gattggttat agaccaacag aagattccaa    1560
agaattttca tgagatcagc taagttgcac caactttgaa gtctgatttt cctggacagt    1620
tttctgcttt aatttcatga aaagattatg atctcagaaa ttgtatctta gttggtatca    1680
accaaatgga gtgacttagt gtacatgaaa gcgtaaagag gatgtgtggc attttcactt    1740
ttggcttgta agtacagac ttttttttt ttttaaacaa aaaaagcatt gtaacttatg    1800
aaccttaca tccagatagg ttaccagtaa cggaacagta tccagtactc ctggttccta    1860
ggtgagcagg tgatgcccca gggacctttg tagccacttc acttttttc ttttctctgc    1920
cttggtatag catatgtttt tgtaagttta tgcatacagt aattttaagt aatttcagaa    1980
gaaattctgc aagcttttca aaattggact taaaatctaa ttcaaactaa tagaattaat    2040
ggaatatgta aatagaaacg tgtatatttt ttatgaaaca ttacagttag agatttttaa    2100
ataaagaatt ttaaaactcg aaaaaaaaaa aaaaaaa                              2138
```

<210> SEQ ID NO 111
<211> LENGTH: 2431
<212> TYPE: PRT
<213> ORGANISM: Homo sapiens

<400> SEQUENCE: 111

Met Thr Thr Leu Leu Trp Val Phe Val Thr Leu Arg Val Ile Thr Ala
1               5                   10                  15

Ala Val Thr Val Glu Thr Ser Asp His Asp Asn Ser Leu Ser Val Ser
                20                  25                  30

Ile Pro Gln Pro Ser Pro Leu Arg Val Leu Leu Gly Thr Ser Leu Thr

```
                35                  40                  45
Ile Pro Cys Tyr Phe Ile Asp Pro Met His Pro Val Thr Thr Ala Pro
 50                  55                  60

Ser Thr Ala Pro Leu Ala Pro Arg Ile Lys Trp Ser Arg Val Ser Lys
 65                  70                  75                  80

Glu Lys Glu Val Val Leu Leu Val Ala Thr Glu Gly Arg Val Arg Val
                 85                  90                  95

Asn Ser Ala Tyr Gln Asp Lys Val Ser Leu Pro Asn Tyr Pro Ala Ile
                100                 105                 110

Pro Ser Asp Ala Thr Leu Glu Val Gln Ser Leu Arg Ser Asn Asp Ser
                115                 120                 125

Gly Val Tyr Arg Cys Glu Val Met His Gly Ile Glu Asp Ser Glu Ala
                130                 135                 140

Thr Leu Glu Val Val Lys Gly Ile Val Phe His Tyr Arg Ala Ile
145                 150                 155                 160

Ser Thr Arg Tyr Thr Leu Asp Phe Asp Arg Ala Gln Arg Ala Cys Leu
                165                 170                 175

Gln Asn Ser Ala Ile Ile Ala Thr Pro Glu Gln Leu Gln Ala Ala Tyr
                180                 185                 190

Glu Asp Gly Phe His Gln Cys Asp Ala Gly Trp Leu Ala Asp Gln Thr
                195                 200                 205

Val Arg Tyr Pro Ile His Thr Pro Arg Glu Gly Cys Tyr Gly Asp Lys
210                 215                 220

Asp Glu Phe Pro Gly Val Arg Thr Tyr Gly Ile Arg Asp Thr Asn Glu
225                 230                 235                 240

Thr Tyr Asp Val Tyr Cys Phe Ala Glu Glu Met Glu Gly Glu Val Phe
                245                 250                 255

Tyr Ala Thr Ser Pro Glu Lys Phe Thr Phe Gln Glu Ala Ala Asn Glu
                260                 265                 270

Cys Arg Arg Leu Gly Ala Arg Leu Ala Thr Thr Gly Gln Leu Tyr Leu
                275                 280                 285

Ala Trp Gln Ala Gly Met Asp Met Cys Ser Ala Gly Trp Leu Ala Asp
290                 295                 300

Arg Ser Val Arg Tyr Pro Ile Ser Lys Ala Arg Pro Asn Cys Gly Gly
305                 310                 315                 320

Asn Leu Leu Gly Val Arg Thr Val Tyr Val His Ala Asn Gln Thr Gly
                325                 330                 335

Tyr Pro Asp Pro Ser Ser Arg Tyr Asp Ala Ile Cys Tyr Thr Gly Glu
                340                 345                 350

Asp Phe Val Asp Ile Pro Glu Asn Phe Phe Gly Val Gly Gly Glu Glu
                355                 360                 365

Asp Ile Thr Val Gln Thr Val Thr Trp Pro Asp Met Glu Leu Pro Leu
                370                 375                 380

Pro Arg Asn Ile Thr Glu Gly Glu Ala Arg Gly Ser Val Ile Leu Thr
385                 390                 395                 400

Val Lys Pro Ile Phe Glu Val Ser Pro Ser Pro Leu Glu Pro Glu Glu
                405                 410                 415

Pro Phe Thr Phe Ala Pro Glu Ile Gly Ala Thr Ala Phe Ala Glu Val
                420                 425                 430

Glu Asn Glu Thr Gly Glu Ala Thr Arg Pro Trp Gly Phe Pro Thr Pro
                435                 440                 445

Gly Leu Gly Pro Ala Thr Ala Phe Thr Ser Glu Asp Leu Val Val Gln
                450                 455                 460
```

```
Val Thr Ala Val Pro Gly Gln Pro His Leu Pro Gly Val Val Phe
465                 470                 475                 480

His Tyr Arg Pro Gly Pro Thr Arg Tyr Ser Leu Thr Phe Glu Glu Ala
                    485                 490                 495

Gln Gln Ala Cys Leu Arg Thr Gly Ala Val Ile Ala Ser Pro Glu Gln
                500                 505                 510

Leu Gln Ala Ala Tyr Glu Ala Gly Tyr Glu Gln Cys Asp Ala Gly Trp
            515                 520                 525

Leu Arg Asp Gln Thr Val Arg Tyr Pro Ile Val Ser Pro Arg Thr Pro
        530                 535                 540

Cys Val Gly Asp Lys Asp Ser Ser Pro Gly Val Arg Thr Tyr Gly Val
545                 550                 555                 560

Arg Pro Ser Thr Glu Thr Tyr Asp Val Tyr Cys Phe Val Asp Arg Leu
                565                 570                 575

Glu Gly Glu Val Phe Phe Ala Thr Arg Leu Glu Gln Phe Thr Phe Gln
                580                 585                 590

Glu Ala Leu Glu Phe Cys Glu Ser His Asn Ala Thr Leu Ala Thr Thr
            595                 600                 605

Gly Gln Leu Tyr Ala Ala Trp Ser Arg Gly Leu Asp Lys Cys Tyr Ala
        610                 615                 620

Gly Trp Leu Ala Asp Gly Ser Leu Arg Tyr Pro Ile Val Thr Pro Arg
625                 630                 635                 640

Pro Ala Cys Gly Gly Asp Lys Pro Gly Val Arg Thr Val Tyr Leu Tyr
                645                 650                 655

Pro Asn Gln Thr Gly Leu Pro Asp Pro Leu Ser Arg His His Ala Phe
                660                 665                 670

Cys Phe Arg Gly Ile Ser Ala Val Pro Ser Pro Gly Glu Glu Glu Gly
            675                 680                 685

Gly Thr Pro Thr Ser Pro Ser Gly Val Glu Glu Trp Ile Val Thr Gln
        690                 695                 700

Val Val Pro Gly Val Ala Ala Val Pro Val Glu Glu Glu Thr Thr Ala
705                 710                 715                 720

Val Pro Ser Gly Glu Thr Thr Ala Ile Leu Glu Phe Thr Thr Glu Pro
                725                 730                 735

Glu Asn Gln Thr Glu Trp Glu Pro Ala Tyr Thr Pro Val Gly Thr Ser
                740                 745                 750

Pro Leu Pro Gly Ile Leu Pro Thr Trp Pro Thr Gly Ala Ala Thr
                755                 760                 765

Glu Glu Ser Thr Glu Gly Pro Ser Ala Thr Glu Val Pro Ser Ala Ser
770                 775                 780

Glu Glu Pro Ser Pro Ser Glu Val Pro Phe Pro Ser Glu Glu Pro Ser
785                 790                 795                 800

Pro Ser Glu Glu Pro Phe Pro Ser Val Arg Pro Phe Pro Ser Val Glu
                805                 810                 815

Leu Phe Pro Ser Glu Glu Pro Phe Pro Ser Lys Glu Pro Ser Pro Ser
                820                 825                 830

Glu Glu Pro Ser Ala Ser Glu Glu Pro Tyr Thr Pro Ser Pro Pro Val
                835                 840                 845

Pro Ser Trp Thr Glu Leu Pro Ser Ser Gly Glu Glu Ser Gly Ala Pro
                850                 855                 860

Asp Val Ser Gly Asp Phe Thr Gly Ser Gly Asp Val Ser Gly His Leu
865                 870                 875                 880
```

Asp Phe Ser Gly Gln Leu Ser Gly Asp Arg Ala Ser Gly Leu Pro Ser
                885                 890                 895

Gly Asp Leu Asp Ser Ser Gly Leu Thr Ser Thr Val Gly Ser Gly Leu
            900                 905                 910

Pro Val Glu Ser Gly Leu Pro Ser Gly Asp Glu Glu Arg Ile Glu Trp
            915                 920                 925

Pro Ser Thr Pro Thr Val Gly Glu Leu Pro Ser Gly Ala Glu Ile Leu
            930                 935                 940

Glu Gly Ser Ala Ser Gly Val Gly Asp Leu Ser Gly Leu Pro Ser Gly
945                 950                 955                 960

Glu Val Leu Glu Thr Ser Ala Ser Gly Val Gly Asp Leu Ser Gly Leu
            965                 970                 975

Pro Ser Gly Glu Val Leu Glu Thr Thr Ala Pro Gly Val Glu Asp Ile
            980                 985                 990

Ser Gly Leu Pro Ser Gly Glu Val Leu Glu Thr Thr Ala Pro Gly Val
            995                 1000                1005

Glu Asp Ile Ser Gly Leu Pro Ser Gly Glu Val Leu Glu Thr Thr
        1010                1015                1020

Ala Pro Gly Val Glu Asp Ile Ser Gly Leu Pro Ser Gly Glu Val
        1025                1030                1035

Leu Glu Thr Thr Ala Pro Gly Val Glu Asp Ile Ser Gly Leu Pro
        1040                1045                1050

Ser Gly Glu Val Leu Glu Thr Thr Ala Pro Gly Val Glu Asp Ile
        1055                1060                1065

Ser Gly Leu Pro Ser Gly Glu Val Leu Glu Thr Thr Ala Pro Gly
        1070                1075                1080

Val Glu Asp Ile Ser Gly Leu Pro Ser Gly Glu Val Leu Glu Thr
        1085                1090                1095

Ala Ala Pro Gly Val Glu Asp Ile Ser Gly Leu Pro Ser Gly Glu
        1100                1105                1110

Val Leu Glu Thr Ala Ala Pro Gly Val Glu Asp Ile Ser Gly Leu
        1115                1120                1125

Pro Ser Gly Glu Val Leu Glu Thr Ala Ala Pro Gly Val Glu Asp
        1130                1135                1140

Ile Ser Gly Leu Pro Ser Gly Glu Val Leu Glu Thr Ala Ala Pro
        1145                1150                1155

Gly Val Glu Asp Ile Ser Gly Leu Pro Ser Gly Glu Val Leu Glu
        1160                1165                1170

Thr Ala Ala Pro Gly Val Glu Asp Ile Ser Gly Leu Pro Ser Gly
        1175                1180                1185

Glu Val Leu Glu Thr Ala Ala Pro Gly Val Glu Asp Ile Ser Gly
        1190                1195                1200

Leu Pro Ser Gly Glu Val Leu Glu Thr Ala Ala Pro Gly Val Glu
        1205                1210                1215

Asp Ile Ser Gly Leu Pro Ser Gly Glu Val Leu Glu Thr Ala Ala
        1220                1225                1230

Pro Gly Val Glu Asp Ile Ser Gly Leu Pro Ser Gly Glu Val Leu
        1235                1240                1245

Glu Thr Ala Ala Pro Gly Val Glu Asp Ile Ser Gly Leu Pro Ser
        1250                1255                1260

Gly Glu Val Leu Glu Thr Ala Ala Pro Gly Val Glu Asp Ile Ser
        1265                1270                1275

Gly Leu Pro Ser Gly Glu Val Leu Glu Thr Ala Ala Pro Gly Val

```
                  1280                1285               1290

Glu Asp Ile Ser Gly Leu Pro Ser Gly Glu Val Leu Glu Thr Ala
    1295                1300               1305

Ala Pro Gly Val Glu Asp Ile Ser Gly Leu Pro Ser Gly Glu Val
    1310                1315               1320

Leu Glu Thr Ala Ala Pro Gly Val Glu Asp Ile Ser Gly Leu Pro
    1325                1330               1335

Ser Gly Glu Val Leu Glu Thr Ala Ala Pro Gly Val Glu Asp Ile
    1340                1345               1350

Ser Gly Leu Pro Ser Gly Glu Val Leu Glu Thr Ala Ala Pro Gly
    1355                1360               1365

Val Glu Asp Ile Ser Gly Leu Pro Ser Gly Glu Val Leu Glu Thr
    1370                1375               1380

Ala Ala Pro Gly Val Glu Asp Ile Ser Gly Leu Pro Ser Gly Glu
    1385                1390               1395

Val Leu Glu Thr Thr Ala Pro Gly Val Glu Ile Ser Gly Leu
    1400                1405               1410

Pro Ser Gly Glu Val Leu Glu Thr Thr Ala Pro Gly Val Asp Glu
    1415                1420               1425

Ile Ser Gly Leu Pro Ser Gly Glu Val Leu Glu Thr Thr Ala Pro
    1430                1435               1440

Gly Val Glu Glu Ile Ser Gly Leu Pro Ser Gly Glu Val Leu Glu
    1445                1450               1455

Thr Ser Thr Ser Ala Val Gly Asp Leu Ser Gly Leu Pro Ser Gly
    1460                1465               1470

Gly Glu Val Leu Glu Ile Ser Val Ser Gly Val Glu Asp Ile Ser
    1475                1480               1485

Gly Leu Pro Ser Gly Glu Val Val Glu Thr Ser Ala Ser Gly Ile
    1490                1495               1500

Glu Asp Val Ser Glu Leu Pro Ser Gly Glu Gly Leu Glu Thr Ser
    1505                1510               1515

Ala Ser Gly Val Glu Asp Leu Ser Arg Leu Pro Ser Gly Glu Glu
    1520                1525               1530

Val Leu Glu Ile Ser Ala Ser Gly Phe Gly Asp Leu Ser Gly Leu
    1535                1540               1545

Pro Ser Gly Gly Glu Gly Leu Glu Thr Ser Ala Ser Glu Val Gly
    1550                1555               1560

Thr Asp Leu Ser Gly Leu Pro Ser Gly Arg Glu Gly Leu Glu Thr
    1565                1570               1575

Ser Ala Ser Gly Ala Glu Asp Leu Ser Gly Leu Pro Ser Gly Lys
    1580                1585               1590

Glu Asp Leu Val Gly Ser Ala Ser Gly Asp Leu Asp Leu Gly Lys
    1595                1600               1605

Leu Pro Ser Gly Thr Leu Gly Ser Gly Gln Ala Pro Glu Thr Ser
    1610                1615               1620

Gly Leu Pro Ser Gly Phe Ser Gly Glu Tyr Ser Gly Val Asp Leu
    1625                1630               1635

Gly Ser Gly Pro Pro Ser Gly Leu Pro Asp Phe Ser Gly Leu Pro
    1640                1645               1650

Ser Gly Phe Pro Thr Val Ser Leu Val Asp Ser Thr Leu Val Glu
    1655                1660               1665

Val Val Thr Ala Ser Thr Ala Ser Glu Leu Glu Gly Arg Gly Thr
    1670                1675               1680
```

```
Ile Gly Ile Ser Gly Ala Gly Glu Ile Ser Gly Leu Pro Ser Ser
    1685            1690            1695

Glu Leu Asp Ile Ser Gly Arg Ala Ser Gly Leu Pro Ser Gly Thr
    1700            1705            1710

Glu Leu Ser Gly Gln Ala Ser Gly Ser Pro Asp Val Ser Gly Glu
    1715            1720            1725

Ile Pro Gly Leu Phe Gly Val Ser Gly Gln Pro Ser Gly Phe Pro
    1730            1735            1740

Asp Thr Ser Gly Glu Thr Ser Gly Val Thr Glu Leu Ser Gly Leu
    1745            1750            1755

Ser Ser Gly Gln Pro Gly Ile Ser Gly Glu Ala Ser Gly Val Leu
    1760            1765            1770

Tyr Gly Thr Ser Gln Pro Phe Gly Ile Thr Asp Leu Ser Gly Glu
    1775            1780            1785

Thr Ser Gly Val Pro Asp Leu Ser Gly Gln Pro Ser Gly Leu Pro
    1790            1795            1800

Gly Phe Ser Gly Ala Thr Ser Gly Val Pro Asp Leu Val Ser Gly
    1805            1810            1815

Thr Thr Ser Gly Ser Gly Glu Ser Ser Gly Ile Thr Phe Val Asp
    1820            1825            1830

Thr Ser Leu Val Glu Val Ala Pro Thr Thr Phe Lys Glu Glu Glu
    1835            1840            1845

Gly Leu Gly Ser Val Glu Leu Ser Gly Leu Pro Ser Gly Glu Ala
    1850            1855            1860

Asp Leu Ser Gly Lys Ser Gly Met Val Asp Val Ser Gly Gln Phe
    1865            1870            1875

Ser Gly Thr Val Asp Ser Ser Gly Phe Thr Ser Gln Thr Pro Glu
    1880            1885            1890

Phe Ser Gly Leu Pro Ser Gly Ile Ala Glu Val Ser Gly Glu Ser
    1895            1900            1905

Ser Arg Ala Glu Ile Gly Ser Ser Leu Pro Ser Gly Ala Tyr Tyr
    1910            1915            1920

Gly Ser Gly Thr Pro Ser Ser Phe Pro Thr Val Ser Leu Val Asp
    1925            1930            1935

Arg Thr Leu Val Glu Ser Val Thr Gln Ala Pro Thr Ala Gln Glu
    1940            1945            1950

Ala Gly Glu Gly Pro Ser Gly Ile Leu Glu Leu Ser Gly Ala His
    1955            1960            1965

Ser Gly Ala Pro Asp Met Ser Gly Glu His Ser Gly Phe Leu Asp
    1970            1975            1980

Leu Ser Gly Leu Gln Ser Gly Leu Ile Glu Pro Ser Gly Glu Pro
    1985            1990            1995

Pro Gly Thr Pro Tyr Phe Ser Gly Asp Phe Ala Ser Thr Thr Asn
    2000            2005            2010

Val Ser Gly Glu Ser Ser Val Ala Met Gly Thr Ser Gly Glu Ala
    2015            2020            2025

Ser Gly Leu Pro Glu Val Thr Leu Ile Thr Ser Glu Phe Val Glu
    2030            2035            2040

Gly Val Thr Glu Pro Thr Ile Ser Gln Glu Leu Gly Gln Arg Pro
    2045            2050            2055

Pro Val Thr His Thr Pro Gln Leu Phe Glu Ser Ser Gly Lys Val
    2060            2065            2070
```

```
Ser Thr Ala Gly Asp Ile Ser Gly Ala Thr Pro Val Leu Pro Gly
2075                2080                2085

Ser Gly Val Glu Val Ser Ser Val Pro Glu Ser Ser Ser Glu Thr
2090                2095                2100

Ser Ala Tyr Pro Glu Ala Gly Phe Gly Ala Ser Ala Ala Pro Glu
2105                2110                2115

Ala Ser Arg Glu Asp Ser Gly Ser Pro Asp Leu Ser Glu Thr Thr
2120                2125                2130

Ser Ala Phe His Glu Ala Asn Leu Glu Arg Ser Ser Gly Leu Gly
2135                2140                2145

Val Ser Gly Ser Thr Leu Thr Phe Gln Glu Gly Glu Ala Ser Ala
2150                2155                2160

Ala Pro Glu Val Ser Gly Glu Ser Thr Thr Thr Ser Asp Val Gly
2165                2170                2175

Thr Glu Ala Pro Gly Leu Pro Ser Ala Thr Pro Thr Ala Ser Gly
2180                2185                2190

Asp Arg Thr Glu Ile Ser Gly Asp Leu Ser Gly His Thr Ser Gln
2195                2200                2205

Leu Gly Val Val Ile Ser Thr Ser Ile Pro Glu Ser Glu Trp Thr
2210                2215                2220

Gln Gln Thr Gln Arg Pro Ala Glu Thr His Leu Glu Ile Glu Ser
2225                2230                2235

Ser Ser Leu Leu Tyr Ser Gly Glu Glu Thr His Thr Val Glu Thr
2240                2245                2250

Ala Thr Ser Pro Thr Asp Ala Ser Ile Pro Ala Ser Pro Glu Trp
2255                2260                2265

Lys Arg Glu Ser Glu Ser Thr Ala Ala Asp Gln Glu Val Cys Glu
2270                2275                2280

Glu Gly Trp Asn Lys Tyr Gln Gly His Cys Tyr Arg His Phe Pro
2285                2290                2295

Asp Arg Glu Thr Trp Val Asp Ala Glu Arg Arg Cys Arg Glu Gln
2300                2305                2310

Gln Ser His Leu Ser Ser Ile Val Thr Pro Glu Glu Gln Glu Phe
2315                2320                2325

Val Asn Asn Asn Ala Gln Asp Tyr Gln Trp Ile Gly Leu Asn Asp
2330                2335                2340

Arg Thr Ile Glu Gly Asp Phe Arg Trp Ser Asp Gly His Pro Met
2345                2350                2355

Gln Phe Glu Asn Trp Arg Pro Asn Gln Pro Asp Asn Phe Phe Ala
2360                2365                2370

Ala Gly Glu Asp Cys Val Val Met Ile Trp His Glu Lys Gly Glu
2375                2380                2385

Trp Asn Asp Val Pro Cys Asn Tyr His Leu Pro Phe Thr Cys Lys
2390                2395                2400

Lys Gly Thr Ala Thr Thr Tyr Lys Arg Arg Leu Gln Lys Arg Ser
2405                2410                2415

Ser Arg His Pro Arg Arg Ser Arg Pro Ser Thr Ala His
2420                2425                2430
```

<210> SEQ ID NO 112
<211> LENGTH: 8543
<212> TYPE: DNA
<213> ORGANISM: Homo sapiens

<400> SEQUENCE: 112

```
cacctacctc cccgccgctc cagaggggc tcgcagagct gaggacgcgc gcagcgctgc    60
tcaaggtctc tctctctcag caccctcgcc ggccggcgtc tgacgcgggt gccagggtct   120
ccgggcacct ttcagtgtcc attccctcag ccagccagga ctccgcaacc cagcagttgc   180
cgctgcggcc acagcccgag gggacctgcg gacaggacgc cggcaggagg aggggtgcgc   240
agcgcccgcg cagagcgtct ccctcgctac gcagcgagac ccgggcctcc cggccccagg   300
agccccagc tgcctcgcca ggtgtgtggg actgaagttc ttggagaagg gagtccaact    360
cttcaaggtg aactatgacc actttactct gggttttcgt gactctgagg gtcatcactg   420
cagctgtcac tgtagaaact tcagaccatg acaactcgct gagtgtcagc atcccccaac   480
cgtccccgct gagggtcctc ctggggacct ccctcaccat ccctgctat ttcatcgacc    540
ccatgcaccc tgtgaccacc gcccttcta ccgccccact ggcccaaga atcaagtgga    600
gccgtgtgtc caaggagaag gaggtagtgc tgctggtggc cactgaaggg cgcgtgcggg   660
tcaacagtgc ctatcaggac aaggtctcac tgcccaacta cccggccatc ccagtgacg    720
ccaccttgga agtccagagc ctgcgctcca atgactctgg ggtctaccgc tgcgaggtga   780
tgcatggcat cgaggacagc gaggccaccc tggaagtcgt ggtgaaaggc atcgtgttcc   840
attacagagc catctctaca cgctacaccc tcgactttga cagggcgcag cgggcctgcc   900
tgcagaacag tgccatcatt gccacgcctg agcagctgca ggccgcctac gaagacggct   960
tccaccagtg tgacgccggc tggctggctg accagactgt cagataccc atccacactc    1020
cccgggaagt ctgctatgga gacaaggatg agtttcctgg tgtgaggacg tatggcatcc   1080
gagacaccaa cgagacctat gatgtgtact gcttcgccga ggagatggag ggtgaggtct   1140
tttatgcaac atctccagag aagttcacct tccaggaagc agccaatgag tgccggcggc   1200
tgggtgcccg gctggccacc acgggccagc tctacctggc ctggcaggct ggcatggaca   1260
tgtgcagcgc cggctggctg gccgaccgca gcgtgcgcta ccccatctcc aaggcccggc   1320
ccaactgcgg tggcaacctc ctgggcgtga ggaccgtcta cgtgcatgcc aaccagacgg   1380
gctaccccga cccctcatcc cgctacgacg ccatctgcta cacaggtgaa gactttgtgg   1440
acatcccaga aaacttcttt ggagtggggg gtgaggagga catcaccgtc cagacagtga   1500
cctggcctga catggagctg ccactgcctc gaaacatcac tgagggtgaa gcccgaggca   1560
gcgtgatcct taccgtaaag cccatcttcg aggtctcccc cagtcccctg gaacccgagg   1620
agcccttcac gtttgcccct gaaataggg ccactgcctt cgctgaggtt gagaatgaga    1680
ctggagaggc caccaggccc tggggctttc ccacacctgg cctgggccct gccacggcat   1740
tcaccagtga ggacctcgtc gtgcaggtga ccgctgtccc tgggcagccg catttgccag   1800
gggggtcgt cttccactac cgcccgggac ccacccgcta ctcgctgacc tttgaggagg   1860
cacagcaggc ctgcctgcgc acggggggcgg tcattgcctc gccggagcag ctccaggccg   1920
cctacgaagc aggctatgag cagtgtgacg ccggctggct gcgggaccag accgtcagat   1980
accccattgt gagccccggg accccatgcg tgggtgacaa ggacagcagc cagggggtca   2040
ggacctatgg cgtgcgccca tcaacagaga cctacgatgt ctactgcttt gtagacagac   2100
ttgaggggga ggtgttcttc gccacacgcc ttgagcagtt caccttccag gaagcactgg   2160
agttctgtga atctcacaat gctacgctgg ccaccacggg ccagctctac gccgcctgga   2220
gccgcggcct ggacaagtgc tatgccggct ggctggccga cggcagcctc cgctacccca   2280
tcgtcacccc aaggcctgcc tgcggtgggg acaagccagg cgtgagaacg gtctacctct   2340
```

```
accctaacca gacgggcctc ccagacccac tgtcccggca ccatgccttc tgcttccgag    2400
gcatttcagc ggttccttct ccaggagaag aagagggtgg cacacccaca tcaccctctg    2460
gtgtggagga gtggatcgtg acccaagtgg ttcctggtgt ggctgctgtc cccgtagaag    2520
aggagacaac tgctgtaccc tcaggggaga ctactgccat cctagagttc accaccgagc    2580
cagaaaacca gacagaatgg gaaccagcct ataccccagt gggcacatcc ccgctgccag    2640
ggatccttcc tacttggcct cccactggcg cagcaacaga ggaaagtaca gaaggccctt    2700
ctgcaactga agtgccctct gcctcagagg aaccatcccc ctcagaggtg ccattcccct    2760
cagaggagcc atcccctca gaggaaccat tccctcagt gaggccattc ccctcagtgg    2820
agctgttccc ctcagaggag ccattcccct ccaaggagcc atcccctca gaggaaccat    2880 cagcctcgga gagccgtat acaccttcac ccccgtgcc cagctggact gagctgccca    2940
gctctgggga ggaatctggg gcccctgatg tcagtggtga cttcacaggc agtggagatg    3000
tttcaggaca ccttgacttc agtgggcagc tgtcagggga cagggcaagt ggactgccct    3060
ctggagacct ggactccagt ggtcttactt ccacagtggg ctcaggcctg cctgtggaaa    3120
gtggactacc ctcaggggat gaagagagaa ttgagtggcc cagcactcct acggttggtg    3180
aactgccctc tggagctgag atcctagagg gctctgcctc tggagttggg gatctcagtg    3240
gacttccttc tggagaagtt ctagagacct ctgcctctgg agtaggagac ctcagtgggc    3300
ttccttctgg agaagttcta gagaccactg ccctggagt agaggacatc agcgggcttc    3360
cttctggaga agttctagag accactgccc ctggagtaga ggacatcagc gggcttcctt    3420
ctggagaagt tctagagacc actgcccctg gagtagagga catcagcggg cttccttctg    3480 agaagttct agagaccact gccctggag tagaggacat cagcgggctt ccttctggag    3540
aagttctaga gaccactgcc cctggagtag aggacatcag cgggcttcct tctggagaag    3600
ttctagagac cactgcccct ggagtagagg acatcagcgg gcttccttct ggagaagttc    3660
tagagaccgt gcccctgga gtagaggaca tcagcgggct tccttctgga gaagttctag    3720
agaccgctgc cctggagta gaggacatca gcgggcttcc ttctggagaa gttctagaga    3780
ccgctgcccc tggagtagag gacatcagcg ggcttcctc tggagaagtt ctagagaccg    3840
ctgcccctgg agtagaggac atcagcgggc ttccttctgg agaagttcta gagaccgctg    3900
cccctggagt agaggacatc agcgggcttc cttctggaga agttctagag accgctgccc    3960
ctggagtaga ggacatcagc gggcttcctt ctggagaagt tctagagacc gctgcccctg    4020
gagtagagga catcagcggg cttccttctg gagaagttct agagactgct gcccctggag    4080
tagaggacat cagcgggctt ccttctggag aagttctaga gactgctgcc cctggagtag    4140
aggacatcag cgggcttcct tctggagaag ttctagagac tgctgcccct ggagtagagg    4200
acatcagcgg gcttccttct ggagaagttc tagagactgc tgcccctgga gtagaggaca    4260
tcagcgggct tccttctgga gaagttctag agactgctgc cctggagta gaggacatca    4320 gcgggcttcc ttctggagaa gttctagaga ctgctgcccc tggagtagag gacatcagcg    4380
ggcttccttc tggagaagtt ctagagactg ctgcccctgg agtagaggac atcagcgggc    4440
ttccttctgg agaagttcta gagactgctg cccctggagt agaggacatc agcgggcttc    4500
cttctggaga agttctagag actgctgccc ctggagtaga ggacatcagc gggcttcctt    4560
ctggagaagt tctagagact actgcccctg gagtagagga gatcagcggg cttccttctg    4620 agaagttct agagactact gccctggag tagatgagat cagtgggctt ccttctggag    4680
aagttctaga gactactgcc cctggagtag aggagatcag cgggcttcct tctggagaag    4740
```

```
ttctagagac ttctacctct gcggtagggg acctcagtgg acttccttct ggaggagaag    4800
ttctagagat ttctgtctct ggagtagagg acatcagtgg gcttccttct ggagaggttg    4860
tagagacttc tgcctctgga atagaggatg tcagtgaact tccttcagga aaggtctag     4920 agacctctgc ttctggagta gaggacctca gcaggctccc ttctggagaa aagttctag     4980 agatttctgc ctctggattt ggggacctca gtggacttcc ttctggagga aaggtctag     5040 agacctctgt ttctgaagta gggactgacc tcagtgggct tccttctgga agggagggtc    5100
tagagacttc agcttctgga gctgaggacc tcagtgggtt gccttctgga aagaagact     5160 tggtggggtc agcttctgga gacttggact tgggcaaact gccttctgga actctaggaa    5220
gtgggcaagc tccagaaaca agtggtcttc cctctggatt tagtggtgag tattctgggg    5280
tggaccttgg aagtggccca ccctctggcc tgcctgactt tagtggactt ccatctggat    5340
tcccaactgt ttccctagtg gattctacat tggtggaagt ggtcacagcc tccactgcaa    5400
gtgaactgga agggagggga accattggca tcagtggtgc aggagaaata tctggactgc    5460
cctccagtga gctggacatt agtgggagag ctagtggact cccttcagga actgaactca    5520
gtggccaagc atctgggtct cctgatgtca gtggggaaat acctggactc tttggtgtca    5580
gtggacagcc atcagggttt cctgacacta gtggggaaac atctggagtg actgagctta    5640
gcgggctgtc ctctggacaa ccaggtatta gtggagaagc atctggagtt ctttatggca    5700
ctagtcaacc ctttggcata actgatctga gtggagaaac atctggggtc cctgatctca    5760
gtgggcagcc ttcagggtta ccaggttca gtggggcaac atcaggagtc cctgacctgg     5820
tttctggtac cacgagtggc agcggtgaat cttctgggat tacatttgtg gacaccagtt    5880
tggttgaagt ggcccctact acatttaaag aagaagaagg cttagggtct gtggaactca    5940
gtggcctccc ttccggagag gcagatctgt caggcaaatc tgggatggtg gatgtcagtg    6000
gacagttttc tggaacagtc gattccagtg ggtttacatc ccagactccg gaattcagtg    6060
gcctaccaag tggcatagct gaggtcagtg gagaatcctc cagagctgag attgggagca    6120
gcctgccctc gggagcatat tatggcagtg gaactccatc tagtttcccc actgtctctc    6180
ttgtagacag aactttggtg gaatctgtaa cccaggctcc aacagcccaa gaggcaggag    6240
aagggccttc tggcattta gaactcagtg gtgctcattc tggagcacca gacatgtctg      6300
gggagcattc tggatttctg gacctaagtg ggctgcagtc cgggctgata gagcccagcg    6360
gagagccacc aggtactcca tattttagtg gggattttgc cagcaccacc aatgtaagtg    6420
gagaatcctc tgtagccatg ggcaccagtg gagaggcctc aggacttcca gaagttactt    6480
taatcacttc tgagttcgtg gagggtgtta ctgaaccaac tatttctcag gaactaggcc    6540
aaaggccccc tgtgacacac acaccccagc tttttgagtc cagtgaaaaa gtctccacag    6600
ctggggacat tagtggagct acccccagtgc tccctgggtc tggagtagaa gtatcatcag   6660
tcccagaatc tagcagtgag acgtccgcct atcctgaagc tgggttcggg gcatctgccg    6720
cccctgaggc cagcagagaa gattctgggt ccctgatct gagtgaaacc acctctgcat     6780
tccacgaagc taaccttgag agatcctctg gcctaggagt gagcggcagc actttgacat    6840
ttcaagaagg cgaggcgtcc gctgcccag aagtgagtgg agaatccacc accaccagtg     6900
atgtggggac agaggcacca ggcttgcctt cagccactcc cacggcttct ggagacagga    6960
ctgaaatcag cggagacctg tctggtcaca cctcgcagct gggcgttgtc atcagcacca    7020
gcatcccaga gtctgagtgg acccagcaga cccagcgccc tgcagagacg catctagaaa    7080
```

```
ttgagtcctc aagcctcctg tactcaggag aagagactca cacagtcgaa acagccacct    7140
ccccaacaga tgcttccatc ccagcttctc cggaatggaa acgtgaatca gaatcaactg    7200
ctgcagacca ggaggtatgt gaggagggct ggaacaagta ccagggccac tgttaccgcc    7260
acttcccgga ccgcgagacc tgggtggatg ctgagcgccg tgtcgggag cagcagtcac     7320 acctgagcag catcgtcacc cccgaggagc aggagtttgt caacaacaat gcccaagact    7380
accagtggat cggcctgaac gacaggacca tcgaagggga cttccgctgg tcagatggac    7440
accccatgca atttgagaac tggcgcccca accagcctga caactttttt gccgctggag    7500
aggactgtgt ggtgatgatc tggcacgaga agggcgagtg gaatgatgtt ccctgcaatt    7560
accacctccc cttcacgtgt aaaaagggca cagccaccac ctacaaacgc agactacaga    7620
agcggagctc acggcaccct cggaggagcc gccccagcac agcccactga aaagagcttc    7680
caggacgcac ccaggacgct gagcccagga gcctgccagg ctgacgtgca tcccacccag    7740
acggtgtcct cttcttgtcg cttttgtca tataaggaat cccattaaag aaggaaaaaa     7800
ataaatccca catttgtgta tgcacccact caccctcca aatcagcaaa accgcatcta     7860
atttgtccgc cgaatgccaa agcaaagcaa acttattata accttggac tgagtttaga     7920 gacatttctt caatttccca tcgtgccttt ccagggacca gtgcagggac agggggagaa    7980 ggggagggt taagttaaat aaagaagatt attttttgttt cctgactta tccaagagca    8040 gtgcaatcgt tggttatttc acctccaggg agagctaggg aggagggagg agggctccaa    8100
aggagctgga aggagcagag gcctgagagc aggaagaact cggaaccgca gctgaatgta    8160
ttggatgaga aggagccagg agggctacac catctgtatg agggaaaagc cttgggggag    8220
aggggtgggt tcctgcctcc tgccgagggt aagccggcag agagagccaa tcagagggac    8280
ctccgctgcc tggagttgg gttcctcca agggtccctc tttcagtgtc ctctctctca     8340
cctgggtctg ccaccctaac aggtggcaac tcggcagggc tgctgggggc acttcctgcc    8400 cagtggggg tgccgcccaa ccttctcccc tccccacccc cgcccccggg accgtgcagg    8460
caccagggtt ccgtgcacct atttatattt ttgaaaactg aagattataa tattataata    8520
ataataaaga cattggaaga gat                                            8543
```

<210> SEQ ID NO 113
<211> LENGTH: 1487
<212> TYPE: PRT
<213> ORGANISM: Homo sapiens

<400> SEQUENCE: 113

```
Met Ile Arg Leu Gly Ala Pro Gln Thr Leu Val Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110
```

```
Lys Asp Ile Val Gly Pro Lys Gly Pro Pro Gly Pro Gln Gly Pro Ala
            115                 120                 125

Gly Glu Gln Gly Pro Arg Gly Asp Arg Gly Asp Lys Gly Glu Lys Gly
130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
            195                 200                 205

Arg Gly Pro Pro Gly Pro Ala Gly Ala Pro Gly Pro Gln Gly Phe Gln
210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
            275                 280                 285

His Arg Gly Tyr Pro Gly Leu Asp Gly Ala Lys Gly Glu Ala Gly Ala
            290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
            355                 360                 365

Gly Ala Pro Gly Ala Lys Gly Glu Ala Gly Pro Thr Gly Ala Arg Gly
370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
```

```
                530             535             540
Asn Gly Asp Pro Gly Arg Pro Gly Glu Pro Gly Leu Pro Gly Ala Arg
545                 550             555                 560

Gly Leu Thr Gly Arg Pro Gly Asp Ala Gly Pro Gln Gly Lys Val Gly
                565             570                 575

Pro Ser Gly Ala Pro Gly Glu Asp Gly Arg Pro Gly Pro Pro Gly Pro
                580             585                 590

Gln Gly Ala Arg Gly Gln Pro Gly Val Met Gly Phe Pro Gly Pro Lys
                595             600             605

Gly Ala Asn Gly Glu Pro Gly Lys Ala Gly Glu Lys Gly Leu Pro Gly
                610             615             620

Ala Pro Gly Leu Arg Gly Leu Pro Gly Lys Asp Gly Glu Thr Gly Ala
625                 630             635                 640

Ala Gly Pro Pro Gly Pro Ala Gly Pro Ala Gly Glu Arg Gly Glu Gln
                645             650             655

Gly Ala Pro Gly Pro Ser Gly Phe Gln Gly Leu Pro Gly Pro Pro Gly
                660             665             670

Pro Pro Gly Glu Gly Gly Lys Pro Gly Asp Gln Gly Val Pro Gly Glu
                675             680             685

Ala Gly Ala Pro Gly Leu Val Gly Pro Arg Gly Glu Arg Gly Phe Pro
690                 695             700

Gly Glu Arg Gly Ser Pro Gly Ala Gln Gly Leu Gln Gly Pro Arg Gly
705                 710             715                 720

Leu Pro Gly Thr Pro Gly Thr Asp Gly Pro Lys Gly Ala Ser Gly Pro
                725             730             735

Ala Gly Pro Pro Gly Ala Gln Gly Pro Pro Gly Leu Gln Gly Met Pro
                740             745             750

Gly Glu Arg Gly Ala Ala Gly Ile Ala Gly Pro Lys Gly Asp Arg Gly
                755             760             765

Asp Val Gly Glu Lys Gly Pro Glu Gly Ala Pro Gly Lys Asp Gly Gly
770                 775             780

Arg Gly Leu Thr Gly Pro Ile Gly Pro Pro Gly Pro Ala Gly Ala Asn
785                 790             795                 800

Gly Glu Lys Gly Glu Val Gly Pro Pro Gly Pro Ala Gly Ser Ala Gly
                805             810             815

Ala Arg Gly Ala Pro Gly Glu Arg Gly Glu Thr Gly Pro Pro Gly Pro
                820             825             830

Ala Gly Phe Ala Gly Pro Pro Gly Ala Asp Gly Gln Pro Gly Ala Lys
                835             840             845

Gly Glu Gln Gly Glu Ala Gly Gln Lys Gly Asp Ala Gly Ala Pro Gly
850                 855             860

Pro Gln Gly Pro Ser Gly Ala Pro Gly Pro Gln Gly Pro Thr Gly Val
865                 870             875                 880

Thr Gly Pro Lys Gly Ala Arg Gly Ala Gln Gly Pro Pro Gly Ala Thr
                885             890             895

Gly Phe Pro Gly Ala Ala Gly Arg Val Gly Pro Pro Gly Ser Asn Gly
                900             905             910

Asn Pro Gly Pro Pro Gly Pro Pro Gly Pro Ser Gly Lys Asp Gly Pro
                915             920             925

Lys Gly Ala Arg Gly Asp Ser Gly Pro Pro Gly Arg Ala Gly Glu Pro
930                 935             940

Gly Leu Gln Gly Pro Ala Gly Pro Pro Gly Glu Lys Gly Glu Pro Gly
945                 950             955                 960
```

-continued

```
Asp Asp Gly Pro Ser Gly Ala Glu Gly Pro Pro Gly Pro Gln Gly Leu
            965                 970                 975
Ala Gly Gln Arg Gly Ile Val Gly Leu Pro Gly Gln Arg Gly Glu Arg
            980                 985                 990
Gly Phe Pro Gly Leu Pro Gly Pro Ser Gly Glu Pro Gly Lys Gln Gly
            995                1000                1005
Ala Pro Gly Ala Ser Gly Asp Arg Gly Pro Pro Gly Pro Val Gly
        1010                1015                1020
Pro Pro Gly Leu Thr Gly Pro Ala Gly Glu Pro Gly Arg Glu Gly
        1025                1030                1035
Ser Pro Gly Ala Asp Gly Pro Pro Gly Arg Asp Gly Ala Ala Gly
        1040                1045                1050
Val Lys Gly Asp Arg Gly Glu Thr Gly Ala Val Gly Ala Pro Gly
        1055                1060                1065
Ala Pro Gly Pro Pro Gly Ser Pro Gly Pro Ala Gly Pro Thr Gly
        1070                1075                1080
Lys Gln Gly Asp Arg Gly Glu Ala Gly Ala Gln Gly Pro Met Gly
        1085                1090                1095
Pro Ser Gly Pro Ala Gly Ala Arg Gly Ile Gln Gly Pro Gln Gly
        1100                1105                1110
Pro Arg Gly Asp Lys Gly Glu Ala Gly Glu Pro Gly Glu Arg Gly
        1115                1120                1125
Leu Lys Gly His Arg Gly Phe Thr Gly Leu Gln Gly Leu Pro Gly
        1130                1135                1140
Pro Pro Gly Pro Ser Gly Asp Gln Gly Ala Ser Gly Pro Ala Gly
        1145                1150                1155
Pro Ser Gly Pro Arg Gly Pro Pro Gly Pro Val Gly Pro Ser Gly
        1160                1165                1170
Lys Asp Gly Ala Asn Gly Ile Pro Gly Pro Ile Gly Pro Pro Gly
        1175                1180                1185
Pro Arg Gly Arg Ser Gly Glu Thr Gly Pro Ala Gly Pro Pro Gly
        1190                1195                1200
Asn Pro Gly Pro Pro Gly Pro Pro Gly Pro Pro Gly Pro Gly Ile
        1205                1210                1215
Asp Met Ser Ala Phe Ala Gly Leu Gly Pro Arg Glu Lys Gly Pro
        1220                1225                1230
Asp Pro Leu Gln Tyr Met Arg Ala Asp Gln Ala Ala Gly Gly Leu
        1235                1240                1245
Arg Gln His Asp Ala Glu Val Asp Ala Thr Leu Lys Ser Leu Asn
        1250                1255                1260
Asn Gln Ile Glu Ser Ile Arg Ser Pro Glu Gly Ser Arg Lys Asn
        1265                1270                1275
Pro Ala Arg Thr Cys Arg Asp Leu Lys Leu Cys His Pro Glu Trp
        1280                1285                1290
Lys Ser Gly Asp Tyr Trp Ile Asp Pro Asn Gln Gly Cys Thr Leu
        1295                1300                1305
Asp Ala Met Lys Val Phe Cys Asn Met Glu Thr Gly Glu Thr Cys
        1310                1315                1320
Val Tyr Pro Asn Pro Ala Asn Val Pro Lys Lys Asn Trp Trp Ser
        1325                1330                1335
Ser Lys Ser Lys Glu Lys Lys His Ile Trp Phe Gly Glu Thr Ile
        1340                1345                1350
```

-continued

```
Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
    1415                1420                1425

Phe Thr Tyr Thr Ala Leu Lys Asp Gly Cys Thr Lys His Thr Gly
    1430                1435                1440

Lys Trp Gly Lys Thr Val Ile Glu Tyr Arg Ser Gln Lys Thr Ser
    1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485
```

<210> SEQ ID NO 114
<211> LENGTH: 5059
<212> TYPE: DNA
<213> ORGANISM: Homo sapiens

<400> SEQUENCE: 114

```
gcagagcgct gctgggctgc cgggtctccc gcttccccct cctgctccaa gggcctcctg      60
catgagggcg cggtagagac ccggacccgc gccgtgctcc tgccgtttcg ctgcgctccg     120
cccgggcccg gctcagccag gccccgcggt gagccatgat tcgcctcggg gctccccaga     180
cgctggtgct gctgacgctg ctcgtcgccg ctgtccttcg gtgtcagggc caggatgtcc     240
aggaggctgg cagctgtgtg caggatgggc agaggtataa tgataaggat gtgtggaagc     300
cggagccctg ccggatctgt gtctgtgaca ctgggactgt cctctgcgac gacataatct     360
gtgaagacgt gaaagactgc ctcagccctg agatcccctt cggagagtgc tgccccatct     420
gcccaactga cctcgccact gccagtgggc aaccaggacc aaagggacag aaaggagaac     480
ctggagacat caaggatatt gtaggaccca aggacctcc tgggcctcag ggacctgcag     540
gggaacaagg acccagaggg gatcgtggtg acaaaggtga aaaaggtgcc cctgacctc     600
gtggcagaga tggagaacct gggacccctg gaaatcctgg cccccctggt cctcccggcc     660
cccctggtcc ccctggtctt ggtggaaact ttgctgccca gatggctgga ggatttgatg     720
aaaaggctgg tggcgcccag ttgggagtaa tgcaaggacc aatgggcccc atgggacctc     780
gaggacctcc aggccctgca ggtgctcctg gcctcaagg atttcaaggc aatcctggtg     840
aacctggtga acctggtgtc tctggtccca tgggtcccg tggtcctcct ggtccccctg     900
gaaagcctgg tgatgatggt gaagctggaa aacctggaaa agctggtgaa agggtccgc     960
ctggtcctca gggtgctcgt ggtttcccag gaaccccagg ccttcctggt gtcaaaggtc    1020
acagaggtta tccaggcctg gacggtgcta agggagaggc gggtgctcct ggtgtgaagg    1080
gtgagagtgg ttccccgggt gagaacggat ctccgggccc aatgggtcct cgtggcctgc    1140
ctggtgaaag aggacggact ggccctgctg gcgctgcggg tgcccgaggc aacgatggtc    1200
agccaggccc cgcagggcct ccgggtcctg tcggtcctgc tggtggtcct ggcttccctg    1260
gtgctcctgg agccaagggt gaagccggcc ccactggtgc ccgtggtcct gaaggtgctc    1320
```

```
aaggtcctcg cggtgaacct ggtactcctg ggtcccctgg gcctgctggt gcctccggta   1380
accctggaac agatggaatt cctggagcca aaggatctgc tggtgctcct ggcattgctg   1440
gtgctcctgg cttccctggg ccacggggcc ctcctggccc tcaaggtgca actggtcctc   1500
tgggcccgaa aggtcagacg ggtgaacctg gtattgctgg cttcaaaggt gaacaaggcc   1560
ccaagggaga acctggccct gctggccccc agggagcccc tggacccgct ggtgaagaag   1620
gcaagagagg tgcccgtgga gagcctggtg gcgttgggcc catcggtccc cctggagaaa   1680
gaggtgctcc cggcaaccgc ggtttcccag gtcaagatgg tctggcaggt cccaagggag   1740
cccctggaga gcgagggccc agtggtcttg ctggccccaa gggagccaac ggtgaccctg   1800
gccgtcctgg agaacctggc cttcctggag cccggggtct cactggccgc cctggtgatg   1860
ctggtcctca aggcaaagtt ggcccttctg gagcccctgg tgaagatggt cgtcctggac   1920
ctccaggtcc tcagggggct cgtgggcagc ctggtgtcat gggtttccct ggccccaaag   1980
gtgccaacgg tgagcctggc aaagctggtg agaagggact gcctggtgct cctggtctga   2040
ggggtcttcc tggcaaagat ggtgagacag gtgctgcagg accccctggc cctgctggac   2100
ctgctggtga acgaggcgag cagggtgctc ctgggccatc tgggttccag ggacttcctg   2160
gccctcctgg tcccccaggt gaaggtgaaa accaggtgga ccaggtgttt cccggtgaag   2220
ctggagcccc tggcctcgtg gtcccaggg  gtgaacgagg tttcccaggt gaacgtggct   2280
ctcccggtgc ccagggcctc cagggtcccc gtggcctccc cggcactcct ggcactgatg   2340
gtcccaaagg tgcatctggc ccagcaggcc ccctggggc tcagggccct ccaggtcttc   2400
agggaatgcc tggcgagagg ggagcagctg gtatcgctgg gcccaaaggc gacaggggtg   2460
acgttggtga aaaggccct gagggagccc ctggaaagga tggtggacga ggcctgacag   2520
gtcccattgg cccccctggc ccagctggtg ctaatggcga aaggggagaa gttggacctc   2580
ctggtcctgc aggaagtgct ggtgctcgtg gcgctccggg tgaacgtgga gagactgggc   2640
cccccggacc agcgggattt gctgggcctc ctggtgctga tggccagcct ggggccaagg   2700
gtgagcaagg agaggccggc cagaaaggcg atgctggtgc cctggtcct cagggcccct   2760 ctggagcacc tgggcctcag gtcctactg gagtgactgg tcctaaagga gcccgaggtg   2820
cccaaggccc cccgggagcc actggattcc ctggagctgc tggccgcgtt ggaccccag   2880 gctccaatgg caaccctgga cccctggtc ccctggtcc ttctggaaaa gatggtccca   2940
aaggtgctcg aggagacagc ggccccctg gccgagctgg tgaacccggc ctccaaggtc   3000
ctgctggacc ccctggcgag aagggagagc tggagatga cggtccctct ggtgccgaag   3060
gtccaccagg tccccagggt ctggctggtc agagaggcat cgtcggtctg cctgggcaac   3120
gtggtgagag aggattccct ggcttgcctg gccgtcggg tgagcccggc aagcagggtg   3180
ctcctggagc atctggagac agaggtcctc ctggcccgt gggtcctcct ggcctgacgg   3240
gtcctgcagg tgaacctgga cgagagggaa gcccggtgc tgatggcccc cctggcagag   3300
atggcgctgc tggagtcaag ggtgatcgtg gtgagactgg tgctgtggga gctcctggag   3360
cccctgggcc ccctggctcc cctggccccg ctggtccaac tggcaagcaa ggagacagag   3420
gagaagctgc tgcacaaggc cccatgggac cctcaggacc agctggagcc cggggaatcc   3480
agggtcctca aggccccaga ggtgacaaag agaggctgg agagcctggc gagagaggcc   3540
tgaagggaca ccgtggcttc actggtctgc agggtctgcc cggccctcct ggtccttctg   3600
gagaccaagg tgcttctggt cctgctggtc cttctggccc tagaggtcct cctggccccg   3660
tcggtccctc tggcaaagat ggtgctaatg gaatccctgg ccccattggg cctcctggtc   3720
```

```
cccgtggacg atcaggcgaa accggccctg ctggtcctcc tggaaatcct ggaccccctg   3780
gtcctccagg tcccctggc cctggcatcg acatgtccgc ctttgctggc ttaggcccga   3840
gagagaaggg ccccgacccc ctgcagtaca tgcgggccga ccaggcagcc ggtggcctga   3900
gacagcatga cgccgaggtg gatgccacac tcaagtccct caacaaccag attgagagca   3960
tccgcagccc cgagggctcc cgcaagaacc ctgctcgcac ctgcagagac ctgaaactct   4020
gccaccctga gtggaagagt ggagactact ggattgaccc caaccaaggc tgcaccttgg   4080
acgccatgaa ggttttctgc aacatggaga ctggcgagac ttgcgtctac cccaatccag   4140
caaacgttcc caagaagaac tggtggagca gcaagagcaa ggagaagaaa cacatctggt   4200
ttggagaaac catcaatggt ggcttccatt tcagctatgg agatgacaat ctggctccca   4260
acactgccaa cgtccagatg accttcctac gcctgctgtc cacggaaggc tcccagaaca   4320
tcacctacca ctgcaagaac agcattgcct atctggacga agcagctggc aacctcaaga   4380
aggccctgct catccagggc tccaatgacg tggagatccg ggcagagggc aatagcaggt   4440
tcacgtacac tgccctgaag gatggctgca cgaaacatac cggtaagtgg ggcaagactg   4500
ttatcgagta ccggtcacag aagacctcac gcctccccat cattgacatt gcacccatgg   4560
acataggagg gcccgagcag gaattcggtg tggacatagg gccggtctgc ttcttgtaaa   4620
aacctgaacc cagaaacaac acaatccgtt gcaaacccaa aggacccaag tactttccaa   4680
tctcagtcac tctaggactc tgcactgaat ggctgacctg acctgatgtc cattcatccc   4740
accctctcac agttcggact tttctcccct ctctttctaa gagacctgaa ctgggcagac   4800
tgcaaaataa aatctcggtg ttctatttat ttattgtctt cctgtaagac cttcgggtca   4860
aggcagaggc aggaaactaa ctggtgtgag tcaaatgccc cctgagtgac tgcccccagc   4920
ccaggccaga agacctccct tcaggtgccg ggcgcaggaa ctgtgtgtgt cctacacaat   4980
ggtgctattc tgtgtcaaac acctctgtat tttttaaaac atcaattgat attaaaaatg   5040
aaaagattat tggaaagta                                               5059
```